(12) United States Patent
Van Rooijen et al.

(10) Patent No.: US 12,409,137 B2
(45) Date of Patent: Sep. 9, 2025

(54) MODIFICATION OF PLANT MESSENGER PACKS WITH CHARGED LIPIDS

(71) Applicant: Flagship Pioneering Innovations VI, LLC, Cambridge, MA (US)

(72) Inventors: Maria Helena Christine Van Rooijen, Cambridge, MA (US); Hok Hei Tam, Newton, MA (US); Maier Steve Avendaño Amado, Cambridge, MA (US); Barry Andrew Martin, Boston, MA (US); Ignacio Martinez, Lexington, MA (US); Piotr Stanislaw Kowalski, Cork (IE); Nataliya Vladimirovna Nukolova, Cambridge, MA (US); John Patrick Casey, Jr., Boston, MA (US); Siddharth Dilipkumar Patel, Cambridge, MA (US); Roman Lvovitch Bogorad, Newton, MA (US)

(73) Assignee: Flagship Pioneering Innovations VI, LLC, Cambridge, MA (US)

( * ) Notice: Subject to any disclaimer, the term of this patent is extended or adjusted under 35 U.S.C. 154(b) by 633 days.

(21) Appl. No.: 17/637,278

(22) PCT Filed: Aug. 24, 2020

(86) PCT No.: PCT/US2020/047606
§ 371 (c)(1),
(2) Date: Feb. 22, 2022

(87) PCT Pub. No.: WO2021/041301
PCT Pub. Date: Mar. 4, 2021

(65) Prior Publication Data
US 2022/0304930 A1    Sep. 29, 2022

Related U.S. Application Data

(60) Provisional application No. 62/981,968, filed on Feb. 26, 2020, provisional application No. 62/981,989, (Continued)

(51) Int. Cl.
| | | |
|---|---|---|
| A61K 9/1272 | (2025.01) |
| A61K 47/60 | (2017.01) |
| C12N 15/88 | (2006.01) |

(52) U.S. Cl.
CPC ............ *A61K 9/1272* (2013.01); *A61K 47/60* (2017.08); *C12N 15/88* (2013.01)

(58) Field of Classification Search
CPC ...... A61K 9/1272; A61K 47/60; C12N 15/88; C12N 15/87; A01N 25/30
See application file for complete search history.

(56) References Cited

U.S. PATENT DOCUMENTS

| | | |
|---|---|---|
| 2011/0203013 A1 | 8/2011 | Peterson et al. |
| 2018/0169016 A1 | 6/2018 | DeRosa et al. |
| 2018/0221402 A1* | 8/2018 | Prieve ................ A61K 31/4745 |

FOREIGN PATENT DOCUMENTS

| | | |
|---|---|---|
| JP | 2014-185090 A | 10/2014 |
| WO | WO-2016/118697 A1 | 7/2016 |
| WO | WO-2020/041783 A1 | 2/2020 |

OTHER PUBLICATIONS

Wang et al, "Delivery of therapeutic agents by nanoparticles made of grapefruit-derived lipids", Nat. Comm., 2013, 4:1867, pp. 1-11. (Year: 2013).*

(Continued)

*Primary Examiner* — Marianne C Seidel
*Assistant Examiner* — Joshua A Atkinson
(74) *Attorney, Agent, or Firm* — Clark & Elbing LLP

(57) ABSTRACT

Disclosed herein are compositions including a plurality of plant messenger packs, (e.g., including a plant extracellular
(Continued)

vesicle (EV), or segment, portion, or extract thereof), that are modified to have enhanced cell uptake (e.g., animal plant cell uptake, bacterial cell uptake, or fungal cell uptake), e.g., for use in a variety of agricultural or therapeutic methods.

15 Claims, 21 Drawing Sheets

Specification includes a Sequence Listing.

Related U.S. Application Data filed on Feb. 26, 2020, provisional application No. 62/891,330, filed on Aug. 24, 2019, provisional application No. 62/891,329, filed on Aug. 24, 2019.

(56) References Cited

OTHER PUBLICATIONS

Uemura et al, "The efficiency of lipid nanoparticles with an original cationic lipid as a siRNA delivery system for macrophages and dendritic cells", Pharm. Dev. Tech. 2019, 24, 3, pp. 263-268. First published May 8, 2018. (Year: 2019).*

Love et al., "Lipid-like materials for low-dose, in vivo gene silencing," Proc Natl Acad Sci USA. 107(5):1864-9 (Feb. 2010) (7 pages).

Extended European Search Report for European Patent Application No. 20859434.1, dated Aug. 23, 2023 (9 pages).

Ci et al., "Biodistribution of Lipid 5, mRNA, and Its Translated Protein Following Intravenous Administration of mRNA-Encapsulated Lipid Nanoparticles in Rats," Drug Metab Dispos. 51(7):813-823 (May 2023).

Sabnis et al., "A Novel Amino Lipid Series for mRNA Delivery: Improved Endosomal Escape and Sustained Pharmacology and Safety in Non-human Primates," Molecular Therapy. 26(6): 1509-1519 (Jun. 2018).

\* cited by examiner

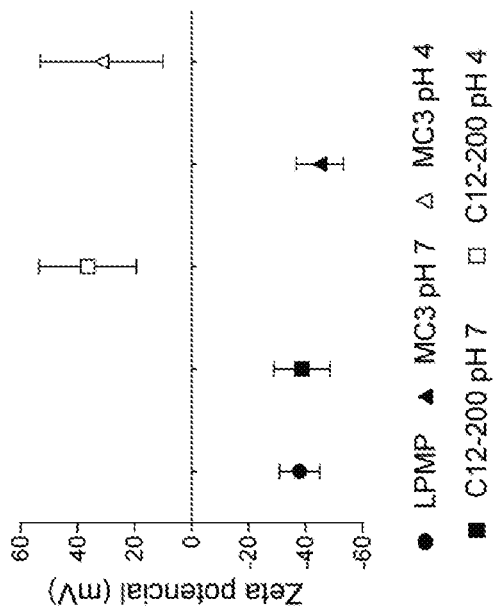
FIG. 3A
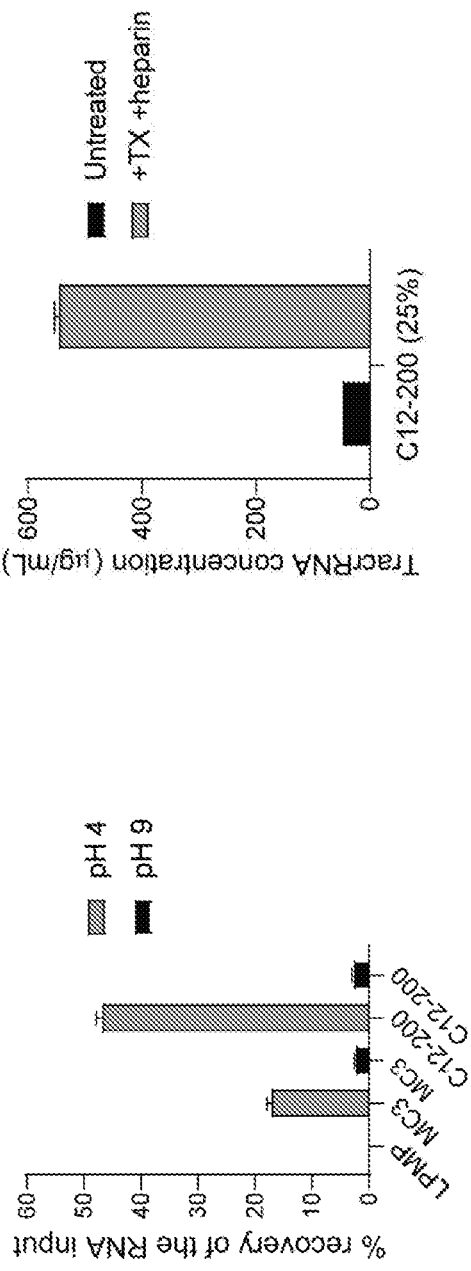
FIG. 3B
FIG. 3C

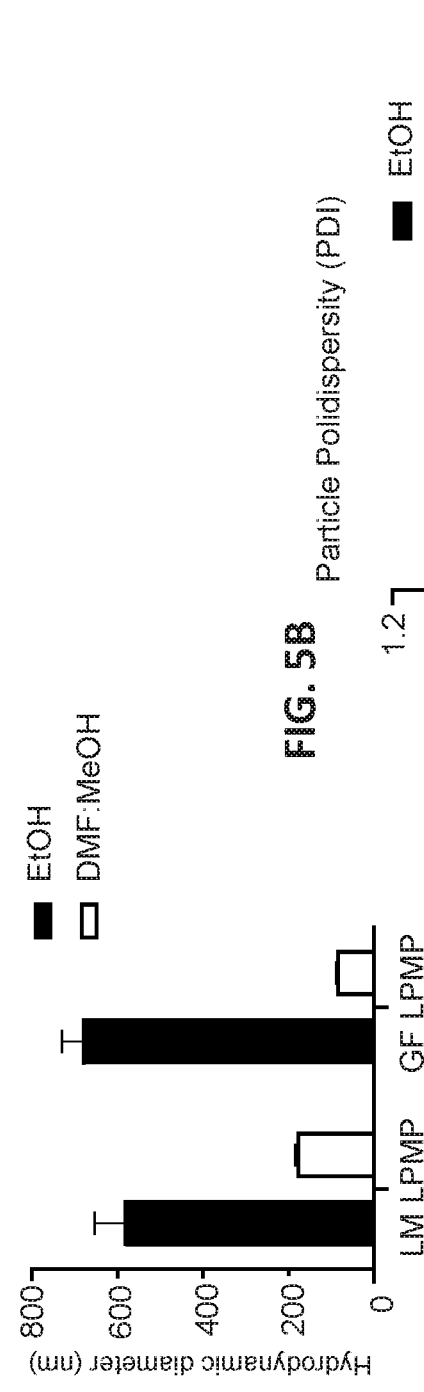
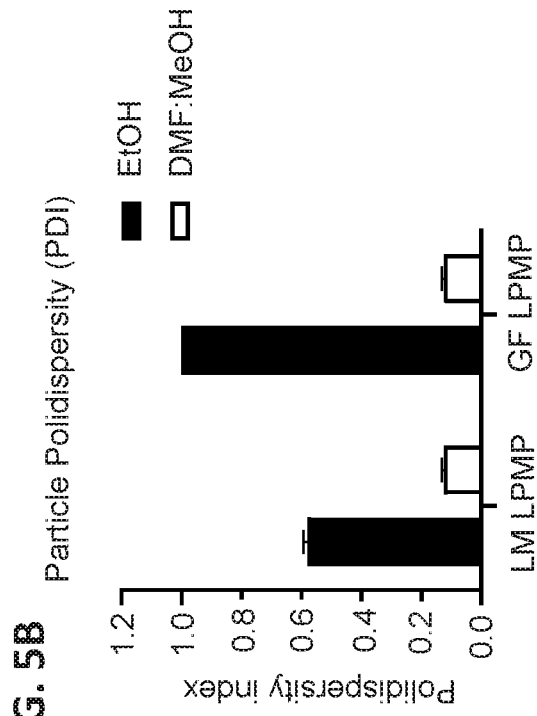
FIG. 5A
FIG. 5B

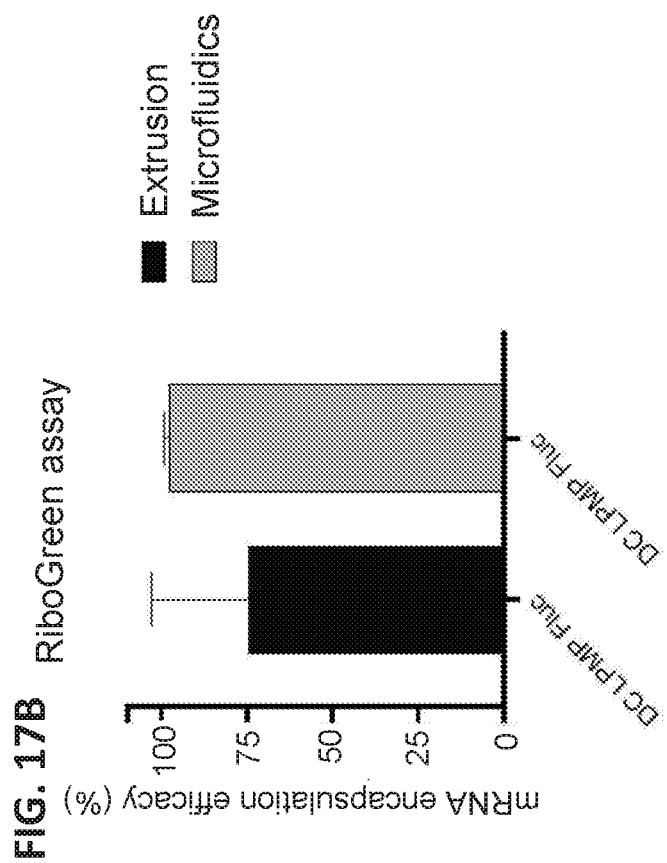
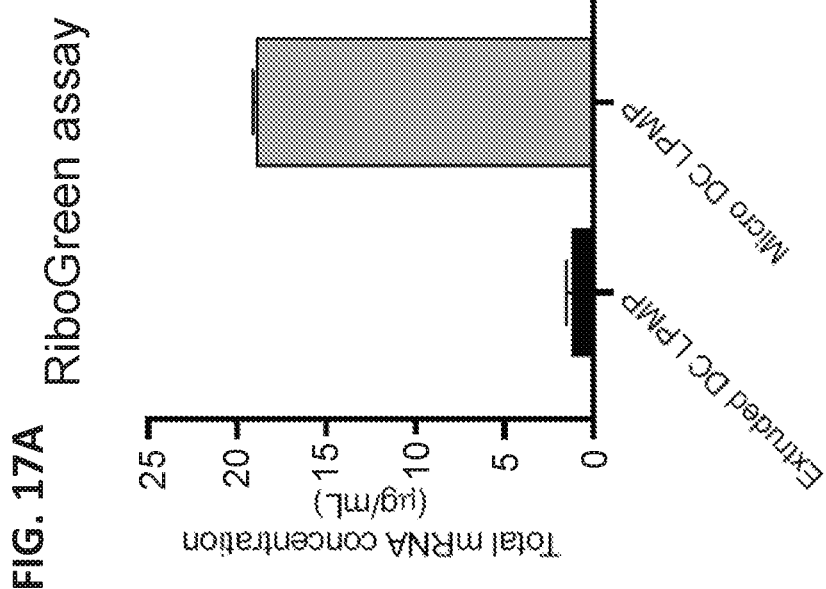
FIG. 17A
FIG. 17B

MODIFICATION OF PLANT MESSENGER PACKS WITH CHARGED LIPIDS

SEQUENCE LISTING

The instant application contains a Sequence Listing which has been submitted electronically in ASCII format and is hereby incorporated by reference in its entirety. Said ASCII copy, created on Aug. 20, 2020, is named 51296-044WO1_Sequence_Listing_8_20_20_ST25 and is 3,013 bytes in size.

BACKGROUND

Delivery of heterologous functional agents (e.g., agricultural or therapeutic agents) can be limited by the degree to which the agent can penetrate cell barriers and thereby effectively act on an organism. For example, the barrier formed by the plant cell wall, bacterial cell wall, or fungal cell wall, or by the cell membrane and/or extracellular matrix of an animal cell, poses a challenge to cellular uptake of agents useful in agriculture or therapeutic applications. Therefore, there is a need in the art for methods and compositions promoting cellular uptake of agents and for methods of manufacturing plant messenger packs comprising heterologous functional agents.

SUMMARY OF THE INVENTION

In one aspect, provided herein is a method for making lipid reconstructed plant messenger packs (LPMPs), the method comprising reconstituting a film comprising purified PMP lipids in the presence of a synthetic charged lipid, thereby producing a LPMP that comprises the synthetic charged lipid.

In another aspect, provided herein is a method for making lipid reconstructed plant messenger packs (LPMPs), the method comprising reconstituting a film comprising purified PMP lipids in the presence of a synthetic charged lipid, thereby producing a LPMP that comprises the synthetic charged lipid, wherein the synthetic charged lipid is chosen from 1'-((2-(4-(2-((2-(bis(2-hydroxydodecyl)amino)ethyl)(2-hydroxydodecyl)amino)ethyl)piperazin-1-yl)ethyl)azanediyl)bis(dodecan-2-ol) (C12-200), DLin-MC3-DMA (MC3), dioleoyl-3-trimethylammonium propane (DODAP), DC-cholesterol, DOTAP, Ethyl PC, GL67, DLin-KC2-DMA (KC2), MD1 (cKK-E12), OF2, EPC, ZA3-Ep10, TT3, LP01, 5A2-SC8, Lipid 5 (Moderna), a cationic sulfonamide amino lipid, an amphiphilic zwitterionic amino lipid, DODAC, DOBAQ, YSK05, DOBAT, DOBAQ, DOPAT, DOMPAQ, DOAAQ, DMAP-BLP, DLinDMA, DODMA, DOTMA, DSDMA, DOSPA, DODAC, DOBAQ, DMRIE, DOTAP-cholesterol, GL67A, and 98N12-5, or combinations thereof.

In some embodiments, the synthetic charged lipid is chosen from C12-200, MC3, DODAP, DC-cholesterol, DOTAP, Ethyl PC, GL67, KC2, MD1, OF2, EPC, ZA3-Ep10, TT3, LP01, 5A2-SC8, Lipid 5 (Moderna), a cationic sulfonamide amino lipid, and an amphiphilic zwitterionic amino lipid, or combinations thereof.

In some embodiments, the synthetic charged lipid is chosen from C12-200, MC3, DODAP, and DC-cholesterol, or combinations thereof.

In some embodiments, the reconstitution is performed in the presence of a sterol, thereby producing a LPMP that comprises a synthetic charged lipid and a sterol. In some embodiments, the sterol is cholesterol or sitosterol.

In some embodiments, the reconstitution is performed in the presence of a PEGylated lipid, thereby producing a LPMP that comprises a synthetic charged lipid and a PEGylated lipid. In some embodiments, the PEGylated lipid is C14-PEG2k, C18-PEG2k, or DMPE-PEG2k.

In some embodiments, the reconstitution is performed in the presence of a sterol and a PEGylated lipid, thereby producing a LPMP that comprises a synthetic charged lipid, a sterol, and a PEGylated lipid. In some embodiments, the synthetic charged lipid, purified PMP lipids, sterol, and PEGylated lipid comprise about 30%-75%, about 10%-20%, about 35%-50%, and about 1%-3%, respectively, of the lipids in the modified PMP. In some embodiments, the synthetic charged lipid, purified PMP lipids, sterol, and PEGylated lipid are formulated at a molar ratio of 50:10:38.5:1.5.

In some embodiments, the LPMPs comprise a heterologous polynucleotide. In some embodiments, the heterologous polynucleotide is an mRNA, a siRNA or a precursor thereof, a microRNA (miRNA) or a precursor thereof, a viral RNA, or a plasmid. In some embodiments, the encapsulation efficiency of the heterologous polynucleotide by the LPMP is at least 5%, 10%, 15%, 20%, 30%, 40%, 50%, 60%, 70%, 80%, 90%, 95%, 98%, 99%, or more than 99%.

In some embodiments, the LPMP is formulated for delivery to an animal.

In some embodiments, the LPMP is formulated for delivery to a plant.

In another aspect, provided herein is a composition comprising a PMP modified to comprise a synthetic charged lipid.

In another aspect, provided herein is a composition comprising a PMP modified to comprise a synthetic charged lipid, wherein the synthetic charged lipid is chosen from 1'-((2-(4-(2-((2-(bis(2-hydroxydodecyl)amino)ethyl)(2-hydroxydodecyl)amino)ethyl)piperazin-1-yl)ethyl)azanediyl)bis(dodecan-2-ol) (C12-200), DLin-MC3-DMA (MC3), dioleoyl-3-trimethylammonium propane (DODAP), DC-cholesterol, DOTAP, Ethyl PC, GL67, DLin-KC2-DMA (KC2), MD1 (cKK-E12), OF2, EPC, ZA3-Ep10, TT3, LP01, 5A2-SC8, Lipid 5 (Moderna), a cationic sulfonamide amino lipid, an amphiphilic zwitterionic amino lipid, DODAC, DOBAQ, YSK05, DOBAT, DOBAQ, DOPAT, DOMPAQ, DOAAQ, DMAP-BLP, DLinDMA, DODMA, DOTMA, DSDMA, DOSPA, DODAC, DOBAQ, DMRIE, DOTAP-cholesterol, GL67A, and 98N12-5, or combinations thereof.

In another aspect, provided herein is a composition comprising a PMP modified to comprise a synthetic charged lipid, wherein the PMP is modified by reconstituting a lipid film comprising purified PMP lipids in the presence of a synthetic charged lipid, thereby producing a modified PMP that comprises the synthetic charged lipid.

In another aspect, provided herein is a composition comprising a PMP modified to comprise a synthetic charged lipid, wherein the PMP is modified by reconstituting a lipid film comprising purified PMP lipids in the presence of a synthetic charged lipid, thereby producing a modified PMP that comprises the synthetic charged lipid, wherein the synthetic charged lipid is chosen from 1'-((2-(4-(2-((2-(bis(2-hydroxydodecyl)amino)ethyl)(2-hydroxydodecyl)amino)ethyl)piperazin-1-yl)ethyl)azanediyl)bis(dodecan-2-ol) (C12-200), DLin-MC3-DMA (MC3), dioleoyl-3-trimethylammonium propane (DODAP), DC-cholesterol, DOTAP, Ethyl PC, GL67, DLin-KC2-DMA (KC2), MD1 (cKK-E12), OF2, EPC, ZA3-Ep10, TT3, LP01, 5A2-SC8, Lipid 5 (Moderna), a cationic sulfonamide amino lipid, an amphiphilic zwitterionic amino lipid, DODAC, DOBAQ, YSK05, DOBAT, DOBAQ, DOPAT, DOMPAQ, DOAAQ, DMAP-BLP, DLinDMA, DODMA, DOTMA, DSDMA, DOSPA, DODAC, DOBAQ, DMRIE, DOTAP-cholesterol, GL67A, and 98N12-5, or combinations thereof.

In some embodiments, the synthetic charged lipid is chosen from C12-200, MC3, DODAP, DC-cholesterol, DOTAP, Ethyl PC, GL67, KC2, MD1, OF2, EPC, ZA3-Ep10, TT3, LP01, 5A2-SC8, Lipid 5 (Moderna), a cationic sulfonamide amino lipid, and an amphiphilic zwitterionic amino lipid, or combinations thereof.

In some embodiments, the synthetic charged lipid is chosen from C12-200, MC3, DODAP, and DC-cholesterol, or combinations thereof.

In some embodiments, the modified PMP further comprises a sterol.

In some embodiments, the modified PMP further comprises a PEGylated lipid.

In some embodiments, the modified PMP further comprises a sterol and a PEGylated lipid.

In some embodiments, the sterol is cholesterol or sitosterol.

In some embodiments, the PEGylated lipid is C14-PEG2k, C18-PEG2k, or DMPE-PEG2k.

In some embodiments, the synthetic charged lipid, purified PMP lipids, sterol, and PEGylated lipid comprise about 30%-75%, about 10%-20%, about 35%-50%, and about 1%-3%, respectively, of the lipids in the modified PMP. In some embodiments, the synthetic charged lipid, purified PMP lipids, sterol, and PEGylated lipid are formulated at a molar ratio of 50:10:38.5:1.5.

In some embodiments, the synthetic charged lipid is C12-200. In some embodiments, a lipid membrane of the modified PMPs comprises 25% C12-200.

In some embodiments, the synthetic charged lipid is MC3. In some embodiments, a lipid membrane of the modified PMPs comprises 40% MC3.

In some embodiments, the synthetic charged lipid is DC-cholesterol. In some embodiments, a lipid membrane of the modified PMPs comprises 20% DC-cholesterol. In some embodiments, a lipid membrane of the modified PMPs comprises 40% DC-cholesterol.

In some embodiments, the synthetic charged lipid is DOTAP. In some embodiments, a lipid membrane of the modified PMPs comprises 25% DOTAP.

In some embodiments, the synthetic charged lipid is an ionizable lipid and the composition has a zeta potential of greater than −40 mV at pH 4 when in the absence of cargo. In some embodiments, the composition has a zeta potential of greater than 0 mV at pH 4 when in the absence of cargo. In some embodiments, the composition has a zeta potential of greater than 20 mV at pH 4 when in the absence of cargo. In some embodiments, the composition has a zeta potential of greater than 30 mV at pH 4 when in the absence of cargo. In some embodiments, the composition has a zeta potential of about 40 mV at pH 4 when in the absence of cargo. In some embodiments, the composition has a zeta potential of greater than −30 mV when in the absence of cargo. In some embodiments, the composition has a zeta potential of greater than −20 mV when in the absence of cargo. In some embodiments, the composition has a zeta potential of greater than −5 mV when in the absence of cargo. In some embodiments, the composition has a zeta potential of greater than 0 mV when in the absence of cargo. In some embodiments, the composition has a zeta potential of about 30 mV when in the absence of cargo.

In some embodiments, the modified PMPs comprise a heterologous functional agent. In some embodiments, the heterologous functional agent is encapsulated by the modified PMPs. In some embodiments, the heterologous functional agent is embedded on the surface of the modified PMPs. In some embodiments, the heterologous functional agent is conjugated to the surface of the modified PMPs.

In some embodiments, the heterologous functional agent is a polynucleotide. In some embodiments, the polynucleotide is chosen from an mRNA, an siRNA or siRNA precursor, a microRNA (miRNA) or miRNA precursor, a plasmid, a Dicer substrate small interfering RNA (dsiRNA), a short hairpin RNA (shRNA), an asymmetric interfering RNA (aiRNA), a peptide nucleic acid (PNA), a morpholino, a locked nucleic acid (LNA), a piwi-interacting RNA (piRNA), a ribozyme, a deoxyribozyme (DNAzyme), an aptamer, a circular RNA (circRNA), a guide RNA (gRNA), or a DNA molecule encoding any of these RNAs. In some embodiments, the polynucleotide is an mRNA. In some embodiments, the polynucleotide is an siRNA or a precursor thereof. In some embodiments, the polynucleotide is a plasmid. In some embodiments, the encapsulation efficiency of the polynucleotide by the modified PMP is at least 5%, 10%, 15%, 20%, 30%, 40%, 50%, 60%, 70%, 80%, 90%, 95%, 98%, 99%, or more than 99%.

In some embodiments, the modified PMPs are lipid reconstructed PMPs (LPMPs). In some embodiments, the LPMP is produced by a method comprising lipid extrusion. In some embodiments, the LPMP is produced by a method comprising processing a solution comprising a lipid extract of the PMPs in a microfluidics device comprising an aqueous phase, thereby producing the LPMPs. In some embodiments, the aqueous phase comprises a heterologous functional agent.

In some embodiments, the modified PMPs have increased cell uptake. In some embodiments, the increased cell uptake is an increased cell uptake of at least 1%, 2%, 5%, 10%, 15%, 20%, 30%, 40%, 50%, 60%, 70%, 80%, 90%, or 100% relative to the cell uptake of the unmodified PMP. In some embodiments, the cell is a mammalian cell. In some embodiments, the mammalian cell is a human cell. In some embodiments, the cell is a plant cell. In some embodiments, the cell is a bacterial cell. In some embodiments, the cell is a fungal cell.

In another aspect, provided herein is a method for delivering a PMP to a target cell, the method comprising introducing a composition that comprises a PMP comprising a synthetic charged lipid to the target cell.

In another aspect, provided herein is a method for delivering a PMP to a target cell, the method comprising introducing a composition that comprises a PMP comprising a synthetic charged lipid to the target cell, wherein the synthetic charged lipid is chosen from 1′-((2-(4-(2-((2-(bis(2-hydroxydodecyl)amino)ethyl) (2-hydroxydodecyl)amino) ethyl)piperazin-1-yl)ethyl)azanediyl)bis(dodecan-2-ol) (C12-200), DLin-MC3-DMA (MC3), dioleoyl-3-trimethyl-ammonium propane (DODAP), DC-cholesterol, DOTAP, Ethyl PC, GL67, DLin-KC2-DMA (KC2), MD1 (cKK-E12), OF2, EPC, ZA3-Ep10, TT3, LP01, 5A2-SC8, Lipid 5 (Moderna), a cationic sulfonamide amino lipid, an amphiphilic zwitterionic amino lipid, DODAC, DOBAQ, YSK05, DOBAT, DOBAQ, DOPAT, DOMPAQ, DOAAQ, DMAP-BLP, DLinDMA, DODMA, DOTMA, DSDMA, DOSPA, DODAC, DOBAQ, DMRIE, DOTAP-cholesterol, GL67A, and 98N12-5, or combinations thereof.

In some embodiments, the synthetic charged lipid is chosen from C12-200, MC3, DODAP, DC-cholesterol, DOTAP, Ethyl PC, GL67, KC2, MD1, OF2, EPC, ZA3-Ep10, TT3, LP01, 5A2-SC8, Lipid 5 (Moderna), a cationic sulfonamide amino lipid, and an amphiphilic zwitterionic amino lipid, or combinations thereof. In some embodiments, the synthetic charged lipid is chosen from C12-200, MC3, DODAP, and DC-cholesterol, or combinations thereof.

In some embodiments, the PMP further comprises a sterol. In some embodiments, the PMP further comprises a PEGylated lipid.

In some embodiments, the PMP further comprises a sterol and a PEGylated lipid. In some embodiments, the sterol is cholesterol or sitosterol. In some embodiments, the PEGylated lipid is C14-PEG2k, C18-PEG2k, or DMPE-PEG2k. In some embodiments, the synthetic charged lipid, purified PMP lipids, sterol, and PEGylated lipid comprise about 30%-75%, about 10%-20%, about 35%-50%, and about 1%-3%, respectively, of the lipids in the PMP. In some embodiments, the synthetic charged lipid, purified PMP lipids, sterol, and PEGylated lipid are formulated at a molar ratio of 50:10:38.5:1.5.

In some embodiments, the synthetic charged lipid is C12-200. In some embodiments, a lipid membrane of the modified PMPs comprises 25% C12-200.

In some embodiments, the synthetic charged lipid is MC3. In some embodiments, a lipid membrane of the modified PMPs comprises 40% MC3.

In some embodiments, the synthetic charged lipid is DC-cholesterol. In some embodiments, a lipid membrane of the modified PMPs comprises 20% DC-cholesterol. In some embodiments, a lipid membrane of the modified PMPs comprises 40% DC-cholesterol.

In some embodiments, the synthetic charged lipid is DOTAP. In some embodiments, a lipid membrane of the modified PMPs comprises 25% DOTAP.

In some embodiments, the synthetic charged lipid is an ionizable lipid and the composition comprising the PMP has a zeta potential of greater than −40 mV at pH 4 when in the absence of cargo. In some embodiments, the composition comprising the PMP has a zeta potential of greater than 0 mV at pH 4 when in the absence of cargo. In some embodiments, the composition comprising the PMP has a zeta potential of greater than 20 mV at pH 4 when in the absence of cargo. In some embodiments, the composition comprising the PMP has a zeta potential of greater than 30 mV at pH 4 when in the absence of cargo. In some embodiments, the composition comprising the PMP has a zeta potential of about 40 mV at pH 4 when in the absence of cargo. In some embodiments, the composition comprising the PMP has a zeta potential of greater than −30 mV when in the absence of cargo. In some embodiments, the composition comprising the PMP has a zeta potential of greater than −20 mV when in the absence of cargo. In some embodiments, the composition comprising the PMP has a zeta potential of greater than −5 mV when in the absence of cargo. In some embodiments, the composition comprising the PMP has a zeta potential of greater than 0 mV when in the absence of cargo. In some embodiments, the composition comprising the PMP has a zeta potential of about 30 mV when in the absence of cargo.

In some embodiments, the PMP comprises a heterologous functional agent. In some embodiments, the heterologous functional agent is encapsulated by the PMP. In some embodiments, the heterologous functional agent is embedded on the surface of the PMP. In some embodiments, the heterologous functional agent is conjugated to the surface of the PMP.

In some embodiments, the heterologous functional agent is a polynucleotide. In some embodiments, the polynucleotide is chosen from an mRNA, an siRNA or siRNA precursor, a miRNA or miRNA precursor, a plasmid, a dsiRNA, a shRNA, an aiRNA, a PNA, a morpholino, a LNA, a piRNA, a ribozyme, a DNAzyme, an aptamer, a circRNA, a gRNA, or a DNA molecule encoding any of these RNAs. In some embodiments, the polynucleotide is an mRNA. In some embodiments, the polynucleotide is an siRNA or a precursor thereof. In some embodiments, the polynucleotide is a plasmid. In some embodiments, the encapsulation efficiency of the polynucleotide by the PMP is at least 5%, 10%, 15%, 20%, 30%, 40%, 50%, 60%, 70%, 80%, 90%, 95%, 98%, 99%, or more than 99%.

In some embodiments, the PMP is a lipid reconstructed PMP (LPMP).

In some embodiments, the PMP has increased cell uptake. In some embodiments, the increased cell uptake is an increased cell uptake of at least 1%, 2%, 5%, 10%, 15%, 20%, 30%, 40%, 50%, 60%, 70%, 80%, 90%, or 100% relative to the cell uptake of the unmodified PMP. In some embodiments, the cell is a mammalian cell. In some embodiments, the mammalian cell is a human cell. In some embodiments, the cell is a plant cell. In some embodiments, the cell is a bacterial cell. In some embodiments, the cell is a fungal cell.

In another aspect, provided herein is a method of increasing the fitness of a plant, the method comprising delivering to the plant an effective amount of any one of the above compositions, wherein the method increases the fitness of the plant relative to an untreated plant.

In some embodiments, the modified PMP comprises an agricultural agent.

In some embodiments, the plant is a plant of agricultural or horticultural importance. In some embodiments, the plant is a soybean plant, a wheat plant, or a corn plant.

In another aspect, provided herein is a method of decreasing the fitness of a plant, the method comprising delivering to the plant an effective amount of any of the above compositions, wherein the method decreases the fitness of the plant relative to an untreated plant.

In some embodiments, the modified PMP comprises an agricultural agent.

In some embodiments, the plant is a weed.

In some embodiments, the composition is delivered to a leaf, seed, embryo, ovule, meristem, microspore, root, fruit, shoot, pollen, or flower of the plant.

In another aspect, provided herein is a method of increasing the fitness of a mammal, the method comprising delivering to the mammal an effective amount of any one of the above compositions, wherein the method increases the fitness of the mammal relative to an untreated mammal.

In some embodiments, the modified PMP comprises a heterologous therapeutic agent.

In some embodiments, the mammal is a human.

In another aspect, provided herein is a composition comprising a plurality of modified PMPs having a zeta potential of greater than or equal to −30 mV when in the absence of cargo.

In another aspect, provided herein is a composition comprising a plurality of modified PMPs having a zeta potential of greater than −40 mV at pH 4 when in the absence of cargo.

In some embodiments, the composition has a net positive zeta potential when in the absence of cargo.

In some embodiments, the composition comprises an exogenous lipid. In some embodiments, the exogenous lipid is an ionizable lipid. In some embodiments, the ionizable lipid is C12-200. In some embodiments, the ionizable lipid is MC3. In some embodiments, the exogenous lipid is a cationic lipid. In some embodiments, the cationic lipid is DOTAP. In some embodiments, the cationic lipid is DC-cholesterol.

In some embodiments, the composition has a zeta potential of greater than 0 mV at pH 4 when in the absence of cargo. In some embodiments, the composition has a zeta potential of greater than 20 mV at pH 4 when in the absence of cargo. In some embodiments, the composition has a zeta potential of about 40 mV at pH 4 when in the absence of cargo.

In some embodiments, the modified PMPs further comprise a cargo. In some embodiments, the cargo is a heterologous functional agent. In some embodiments, the heterologous functional agent is a polynucleotide. In some embodiments, the polynucleotide is chosen from an mRNA, an siRNA or siRNA precursor, a miRNA or miRNA precursor, a plasmid, a dsiRNA, a shRNA, an aiRNA, a PNA, a morpholino, a LNA, a piRNA, a ribozyme, a DNAzyme, an aptamer, a circRNA, a gRNA, or a DNA molecule encoding any of these RNAs.

In some embodiments, zeta potential is measured by electrophoretic light scattering.

In another aspect, provided herein is a method for delivering a cargo to a cell, the method comprising contacting a cell with any one of the compositions provided herein.

In another aspect, provided herein is a method for increasing uptake of a cargo by a cell, the method comprising contacting a cell with any one of the compositions provided herein.

In another aspect, provided herein is a method for fusing a composition to a cell, the method comprising contacting a cell with any one of the compositions provided herein.

In another aspect, provided herein is a method for delivering a composition to a cell wall, the method comprising contacting a cell with any one of the compositions provided herein.

In another aspect, provided herein is a method for modulating gene expression in a cell, the method comprising contacting a cell with any one of the compositions provided herein.

In another aspect, provided herein is a composition comprising a plurality of lipid reconstructed PMPs (LPMPs), wherein the LPMPs are produced by a process comprising the steps of (a) providing a plurality of purified PMPs; (b) processing the plurality of PMPs to produce a lipid film; (c) reconstituting the lipid film in an organic solvent, wherein the organic solvent is dimethylformamide:methanol (DMF:MeOH), thereby producing a lipid solution; and (d) processing the lipid solution of step (c) in a microfluidics device comprising an aqueous phase, thereby producing the LPMPs.

In some embodiments, the LPMPs further comprise an exogenous lipid. In some embodiments, the exogenous lipid is added to the preparation prior to step (b). In some embodiments, the exogenous lipid is a synthetic charged lipid. In some embodiments, the synthetic charged lipid is chosen from 1'-((2-(4-(2-((2-(bis(2-hydroxydodecyl)amino) ethyl) (2-hydroxydodecyl)amino)ethyl)piperazin-1-yl) ethyl)azanediyl)bis(dodecan-2-ol) (C12-200), DLin-MC3-DMA (MC3), dioleoyl-3-trimethylammonium propane (DODAP), DC-cholesterol, DOTAP, Ethyl PC, GL67, DLin-KC2-DMA (KC2), MD1 (cKK-E12), OF2, EPC, ZA3-Ep10, TT3, LP01, 5A2-SC8, Lipid 5 (Moderna), a cationic sulfonamide amino lipid, an amphiphilic zwitterionic amino lipid, DODAC, DOBAQ, YSK05, DOBAT, DOBAQ, DOPAT, DOMPAQ, DOAAQ, DMAP-BLP, DLinDMA, DODMA, DOTMA, DSDMA, DOSPA, DODAC, DOBAQ, DMRIE, DOTAP-cholesterol, GL67A, and 98N12-5, or combinations thereof. In some embodiments, the synthetic charged lipid is chosen from C12-200, MC3, DODAP, DC-cholesterol, DOTAP, Ethyl PC, GL67, KC2, MD1, OF2, EPC, ZA3-Ep10, TT3, LP01, 5A2-SC8, Lipid 5 (Moderna), a cationic sulfonamide amino lipid, and an amphiphilic zwitterionic amino lipid, or combinations thereof. In some embodiments, the synthetic charged lipid is chosen from C12-200, MC3, DODAP, and DC-cholesterol, or combinations thereof.

In some embodiments, the aqueous phase comprises a citrate buffer having a pH of about 3.2.

In some embodiments, the aqueous phase and the lipid solution are mixed at a 3:1 volumetric ratio.

In some embodiments, the LPMPs comprise a heterologous functional agent. In some embodiments, the heterologous functional agent is a polynucleotide. In some embodiments, the polynucleotide is chosen from an mRNA, an siRNA or siRNA precursor, a miRNA or miRNA precursor, a plasmid, a dsiRNA, a shRNA, an aiRNA, a PNA, a morpholino, a LNA, a piRNA, a ribozyme, a DNAzyme, an aptamer, a circRNA, a gRNA, or a DNA molecule encoding any of these RNAs.

In some embodiments, the heterologous functional agent is comprised by the aqueous phase.

In some embodiments, the LPMPs further comprise a sterol. In some embodiments, the LPMPs further comprise a PEGylated lipid. In some embodiments, the LPMPs further comprise a sterol and a PEGylated lipid. In some embodiments, the sterol is cholesterol or sitosterol. In some embodiments, the PEGylated lipid is C14-PEG2k, C18-PEG2k, or DMPE-PEG2k.

In another aspect, provided herein is a method for making LPMPs, the method comprising (a) providing a plurality of purified PMPs; (b) processing the plurality of PMPs to produce a lipid film; (c) reconstituting the lipid film in an organic solvent, wherein the organic solvent is dimethylformamide:methanol (DMF:MeOH), thereby producing a lipid solution; and (d) processing the lipid solution of step (c) in a microfluidics device comprising an aqueous phase, thereby producing the LPMPs.

In some embodiments, the LPMPs further comprise an exogenous lipid.

In some embodiments, the exogenous lipid is added to the preparation prior to step (b).

In some embodiments, the exogenous lipid is a synthetic charged lipid. In some embodiments, the synthetic charged lipid is chosen from 1'-((2-(4-(2-((2-(bis(2-hydroxydodecyl) amino)ethyl) (2-hydroxydodecyl)amino)ethyl)piperazin-1-yl)ethyl)azanediyl)bis(dodecan-2-ol) (C12-200), DLin-MC3-DMA (MC3), dioleoyl-3-trimethylammonium propane (DODAP), DC-cholesterol, DOTAP, Ethyl PC, GL67, DLin-KC2-DMA (KC2), MD1 (cKK-E12), OF2, EPC, ZA3-Ep10, TT3, LP01, 5A2-SC8, Lipid 5 (Moderna), a cationic sulfonamide amino lipid, an amphiphilic zwitterionic amino lipid, DODAC, DOBAQ, YSK05, DOBAT, DOBAQ, DOPAT, DOMPAQ, DOAAQ, DMAP-BLP, DLinDMA, DODMA, DOTMA, DSDMA, DOSPA, DODAC, DOBAQ, DMRIE, DOTAP-cholesterol, GL67A, and 98N12-5, or combinations thereof. In some embodiments, the synthetic charged lipid is chosen from C12-200, MC3, DODAP, DC-cholesterol, DOTAP, Ethyl PC, GL67, KC2, MD1, OF2, EPC, ZA3-Ep10, TT3, LP01, 5A2-SC8, Lipid 5 (Moderna), a cationic sulfonamide amino lipid, and an amphiphilic zwitterionic amino lipid, or combinations thereof. In some embodiments, the synthetic charged lipid is chosen from C12-200, MC3, DODAP, and DC-cholesterol, or combinations thereof.

In some embodiments, the aqueous phase comprises water, PBS, or a citrate buffer.

In some embodiments, the aqueous phase and the lipid solution are mixed at a 3:1 volumetric ratio.

In some embodiments, the LPMPs comprise a heterologous functional agent. In some embodiments, the heterologous functional agent is a polynucleotide. In some embodiments, the polynucleotide is chosen from an mRNA, an siRNA or siRNA precursor, a miRNA or miRNA precursor, a plasmid, a dsiRNA, a shRNA, an aiRNA, a PNA, a morpholino, a LNA, a piRNA, a ribozyme, a DNAzyme, an aptamer, a circRNA, a gRNA, or a DNA molecule encoding any of these RNAs.

In some embodiments, the heterologous functional agent is comprised by the aqueous phase.

In some embodiments, the LPMPs further comprise a sterol. In some embodiments, the LPMPs further comprise a PEGylated lipid. In some embodiments, the LPMPs further comprise a sterol and a PEGylated lipid. In some embodiments, the sterol is cholesterol or sitosterol. In some embodiments, the PEGylated lipid is C14-PEG2k, C18-PEG2k, or DMPE-PEG2k.

Other features and advantages of the invention will be apparent from the following Detailed Description and the Claims.

Definitions

As used herein, an "agriculturally acceptable" carrier or excipient is one that is suitable for use in agriculture, e.g., for use on plants. In certain embodiments, the agriculturally acceptable carrier or excipient does not have undue adverse side effects to the plants, the environment, or to humans or animals who consume the resulting agricultural products derived therefrom commensurate with a reasonable benefit/risk ratio.

As used herein, "delivering" or "contacting" refers to applying to a plant, animal, fungus, or bacterium, a PMP composition either directly on the plant, animal, fungus, or bacterium, or adjacent to the plant, animal, fungus, or bacterium, in a region where the composition is effective to alter the fitness of the plant, animal, fungus, or bacterium. In methods where the composition is directly contacted with a plant, animal, fungus, or bacterium, the composition may be contacted with the entire plant, animal, fungus, or bacterium or with only a portion of the plant, animal, fungus, or bacterium.

As used herein, "decreasing the fitness of a plant" refers to any disruption of the physiology of a plant (e.g., a weed) as a consequence of administration of a composition described herein (e.g., a PMP composition including modified PMPs, optionally including a heterologous functional agent), including, but not limited to, decreasing a population of a plant (e.g., a weed) by about 10%, 20%, 30%, 40%, 50%, 60%, 70%, 80%, 90%, 95%, 99%, 100% or more. A decrease in plant fitness can be determined in comparison to a plant to which the composition has not been administered.

As used herein, the term "effective amount," "effective concentration," or "concentration effective to" refers to an amount of a modified PMP, or a heterologous functional agent therein, sufficient to effect the recited result or to reach a target level (e.g., a predetermined or threshold level) in or on a target organism.

As used herein, "increasing the fitness of a plant" refers to an increase in the production of the plant, for example, an improved yield, improved vigor of the plant, or improved quality of the harvested product from the plant as a consequence of administration of a composition described herein (e.g., a PMP composition including modified PMPs, optionally including a heterologous functional agent). An improved yield of a plant relates to an increase in the yield of a product (e.g., as measured by plant biomass, grain, seed or fruit yield, protein content, carbohydrate or oil content or leaf area) of the plant by a measurable amount over the yield of the same product of the plant produced under the same conditions, but without the application of the instant compositions or compared with application of conventional agricultural agents. For example, yield can be increased by at least about 0.5%, about 1%, about 2%, about 3%, about 4%, about 5%, about 10%, about 20%, about 30%, about 40%, about 50%, about 60%, about 70%, about 80%, about 90%, about 100%, or more than 100%. Yield can be expressed in terms of an amount by weight or volume of the plant or a product of the plant on some basis. The basis can be expressed in terms of time, growing area, weight of plants produced, or amount of a raw material used. An increase in the fitness of plant can also be measured by other means, such as an increase or improvement of the vigor rating, increase in the stand (the number of plants per unit of area), increase in plant height, increase in stalk circumference, increase in plant canopy, improvement in appearance (such as greener leaf color as measured visually), improvement in root rating, increase in seedling emergence, protein content, increase in leaf size, increase in leaf number, fewer dead basal leaves, increase in tiller strength, decrease in nutrient or fertilizer requirements, increase in seed germination, increase in tiller productivity, increase in flowering, increase in seed or grain maturatutin or seed maturity, fewer plant verse (lodging), increased shoot growth, or any combination of these factors, by a measurable or noticeable amount over the same factor of the plant produced under the same conditions, but without the administration of the instant compositions or with application of conventional agricultural agents.

As used herein, the term "heterologous" refers to an agent that is either (1) exogenous to the plant (e.g., originating from a source that is not the plant from which the PMP is produced) or (2) endogenous to the plant from which the PMP is produced, but is present in the PMP (e.g., using loading, genetic engineering, in vitro or in vivo approaches) at a concentration that is higher than that found in nature (e.g., as found in a naturally-occurring plant extracellular vesicle).

As used herein, the term "functional agent" refers to an agent (e.g., an agricultural agent (e.g., pesticidal agent, fertilizing agent, herbicidal agent, plant-modifying agent) or a therapeutic agent (e.g., an antifungal agent, an antibacterial agent, a virucidal agent, an anti-viral agent, an insecticidal agent, a nematicidal agent, an antiparasitic agent, or an insect repellent)) that is or can be associated with PMPs (e.g., loaded into or onto PMPs (e.g., encapsulated by, embedded in, or conjugated to PMPs)) using in vivo or in vitro methods and is capable of effecting the recited result (e.g., increasing or decreasing the fitness of a plant, plant pest, plant symbiont, animal (e.g., human) pathogen, or animal pathogen vector) in accordance with the present compositions or methods. In some aspects, the functional agent is a polynucleotide.

As used herein, the term "agricultural agent" refers to an agent that can act on a plant, a plant pest, or a plant symbiont, such as a pesticidal agent, pest repellent, fertilizing agent, plant-modifying agent, or plant-symbiont modifying agent.

As used herein, the term "fertilizing agent" refers to an agent that is capable of increasing the fitness of a plant (e.g., a plant nutrient or a plant growth regulator) or a plant symbiont (e.g., a nucleic acid or a peptide).

As used herein, the term "pesticidal agent" refers to an agent, composition, or substance therein, that controls or decreases the fitness (e.g., kills or inhibits the growth, proliferation, division, reproduction, or spread) of an agricultural, environmental, or domestic/household pest, such as an insect, mollusk, nematode, fungus, bacterium, weed, or virus. Pesticides are understood to include naturally occurring or synthetic insecticides (larvicides or adulticides), insect growth regulators, acaricides (miticides), molluscicides, nematicides, ectoparasiticides, bactericides, fungicides, or herbicides. The term "pesticidal agent" may further encompass other bioactive molecules such as antibiotics, antivirals pesticides, antifungals, antihelminthics, nutrients, and/or agents that stun or slow insect movement.

As used herein, the term "plant-modifying agent" refers to an agent that can alter the genetic properties (e.g., increase gene expression, decrease gene expression, or otherwise alter the nucleotide sequence of DNA or RNA), epigenetic properties, or biochemical properties of a plant in a manner that results in a change (e.g., increase or decrease) in plant fitness.

As used herein, the term "therapeutic agent" refers to an agent that can act on an animal, e.g., a mammal (e.g., a human), an animal pathogen, or a pathogen vector, such as an antifungal agent, an antibacterial agent, a virucidal agent, an anti-viral agent, an insecticidal agent, a nematicidal agent, an antiparasitic agent, or an insect repellent.

As used herein, the term "formulated for delivery to a plant" refers to a PMP composition that includes an agriculturally acceptable carrier. As used herein, an "agriculturally acceptable" carrier or excipient is one that is suitable for use in agriculture without undue adverse side effects to the plants, the environment, or to humans or animals who consume the resulting agricultural products derived therefrom commensurate with a reasonable benefit/risk ratio. Non-limiting examples of agriculturally acceptable carriers or excipients are known in the art; see, e.g., the Compendium of Herbicide Adjuvants, ppp[dot]purdue[dot]edu/wp-content/uploads/2016/11/PPP-115[dot]pdf.

As defined herein, the term "nucleic acid" and "polynucleotide" are interchangeable and refer to RNA or DNA that is linear or branched, single or double stranded, or a hybrid thereof, regardless of length (e.g., at least 2, 3, 4, 5, 6, 7, 8, 9, 10, 20, 30, 40, 50, 100, 150, 200, 250, 500, 1000, or more nucleic acids). The term also encompasses RNA/DNA hybrids. Nucleotides are typically linked in a nucleic acid by phosphodiester bonds, although the term "nucleic acid" also encompasses nucleic acid analogs having other types of linkages or backbones (e.g., phosphoramide, phosphorothioate, phosphorodithioate, O-methylphosphoroamidate, morpholino, locked nucleic acid (LNA), glycerol nucleic acid (GNA), threose nucleic acid (TNA), and peptide nucleic acid (PNA) linkages or backbones, among others). The nucleic acids may be single-stranded, double-stranded, or contain portions of both single-stranded and double-stranded sequence. A nucleic acid can contain any combination of deoxyribonucleotides and ribonucleotides, as well as any combination of bases, including, for example, adenine, thymine, cytosine, guanine, uracil, and modified or non-canonical bases (including, e.g., hypoxanthine, xanthine, 7-methylguanine, 5,6-dihydrouracil, 5-methylcytosine, and 5 hydroxymethylcytosine).

As used herein, the term "pest" refers to organisms that cause damage to plants or other organisms, are present where they are not wanted, or otherwise are detrimental to humans, for example, by negatively impacting human agricultural methods or products. Pests may include, for example, invertebrates (e.g., insects, nematodes, or mollusks), microorganisms (e.g., phytopathogens, endophytes, obligate parasites, facultative parasites, or facultative saprophytes), such as bacteria, fungi, or viruses; or weeds.

As used herein, the term "pesticidal agent" or "pesticide" refers to an agent, composition, or substance therein, that controls or decreases the fitness (e.g., kills or inhibits the growth, proliferation, division, reproduction, or spread) of an agricultural, environmental, or domestic/household pest, such as an insect, mollusk, nematode, fungus, bacterium, weed, or virus. Pesticides are understood to encompass naturally occurring or synthetic insecticides (larvicides or adulticides), insect growth regulators, acaricides (miticides), molluscicides, nematicides, ectoparasiticides, bactericides, fungicides, or herbicides. The term "pesticidal agent" may further encompass other bioactive molecules such as antibiotics, antivirals pesticides, antifungals, antihelminthics, nutrients, and/or agents that stun or slow insect movement.

The pesticidal agent may be heterologous. As used herein, the term "heterologous" refers to an agent (e.g., a polynucleotide or a pesticidal agent) that is either (1) exogenous to the plant (e.g., originating from a source that is not the plant or plant part from which the PMP is produced) (e.g., added the PMP using loading approaches described herein) or (2) endogenous to the plant cell or tissue from which the PMP is produced, but present in the PMP (e.g., added to the PMP using loading approaches described herein, genetic engineering, in vitro or in vivo approaches) at a concentration that is higher than that found in nature (e.g., higher than a concentration found in a naturally-occurring plant extracellular vesicle).

As used herein, the term "repellent" refers to an agent, composition, or substance therein, that deters pests from approaching or remaining on a plant. A repellent may, for example, decrease the number of pests on or in the vicinity of a plant, but may not necessarily kill or decrease the fitness of the pest.

As used herein, the term "peptide," "protein," or "polypeptide" encompasses any chain of naturally or non-naturally occurring amino acids (either D- or L-amino acids), regardless of length (e.g., at least 2, 3, 4, 5, 6, 7, 10, 12, 14, 16, 18, 20, 25, 30, 40, 50, 100, or more amino acids), the presence or absence of post-translational modifications (e.g., glycosylation or phosphorylation), or the presence of, e.g., one or more non-amino acyl groups (for example, sugar, lipid, etc.) covalently linked to the peptide, and includes, for example, natural proteins, synthetic, or recombinant polypeptides and peptides, hybrid molecules, peptoids, or peptidomimetics.

As used herein, "percent identity" between two sequences is determined by the BLAST 2.0 algorithm, which is described in Altschul et al., (1990) *J. Mol. Biol.* 215:403-410. Software for performing BLAST analyses is publicly available through the National Center for Biotechnology Information.

As used herein, the term "plant" refers to whole plants, plant organs, plant tissues, seeds, plant cells, seeds, and progeny of the same. Plant cells include, without limitation, cells from seeds, suspension cultures, embryos, meristematic regions, callus tissue, leaves, roots, shoots, gametophytes, sporophytes, pollen, and microspores. Plant parts include differentiated and undifferentiated tissues including, but not limited to the following: roots, stems, shoots, leaves, pollen, seeds, fruit, harvested produce, tumor tissue, sap (e.g., xylem sap and phloem sap), and various forms of cells and culture (e.g., single cells, protoplasts, embryos, and callus tissue). The plant tissue may be in a plant or in a plant organ, tissue, or cell culture.

As used herein, the term "modified PMPs" refers to a composition including a plurality of PMPs, wherein the PMPs include one or more heterologous agents (e.g., one or more exogenous lipids, such as a charged lipid (e.g., an ionizable and/or cationic lipid, e.g., a PMP comprising a charged lipid and a sterol and/or a PEGylated lipid) capable of increasing cell uptake (e.g., animal cell uptake, plant cell uptake, bacterial cell uptake, or fungal cell uptake) of the PMP, or a portion or component thereof (e.g., a heterologous functional agent carried by the PMP), relative to an unmodified PMP; capable of enabling or increasing delivery of a heterologous functional agent (e.g., an agricultural or therapeutic agent) by the PMP to a cell, and/or capable of enabling or increasing loading (e.g., loading efficiency or loading capacity) of a heterologous functional agent (e.g., an agricultural or therapeutic agent). The PMPs may be modified in vitro or in vivo.

As used herein, the term "unmodified PMPs" refers to a composition including a plurality of PMPs that lack a heterologous cell uptake agent capable of increasing cell uptake (e.g., animal cell uptake, plant cell uptake, bacterial cell uptake, or fungal cell uptake) of the PMP.

As used herein, the term "cell uptake" refers to uptake of a PMP or a portion or component thereof (e.g., a heterologous functional agent carried by the PMP) by a cell, such as an animal cell, a plant cell, bacterial cell, or fungal cell. For example, uptake can involve transfer of the PMP or a portion of component thereof from the extracellular environment into or across the cell membrane, the cell wall, the extracellular matrix, or into the intracellular environment of the cell). Cell uptake of PMPs may occur via active or passive cellular mechanisms. Cell uptake includes aspects in which the entire PMP (e.g., LPMP) is taken up by a cell, e.g., taken up by endocytosis. In embodiments, one or more heterologous functional agents (e.g., polynucleotides) are exposed to the cytoplasm of the target cell following endocytosis and endosomal escape. In embodiments, a modified PMP (e.g., a PMP comprising a charged lipid (e.g., ionizable lipid and/or cationic lipid), e.g., a PMP comprising a charged lipid and a sterol and/or a PEGylated lipid) has an increased rate of endosomal escape relative to an unmodified PMP. Cell uptake also includes aspects in which the PMP (e.g., LPMP) fuses with the membrane of the target cell. In embodiments, one or more heterologous functional agents (e.g., polynucleotides) are exposed to the cytoplasm of the target cell following membrane fusion. In embodiments, a modified PMP (e.g., a PMP comprising a charged lipid (e.g., an ionizable lipid and/or cationic lipid), e.g., a PMP comprising a charged lipid and a sterol and/or a PEGylated lipid) has an increased rate of fusion with the membrane of the target cell (e.g., is more fusogenic) relative to an unmodified PMP.

As used herein, the term "cell-penetrating agent" refers to agents that alter properties (e.g., permeability) of the cell wall, extracellular matrix, or cell membrane of a cell (e.g., an animal cell, a plant cell, a bacterial cell, or a fungal cell) in a manner that promotes increased cell uptake relative to a cell that has not been contacted with the agent.

As used herein, the term "plant extracellular vesicle", "plant EV", or "EV" refers to an enclosed lipid-bilayer structure naturally occurring in a plant. Optionally, the plant EV includes one or more plant EV markers. As used herein, the term "plant EV marker" refers to a component that is naturally associated with a plant, such as a plant protein, a plant nucleic acid, a plant small molecule, a plant lipid, or a combination thereof, including but not limited to any of the plant EV markers listed in the Appendix. In some instances, the plant EV marker is an identifying marker of a plant EV but is not a pesticidal agent. In some instances, the plant EV marker is an identifying marker of a plant EV and also a pesticidal agent (e.g., either associated with or encapsulated by the plurality of PMPs, or not directly associated with or encapsulated by the plurality of PMPs).

As used herein, the term "plant messenger pack" or "PMP" refers to a lipid structure (e.g., a lipid bilayer, unilamellar, multilamellar structure; e.g., a vesicular lipid structure), that is about 5-2000 nm (e.g., at least 5-1000 nm, at least 5-500 nm, at least 400-500 nm, at least 25-250 nm, at least 50-150 nm, or at least 70-120 nm) in diameter that is derived from (e.g., enriched, isolated or purified from) a plant source or segment, portion, or extract thereof, including lipid or non-lipid components (e.g., peptides, nucleic acids, or small molecules) associated therewith and that has been enriched, isolated or purified from a plant, a plant part, or a plant cell, the enrichment or isolation removing one or more contaminants or undesired components from the source plant. PMPs may be highly purified preparations of naturally occurring EVs. Preferably, at least 1% of contaminants or undesired components from the source plant are removed (e.g., at least 2%, 5%, 10%, 15%, 20%, 25%, 30%, 40%, 45%, 50%, 55%, 60%, 70%, 80%, 90%, 95%, 96%, 98%, 99%, or 100%) of one or more contaminants or undesired components from the source plant, e.g., plant cell wall components; pectin; plant organelles (e.g., mitochondria; plastids such as chloroplasts, leucoplasts or amyloplasts; and nuclei); plant chromatin (e.g., a plant chromosome); or plant molecular aggregates (e.g., protein aggregates, protein-nucleic acid aggregates, lipoprotein aggregates, or lipido-proteic structures). Preferably, a PMP is at least 30% pure (e.g., at least 40% pure, at least 50% pure, at least 60% pure, at least 70% pure, at least 80% pure, at least 90% pure, at least 99% pure, or 100% pure) relative to the one or more contaminants or undesired components from the source plant as measured by weight (w/w), spectral imaging (% transmittance), or conductivity (S/m).

In some instances, the PMP is a lipid reconstructed PMP (LPMP). As used herein, the terms "lipid reconstructed PMP" and "LPMP" refer to a PMP that has been derived from a lipid structure (e.g., a lipid bilayer, unilamellar, multilamellar structure; e.g., a vesicular lipid structure) derived from (e.g., enriched, isolated or purified from) a plant source, wherein the lipid structure is disrupted (e.g., disrupted by lipid extraction) and reassembled or reconstituted in a liquid phase (e.g., a liquid phase containing a cargo) using standard methods, e.g., reconstituted by a method comprising lipid film hydration and/or solvent injection, to produce the LPMP, as is described herein. The method may, if desired, further comprise sonication, freeze/thaw treatment, and/or lipid extrusion, e.g., to reduce the size of the reconstituted PMPs. Alternatively, LPMPs may be produced using a microfluidic device (such as a Nano-Assemblr® IGNITE™ microfluidic instrument (Precision NanoSystems)). A PMP (e.g., a LPMP) may comprise between 10% and 100% lipids derived from the lipid structure from the plant source, e.g., may contain at least 10%, at least 20%, at least 30%, at least 40%, at least 50%, at least 60%, at least 70%, at least 80%, at least 90%, at least 95%, or 100% lipids derived from the lipid structure from the plant source. A PMP (e.g., a LPMP) may comprise all or a fraction of the lipid species present in the lipid structure from the plant source, e.g., it may contain at least 10%, at least 20%, at least 30%, at least 40%, at least 50%, at least 60%, at least 70%, at least 80%, at least 90%, or 100% of the lipid species present in the lipid structure from the plant source. A PMP (e.g., a LPMP) may comprise none, a fraction, or all of the protein species present in the lipid structure from the plant source, e.g., may contain 0%, less than 1%, less than 5%, less than 10%, less than 15%, less than 20%, less than 30%, less than 40%, less than 50%, less than 60%, less than 70%, less than 80%, less than 90%, less than 100%, or 100% of the protein species present in the lipid structure from the plant source. In some instances, the lipid bilayer of the PMP (e.g., LPMP) does not contain proteins. In some instances, the lipid structure of the PMP (e.g., LPMP) contains a reduced amount of proteins relative to the lipid structure from the plant source.

PMPs (e.g., LPMPs) may optionally include exogenous lipids, e.g., lipids that are exogenous to the plant (e.g., originating from a source that is not the plant or plant part from which the PMP is produced) (e.g., added the PMP using methods described herein). The lipid composition of the PMP may include 0%, less than 1%, or at least 1%, 2%, 5%, 10%, 15%, 20%, 25%, 30%, 40%, 50%, 60%, 70%, 80%, 90%, 95%, or more than 95% exogenous lipid. Exemplary exogenous lipids include charged lipids (e.g., ionizable and/or cationic lipids). The exogenous lipid may be a cell-penetrating agent, may be capable of increasing delivery of a heterologous functional agent (e.g., an agricultural or therapeutic agent) by the PMP to a cell, and/or may be capable of increasing loading (e.g., loading efficiency or loading capacity) of a heterologous functional agent (e.g., an agricultural or therapeutic agent). Further exemplary exogenous lipids include sterols and PEGylated lipids.

PMPs may optionally include additional agents, such as heterologous functional agents, e.g., cell-penetrating agents, pesticidal agents, fertilizing agents, plant-modifying agents, therapeutic agents, polynucleotides, polypeptides, or small molecules. The PMPs can carry or associate with additional agents (e.g., heterologous functional agents) in a variety of ways to enable delivery of the agent to a target plant, e.g., by encapsulating the agent, incorporation of the agent in the lipid bilayer structure, or association of the agent (e.g., by conjugation) with the surface of the lipid bilayer structure. Heterologous functional agents can be incorporated into the PMPs either in vivo (e.g., in planta) or in vitro (e.g., in tissue culture, in cell culture, or synthetically incorporated).

As used herein, the term "charged lipid" refers to an amphiphilic molecule (e.g., a lipid or a lipidoid, e.g., a synthetic lipid or lipidoid) containing a group (e.g., a head group) that is charged (e.g., is cationic) or that can be ionized under a given condition (e.g., pH) to produce one or more electrically charged species. Charged lipids include ionizable lipids and cationic lipids. In some embodiments, the charged lipid is a positively charged lipid. Exemplary synthetic charged lipids include 1'-((244424(2-(bis(2-hydroxydodecyl)amino)ethyl) (2-hydroxydodecyl)amino) ethyl)piperazin-1-yl)ethyl)azanediyl)bis(dodecan-2-ol) (C12-200), DLin-MC3-DMA (MC3), dioleoyl-3-trimethylammonium propane (DODAP), DC-cholesterol, DOTAP, Ethyl PC, GL67, DLin-KC2-DMA (KC2), MD1 (cKK-E12), OF2, EPC, ZA3-Ep10, TT3, LP01, 5A2-SC8, Lipid 5 (Moderna), a cationic sulfonamide amino lipid, an amphiphilic zwitterionic amino lipid, DODAC, DOBAQ, YSK05, DOBAT, DOBAQ, DOPAT, DOMPAQ, DOAAQ, DMAP-BLP, DLinDMA, DODMA, DOTMA, DSDMA, DOSPA, DODAC, DOBAQ, DMRIE, DOTAP-cholesterol, GL67A, and 98N12-5.

As used herein, the term "ionizable lipid" refers to an amphiphilic molecule (e.g., a lipid or a lipidoid, e.g., a synthetic lipid or lipidoid) containing a group (e.g., a head group) that can be ionized, e.g., dissociated to produce one or more electrically charged species, under a given condition (e.g., pH). Exemplary synthetic ionizable lipids include, but are not limited to [1,1'-((2-(4-(2-((2-(bis(2-hydroxydodecyl) amino)ethyl) (2-hydroxydodecyl)amino)ethyl)piperazin-1-yl)ethyl)azanediyl)bis(dodecan-2-ol)] (C12-200), [(6Z,9Z, 28Z,31Z)-Heptatriaconta-6,9,28,31-tetraen-19-yl 4-(dimethylamino)butanoate] (DLin-MC3-DMA (MC3)), and 18:1 DAP 1,2-dioleoyl-3-dimethylammonium-propane (DODAP).

As used herein, the term "cationic lipid" refers to an amphiphilic molecule (e.g., a lipid or a lipidoid, e.g., a synthetic lipid or lipidoid) containing a cationic group (e.g., a cationic head group). Exemplary synthetic cationic lipids include, but are not limited to DC-cholesterol, dioleoyl-3-trimethylammonium propane (DOTAP), 1-palmitoyl-2-oleoyl-sn-glycero-3-ethylphosphocholine (chloride salt) (Ethyl PC), and $N^4$—Cholesteryl-Spermine HCl Salt (GL67).

As used herein, the term "lipidoid" refers to a molecule having one or more characteristics of a lipid.

As used herein, the term "stable PMP composition" (e.g., a composition including loaded or non-loaded PMPs) refers to a PMP composition that over a period of time (e.g., at least 24 hours, at least 48 hours, at least 1 week, at least 2 weeks, at least 3 weeks, at least 4 weeks, at least 30 days, at least 60 days, or at least 90 days) retains at least 5% (e.g., at least 5%, 10%, 15%, 20%, 25%, 30%, 35%, 40%, 45%, 50%, 55%, 60%, 65%, 70%, 75%, 80%, 85%, 90%, 95%, or 100%) of the initial number of PMPs (e.g., PMPs per mL of solution) relative to the number of PMPs in the PMP composition (e.g., at the time of production or formulation) optionally at a defined temperature range (e.g., a temperature of at least 24° C. (e.g., at least 24° C., 25° C., 26° C., 27° C., 28° C., 29° C., or 30° C.), at least 20° C. (e.g., at least 20° C., 21° C., 22° C., or 23° C.), at least 4° C. (e.g., at least 5° C., 10° C., or 15° C.), at least −20° C. (e.g., at least −20° C., −15° C., −10° C., −5° C., or 0° C.), or −80° C. (e.g., at least −80° C., −70° C., −60° C., −50° C., −40° C., or −30° C.)); or retains at least 5% (e.g., at least 5%, 10%, 15%, 20%, 25%, 30%, 35%, 40%, 45%, 50%, 55%, 60%, 65%, 70%, 75%, 80%, 85%, 90%, 95%, or 100%) of its activity (e.g., cell wall penetrating activity and/or pesticidal and/or repellent activity) relative to the initial activity of the PMP (e.g., at the time of production or formulation) optionally at a defined temperature range (e.g., a temperature of at least 24° C. (e.g., at least 24° C., 25° C., 26° C., 27° C., 28° C., 29° C., or 30° C.), at least 20° C. (e.g., at least 20° C., 21° C., 22° C., or 23° C.), at least 4° C. (e.g., at least 5° C., 10° C., or 15° C.), at least −20° C. (e.g., at least −20° C., −15° C., −10° C., −5° C., or 0° C.), or −80° C. (e.g., at least −80° C., −70° C., −60° C., −50° C., −40° C., or −30° C.)).

As used herein, the term "formulated for delivery to an animal" refers to a PMP composition that includes a pharmaceutically acceptable carrier. As used herein, a "pharmaceutically acceptable" carrier or excipient is one that is suitable for administration to an animal (e.g., human), e.g., without undue adverse side effects to the animal (e.g., human).

As used herein, the term "untreated" refers to a plant, animal, fungus, or bacterium that has not been contacted with or delivered a PMP composition herein, including a separate plant, animal, fungus, or bacterium that has not been delivered the PMP composition, the same plant, animal, fungus, or bacterium undergoing treatment assessed at a time point prior to delivery of the PMP composition, or the same plant, animal, fungus, or bacterium undergoing treatment assessed at an untreated part of the plant, animal, fungus, or bacterium.

BRIEF DESCRIPTION OF THE DRAWINGS

FIG. 3A is a graph showing the zeta potential (mV) of LPMPs not comprising added lipids (LPMPs) at pH 7, LPMPs comprising 40% MC3 at pH 4 and pH 7, and LPMPs comprising 25% C12-200 at pH 4 and pH 7. Data are presented as Mean±SD.

FIG. 3B is a bar graph showing the percent of ATTO 550-labeled TracrRNA input that was recovered from LPMPs following loading of LPMPs from lemon lipids not comprising added lipids (LPMPs) at pH 7, LPMPs comprising 40% MC3 at pH 4 and pH 9, and LPMPs comprising 25% C12-200 at pH 4 and pH 9. Data are presented as Mean±SD.

FIG. 3C is a bar graph showing sgRNA concentration (µg/mL) in LPMPs comprising 25% C12-200 that have not been treated or have been lysed using Triton™ X-100 and heparin (+TX+heparin), as measured using a Quant-iT™ RiboGreen® analysis.

FIG. 5A is a bar graph showing the hydrodynamic diameter in nanometers (nm) of lipid-reconstructed PMPs (LPMPs) from grapefruit (GF) and lemon (LM), formulated using microfluidics (NanoAssemblr) in the organic phase solvent ethanol (EtOH) or dimethylformamide:methanol (DMF:MeOH) as measured using DLS. Data are presented as Mean±SD.

FIG. 5B is a bar graph showing the polydispersity of LPMPs from grapefruit (GF) and lemon (LM), formulated using microfluidics (NanoAssemblr) in EtOH or DMF:MeOH as measured using DLS. Data are presented as Mean±SD.

FIG. 17A is a bar graph showing total mRNA concentration (µg/mL) in LPMPs comprising DC-cholesterol that have been formulated with 35 µg of firefly luciferase (Fluc) mRNA per 1 mg of PMP lipid using extrusion or microfluidics, as measured using a Quant-iT™ RiboGreen® analysis. Data are presented as Mean±SD.

FIG. 17B is a bar graph showing the mRNA encapsulation efficacy (% difference in mRNA concentrations between intact and lysed (+Triton® X-100+Heparin) vesicles) for the LPMPs of FIG. 8A. Data are presented as Mean±SD.

DETAILED DESCRIPTION

Figure 1:
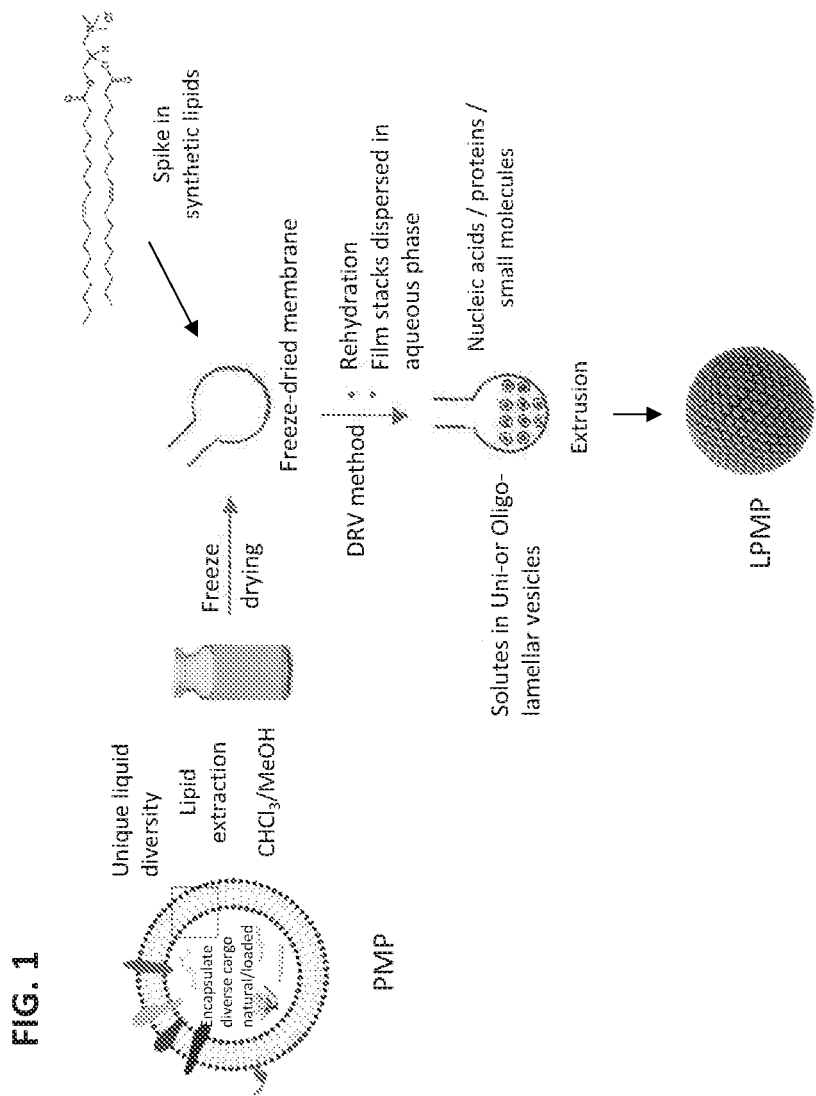
FIG. 1 is a schematic diagram showing a workflow for preparation of lipid reconstructed PMPs (LPMPs) from grapefruit and lemon PMPs.
Figure 2:
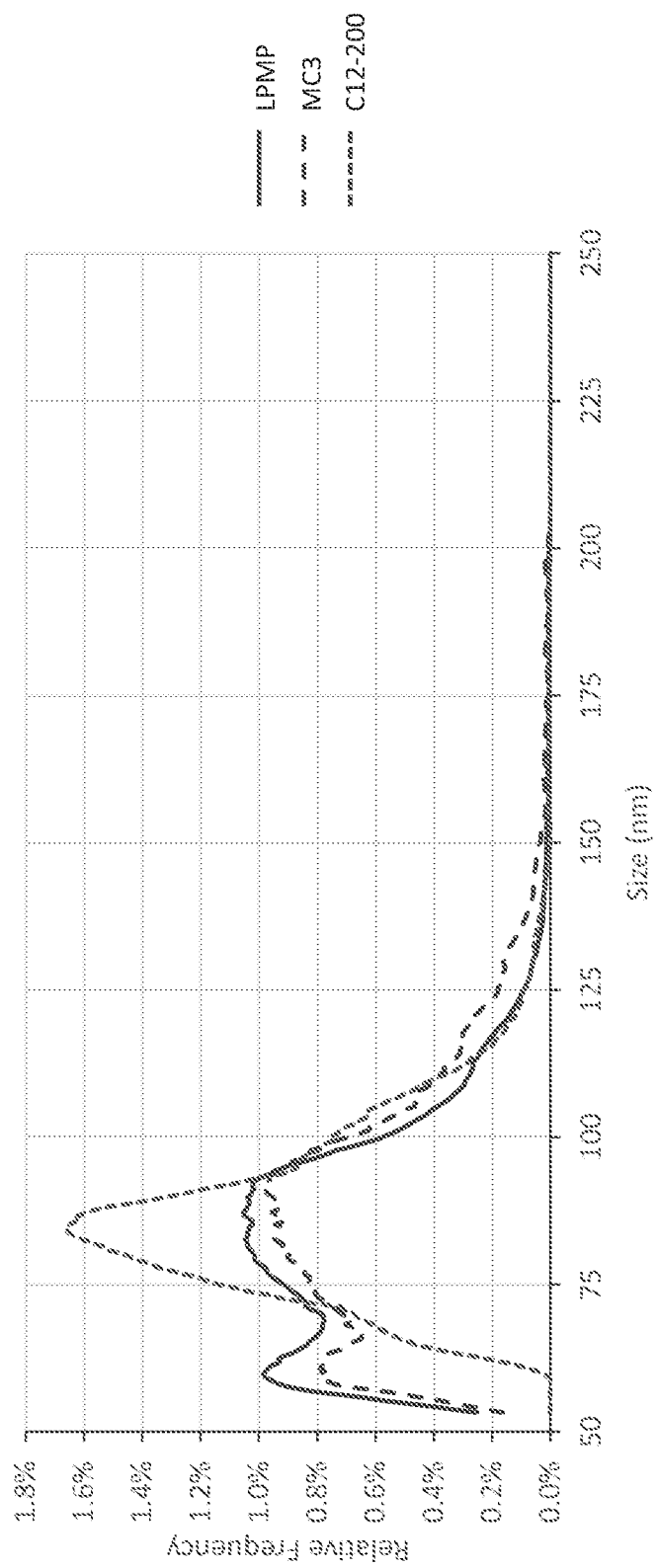
FIG. 2 is a graph showing the relative frequency of particles of a given size (nm) in unmodified LPMPs; LPMPs with added MC3; and LPMPs with added C12-200. Data were acquired by NanoFCM using concentration and size standards provided by the manufacturer.

Featured herein are modified plant messenger packs (PMPs). PMPs are lipid assemblies produced wholly or in part from plant extracellular vesicles (EVs), or segments, portions, or extracts thereof. PMPs can optionally include additional agents (e.g., heterologous functional agents, (e.g., a heterologous agricultural agent (e.g., pesticidal agent, fertilizing agent, herbicidal agent, plant-modifying agent) or a heterologous therapeutic agent (e.g., an antifungal agent, an antibacterial agent, a virucidal agent, an anti-viral agent, an insecticidal agent, a nematicidal agent, an antiparasitic agent, or an insect repellent)). The modified PMPs and related compositions and methods described herein can be used in a variety of agricultural and therapeutic methods.

I. Modified Plant Messenger Pack Compositions

The PMP compositions described herein include a plurality of modified plant messenger packs (PMPs). A PMP is a lipid (e.g., lipid bilayer, unilamellar, or multilamellar structure) structure that includes a plant EV, or segment, portion, or extract (e.g., lipid extract) thereof. Plant EVs refer to an enclosed lipid-bilayer structure that naturally occurs in a plant and that is about 5-2000 nm in diameter. Plant EVs can originate from a variety of plant biogenesis pathways. In nature, plant EVs can be found in the intracellular and extracellular compartments of plants, such as the plant apoplast, the compartment located outside the plasma membrane and formed by a continuum of cell walls and the extracellular space. Alternatively, PMPs can be enriched plant EVs found in cell culture media upon secretion from plant cells. Plant EVs can be separated from plants, thereby providing PMPs, by a variety of methods further described herein. Further, the PMPs can optionally include a heterologous functional agent, (e.g., a heterologous agricultural agent (e.g., pesticidal agent, fertilizing agent, herbicidal agent, plant-modifying agent) or a heterologous therapeutic agent (e.g., a cell-penetrating agent, an antifungal agent, an antibacterial agent, a virucidal agent, an anti-viral agent, an insecticidal agent, a nematicidal agent, an antiparasitic agent, or an insect repellent)), which can be introduced in vivo or in vitro. In some aspects, the heterologous functional agent is at least one nucleic acid (e.g., a DNA or an RNA, e.g., a mRNA or an siRNA) or a small molecule.

PMPs can include plant EVs, or segments, portions, or extracts, thereof. Optionally, PMPs can also include exogenous lipids (e.g., sterols (e.g., cholesterol or sitosterol), charged lipids (e.g., ionizable and/or cationic lipids), and/or PEGylated lipids) in addition to lipids derived from plant EVs. In some embodiments, the plant EVs are about 5-1000 nm in diameter. For example, the PMP can include a plant EV, or segment, portion, or extract thereof, that has a mean diameter of about 5-50 nm, about 50-100 nm, about 100-150 nm, about 150-200 nm, about 200-250 nm, about 250-300 nm, about 300-350 nm, about 350-400 nm, about 400-450 nm, about 450-500 nm, about 500-550 nm, about 550-600 nm, about 600-650 nm, about 650-700 nm, about 700-750 nm, about 750-800 nm, about 800-850 nm, about 850-900 nm, about 900-950 nm, about 950-1000 nm, about 1000-1250 nm, about 1250-1500 nm, about 1500-1750 nm, or about 1750-2000 nm. In some instances, the PMP includes a plant EV, or segment, portion, or extract thereof, that has a mean diameter of about 5-950 nm, about 5-900 nm, about 5-850 nm, about 5-800 nm, about 5-750 nm, about 5-700 nm, about 5-650 nm, about 5-600 nm, about 5-550 nm, about 5-500 nm, about 5-450 nm, about 5-400 nm, about 5-350 nm, about 5-300 nm, about 5-250 nm, about 5-200 nm, about 5-150 nm, about 5-100 nm, about 5-50 nm, or about 5-25 nm. In certain instances, the plant EV, or segment, portion, or extract thereof, has a mean diameter of about 50-200 nm. In certain instances, the plant EV, or segment, portion, or extract thereof, has a mean diameter of about 50-300 nm. In certain instances, the plant EV, or segment, portion, or extract thereof, has a mean diameter of about 200-500 nm. In certain instances, the plant EV, or segment, portion, or extract thereof, has a mean diameter of about 30-150 nm.

In some instances, the PMP may include a plant EV, or segment, portion, or extract thereof, that has a mean diameter of at least 5 nm, at least 50 nm, at least 100 nm, at least 150 nm, at least 200 nm, at least 250 nm, at least 300 nm, at least 350 nm, at least 400 nm, at least 450 nm, at least 500 nm, at least 550 nm, at least 600 nm, at least 650 nm, at least 700 nm, at least 750 nm, at least 800 nm, at least 850 nm, at least 900 nm, at least 950 nm, or at least 1000 nm. In some instances, the PMP includes a plant EV, or segment, portion, or extract thereof, that has a mean diameter less than 1000 nm, less than 950 nm, less than 900 nm, less than 850 nm, less than 800 nm, less than 750 nm, less than 700 nm, less than 650 nm, less than 600 nm, less than 550 nm, less than 500 nm, less than 450 nm, less than 400 nm, less than 350 nm, less than 300 nm, less than 250 nm, less than 200 nm, less than 150 nm, less than 100 nm, or less than 50 nm. A variety of methods (e.g., a dynamic light scattering method) standard in the art can be used to measure the particle diameter of the plant EV, or segment, portion, or extract thereof.

In some instances, the PMP may include a plant EV, or segment, portion, or extract thereof, that has a mean surface area of 77 nm$^2$ to 3.2×10$^6$ nm$^2$ (e.g., 77-100 nm$^2$, 100-1000 nm$^2$, 1000-1×10$^4$ nm$^2$, 1×10$^4$-1×10$^5$ nm$^2$, 1×10$^5$-1×10$^6$ nm$^2$, or 1×10$^6$-3.2×10$^6$ nm$^2$). In some instances, the PMP may include a plant EV, or segment, portion, or extract thereof, that has a mean volume of 65 nm$^3$ to 5.3×10$^8$ nm$^3$ (e.g., 65-100 nm$^3$, 100-1000 nm$^3$, 1000-1×10$^4$ nm$^3$, 1×10$^4$-1×10$^5$ nm$^3$, 1×10$^5$-1×10$^6$ nm$^3$, 1×10$^6$-1×10$^7$ nm$^3$, 1×10$^7$-1×10$^8$ nm$^3$, 1×10$^8$-5.3×10$^8$ nm$^3$). In some instances, the PMP may include a plant EV, or segment, portion, or extract thereof, that has a mean surface area of at least 77 nm$^2$, (e.g., at least 77 nm$^2$, at least 100 nm$^2$, at least 1000 nm$^2$, at least 1×10$^4$ nm$^2$, at least 1×10$^5$ nm$^2$, at least 1×10$^6$ nm$^2$, or at least 2×10$^6$ nm$^2$). In some instances, the PMP may include a plant EV, or segment, portion, or extract thereof, that has a mean volume of at least 65 nm$^3$ (e.g., at least 65 nm$^3$, at least 100 nm$^3$, at least 1000 nm$^3$, at least 1×10$^4$ nm$^3$, at least 1×10$^5$ nm$^3$, at least 1×10$^6$ nm$^3$, at least 1×10$^7$ nm$^3$, at least 1×10$^8$ nm$^3$, at least 2×10$^8$ nm$^3$, at least 3×10$^8$ nm$^3$, at least 4×10$^8$ nm$^3$, or at least 5×10$^8$ nm$^3$.

In some instances, the PMP can have the same size as the plant EV or segment, extract, or portion thereof. Alternatively, the PMP may have a different size than the initial plant EV from which the PMP is produced. For example, the PMP may have a diameter of about 5-2000 nm in diameter. For example, the PMP can have a mean diameter of about 5-50 nm, about 50-100 nm, about 100-150 nm, about 150-200 nm, about 200-250 nm, about 250-300 nm, about 300-350 nm, about 350-400 nm, about 400-450 nm, about 450-500 nm, about 500-550 nm, about 550-600 nm, about 600-650 nm, about 650-700 nm, about 700-750 nm, about 750-800 nm, about 800-850 nm, about 850-900 nm, about 900-950 nm, about 950-1000 nm, about 1000-1200 nm, about 1200-1400 nm, about 1400-1600 nm, about 1600-1800 nm, or about 1800-2000 nm. In some instances, the PMP may have a mean diameter of at least 5 nm, at least 50 nm, at least 100 nm, at least 150 nm, at least 200 nm, at least 250 nm, at least 300 nm, at least 350 nm, at least 400 nm, at least 450 nm, at least 500 nm, at least 550 nm, at least 600 nm, at least 650 nm, at least 700 nm, at least 750 nm, at least 800 nm, at least 850 nm, at least 900 nm, at least 950 nm, at least 1000 nm, at least 1200 nm, at least 1400 nm, at least 1600 nm, at least 1800 nm, or about 2000 nm. A variety of methods (e.g., a dynamic light scattering method) standard in the art can be used to measure the particle diameter of the PMPs. In some instances, the size of the PMP is determined following loading of heterologous functional agents, or following other modifications to the PMPs.

In some instances, the PMP may have a mean surface area of 77 nm$^2$ to 1.3×10$^7$ nm$^2$ (e.g., 77-100 nm$^2$, 100-1000 nm$^2$, 1000-1×10$^4$ nm$^2$, 1×10$^4$-1×10$^5$ nm$^2$, 1×10$^5$-1×10$^6$ nm$^2$, or 1×10$^6$-1.3×10$^7$ nm$^2$). In some instances, the PMP may have a mean volume of 65 nm$^3$ to 4.2×10$^9$ nm$^3$ (e.g., 65-100 nm$^3$, 100-1000 nm$^3$, 1000-1×10$^4$ nm$^3$, 1×10$^4$-1×10$^5$ nm$^3$, 1×10$^5$-1×10$^6$ nm$^3$, 1×10$^6$-1×10$^7$ nm$^3$, 1×10$^7$-1×10$^8$ nm$^3$, 1×10$^8$-1×10$^9$ nm$^3$, or 1×10$^9$-4.2×10$^9$ nm$^3$). In some instances, the PMP has a mean surface area of at least 77 nm$^2$, (e.g., at least 77 nm$^2$, at least 100 nm$^2$, at least 1000 nm$^2$, at least 1×10$^4$ nm$^2$, at least 1×10$^5$ nm$^2$, at least 1×10$^6$ nm$^2$, or at least 1×10$^7$ nm$^2$). In some instances, the PMP has a mean volume of at least 65 nm$^3$ (e.g., at least 65 nm$^3$, at least 100 nm$^3$, at least 1000 nm$^3$, at least 1×10$^4$ nm$^3$, at least 1×10$^5$ nm$^3$, at least 1×10$^6$ nm$^3$, at least 1×10$^7$ nm$^3$, at least 1×10$^8$ nm$^3$, at least 1×10$^9$ nm$^3$, at least 2×10$^9$ nm$^3$, at least 3×10$^9$ nm$^3$, or at least 4×10$^9$ nm$^3$).

In some instances, the PMP may include an intact plant EV. Alternatively, the PMP may include a segment, portion, or extract of the full surface area of the vesicle (e.g., a segment, portion, or extract including less than 100% (e.g., less than 90%, less than 80%, less than 70%, less than 60%, less than 50%, less than 40%, less than 30%, less than 20%, less than 10%, less than 10%, less than 5%, or less than 1%) of the full surface area of the vesicle) of a plant EV. The segment, portion, or extract may be any shape, such as a circumferential segment, spherical segment (e.g., hemisphere), curvilinear segment, linear segment, or flat segment. In instances where the segment is a spherical segment of the vesicle, the spherical segment may represent one that arises from the splitting of a spherical vesicle along a pair of parallel lines, or one that arises from the splitting of a spherical vesicle along a pair of non-parallel lines. Accordingly, the plurality of PMPs can include a plurality of intact plant EVs, a plurality of plant EV segments, portions, or extracts, or a mixture of intact and segments of plant EVs. One skilled in the art will appreciate that the ratio of intact to segmented plant EVs will depend on the particular isolation method used. For example, grinding or blending a plant, or part thereof, may produce PMPs that contain a higher percentage of plant EV segments, portions, or extracts than a non-destructive extraction method, such as vacuum-infiltration.

In instances where, the PMP includes a segment, portion, or extract of a plant EV, the EV segment, portion, or extract may have a mean surface area less than that of an intact vesicle, e.g., a mean surface area less than 77 nm$^2$, 100 nm$^2$, 1000 nm$^2$, 1×10$^4$ nm$^2$, 1×10$^5$ nm$^2$, 1×10$^6$ nm$^2$, or 3.2×10$^6$ nm$^2$). In some instances, the EV segment, portion, or extract has a surface area of less than 70 nm$^2$, 60 nm$^2$, 50 nm$^2$, 40 nm$^2$, 30 nm$^2$, 20 nm$^2$, or 10 nm$^2$). In some instances, the PMP may include a plant EV, or segment, portion, or extract thereof, that has a mean volume less than that of an intact vesicle, e.g., a mean volume of less than 65 nm$^3$, 100 nm$^3$, 1000 nm$^3$, 1×10$^4$ nm$^3$, 1×10$^5$ nm$^3$, 1×10$^6$ nm$^3$, 1×10$^7$ nm$^3$, 1×10$^8$ nm$^3$, or 5.3×10$^8$ nm$^3$).

In instances where the PMP includes an extract of a plant EV, e.g., in instances where the PMP includes lipids extracted (e.g., with chloroform) from a plant EV, the PMP may include at least 1%, 2%, 5%, 10%, 20%, 30%, 40%, 50%, 60%, 70%, 80%, 90%, 95%, 99%, or more than 99%, of lipids extracted (e.g., with chloroform) from a plant EV. The PMPs in the plurality may include plant EV segments and/or plant EV-extracted lipids or a mixture thereof.

Further outlined herein are details regarding methods of producing modified PMPs, plant EV markers that can be associated with PMPs, and formulations for compositions including PMPs.

A. Production Methods

PMPs may be produced from plant EVs, or a segment, portion or extract (e.g., lipid extract) thereof, that occur naturally in plants, or parts thereof, including plant tissues or plant cells. An exemplary method for producing PMPs includes (a) providing an initial sample from a plant, or a part thereof, wherein the plant or part thereof comprises EVs; and (b) isolating a crude PMP fraction from the initial sample, wherein the crude PMP fraction has a decreased level of at least one contaminant or undesired component from the plant or part thereof relative to the level in the initial sample. The method can further include an additional step (c) comprising purifying the crude PMP fraction, thereby producing a plurality of pure PMPs, wherein the plurality of pure PMPs have a decreased level of at least one contaminant or undesired component from the plant or part thereof relative to the level in the crude EV fraction. Each production step is discussed in further detail, below. Exemplary methods regarding the isolation and purification of PMPs is found, for example, in Rutter and Innes, *Plant Physiol.* 173(1): 728-741, 2017; Rutter et al, *Bio. Protoc.* 7(17): e2533, 2017; Regente et al, *J of Exp. Biol.* 68(20): 5485-5496, 2017; Mu et al, *Mol. Nutr. Food Res.*, 58, 1561-1573, 2014, and Regente et al, *FEBS Letters.* 583: 3363-3366, 2009, each of which is herein incorporated by reference.

In some instances, a plurality of PMPs may be isolated from a plant by a process which includes the steps of: (a) providing an initial sample from a plant, or a part thereof, wherein the plant or part thereof comprises EVs; (b) isolating a crude PMP fraction from the initial sample, wherein the crude PMP fraction has a decreased level of at least one contaminant or undesired component from the plant or part thereof relative to the level in the initial sample (e.g., a level that is decreased by at least 1%, 2%, 5%, 10%, 15%, 20%, 25%, 30%, 40%, 45%, 50%, 55%, 60%, 70%, 80%, 90%, 95%, 96%, 98%, 99%, or 100%); and (c) purifying the crude PMP fraction, thereby producing a plurality of pure PMPs, wherein the plurality of pure PMPs have a decreased level of at least one contaminant or undesired component from the plant or part thereof relative to the level in the crude EV fraction (e.g., a level that is decreased by at least 1%, 2%, 5%, 10%, 15%, 20%, 25%, 30%, 40%, 45%, 50%, 55%, 60%, 70%, 80%, 90%, 95%, 96%, 98%, 99%, or 100%).

The PMPs provided herein can include a plant EV, or segment, portion, or extract thereof, produced from a variety of plants. PMPs may be produced from any genera of plants (vascular or nonvascular), including but not limited to angiosperms (monocotyledonous and dicotyledonous plants), gymnosperms, ferns, selaginellas, horsetails, psilophytes, lycophytes, algae (e.g., unicellular or multicellular, e.g., archaeplastida), or bryophytes. In certain instances, PMPs can be produced using a vascular plant, for example monocotyledons or dicotyledons or gymnosperms. For example, PMPs can be produced using alfalfa, apple, *Arabidopsis*, banana, barley, a *Brassica* species (e.g., *Arabidopsis thaliana* or *Brassica napus*), canola, castor bean, chicory, *chrysanthemum*, clover, cocoa, coffee, cotton, cottonseed, corn, *crambe*, cranberry, cucumber, dendrobium, *dioscorea*, *eucalyptus*, fescue, flax, *gladiolus*, liliacea, linseed, millet, muskmelon, mustard, oat, oil palm, oilseed rape, *papaya*, peanut, pineapple, ornamental plants, *Phaseolus*, potato, rapeseed, rice, rye, ryegrass, safflower, sesame, sorghum, soybean, sugarbeet, sugarcane, sunflower, strawberry, tobacco, tomato, turfgrass, wheat or vegetable crops such as lettuce, celery, broccoli, cauliflower, cucurbits; fruit and nut trees, such as apple, pear, peach, orange, grapefruit, lemon, lime, almond, pecan, walnut, hazel; vines, such as grapes, kiwi, hops; fruit shrubs and brambles, such as raspberry, blackberry, gooseberry; forest trees, such as ash, pine, fir, maple, oak, chestnut, popular; with alfalfa, canola, castor bean, corn, cotton, *crambe*, flax, linseed, mustard, oil palm, oilseed rape, peanut, potato, rice, safflower, sesame, soybean, sugarbeet, sunflower, tobacco, tomato, or wheat.

PMPs may be produced using a whole plant (e.g., a whole rosettes or seedlings) or alternatively from one or more plant parts (e.g., leaf, seed, root, fruit, vegetable, pollen, phloem sap, or xylem sap). For example, PMPs can be produced using shoot vegetative organs/structures (e.g., leaves, stems, or tubers), roots, flowers and floral organs/structures (e.g., pollen, bracts, sepals, petals, stamens, carpels, anthers, or ovules), seed (including embryo, endosperm, or seed coat), fruit (the mature ovary), sap (e.g., phloem or xylem sap), plant tissue (e.g., vascular tissue, ground tissue, tumor tissue, or the like), and cells (e.g., single cells, protoplasts, embryos, callus tissue, guard cells, egg cells, or the like), or progeny of same. For instance, the isolation step may involve (a) providing a plant, or a part thereof. In some examples, the plant part is an *Arabidopsis* leaf. The plant may be at any stage of development. For example, the PMPs can be produced using seedlings, e.g., 1 week, 2 week, 3 week, 4 week, 5 week, 6 week, 7 week, or 8 week old seedlings (e.g., *Arabidopsis* seedlings). Other exemplary PMPs can include PMPs produced using roots (e.g., ginger roots), fruit juice (e.g., grapefruit juice), vegetables (e.g., broccoli), pollen (e.g., olive pollen), phloem sap (e.g., *Arabidopsis* phloem sap), or xylem sap (e.g., tomato plant xylem sap).

PMPs can be produced using a plant, or part thereof, by a variety of methods. Any method that allows release of the EV-containing apoplastic fraction of a plant, or an otherwise extracellular fraction that contains PMPs comprising secreted EVs (e.g., cell culture media) is suitable in the present methods. EVs can be separated from the plant or plant part by either destructive (e.g., grinding or blending of a plant, or any plant part) or non-destructive (washing or vacuum infiltration of a plant or any plant part) methods. For instance, the plant, or part thereof, can be vacuum-infiltrated, ground, blended, or a combination thereof to isolate EVs from the plant or plant part, thereby producing PMPs. For instance, the isolating step may involve vacuum infiltrating the plant (e.g., with a vesicle isolation buffer) to release and collect the apoplastic fraction. Alternatively, the isolating step may involve grinding or blending the plant to release the EVs, thereby producing PMPs.

Upon isolating the plant EVs, thereby producing PMPs, the PMPs can be separated or collected into a crude PMP fraction (e.g., an apoplastic fraction). For instance, the separating step may involve separating the plurality of PMPs into a crude PMP fraction using centrifugation (e.g., differential centrifugation or ultracentrifugation) and/or filtration to separate the plant PMP-containing fraction from large contaminants, including plant tissue debris or plant cells. As such, the crude PMP fraction will have a decreased number of large contaminants, including plant tissue debris or plant cells, as compared to the initial sample from the plant or plant part. Depending on the method used, the crude PMP fraction may additionally comprise a decreased level of plant cell organelles (e.g., nuclei, mitochondria or chloroplasts), as compared to the initial sample from the plant or plant part.

In some instances, the isolating step may involve separating the plurality of PMPs into a crude PMP fraction using centrifugation (e.g., differential centrifugation or ultracentrifugation) and/or filtration to separate the PMP-containing fraction from plant cells or cellular debris. In such instances, the crude PMP fraction will have a decreased number of plant cells or cellular debris, as compared to the initial sample from the source plant or plant part.

The crude PMP fraction can be further purified by additional purification methods to produce a plurality of pure PMPs. For example, the crude PMP fraction can be separated from other plant components by ultracentrifugation, e.g., using a density gradient (iodixanol or sucrose) and/or use of other approaches to remove aggregated components (e.g., precipitation or size-exclusion chromatography). The resulting pure PMPs may have a decreased level of contaminants or other undesired components from the source plant (e.g., one or more non-PMP components, such as protein aggregates, nucleic acid aggregates, protein-nucleic acid aggregates, free lipoproteins, lipido-proteic structures), nuclei, cell wall components, cell organelles, or a combination thereof) relative to one or more fractions generated during the earlier separation steps, or relative to a pre-established threshold level, e.g., a commercial release specification. For example, the pure PMPs may have a decreased level (e.g., by about 5%, 10%, 15%, 20%, 30%, 40%, 50%, 60%, 70%, 80%, 90%, 100%, or more than 100%; or by about 2× fold, 4× fold, 5× fold, 10× fold, 20× fold, 25× fold, 50× fold, 75× fold, 100× fold, or more than 100× fold) of plant organelles or cell wall components relative to the level in the initial sample. In some instances, the pure PMPs are substantially free (e.g., have undetectable levels) of one or more non-PMP components, such as protein aggregates, nucleic acid aggregates, protein-nucleic acid aggregates, free lipoproteins, lipido-proteic structures), nuclei, cell wall components, cell organelles, or a combination thereof. Further examples of the releasing and separation steps can be found in Example 1. The PMPs may be at a concentration of, e.g., $1\times10^9$, $5\times10^9$, $1\times10^{10}$, $5\times10^{10}$, $5\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, or more than $1\times10^{13}$ PMPs/mL.

For example, protein aggregates may be removed from PMPs. For example, the PMPs can be taken through a range of pHs (e.g., as measured using a pH probe) to precipitate out protein aggregates in solution. The pH can be adjusted to, e.g., pH 3, pH 5, pH 7, pH 9, or pH 11 with the addition of, e.g., sodium hydroxide or hydrochloric acid. Once the solution is at the specified pH, it can be filtered to remove particulates. Alternatively, the PMPs can be flocculated using the addition of charged polymers, such as Polymin-P or Praestol 2640. Briefly, Polymin-P or Praestol 2640 is added to the solution and mixed with an impeller. The solution can then be filtered to remove particulates. Alternatively, aggregates can be solubilized by increasing salt concentration. For example NaCl can be added to the PMPs until it is at, e.g., 1 mol/L. The solution can then be filtered to isolate the PMPs. Alternatively, aggregates are solubilized by increasing the temperature. For example, the PMPs can be heated under mixing until the solution has reached a uniform temperature of, e.g., 50° C. for 5 minutes. The PMP mixture can then be filtered to isolate the PMPs. Alternatively, soluble contaminants from PMP solutions can be separated by size-exclusion chromatography column according to standard procedures, where PMPs elute in the first fractions, whereas proteins and ribonucleoproteins and some lipoproteins are eluted later. The efficiency of protein aggregate removal can be determined by measuring and comparing the protein concentration before and after removal of protein aggregates via BCA/Bradford protein quantification.

Any of the production methods described herein can be supplemented with any quantitative or qualitative methods known in the art to characterize or identify the PMPs at any step of the production process. PMPs may be characterized by a variety of analysis methods to estimate PMP yield, PMP concentration, PMP purity, PMP composition, or PMP sizes. PMPs can be evaluated by a number of methods known in the art that enable visualization, quantitation, or qualitative characterization (e.g., identification of the composition) of the PMPs, such as microscopy (e.g., transmission electron microscopy), dynamic light scattering, nanoparticle tracking, spectroscopy (e.g., Fourier transform infrared analysis), or mass spectrometry (protein and lipid analysis). In certain instances, methods (e.g., mass spectroscopy) may be used to identify plant EV markers present on the PMP, such as markers disclosed in the Appendix. To aid in analysis and characterization, of the PMP fraction, the PMPs can additionally be labelled or stained. For example, the PMPs can be stained with 3,3'-dihexyloxacarbocyanine iodide (DIOC6), a fluorescent lipophilic dye, PKH67 (Sigma Aldrich); Alexa Fluor® 488 (Thermo Fisher Scientific), or DyLight™ 800 (Thermo Fisher). In the absence of sophisticated forms of nanoparticle tracking, this relatively simple approach quantifies the total membrane content and can be used to indirectly measure the concentration of PMPs (Rutter and Innes, *Plant Physiol.* 173(1): 728-741, 2017; Rutter et al, *Bio. Protoc.* 7(17): e2533, 2017). For more precise measurements, and to assess the size distributions of PMPs, nanoparticle tracking can be used.

During the production process, the PMPs can optionally be prepared such that the PMPs are at an increased concentration (e.g., by about 5%, 10%, 15%, 20%, 30%, 40%, 50%, 60%, 70%, 80%, 90%, 100%, or more than 100%; or by about 2× fold, 4× fold, 5× fold, 10× fold, 20× fold, 25× fold, 50× fold, 75× fold, 100× fold, or more than 100× fold) relative to the EV level in a control or initial sample. The PMPs may make up about 0.1% to about 100% of the PMP composition, such as any one of about 0.01% to about 100%, about 1% to about 99.9%, about 0.1% to about 10%, about 1% to about 25%, about 10% to about 50%, about 50% to about 99%, or about 75% to about 100%. In some instances, the composition includes at least any of 0.1%, 0.5%, 1%, 5%, 10%, 20%, 30%, 40%, 50%, 60%, 70%, 80%, 90%, 95%, or more PMPs, e.g., as measured by wt/vol, percent PMP protein composition, and/or percent lipid composition (e.g., by measuring fluorescently labelled lipids); See, e.g., Example 3). In some instances, the concentrated agents are used as commercial products, e.g., the final user may use diluted agents, which have a substantially lower concentration of active ingredient. In some embodiments, the composition is formulated as an agricultural concentrate formulation, e.g., an ultra-low-volume concentrate formulation.

As illustrated by Example 1, PMPs can be produced using a variety of plants, or parts thereof (e.g., the leaf apoplast, seed apoplast, root, fruit, vegetable, pollen, phloem, or xylem sap). For example, PMPs can be released from the apoplastic fraction of a plant, such as the apoplast of a leaf (e.g., apoplast *Arabidopsis thaliana* leaves) or the apoplast of seeds (e.g., apoplast of sunflower seeds). Other exemplary PMPs are produced using roots (e.g., ginger roots), fruit juice (e.g., grapefruit juice), vegetables (e.g., broccoli), pollen (e.g., olive pollen), phloem sap (e.g., *Arabidopsis* phloem sap), xylem sap (e.g., tomato plant xylem sap), or cell culture supernatant (e.g. BY2 tobacco cell culture supernatant). This example further demonstrates the production of PMPs from these various plant sources.

As illustrated by Example 2, PMPs can be purified by a variety of methods, for example, by using a density gradient (iodixanol or sucrose) in conjunction with ultracentrifugation and/or methods to remove aggregated contaminants, e.g., precipitation or size-exclusion chromatography. For instance, Example 2 illustrates purification of PMPs that have been obtained via the separation steps outlined in Example 1. Further, PMPs can be characterized in accordance with the methods illustrated in Example 3.

The PMP can be modified prior to use, as outlined further herein.

B. Modified PMPs and PMP Compositions

Following production of the PMPs, the PMPs may be modified by loading with or formulating with a heterologous agent (e.g., a cell-penetrating agent) that is capable of increasing cell uptake (e.g., animal cell uptake (e.g., mammalian cell uptake, e.g., human cell uptake), plant cell uptake, bacterial cell uptake, or fungal cell uptake) relative to an unmodified PMP. For example, the modified PMPs may include (e.g., be loaded with, e.g., encapsulate or be conjugated to) or be formulated with (e.g., be suspended or resuspended in a solution comprising) a plant cell-penetrating agent, such as a charged lipid (e.g., an ionizable and/or cationic lipid). Each of the modified PMPs may comprise at least 1%, 5%, 10%, 20%, 30%, 40%, 50%, 60%, 70%, 80%, 90%, or more than 90% charged lipid (e.g., ionizable and/or cationic lipid).

In some instances, the heterologous agent is a charged lipid (e.g., a synthetic charged lipid, e.g., an ionizable lipid and/or a cationic lipid). In some embodiments, the synthetic charged lipid is chosen from 1'-((2-(4-(2((2-(bis(2-hydroxydodecyl)amino)ethyl) (2-hydroxydodecyl)amino) ethyl)piperazin-1-yl)ethyl)azanediyl)bis(dodecan-2-ol) (C12-200), DLin-MC3-DMA (MC3), dioleoyl-3-trimethylammonium propane (DODAP), DC-cholesterol, DOTAP, Ethyl PC, GL67, DLin-KC2-DMA (KC2), MD1 (cKK-E12), OF2, EPC, ZA3-Ep10, TT3, LP01, 5A2-SC8, Lipid 5 (Moderna), a cationic sulfonamide amino lipid, an amphiphilic zwitterionic amino lipid, DODAC, DOBAQ, YSK05, DOBAT, DOBAQ, DOPAT, DOMPAQ, DOAAQ, DMAP-BLP, DLinDMA, DODMA, DOTMA, DSDMA, DOSPA, DODAC, DOBAQ, DMRIE, DOTAP-cholesterol, GL67A, and 98N12-5 or a combination thereof. In some embodiments, the synthetic charged lipid is chosen from C12-200, MC3, DODAP, DC-cholesterol, DOTAP, Ethyl PC, GL67, KC2, MD1, OF2, EPC, ZA3-Ep10, TT3, LP01, 5A2-SC8, Lipid 5 (Moderna), a cationic sulfonamide amino lipid, and an amphiphilic zwitterionic amino lipid or a combination thereof. In some embodiments, the synthetic charged lipid is chosen from C12-200, MC3, DODAP, and DC-cholesterol or combinations thereof. In some instances, the charged lipid is an ionizable lipid. In some embodiments, the ionizable lipid is 1,1'-((2-(4-(2-((2-(bis(2-hydroxydodecyl)amino) ethyl) (2-hydroxydodecyl)amino)ethyl)piperazin-1-yl) ethyl)azanediyl)bis(dodecan-2-ol) (C12-200) or (6Z,9Z, 28Z,31Z)-Heptatriaconta-6,9,28,31-tetraen-19-yl 4-(dimethylamino)butanoate, DLin-MC3-DMA (MC3). In some instances, the charged lipid is a cationic lipid. In some embodiments, the cationic lipid is DC-cholesterol or dioleoyl-3-trimethylammonium propane (DOTAP).

In some instances, the PMPs comprise at least 1%, 5%, 10%, 20%, 30%, 40%, 50%, 60%, 70%, 80%, 90%, or more than 90% charged lipid (e.g., ionizable lipid and/or cationic lipid).

In some instances, the PMPs comprise a molar ratio of least 0.1%, 1%, 5%, 10%, 15%, 20%, 25%, 30%, 35%, 40%, 45%, 50%, 55%, 60%, 65%, 70%, 75% 80%, 85%, 90%, or more than 90% charged lipid (e.g., ionizable lipid and/or cationic lipid), e.g., 1%-10%, 10%-20%, 20%-30%, 30%-40%, 40%-50%, 50%-60%, 60%-70%, 70%-80%, or 80%-90% charged lipid, e.g., about 30%-75% charged lipid (e.g., about 30%-75% charged lipid). In some embodiments, the PMP comprises 25% C12-200. In some embodiments, the PMP comprises a molar ratio of 35% C12-200. In some embodiments, the PMP comprises a molar ratio of 50% C12-200. In some embodiments, the PMP comprises 40% MC3. In some embodiments, the PMP comprises a molar ratio of 50% C12-200. In some embodiments, embodiments, the PMP comprises 20% or 40% DC-cholesterol. In some embodiments, the PMP comprises 25% or 40% DOTAP.

The agent may increase uptake of the PMP as a whole or may increase uptake of a portion or component of the PMP, such as a heterologous functional agent (e.g., a heterologous agricultural agent (e.g., pesticidal agent, fertilizing agent, herbicidal agent, plant-modifying agent) or a heterologous therapeutic agent (e.g., an antifungal agent, an antibacterial agent, a virucidal agent, an anti-viral agent, an insecticidal agent, a nematicidal agent, an antiparasitic agent, or an insect repellent)) carried by the PMP. The degree to which cell uptake (e.g., plant cell uptake, bacterial cell uptake, or fungal cell uptake) is increased may vary depending on the plant or plant part to which the composition is delivered, the PMP formulation, and other modifications made to the PMP, For example, the modified PMPs may have an increased cell uptake (e.g., animal cell uptake, plant cell uptake, bacterial cell uptake, or fungal cell uptake) of at least 1%, 2%, 5%, 10%, 15%, 20%, 30%, 40%, 50%, 60%, 70%, 80%, 90%, or 100% relative to an unmodified PMP. In some instances, the increased cell uptake (e.g., animal cell uptake, plant cell uptake, bacterial cell uptake, or fungal cell uptake) is an increased cell uptake of at least 2×-fold, 4×-fold, 5×-fold, 10×-fold, 100×-fold, or 1000×-fold relative to an unmodified PMP.

In some embodiments, a PMP that has been modified with a charged lipid (e.g., an ionizable and/or cationic lipid) more efficiently encapsulates a negatively charged heterologous functional agent (e.g., a polynucleotide) than a PMP that has not been modified with a charged lipid. In some aspects, a PMP that has been modified with a charged lipid has altered biodistribution relative to a PMP that has not been modified with a charged lipid. In some aspects, a PMP that has been modified with a charged lipid has altered (e.g., increased) fusion with an endosomal membrane of a target cell relative to a PMP that has not been modified with a charged lipid.

In another aspect, the PMPs can be modified with other components (e.g., lipids, e.g., sterols, e.g., cholesterol; or small molecules) to further alter the functional and structural characteristics of the PMP. For example, the PMPs can be further modified with stabilizing molecules that increase the stability of the PMPs (e.g., for at least one day at room temperature, and/or stable for at least one week at 4° C.).

In some embodiments, the PMP is modified with a sterol. In some embodiments, the sterol is cholesterol or sitosterol. In some instances, the PMPs comprise a molar ratio of least 1%, 5%, 10%, 15%, 20%, 25%, 30%, 35%, 40%, 45%, 50%, 55%, 60%, or more than 60% sterol (e.g., cholesterol or sitosterol), e.g., 1%-10%, 10%-20%, 20%-30%, 30%-40%, 40%-50%, or 50%-60% sterol. In some embodiments, the PMP comprises a molar ratio of about 35%-50% sterol (e.g., cholesterol or sitosterol), e.g., about 36%, 38.5%, 42.5%, or 46.5% sterol. In some embodiments, the PMP comprises a molar ratio of about 20%-40% sterol.

In some embodiments, a PMP that has been modified with a sterol has altered stability (e.g., increased stability) relative to a PMP that has not been modified with a sterol. In some aspects, a PMP that has been modified with a sterol has a greater rate of fusion with a membrane of a target cell relative to a PMP that has not been modified with a sterol.

In some embodiments, the PMP is modified with a PEGylated lipid. Polyethylene glycol (PEG) length can vary from 1 kDa to 10 kDa; in some aspects, PEG having a length of 2 kDa is used. In some embodiments, the PEGylated lipid is C14-PEG2k, C18-PEG2k, or DMPE-PEG2k. In some instances, the PMPs comprise a molar ratio of at least 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.5%, 4%, 4.5%, 5%, 10%, 20%, 30%, 40%, 50%, or more than 50% PEGylated lipid (e.g., C14-PEG2k, C18-PEG2k, or DMPE-PEG2k), e.g., 0.1%-0.5%, 0.5%-1%, 1%-1.5%, 1.5%-2.5%, 2.5%-3.5%, 3.5%-5%, 5%-10%, 10%-20%, 20%-30%, 30%-40%, or 30%-50% PEGylated lipid. In some embodiments, the PMP comprises a molar ratio of about 0.1%-10% PEGylated lipid (e.g., C14-PEG2k, C18-PEG2k, or DMPE-PEG2k), e.g., about 1%-3% PEGylated lipid, e.g., about 1.5% or about 2.5% PEGylated lipid. In some embodiments, a PMP that has been modified with a PEGylated lipid has altered stability (e.g., increased stability) relative to a PMP that has not been modified with a PEGylated lipid. In some embodiments, a PMP that has been modified with a PEGylated lipid has altered particle size relative to a PMP that has not been modified with a PEGylated lipid. In some embodiments, a PMP that has been modified with a PEGylated lipid is less likely to be phagocytosed than a PMP that has not been modified with a PEGylated lipid. The addition of PEGylated lipids can also affect stability in GI tract and enhance particle migration through mucus. PEG may be used as a method to attach targeting moieties.

In some embodiments, the PMPs are modified with an ionizable lipid (e.g., C12-200 or MC3) and one or both of a sterol (e.g., cholesterol or sitosterol) and a PEGylated lipid (e.g., C14-PEG2k, C18-PEG2k, or DMPE-PEG2k). In embodiments, the modified PMPs comprise a molar ratio of about 5%-50% PMP lipids (e.g., about 10%-20% PMP lipids, e.g., about 10%, 12.5%, 16%, or 20% PMP lipids); about 30%-75% ionizable lipids (e.g., about 35% or about 50% ionizable lipids); about 35%-50% sterol (e.g., about 36%, 38.5%, 42.5%, or 46.5% sterol); and about 0.1%-10% PEGylated lipid (e.g., about 1%-3% PEGylated lipid, e.g., about 1.5% or about 2.5% PEGylated lipid).

In some embodiments, a PMP that has been modified with a cationic lipid and a sterol and/or a PEGylated lipid more efficiently encapsulates a negatively charged cargo (e.g., a nucleic acid) than a PMP that has not been modified with a cationic lipid and a sterol and/or a PEGylated lipid. The modified PMP may have an encapsulation efficiency for the cargo (e.g., nucleic acid, e.g., RNA or DNA) that is at least 5%, 10%, 15%, 20%, 30%, 40%, 50%, 60%, 70%, 80%, 90%, 95%, 98%, 99%, or more than 99%, e.g., may have an encapsulation efficiency of 5%-30%, 30%-50%, 50%-70%, 70%-80%, 80%-90%, 90%-95%, or 95%-100%.

Cell uptake of the modified PMPs can be measured by a variety of methods known in the art. For example, the PMPs, or a component thereof, can be labelled with a marker (e.g., a fluorescent marker) that can be detected in isolated cells to confirm uptake. For example, cell uptake can be detected based on measures of fitness, e.g., fitness of an animal, plant, bacterium, or fungus comprising the treated cell. For instance, efficacy of the present compositions and methods can be determined by comparing fitness changes in organisms treated with the presently modified PMPs relative to treatment of compositions lacking modified PMPs.

In some embodiments, a PMP composition provided herein comprises two or more different modified PMPs, e.g., comprises modified PMPs derived from different unmodified PMPs (e.g., unmodified PMPs from two or more different plant sources) and/or comprises modified PMPs comprising different species and/or different ratios of charged lipids (e.g., ionizable and/or cationic lipids), sterols, and/or PEGylated lipids.

C. Plant EV-Markers

The PMPs of the present compositions and methods may have a range of markers that identify the PMPs as being produced using a plant EV, and/or including a segment, portion, or extract thereof. As used herein, the term "plant EV-marker" refers to a component that is naturally associated with a plant and incorporated into or onto the plant EV in planta, such as a plant protein, a plant nucleic acid, a plant small molecule, a plant lipid, or a combination thereof. Examples of plant EV-markers can be found, for example, in Rutter and Innes, Plant Physio). 173(1): 728-741, 2017; Raimondo et al., *Oncotarget*. 6(23): 19514, 2015; Ju et al., *Mol. Therapy*. 21(7):1345-1357, 2013; Wang et al., *Molecular Therapy*. 22(3): 522-534, 2014; and Regente et al, *J of Exp. Biol.* 68(20): 5485-5496, 2017; each of which is incorporated herein by reference. Additional examples of plant EV-markers are listed in the Appendix, and are further outlined herein.

In some instances, the plant EV marker can include a plant lipid. Examples of plant lipid markers that may be found in the PMPs include phytosterol, campesterol, β-sitosterol, stigmasterol, avenasterol, glycosyl inositol phosphoryl ceramides (GIPCs), glycolipids (e.g., monogalactosyldiacylglycerol (MGDG) or digalactosyldiacylglycerol (DGDG)), or a combination thereof. For instance, the PMP may include GIPCs, which represent the main sphingolipid class in plants and are one of the most abundant membrane lipids in plants. Other plant EV markers may include lipids that accumulate in plants in response to abiotic or biotic stressors (e.g., bacterial or fungal infection), such as phosphatidic acid (PA) or phosphatidylinositol-4-phosphate (PI4P).

Alternatively, the plant EV marker may include a plant protein. In some instances, the protein plant EV marker may be an antimicrobial protein naturally produced by plants, including defense proteins that plants secrete in response to abiotic or biotic stressors (e.g., bacterial or fungal infection). Plant pathogen defense proteins include soluble N-ethylmalemide-sensitive factor association protein receptor protein (SNARE) proteins (e.g., Syntaxin-121 (SYP121; GenBank Accession No.: NP_187788.1 or NP_974288.1), Penetration) (PEN1; GenBank Accession No: NP_567462.1)) or ABC transporter Penetration3 (PEN3; GenBank Accession No: NP_191283.2). Other examples of plant EV markers includes proteins that facilitate the long-distance transport of RNA in plants, including phloem proteins (e.g., Phloem protein2-A1 (PP2-A1), GenBank Accession No: NP_193719.1), calcium-dependent lipid-binding proteins, or lectins (e.g., Jacalin-related lectins, e.g., *Helianthus annuus* jacalin (Helja; GenBank: AHZ86978.1). For example, the RNA binding protein may be Glycine-Rich RNA Binding Protein-7 (GRP7; GenBank Accession Number: NP_179760.1). Additionally, proteins that regulate plasmodesmata function can in some instances be found in plant EVs, including proteins such as Synap-Totgamin A A (GenBank Accession No: NP_565495.1). In some instances, the plant EV marker can include a protein involved in lipid metabolism, such as phospholipase C or phospholipase D. In some instances, the plant protein EV marker is a cellular trafficking protein in plants. In certain instances where the plant EV marker is a protein, the protein marker may lack a signal peptide that is typically associated with secreted proteins. Unconventional secretory proteins seem to share several common features like (i) lack of a leader sequence, (ii) absence of post-translational modifications (PTMs) specific for ER or Golgi apparatus, and/or (iii) secretion not affected by brefeldin A which blocks the classical ER/Golgi-dependent secretion pathway. One skilled in the art can use a variety of tools freely accessible to the public (e.g., SecretomeP Database; SUBA3 (SUBcellular localization database for *Arabidopsis* proteins)) to evaluate a protein for a signal sequence, or lack thereof.

In instances where the plant EV marker is a protein, the protein may have an amino acid sequence having at least 35%, 40%, 45%, 50%, 55%, 60%, 65%, 70%, 75%, 80%, 85%, 90%, 95%, 98%, 99%, or 100% sequence identity to a plant EV marker, such as any of the plant EV markers listed in the Appendix. For example, the protein may have an amino acid sequence having at least 35%, 40%, 45%, 50%, 55%, 60%, 65%, 70%, 75%, 80%, 85%, 90%, 95%, 98%, 99%, or 100% sequence identity to PEN1 from *Arabidopsis thaliana* (GenBank Accession Number: NP_567462.1).

In some instances, the plant EV marker includes a nucleic acid encoded in plants, e.g., a plant RNA, a plant DNA, or a plant PNA. For example, the PMP may include dsRNA, mRNA, a viral RNA, a microRNA (miRNA) or miRNA precursor, or a small interfering RNA (siRNA) or siRNA precursor encoded by a plant. In some instances, the nucleic acid may be one that is associated with a protein that facilitates the long-distance transport of RNA in plants, as discussed herein. In some instances, the nucleic acid plant EV marker may be one involved in host-induced gene silencing (HIGS), which is the process by which plants silence foreign transcripts of plant pests (e.g., pathogens such as fungi). For example, the nucleic acid may be one that silences bacterial or fungal genes. In some instances, the nucleic acid may be a microRNA, such as miR159 or miR166, which target genes in a fungal pathogen (e.g., *Verticillium dahliae*). In some instances, the protein may be one involved in carrying plant defense compounds, such as proteins involved in glucosinolate (GSL) transport and metabolism, including Glucosinolate Transporter-1-1 (GTR1; GenBank Accession No: NP_566896.2), Glucosinolate Transporter-2 (GTR2; NP_201074.1), or Epithiospecific Modifier 1 (ESM1; NP_188037.1).

In instances where the plant EV marker is a nucleic acid, the nucleic acid may have a nucleotide sequence having at least 35%, 40%, 45%, 50%, 55%, 60%, 65%, 70%, 75%, 80%, 85%, 90%, 95%, 98%, 99%, or 100% sequence identity to a plant EV marker, e.g., such as those encoding the plant EV markers listed in the Appendix. For example, the nucleic acid may have a polynucleotide sequence having at least 35%, 40%, 45%, 50%, 55%, 60%, 65%, 70%, 75%, 80%, 85%, 90%, 95%, 98%, 99%, or 100% sequence identity to miR159 or miR166.

In some instances, the plant EV marker includes a compound produced by plants. For example, the compound may be a defense compound produced in response to abiotic or biotic stressors, such as secondary metabolites. One such secondary metabolite that be found in PMPs are glucosinolates (GSLs), which are nitrogen and sulfur-containing secondary metabolites found mainly in Brassicaceae plants. Other secondary metabolites may include allelochemicals.

In some instances, the PMPs may also be identified as being produced using a plant EV based on the lack of certain markers (e.g., lipids, polypeptides, or polynucleotides) that are not typically produced by plants, but are generally associated with other organisms (e.g., markers of animal EVs, bacterial EVs, or fungal EVs). For example, in some instances, the PMP lacks lipids typically found in animal EVs, bacterial EVs, or fungal EVs. In some instances, the PMP lacks lipids typical of animal EVs (e.g., sphingomyelin). In some instances, the PMP does not contain lipids typical of bacterial EVs or bacterial membranes (e.g., LPS). In some instances, the PMP lacks lipids typical of fungal membranes (e.g., ergosterol).

Plant EV markers can be identified using any approaches known in the art that enable identification of small molecules (e.g., mass spectroscopy, mass spectrometry), lipids (e.g., mass spectroscopy, mass spectrometry), proteins (e.g., mass spectroscopy, immunoblotting), or nucleic acids (e.g., PCR analysis). In some instances, a PMP composition described herein includes a detectable amount, e.g., a pre-determined threshold amount, of a plant EV marker described herein.

D. Loading of Agents

The PMPs can be modified to include a heterologous functional agent, e.g., a cell-penetrating agent and/or a heterologous agricultural agent (e.g., pesticidal agent, fertilizing agent, herbicidal agent, plant-modifying agent), a heterologous therapeutic agent (e.g., an antifungal agent, an antibacterial agent, a virucidal agent, an anti-viral agent, an insecticidal agent, a nematicidal agent, an antiparasitic agent, or an insect repellent)), such as those described herein. The PMPs can carry or associate with such agents by a variety of means to enable delivery of the agent to a target organism (e.g., a target animal, plant, bacterium, or fungus), e.g., by encapsulating the agent, incorporation of the component in the lipid bilayer structure, or association of the component (e.g., by conjugation) with the surface of the lipid bilayer structure of the PMP. In some instances, the heterologous functional agent (e.g., cell-penetrating agent) is included in the PMP formulation, as described in Section IB herein.

The heterologous functional agent can be incorporated or loaded into or onto the PMPs by any methods known in the art that allow association, directly or indirectly, between the PMPs and agent. Heterologous functional agent agents can be incorporated into the PMPs by an in vivo method (e.g., in planta, e.g., through production of PMPs from a transgenic plant that comprises the heterologous agent), or in vitro (e.g., in tissue culture, or in cell culture), or both in vivo and in vitro methods.

In instances where the PMPs are loaded with a heterologous functional agent (e.g., a heterologous agricultural agent (e.g., pesticidal agent, fertilizing agent, herbicidal agent, plant-modifying agent) or a heterologous therapeutic agent (e.g., an antifungal agent, an antibacterial agent, a virucidal agent, an anti-viral agent, an insecticidal agent, a nematicidal agent, an antiparasitic agent, or an insect repellent)) in vivo, PMPs may be produced using EVs, or a segments or portions thereof, or an extract containing EVs that has been loaded in planta. In planta methods include expression of the heterologous functional agent (e.g., a heterologous agricultural agent (e.g., pesticidal agent, fertilizing agent, herbicidal agent, plant-modifying agent) or a heterologous therapeutic agent (e.g., an antifungal agent, an antibacterial agent, a virucidal agent, an anti-viral agent, an insecticidal agent, a nematicidal agent, an antiparasitic agent, or an insect repellent)) in a plant that has been genetically modified to express the heterologous functional agent for loading into EVs. In some instances, the heterologous functional agent is exogenous to the plant. Alternatively, the heterologous functional agent may be naturally found in the plant, but engineered to be expressed at an elevated level relative to level of that found in a non-genetically modified plant.

In some instances, the PMPs can be loaded in vitro. The substance may be loaded onto or into (e.g., may be encapsulated by) the PMPs using, but not limited to, physical, chemical, and/or biological methods (e.g., in tissue culture or in cell culture). For example, the heterologous functional agent may be introduced into PMPs by one or more of electroporation, sonication, passive diffusion, stirring, lipid extraction, or extrusion. In some instances, the heterologous functional agent is incorporated into the PMP using a microfluidic device, e.g., using a method in which PMP lipids are provided in an organic phase, the heterologous functional agent is provided in an aqueous phase, and the organic and aqueous phases are combined in the microfluidics device to produce a PMP comprising the heterologous functional agent. Loaded PMPs can be assessed to confirm the presence or level of the loaded agent using a variety of methods, such as HPLC (e.g., to assess small molecules), immunoblotting (e.g., to assess proteins); and/or quantitative PCR (e.g., to assess nucleotides). However, it should be appreciated by those skilled in the art that the loading of a substance of interest into PMPs is not limited to the above-illustrated methods.

In some instances, the heterologous functional agent can be conjugated to the PMP, in which the heterologous functional agent is connected or joined, indirectly or directly, to the PMP. For instance, one or more heterologous functional agents can be chemically-linked to a PMP, such that the one or more heterologous functional agents are joined (e.g., by covalent or ionic bonds) directly to the lipid bilayer of the PMP. In some instances, the conjugation of various heterologous functional agents to the PMPs can be achieved by first mixing the one or more heterologous functional agents with an appropriate cross-linking agent (e.g., N-ethylcarbodiimide ("EDC"), which is generally utilized as a carboxyl activating agent for amide bonding with primary amines and also reacts with phosphate groups) in a suitable solvent. After a period of incubation sufficient to allow the heterologous functional agent to attach to the cross-linking agent, the cross-linking agent/heterologous functional agent mixture can then be combined with the PMPs and, after another period of incubation, subjected to a sucrose gradient (e.g., and 8, 30, 45, and 60% sucrose gradient) to separate the free heterologous functional agent and free PMPs from the heterologous functional agent conjugated to the PMPs. As part of combining the mixture with a sucrose gradient, and an accompanying centrifugation step, the PMPs conjugated to the heterologous functional agent are then seen as a band in the sucrose gradient, such that the conjugated PMPs can then be collected, washed, and dissolved in a suitable solution for use as described herein.

In some instances, the PMPs are stably associated with the heterologous functional agent prior to and following delivery of the PMP, e.g., to a plant. In other instances, the PMPs are associated with the heterologous functional agent such that the heterologous functional agent becomes dissociated from the PMPs following delivery of the PMP, e.g., to a plant.

The PMPs can be loaded or the PMP composition can be formulated with various concentrations of the heterologous functional agent, depending on the particular agent or use. For example, in some instances, the PMPs are loaded or the PMP composition is formulated such that the PMP composition disclosed herein includes about 0.001, 0.01, 0.1, 1.0, 2, 3, 4, 5, 6, 7, 8, 9, 10, 15, 20, 30, 40, 50, 60, 70, 80, 90, or 95 (or any range between about 0.001 and 95) or more wt % of a heterologous functional agent. In some instances, the PMPs are loaded or the PMP composition is formulated such that the PMP composition includes about 95, 90, 80, 70, 60, 50, 40, 30, 20, 15, 10, 9, 8, 7, 6, 5, 4, 3, 2, 1.0, 0.1, 0.01, 0.001 (or any range between about 95 and 0.001) or less wt % of a heterologous functional agent. For example, the PMP composition can include about 0.001 to about 0.01 wt %, about 0.01 to about 0.1 wt %, about 0.1 to about 1 wt %, about 1 to about 5 wt %, or about 5 to about 10 wt %, about 10 to about 20 wt % of the heterologous functional agent. In some instances, the PMP can be loaded or the PMP composition is formulated with about 1, 5, 10, 50, 100, 200, or 500, 1,000, 2,000 (or any range between about 1 and 2,000) or more µg/ml of a heterologous functional agent. A PMP of the invention can be loaded or a PMP composition can be formulated with about 2,000, 1,000, 500, 200, 100, 50, 10, 5, 1 (or any range between about 2,000 and 1) or less µg/ml of a heterologous functional agent.

In some instances, the PMPs are loaded or the PMP composition is formulated such that the PMP composition disclosed herein includes at least 0.001 wt %, at least 0.01 wt %, at least 0.1 wt %, at least 1.0 wt %, at least 2 wt %, at least 3 wt %, at least 4 wt %, at least 5 wt %, at least 6 wt %, at least 7 wt %, at least 8 wt %, at least 9 wt %, at least 10 wt %, at least 15 wt %, at least 20 wt %, at least 30 wt %, at least 40 wt %, at least 50 wt %, at least 60 wt %, at least 70 wt %, at least 80 wt %, at least 90 wt %, or at least 95 wt % of a heterologous functional agent. In some instances, the PMP can be loaded or the PMP composition can be formulated with at least 1 µg/ml, at least 5 µg/ml, at least 10 µg/ml, at least 50 µg/ml, at least 100 µg/ml, at least 200 µg/ml, at least 500 µg/ml, at least 1,000 µg/ml, at least 2,000 µg/ml of a heterologous functional agent.

In some instances, the PMP composition is formulated with the heterologous functional agent by suspending the PMPs in a solution comprising or consisting of the heterologous functional agent, e.g., suspending or resuspending the PMPs by vigorous mixing. The heterologous functional agent (e.g., cell-penetrating agent, e.g., enzyme, detergent, ionic, fluorous, or zwitterionic liquid, or charged lipid (e.g., ionizable and/or cationic lipid) may comprise, e.g., less than 1% or at least 1%, 5%, 10%, 20%, 30%, 40%, 50%, 60%, 70%, 80%, 90%, or 100% of the solution.

Examples of particular heterologous functional agents that can be loaded into the PMPs are further outlined in the section entitled "Heterologous Functional Agents."

E. Production of LPMPs Using Microfluidics

In some aspects, the PMP composition comprises a plurality of lipid reconstructed PMPs (LPMPs), wherein the LPMPs are produced by a process which comprises the steps of (a) providing a plurality of purified PMPs (e.g., PMPs purified as described in Section IA herein); (b) processing the plurality of PMPs to produce a lipid film; (c) reconstituting the lipid film in an organic solvent or solvent combination, thereby producing a lipid solution; and (d) processing the lipid solution of step (c) in a microfluidics device comprising an aqueous phase, thereby producing the LPMPs.

In some instances, processing the plurality of PMPs to produce a lipid film includes extracting lipids from the plurality of PMPs, e.g., extracting lipids using the Bligh-Dyer method (Bligh and Dyer, *J Biolchem Physiol*, 37: 911-917, 1959). The extracted lipids may be provided as a stock solution, e.g., a solution in chloroform:methanol. Producing the lipid film may comprise, e.g., evaporation of the solvent with a stream of inert gas (e.g., nitrogen).

The LPMPs may comprise an exogenous lipid, e.g., a charged lipid (e.g., an ionizable lipid (e.g., C12-200 or MC3) and/or a cationic lipid (e.g., DOTAP or DC cholesterol). In some examples, the charged lipid is chosen from 1'-((2-(4-(2-((2-(bis(2-hydroxydodecyl)amino)ethyl) (2-hydroxydodecyl)amino)ethyl)piperazin-1-yl)ethyl)azanediyl)bis(dodecan-2-ol) (C12-200), DLin-MC3-DMA (MC3), dioleoyl-3-trimethylammonium propane (DODAP), DC-cholesterol, DOTAP, Ethyl PC, GL67, DLin-KC2-DMA (KC2), MD1 (cKK-E12), OF2, EPC, ZA3-Ep10, TT3, LP01, 5A2-SC8, Lipid 5 (Moderna), a cationic sulfonamide amino lipid, an amphiphilic zwitterionic amino lipid, DODAC, DOBAQ, YSK05, DOBAT, DOBAQ, DOPAT, DOMPAQ, DOAAQ, DMAP-BLP, DLinDMA, DODMA, DOTMA, DSDMA, DOSPA, DODAC, DOBAQ, DMRIE, DOTAP-cholesterol, GL67A, and 98N12-5 or a combination thereof. In some examples, the exogenous lipid is added to the preparation prior to step (b), e.g., mixed with extracted PMP lipids prior to step (b). The exogenous lipids may be added to amount to, e.g., 1%, 5%, 10%, 20%, 30%, 40%, 50%, 60%, 70%, 80%, 90%, or more than 90% (w/w) of total lipids in the preparation. In some examples, the exogenous lipid (e.g., charged lipid, e.g., ionizable lipid and/or cationic lipid) is added to amount to 25% or 40% (w/w) of total lipids in the preparation.

In some instances, the LPMPs comprise an exogenous sterol, e.g., sitosterol, sitostanol, R-sitosterol, 7α-hydroxycholesterol, pregnenolone, cholesterol (e.g., ovine cholesterol or cholesterol isolated from plants), stigmasterol, campesterol, fucosterol, or an analog (e.g., a glycoside, ester, or peptide) of any sterol. In some examples, the exogenous sterol is added to the preparation prior to step (b), e.g., mixed with extracted PMP lipids prior to step (b). The exogenous sterol may be added to amount to, e.g., 1%, 5%, 10%, 20%, 30%, 40%, 50%, 60%, 70%, 80%, 90%, or more than 90% (w/w) of total lipids and sterols in the preparation.

In some instances, the LPMPs comprise an exogenous lipid and an exogenous sterol.

In some instances, the organic solvent in which the lipid film is dissolved is dimethylformamide:methanol (DMF: MeOH). Alternatively, the organic solvent or solvent combination may be, e.g., acetonitrile, acetone, ethanol, methanol, dimethylformamide, tetrahydrofuran, 1-buthanol, dimethyl sulfoxide, acetonitrile:ethanol, acetonitrile:methanol, acetone:methanol, methyl tert-butyl ether:propanol, tetrahydrofuran:methanol, dimethyl sulfoxide:methanol, or dimethylformamide:methanol.

The aqueous phase may be any suitable solution, e.g., a citrate buffer (e.g., a citrate buffer having a pH of about 3.2), water, or phosphate-buffered saline (PBS). The aqueous phase may further comprise a heterologous functional agent, e.g., an agent described in Section II herein, e.g., a nucleic acid (e.g., an siRNA or siRNA precursor (e.g., dsRNA), miRNA or miRNA precursor, mRNA, or plasmid (pDNA)) or a small molecule.

The lipid solution and the aqueous phase may be mixed in the microfluidics device at any suitable ratio. In some examples, aqueous phase and the lipid solution are mixed at a 3:1 volumetric ratio.

F. Zeta Potential

The PMP composition comprising a plurality of modified PMPs comprising a charged lipid (e.g., an ionizable lipid, e.g., C12-200 or MC3 and/or a cationic lipid, e.g., DC-cholesterol or DOTAP) may have, e.g., a zeta potential of greater than −30 mV when in the absence of cargo, greater than −20 mV, greater than −5 mV, greater than 0 mV, or about 30 my when in the absence of cargo. In some examples, the PMP composition has a negative zeta potential, e.g., a zeta potential of less than 0 mV, less than −10 mV, less than −20 mV, less than −30 mV, less than −40 mV, or less than −50 mV when in the absence of cargo. In some examples, the PMP composition has a positive zeta potential, e.g., a zeta potential of greater than 0 mV, greater than 10 mV, greater than 20 mV, greater than 30 mV, greater than 40 mV, or greater than 50 mV when in the absence of cargo. In some examples, the PMP composition has a zeta potential of about 0.

The zeta potential of the PMP composition may be measured using any method known in the art. Zeta potentials are generally measured indirectly, e.g., calculated using theoretical models from the data obtained using methods and techniques known in the art, e.g., electrophoretic mobility or dynamic electrophoretic mobility. Electrophoretic mobility is typically measured using microelectrophoresis, electrophoretic light scattering, or tunable resistive pulse sensing. Electrophoretic light scattering is based on dynamic light scattering. Typically, zeta potentials are accessible from dynamic light scattering (DLS) measurements, also known as photon correlation spectroscopy or quasi-elastic light scattering.

G. Formulations i. Agricultural Formulations

To allow ease of application, handling, transportation, storage, and effective activity, PMPs (e.g., modified PMPs as described herein), can be formulated with other substances. PMPs can be formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra-low volume solutions. For further information on formulation types see "Catalogue of Pesticide Formulation Types and International Coding System" Technical Monograph n° 2, 5th Edition by CropLife International (2002).

PMP compositions can be applied as aqueous suspensions or emulsions prepared from concentrated formulations of such agents. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the PMP composition, a carrier, and surfactants. The carrier is usually selected from among the attapulgite clays, the montmorillonite clays, the diatomaceous earths, or the purified silicates. Effective surfactants, including from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates can comprise a suitable concentration of PMPs, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble PMP compositions dispersed in an aqueous carrier at a concentration in the range from about 5% to about 50% by weight. Suspensions are prepared by finely grinding the composition and vigorously mixing it into a carrier comprised of water and surfactants. Ingredients, such as inorganic salts and synthetic or natural gums may also be added, to increase the density and viscosity of the aqueous carrier.

PMP compositions may also be applied as granular compositions that are particularly useful for applications to the soil. Granular compositions usually contain from about 0.5% to about 10% by weight of the PMP composition, dispersed in a carrier that comprises clay or a similar substance. Such compositions are usually prepared by dissolving the formulation in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing the present PMP formulation are prepared by intimately mixing PMPs in powdered form with a suitable dusty agricultural carrier, such as kaolin clay, ground volcanic rock, and the like. Dusts can suitably contain from about 1% to about 10% of the packets. They can be applied as a seed dressing or as a foliage application with a dust blower machine.

It is equally practical to apply the present formulation in the form of a solution in an appropriate organic solvent, usually petroleum oil, such as the spray oils, which are widely used in agricultural chemistry.

PMPs can also be applied in the form of an aerosol composition. In such compositions the packets are dissolved or dispersed in a carrier, which is a pressure-generating propellant mixture. The aerosol composition is packaged in a container from which the mixture is dispensed through an atomizing valve.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer including: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007. For ease of use, this embodiment will be referred to as "OIWE."

Additionally, generally, when the molecules disclosed above are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO (ethylene oxide-propylene oxide) block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the PMP composition on the target. The types of surfactants used for bioenhancement depend generally on the nature and mode of action of the PMP composition. However, they are often non-ionics such as: alkyl ethoxylates; linear aliphatic alcohol ethoxylates; aliphatic amine ethoxylates.

A carrier or diluent in an agricultural formulation is a material added to the PMP composition to give a product of the required strength. Carriers are usually materials with high absorptive capacities, while diluents are usually materials with low absorptive capacities. Carriers and diluents are used in the formulation of dusts, wettable powders, granules, and water-dispersible granules.

Organic solvents are used mainly in the formulation of emulsifiable concentrates, oil-in-water emulsions, suspoemulsions, and ultra low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of PMP composition when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions, and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol, and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g., plant and animal sources. Specific examples are: vegetable oils, seed oils, and esters thereof, also alkoxylated alkyl polyglucosides.

In some instances, PMPs can be freeze-dried or lyophilized. See U.S. Pat. No. 4,311,712. The PMPs can later be reconstituted on contact with water or another liquid. Other components can be added to the lyophilized or reconstituted PMPs, for example, other heterologous functional agents, agriculturally acceptable carriers, or other materials in accordance with the formulations described herein.

Other optional features of the composition include carriers or delivery vehicles that protect the PMP composition against UV and/or acidic conditions. In some instances, the delivery vehicle contains a pH buffer. In some instances, the composition is formulated to have a pH in the range of about 4.5 to about 9.0, including for example pH ranges of about any one of 5.0 to about 8.0, about 6.5 to about 7.5, or about 6.5 to about 7.0.

For further information on agricultural formulations, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

ii. Pharmaceutical Formulations The modified PMPs described herein can be formulated into pharmaceutical compositions, e.g., for administration to an animal (e.g., a human). The pharmaceutical composition may be administered to an animal (e.g., human) with a pharmaceutically acceptable diluent, carrier, and/or excipient. Depending on the mode of administration and the dosage, the pharmaceutical composition of the methods described herein will be formulated into suitable pharmaceutical compositions to permit facile delivery. The single dose may be in a unit dose form as needed.

A PMP composition may be formulated for e.g., oral administration, intravenous administration (e.g., injection or infusion), or subcutaneous administration to an animal. For injectable formulations, various effective pharmaceutical carriers are known in the art (See, e.g., Remington: The Science and Practice of Pharmacy, $22^{nd}$ ed., (2012) and ASHP Handbook on Injectable Drugs, $18^{th}$ ed., (2014)).

Pharmaceutically acceptable carriers and excipients in the present compositions are nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. The compositions may be formulated according to conventional pharmaceutical practice. The concentration of the compound in the formulation will vary depending upon a number of factors, including the dosage of the active agent (e.g., PMP) to be administered, and the route of administration.

For oral administration to an animal, the PMP composition can be prepared in the form of an oral formulation. Formulations for oral use can include tablets, caplets, capsules, syrups, or oral liquid dosage forms containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like. Formulations for oral use may also be provided in unit dosage form as chewable tablets, non-chewable tablets, caplets, capsules (e.g., as hard gelatin capsules wherein the active ingredient is mixed with an inert solid diluent, or as soft gelatin capsules wherein the active ingredient is mixed with water or an oil medium). The compositions disclosed herein may also further include an immediate-release, extended release or delayed-release formulation.

For parenteral administration to an animal, the PMP compositions may be formulated in the form of liquid solutions or suspensions and administered by a parenteral route (e.g., subcutaneous, intravenous, or intramuscular). The pharmaceutical composition can be formulated for injection or infusion. Pharmaceutical compositions for parenteral administration can be formulated using a sterile solution or any pharmaceutically acceptable liquid as a vehicle. Pharmaceutically acceptable vehicles include, but are not limited to, sterile water, physiological saline, or cell culture media (e.g., Dulbecco's Modified Eagle Medium (DMEM), α-Modified Eagles Medium (α-MEM), F-12 medium). Formulation methods are known in the art, see e.g., Gibson (ed.) Pharmaceutical Preformulation and Formulation (2nd ed.) Taylor & Francis Group, CRC Press (2009).

II. Heterologous Functional Agents

The PMPs manufactured herein can further include a heterologous functional agent, such as a heterologous functional agent (e.g., a heterologous agricultural agent (e.g., pesticidal agent, fertilizing agent, herbicidal agent, plant-modifying agent) or a heterologous therapeutic agent (e.g., an antifungal agent, an antibacterial agent, a virucidal agent, an anti-viral agent, an insecticidal agent, a nematicidal agent, an antiparasitic agent, or an insect repellent)). For example, the PMP may encapsulate the heterologous functional agent. Alternatively, the heterologous functional agent can be embedded on or conjugated to the surface of the PMP. In some instances, the PMPs include two or more (e.g., 2, 3, 4, 5, 6, 7, 8, 9, 10, or more than 10) different heterologous functional agents. Heterologous functional agents may be added at any step during the manufacturing process effective to introduce the agent into the manufactured PMPs.

In certain instances, the heterologous functional agent (e.g., a heterologous agricultural agent (e.g., pesticidal agent, fertilizing agent, herbicidal agent, plant-modifying agent, a heterologous nucleic acid, a heterologous polypeptide, or a heterologous small molecule) or a heterologous therapeutic agent (e.g., an antifungal agent, an antibacterial agent, a virucidal agent, an anti-viral agent, a nematicidal agent, an antiparasitic agent, or an insect repellent)) can be modified. For example, the modification can be a chemical modification, e.g., conjugation to a marker, e.g., fluorescent marker or a radioactive marker. In other examples, the modification can include conjugation or operational linkage to a moiety that enhances the stability, delivery, targeting, bioavailability, or half-life of the agent, e.g., a lipid, a glycan, a polymer (e.g., PEG), or a cation moiety.

Examples of heterologous functional agents that can be loaded into the PMPs manufactured herein are outlined below.

A. Heterologous Agricultural Agents

The PMPs manufactured herein can include a heterologous agricultural agent (e.g., an agent that effects a plant or an organism that associates with a plant and can be loaded into a PMP), such as a pesticidal agent, herbicidal agent, fertilizing agent, or a plant-modifying agent.

For example, in some instances, the PMPs may include a pesticidal agent. The pesticidal agent can be an antifungal agent, an antibacterial agent, an insecticidal agent, a molluscicidal agent, a nematicidal agent, a virucidal agent, or a combination thereof. The pesticidal agent can be a chemical agent, such as those well known in the art. Alternatively or additionally, the pesticidal agent can be a peptide, a polypeptide, a nucleic acid, a polynucleotide, or a small molecule. The pesticidal agent may be an agent that can decrease the fitness of a variety of plant pests or can be one that targets one or more specific target plant pests (e.g., a specific species or genus of plant pests).

In some instances, the PMPs may include one or more heterologous fertilizing agents. Examples of heterologous fertilizing agents include plant nutrients or plant growth regulators, such as those well known in the art. Alternatively, or additionally, the fertilizing agent can be a peptide, a polypeptide, a nucleic acid, or a polynucleotide that can increase the fitness of a plant symbiont. The fertilizing agent may be an agent that can increase the fitness of a variety of plants or plant symbionts or can be one that targets one or more specific target plants or plant symbionts (e.g., a specific species or genera of plants or plant symbionts).

In other instances, the PMPs may include one or more heterologous plant-modifying agents. In some instances, the plant-modifying agent can include a peptide or a nucleic acid.

i. Antibacterial Agents

The PMP compositions described herein can further include an antibacterial agent. In some instances, the PMP compositions include two or more (e.g., 2, 3, 4, 5, 6, 7, 8, 9, 10, or more than 10) different antibacterial agents. For example, the antibacterial agent can decrease the fitness of (e.g., decrease growth or kill) a bacterial plant pest (e.g., a bacterial plant pathogen). A PMP composition including an antibiotic as described herein can be contacted with a target pest, or plant infested thereof, in an amount and for a time sufficient to: (a) reach a target level (e.g., a predetermined or threshold level) of antibiotic concentration inside or on the target pest; and (b) decrease fitness of the target pest. The antibacterials described herein may be formulated in a PMP composition for any of the methods described herein, and in certain instances, may be associated with the PMP thereof.

As used herein, the term "antibacterial agent" refers to a material that kills or inhibits the growth, proliferation, division, reproduction, or spread of bacteria, such as phytopathogenic bacteria, and includes bactericidal (e.g., disinfectant compounds, antiseptic compounds, or antibiotics) or bacteriostatic agents (e.g., compounds or antibiotics). Bactericidal antibiotics kill bacteria, while bacteriostatic antibiotics only slow their growth or reproduction.

Bactericides can include disinfectants, antiseptics, or antibiotics. The most used disinfectants can comprise: active chlorine (i.e., hypochlorites (e.g., sodium hypochlorite), chloramines, dichloroisocyanurate and trichloroisocyanurate, wet chlorine, chlorine dioxide etc.), active oxygen (peroxides, such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols are used), phenolic substances (such as phenol (also called carbolic acid), cresols (called Lysole in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants, such as some quaternary ammonium cations (such as benzalkonium chloride, cetyl trimethylammonium bromide or chloride, didecyldimethylammonium chloride, cetylpyridinium chloride, benzethonium chloride) and others, non-quaternary compounds, such as chlorhexidine, glucoprotamine, octenidine dihydrochloride etc.), strong oxidizers, such as ozone and permanganate solutions; heavy metals and their salts, such as colloidal silver, silver nitrate, mercury chloride, phenylmercury salts, copper sulfate, copper oxide-chloride, copper hydroxide, copper octanoate, copper oxychloride sulfate, copper sulfate, copper sulfate pentahydrate, etc. Heavy metals and their salts are the most toxic, and environment-hazardous bactericides and therefore, their use is strongly oppressed or canceled; further, also properly concentrated strong acids (phosphoric, nitric, sulfuric, amidosulfuric, toluenesulfonic acids) and alkalis (sodium, potassium, calcium hydroxides).

As antiseptics (i.e., germicide agents that can be used on human or animal body, skin, mucoses, wounds and the like), few of the above mentioned disinfectants can be used, under proper conditions (mainly concentration, pH, temperature and toxicity toward man/animal). Among them, important are: properly diluted chlorine preparations (i.e., Daquin's solution, 0.5% sodium or potassium hypochlorite solution, pH-adjusted to pH 7-8, or 0.5-1% solution of sodium benzenesulfochloramide (chloramine B)), some iodine preparations, such as iodopovidone in various galenics (ointment, solutions, wound plasters), in the past also Lugol's solution, peroxides as urea perhydrate solutions and pH-buffered 0.1-0.25% peracetic acid solutions, alcohols with or without antiseptic additives, used mainly for skin antisepsis, weak organic acids such as sorbic acid, benzoic acid, lactic acid and salicylic acid some phenolic compounds, such as hexachlorophene, triclosan and Dibromol, and cation-active compounds, such as 0.05-0.5% benzalkonium, 0.5-4% chlorhexidine, 0.1-2% octenidine solutions.

The PMP composition described herein may include an antibiotic. Any antibiotic known in the art may be used. Antibiotics are commonly classified based on their mechanism of action, chemical structure, or spectrum of activity.

The antibiotic described herein may target any bacterial function or growth processes and may be either bacteriostatic (e.g., slow or prevent bacterial growth) or bactericidal (e.g., kill bacteria). In some instances, the antibiotic is a bactericidal antibiotic. In some instances, the bactericidal antibiotic is one that targets the bacterial cell wall (e.g., penicillins and cephalosporins); one that targets the cell membrane (e.g., polymyxins); or one that inhibits essential bacterial enzymes (e.g., rifamycins, lipiarmycins, quinolones, and sulfonamides). In some instances, the bactericidal antibiotic is an aminoglycoside (e.g., kasugamycin). In some instances, the antibiotic is a bacteriostatic antibiotic. In some instances the bacteriostatic antibiotic targets protein synthesis (e.g., macrolides, lincosamides, and tetracyclines). Additional classes of antibiotics that may be used herein include cyclic lipopeptides (such as daptomycin), glycylcyclines (such as tigecycline), oxazolidinones (such as linezolid), or lipiarmycins (such as fidaxomicin). Examples of antibiotics include rifampicin, ciprofloxacin, doxycycline, ampicillin, and polymyxin B. The antibiotic described herein may have any level of target specificity (e.g., narrow- or broad-spectrum). In some instances, the antibiotic is a narrow-spectrum antibiotic, and thus targets specific types of bacteria, such as gram-negative or gram-positive bacteria. Alternatively, the antibiotic may be a broad-spectrum antibiotic that targets a wide range of bacteria.

Other non-limiting examples of antibiotics are found in Table 1. One skilled in the art will appreciate that a suitable concentration of each antibiotic in the composition depends on factors such as efficacy, stability of the antibiotic, number of distinct antibiotics, the formulation, and methods of application of the composition.

TABLE 1

Examples of Antibiotics

| Antibiotics | Action |
| --- | --- |
| Penicillins, cephalosporins, vancomycin | Cell wall synthesis |
| Polymixin, gramicidin | Membrane active agent, disrupt cell membrane |
| Tetracyclines, macrolides, chloramphenicol, clindamycin, spectinomycin | Inhibit protein synthesis |
| Sulfonamides | Inhibit folate-dependent pathways |
| Ciprofloxacin | Inhibit DNA-gyrase |
| Isoniazid, rifampicin, pyrazinamide, ethambutol, (myambutol)l, streptomycin | Antimycobacterial agents | ii. Antifungal Agents

The PMP compositions described herein can further include an antifungal agent. In some instances, the PMP compositions include two or more (e.g., 2, 3, 4, 5, 6, 7, 8, 9, 10, or more than 10) different antifungal agents. For example, the antifungal agent can decrease the fitness of (e.g., decrease growth or kill) a fungal plant pest. A PMP composition including an antifungal as described herein can be contacted with a target fungal pest, or plant infested therewith, in an amount and for a time sufficient to: (a) reach a target level (e.g., a predetermined or threshold level) of antibiotic concentration inside or on the target fungus; and (b) decrease fitness of the target fungus. The antifungals described herein may be formulated in a PMP composition for any of the methods described herein, and in certain instances, may be associated with the PMP thereof.

As used herein, the term "fungicide" or "antifungal agent" refers to a substance that kills or inhibits the growth, proliferation, division, reproduction, or spread of fungi, such as phytopathogenic fungi. Many different types of antifungal agent have been produced commercially. Non limiting examples of antifungal agents include: azoxystrobin, mancozeb, prothioconazole, folpet, tebuconazole, difenoconazole, captan, bupirimate, or fosetyl-Al. Further exemplary fungicides include, but are not limited to, strobilurins, azoxystrobin, dimmrystrobin, enestroburin, fluoxastrobin, kresoxim-methyl, metominostrobin, picoxystrobin, pyraclostrobin, trifloxystrobin, orysastrobin, carboxamides, carboxanilides, benalaxyl, benalaxyl-M, benodanil, carboxin, mebenil, mepronil, fenfuram, fenhexamid, flutolanil, furalaxyl, furcarbanil, furametpyr, metalaxyl, metalaxyl-M (mefenoxam), methfuroxam, metsulfovax, ofurace, oxadixyl, oxycarboxin, penthiopyrad, pyracarbolid, salicylanilide, tecloftalam, thifluzamide, tiadinil, N-biphenylamides, bixafen, boscalid, carboxylic acid morpholides, dimethomorph, flu morph, benzamides, flumetover, fluopicolid (picobenzamid), zoxamid, carboxamides, carpropamid, diclocymet, mandipropamid, silthiofam, azoles, triazoles, bitertanol, bromuconazole, cyproconazole, difenoconazole, diniconazole, enilconazole, epoxiconazole, fenbuconazole, flusilazol, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole, Imidazoles, cyazofamid, imazalil, pefurazoate, prochloraz, triflumizole, benzimidazoles, benomyl, carbendazim, fuberidazole, thiabendazole, ethaboxam, etridiazole, hymexazol, nitrogen-containing heterocyclyl compounds, pyridines, fuazinam, pyrifenox, pyrimidines, bupirimate, cyprodinil, ferimzone, fenarimol, mepanipyrim, nuarimol, pyrimethanil, piperazines, triforine, pyrroles, fludioxonil, fenpiclonil, morpholines, aldimorph, dodemorph, fenpropimorph, tridemorph, dicarboximides, iprodione, procymidone, vinclozolin, acibenzolar-S-methyl, anilazine, captan, captafol, dazomet, diclomezin, fenoxanil, folpet, fenpropidin, famoxadon, fenamidon, octhilinone, probenazole, proquinazid, pyroquilon, quinoxyfen, tricyclazole, carbamates, dithiocarbamates, ferbam, mancozeb, maneb, metiram, metam, propineb, thiram, zineb, ziram, diethofencarb, flubenthiavalicarb, iprovalicarb, propamocarb, guanidines, dodine, iminoctadine, guazatine, kasugamycin, polyoxins, streptomycin, validamycin A, organometallic compounds, fentin salts, sulfur-containing heterocyclyl compounds, isoprothiolane, dithianone, organophosphorous compounds, edifenphos, fosetyl, fosetyl-aluminum, iprobenfos, pyrazophos, tolclofos-methyl, Organochlorine compounds, thiophanate-methyl, chlorothalonil, dichlofluanid, tolylfluanid, flusulfamide, phthalide, hexachlorobenzene, pencycuron, quintozene, nitrophenyl derivatives, binapacryl, dinocap, dinobuton, spiroxamine, cyflufenamid, cymoxanil, metrafenon, N-2-cyanophenyl-3,4-dichloroisothiazol-5-carboxamide (isotianil), N-(3',4',5'-trifluorobiphenyl-2-yl)-3-difluoromethyl-1-methylpyrazole-4-carboxamide, 3-[5-(4-chlorophenyl)-2,3-dimethylisoxazolidin-3-yl]-pyridine, N-(3',4'-dichloro-4-fluorobiphenyl-2-yl)-3-difluoromethyl-1-methylpyrazol-e-4-carboxamide, 5-chloro-7-(4-methylpiperidin-1-yl)-6-(2,4,6-trifluorophenyl)-[1,2,4]tria-zolo[1,5-a]pyrimidine, 2-butoxy-6-iodo-3-propylchromen-4-one, N,N-dimethyl-3-(3-bromo-6-fluoro-2-methylindole-1-sulfonyl)-[1,2,4]triazo-le-1-sulfonamide, methyl-(2-chloro-5-[1-(3-methylbenzyloxyimino)-ethyl]benzyl)carbamate, methyl-(2-chloro-5-[1-(6-methylpyridin-2-ylmethoxy-imino)ethyl]benzyl)carbamate, methyl 3-(4-chlorophenyl)-3-(2-isopropoxycarbonylamino-3-methylbutyryl-amino) propionate, 4-fluorophenyl N-(1-(1-(4-cyanophenyl) ethanesulfonyl)but-2-yl)carbamate, N-(2-(4-[3-(4-chlorophenyl)prop-2-ynyloxy]-3-methoxyphenyl)ethyl)-2-metha-nesulfonylamino-3-methylbutyramide, N-(2-(4-[3-(4-chlorophenyl)prop-2-ynyloxy]-3-methoxyphenyl)ethyl)-2-ethan-esulfonylamino-3-methylbutyramide, N-(4'-bromobiphenyl-2-yl)-4-difluoromethyl-2-methylthiazol-5-carboxamide, N-(4'-trifluoromethylbiphenyl-2-yl)-4-difluoromethyl-2-methylthiazol-5-carboxamide, N-(4'-chloro-3'-fluorobiphenyl-2-yl)-4-difluoromethyl-2-methylthiazol-5-carboxamide, or methyl 2-(ortho-((2,5-dimethylphenyloxy-methylene)phenyl)-3-methoxyacrylate. One skilled in the art will appreciate that a suitable concentration of each antifungal in the composition depends on factors such as efficacy, stability of the antifungal, number of distinct antifungals, the formulation, and methods of application of the composition.

iii. Insecticides

The PMP compositions described herein can further include an insecticide. In some instances, the PMP compositions include two or more (e.g., 2, 3, 4, 5, 6, 7, 8, 9, 10, or more than 10) different insecticide agents. For example, the insecticide can decrease the fitness of (e.g., decrease growth or kill) an insect plant pest. A PMP composition including an insecticide as described herein can be contacted with a target insect pest, or plant infested therewith, in an amount and for a time sufficient to: (a) reach a target level (e.g., a predetermined or threshold level) of insecticide concentration inside or on the target insect; and (b) decrease fitness of the target insect. The insecticides described herein may be formulated in a PMP composition for any of the methods described herein, and in certain instances, may be associated with the PMP thereof.

As used herein, the term "insecticide" or "insecticidal agent" refers to a substance that kills or inhibits the growth, proliferation, reproduction, or spread of insects, such as agricultural insect pests. Non limiting examples of insecticides are shown in Table 2. Additional non-limiting examples of suitable insecticides include biologics, hormones or pheromones such as azadirachtin, *Bacillus* species, *Beauveria* species, codlemone, *Metarrhizium* species, *Paecilomyces* species, *thuringiensis*, and *Verticillium* species, and active compounds having unknown or non-specified mechanisms of action such as fumigants (such as aluminium phosphide, methyl bromide and sulphuryl fluoride) and selective feeding inhibitors (such as cryolite, flonicamid and pymetrozine). One skilled in the art will appreciate that a suitable concentration of each insecticide in the composition depends on factors such as efficacy, stability of the insecticide, number of distinct insecticides, the formulation, and methods of application of the composition.

TABLE 2

Examples of insecticides

| Class | Compounds |
| --- | --- |
| chloronicotinyls/ neonicotinoids | acetamiprid, clothianidin, dinotefuran, imidacloprid, nitenpyram, nithiazine, thiacloprid, thiamethoxam, imidaclothiz, (2E)-1-[(2-chloro-1,3-thiazol-5-yl)methyl]-3,5-dimethyl-N-nitro-1,3,5-tri-azinan-2-imine, acetylcholinesterase (AChE) inhibitors (such as carbamates and organophosphates) |
| carbamates | alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, chloethocarb, dimetilan, ethiofencarb, fenobucarb, fenothiocarb, formetanate, furathiocarb, isoprocarb, metam-sodium, methiocarb, methomyl, metolcarb, oxamyl, phosphocarb, pirimicarb, promecarb, propoxur, thiodicarb, thiofanox, triazamate, trimethacarb, XMC, xylylcarb |
| organophosphates | acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion |
| pyrethroids | acrinathrin, allethrin (d-cis-trans, d-trans), cypermethrin (alpha-, beta-, theta-, zeta-), permethrin (cis-, trans-), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda, cyhalothrin, metofluthrin, phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralocythrin, tralomethrin, transfluthrin, ZXI 8901, pyrethrins (pyrethrum) |
| oxadiazines | indoxacarb, acetylcholine receptor modulators (such as spinosyns) |
| spinosyns | spinosad |
| cyclodiene | camphechlor, chlordane, endosulfan, gamma-HCH, HCH, heptachlor, |
| organochlorines | lindane, methoxychlor |
| fiproles | acetoprole, ethiprole, vaniliprole, fipronil |
| mectins | abamectin, avermectin, emamectin, emamectin-benzoate, fenoxycarb, hydroprene, kinoprene, methoprene, ivermectin, lepimectin, epofenonane, pyriproxifen, milbemectin, milbemycin, triprene |
| diacylhydrazines | chromafenozide, halofenozide, methoxyfenozide, tebufenozide |
| benzoylureas | bistrifluoron, chlorfluazuron, diflubenzuron, fluazuron, flucycloxuron, flufenoxuron, hexaflumuron, lufenuron, novaluron, noviflumuron, penfluoron, teflubenzuron, triflumuron |

TABLE 2-continued

Examples of insecticides

| Class | Compounds |
| --- | --- |
| organotins | azocyclotin, cyhexatin, fenbutatin oxide |
| pyrroles | chlorfenapyr |
| dinitrophenols | binapacyrl, dinobuton, dinocap, DNOC |
| METIs | fenazaquin, fenpyroximate, pyrimidifen, pyridaben, tebufenpyrad, tolfenpyrad, rotenone, acequinocyl, fluacrypyrim, microbial disrupters of the intestinal membrane of insects (such as *Bacillus thuringiensis* strains), inhibitors of lipid synthesis (such as tetronic acids and tetramic acids) |
| tetronic acids | spirodiclofen, spiromesifen, spirotetramat |
| tetramic acids | cis-3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester; CAS Reg. No.: 382608-10-8), carboxamides (such as flonicamid), octopaminergic agonists (such as amitraz), inhibitors of the magnesium-stimulated ATPase (such as propargite), ryanodin receptor agonists (such as phthalamides or rynaxapyr) |
| phthalamides | N2-[1,1-dimethyl-2-(methylsulphonyl)ethyl]-3-iodo-N1-[2-methyl--4-[1,2,2,2-tetrafluoro-1-(trifluoromethyl)ethyl]phenyl]-1,2-benzenedi-carboxamide (i.e., flubendiamide; CAS reg. No.: 272451-65-7) | iv. Nematicide

The PMP compositions described herein can further include a nematicide. In some instances, the PMP compositions include two or more (e.g., 2, 3, 4, 5, 6, 7, 8, 9, 10, or more than 10) different nematicides. For example, the nematicide can decrease the fitness of (e.g., decrease growth or kill) a nematode plant pest. A PMP composition including a nematicide as described herein can be contacted with a target nematode pest, or plant infested therewith, in an amount and for a time sufficient to: (a) reach a target level (e.g., a predetermined or threshold level) of nematicide concentration inside or on the target nematode; and (b) decrease fitness of the target nematode. The nematicides described herein may be formulated in a PMP composition for any of the methods described herein, and in certain instances, may be associated with the PMP thereof.

As used herein, the term "nematicide" or "nematicidal agent" refers to a substance that kills or inhibits the growth, proliferation, reproduction, or spread of nematodes, such as agricultural nematode pests. Non limiting examples of nematicides are shown in Table 3. One skilled in the art will appreciate that a suitable concentration of each nematicide in the composition depends on factors such as efficacy, stability of the nematicide, number of distinct nematicides, the formulation, and methods of application of the composition.

v. Molluscicide

The PMP compositions described herein can further include a molluscicide. In some instances, the PMP compositions include two or more (e.g., 2, 3, 4, 5, 6, 7, 8, 9, 10, or more than 10) different molluscicides. For example, the molluscicide can decrease the fitness of (e.g., decrease growth or kill) a mollusk plant pest. A PMP composition including a molluscicide as described herein can be contacted with a target mollusk pest, or plant infested therewith, in an amount and for a time sufficient to: (a) reach a target level (e.g., a predetermined or threshold level) of molluscicide concentration inside or on the target mollusk; and (b) decrease fitness of the target mollusk. The molluscicides described herein may be formulated in a PMP composition for any of the methods described herein, and in certain instances, may be associated with the PMP thereof.

As used herein, the term "molluscicide" or "molluscicidal agent" refers to a substance that kills or inhibits the growth, proliferation, reproduction, or spread of mollusks, such as agricultural mollusk pests. A number of chemicals can be employed as a molluscicide, including metal salts such as iron(III) phosphate, aluminium sulfate, and ferric sodium EDTA,[3][4], metaldehyde, methiocarb, or acetylcholinesterase inhibitors. One skilled in the art will appreciate that a suitable concentration of each molluscicide in the composition depends on factors such as efficacy, stability of the molluscicide, number of distinct molluscicides, the formulation, and methods of application of the composition.

vi. Virucides

The PMP compositions described herein can further include a virucide. In some instances, the PMP compositions include two or more (e.g., 2, 3, 4, 5, 6, 7, 8, 9, 10, or more than 10) different virucides. For example, the virucide can decrease the fitness of (e.g., decrease or eliminate) a viral plant pathogen. A PMP composition including a virucide as described herein can be contacted with a target virus, or plant infested therewith, in an amount and for a time sufficient to: (a) reach a target level (e.g., a predetermined or

TABLE 3

Examples of Nematicides

| | |
| --- | --- |
| FUMIGANTS | D-D, 1,3-Dichloropropene, Ethylene Dibromide, 1,2-Dibromo-3-Chloropropane, Methyl Bromide, Chloropicrin, Metam Sodium, Dazomet, Methyl Isothiocyanate (MITC), Sodium Tetrathiocarbonate, Chloropicrin, |
| CARBAMATES | Aldicarb, Aldoxycarb, Carbofuran, Oxamyl, Cleothocarb |
| ORGANOPHOSPHATES | Ethoprophos, Fenamiphos, Cadusafos, Fosthiazate, Fensulfothion, Thionazin, Isazofos, |
| BIOCHEMICALS | DITERA ®, CLANDOSAN ®, SINCOCIN ® | threshold level) of virucide concentration; and (b) decrease or eliminate the target virus. The virucides described herein may be formulated in a PMP composition for any of the methods described herein, and in certain instances, may be associated with the PMP thereof.

As used herein, the term "virucide" or "antiviral" refers to a substance that kills or inhibits the growth, proliferation, reproduction, development, or spread of viruses, such as agricultural virus pathogens. A number of agents can be employed as a virucide, including chemicals or biological agents (e.g., nucleic acids, e.g., dsRNA). One skilled in the art will appreciate that a suitable concentration of each virucide in the composition depends on factors such as efficacy, stability of the virucide, number of distinct virucides, the formulation, and methods of application of the composition.

vii. Herbicides

The PMP compositions described herein can further include one or more (e.g., 1, 2, 3, 4, 5, 6, 7, 8, 9, 10, or more than 10) herbicide. For example, the herbicide can decrease the fitness of (e.g., decrease or eliminate) a weed. A PMP composition including an herbicide as described herein can be contacted with a target weed in an amount and for a time sufficient to: (a) reach a target level (e.g., a predetermined or threshold level) of herbicide concentration on the plant and (b) decrease the fitness of the weed. The herbicides described herein may be formulated in a PMP composition for any of the methods described herein, and in certain instances, may be associated with the PMP thereof.

As used herein, the term "herbicide" refers to a substance that kills or inhibits the growth, proliferation, reproduction, or spread of weeds. A number of chemicals can be employed as a herbicides, including Glufosinate, Propaquizofop, Metamitron, Metazachlor, Pendimethalin, Flufenacet, Diflufenican, Clomazone, Nicosulfuron, Mesotrione, Pinoxaden, Sulcotrione, Prosulfocarb, Sulfentrazone, Bifenox, Quinmerac, Triallate, Terbuthylazine, Atrazine, Oxyfluorfen, Diuron, Trifluralin, or Chlorotoluron. Further examples of herbicides include, but are not limited to, benzoic acid herbicides, such as dicamba esters, phenoxyalkanoic acid herbicides, such as 2,4-D, MCPA and 2,4-DB esters, aryloxyphenoxypropionic acid herbicides, such as clodinafop, cyhalofop, fenoxaprop, fluazifop, haloxyfop, and quizalofop esters, pyridinecarboxylic acid herbicides, such as aminopyralid, picloram, and clopyralid esters, pyrimidinecarboxylic acid herbicides, such as aminocyclopyrachlor esters, pyridyloxyalkanoic acid herbicides, such as fluoroxypyr and triclopyr esters, and hydroxybenzonitrile herbicides, such as bromoxynil and ioxynil esters, esters of the arylpyridine carboxylic acids, and arylpyrimidine carboxylic acids of the generic structures disclosed in U.S. Pat. Nos. 7,314,849, 7,300,907, and 7,642,220, each of which is incorporated by reference herein in its entirety. In certain embodiments, the herbicide can be selected from the group consisting of 2,4-D, 2,4-DB, acetochlor, acifluorfen, alachlor, ametryn, amitrole, asulam, atrazine, azafenidin, benefin, bensulfuron, bensulide, bentazon, bromacil, bromoxynil, butylate, carfentrazone, chloramben, chlorimuron, chlorpropham, chlorsulfuron, clethodim, clomazone, clopyralid, cloransulam, cyanazine, cycloate, DCPA, desmedipham, dichlobenil, diclofop, diclosulam, diethatyl, difenzoquat, diflufenzopyr, dimethenamid-p, diquat, diuron, DSMA, endothall, EPTC, ethalfluralin, ethametsulfuron, ethofumesate, fenoxaprop, fluazifop-P, flucarbazone, flufenacet, flumetsulam, flumiclorac, flumioxazin, fluometuron, fluroxypyr, fluthiacet, fomesafen, foramsulfuron, glufosinate, glyphosate, halosulfuron, haloxyfop, hexazinone, imazamethabenz, imazamox, imazapic, imazaquin, imazethapyr, isoxaben, isoxaflutole, lactofen, linuron, MCPA, MCPB, mesotrione, methazole, metolachlor-s, metribuzin, metsulfuron, molinate, MSMA, napropamide, naptalam, nicosulfuron, norflurazon, oryzalin, oxadiazon, oxasulfuron, oxyfluorfen, paraquat, pebulate, pelargonic acid, pendimethalin, phenmedipham, picloram, primisulfuron, prodiamine, prometryn, pronamide, propachlor, propanil, prosulfuron, pyrazon, pyridate, pyrithiobac, quinclorac, quizalofop, rimsulfuron, sethoxydim, siduron, simazine, sulfentrazone, sulfometuron, sulfosulfuron, tebuthiuron, terbacil, thiazopyr, thifensulfuron, thiobencarb, tralkoxydim, triallate, triasulfuron, tribenuron, triclopyr, trifluralin, triflusulfuron, vernolate. One skilled in the art will appreciate that a suitable concentration of each herbicide in the composition depends on factors such as efficacy, stability of the herbicide, number of distinct herbicides, the formulation, and methods of application of the composition.

viii. Repellents

The PMP compositions described herein can further include a repellent. In some instances, the PMP compositions include two or more (e.g., 2, 3, 4, 5, 6, 7, 8, 9, 10, or more than 10) different repellents. For example, the repellent can repel any of the pests described herein (e.g., insects, nematodes, or mollusks); microorganisms (e.g., phytopathogens or endophytes, such as bacteria, fungi, or viruses); or weeds. A PMP composition including a repellent as described herein can be contacted with a target plant, or plant infested therewith, in an amount and for a time sufficient to: (a) reach a target level (e.g., a predetermined or threshold level) of repellent concentration; and (b) decrease the levels of the pest on the plant relative to an untreated plant. The repellent described herein may be formulated in a PMP composition for any of the methods described herein, and in certain instances, may be associated with the PMP thereof.

In some instances, the repellent is an insect repellent. Some examples of well-known insect repellents include: benzil; benzyl benzoate; 2,3,4,5-bis(butyl-2-ene)tetrahydrofurfural (MGK Repellent 11); butoxypolypropylene glycol; N-butylacetanilide; normal-butyl-6,6-dimethyl-5,6-dihydro-1,4-pyrone-2-carboxylate (Indalone); dibutyl adipate; dibutyl phthalate; di-normal-butyl succinate (Tabatrex); N,N-diethyl-meta-toluamide (DEET); dimethyl carbate (endo,endo)-dimethyl bicyclo[2.2.1] hept-5-ene-2,3-dicarboxylate); dimethyl phthalate; 2-ethyl-2-butyl-1,3-propanediol; 2-ethyl-1,3-hexanediol (Rutgers 612); di-normal-propyl isocinchomeronate (MGK Repellent 326); 2-phenylcyclohexanol; p-methane-3,8-diol, and normal-propyl N,N-diethylsuccinamate. Other repellents include citronella oil, dimethyl phthalate, normal-butylmesityl oxide oxalate and 2-ethyl hexanediol-1,3 (See, Kirk-Othmer Encyclopedia of Chemical Technology, 2nd Ed., Vol. 11: 724-728; and The Condensed Chemical Dictionary, 8th Ed., p 756).

An insect repellent may be a synthetic or nonsynthetic insect repellent. Examples of synthetic insect repellents include methyl anthranilate and other anthranilate-based insect repellents, benzaldehyde, DEET (N,N-diethyl-m-toluamide), dimethyl carbate, dimethyl phthalate, icaridin (i.e., picaridin, Bayrepel, and KBR 3023), indalone (e.g., as used in a "6-2-2" mixture (60% Dimethyl phthalate, 20% Indalone, 20% Ethylhexanediol), IR3535 (3-[N-Butyl-N-acetyl]-aminopropionic acid, ethyl ester), metofluthrin, permethrin, SS220, or tricyclodecenyl allyl ether. Examples of natural insect repellents include beautyberry (*Callicarpa*) leaves, birch tree bark, bog myrtle (*Myrica gale*), catnip oil (e.g., nepetalactone), citronella oil, essential oil of the lemon eucalyptus (*Corymbia citriodora*; e.g., p-menthane-3,8-diol (PMD)), neem oil, lemongrass, tea tree oil from the leaves of *Melaleuca alternifolia*, tobacco, or extracts thereof.

ix. Fertilizing Agents

The PMP compositions described herein can further include a heterologous fertilizing agent. In some instances, the heterologous fertilizing agent is associated with the PMPs. For example, a PMP may encapsulate the heterologous fertilizing agent. Additionally, or alternatively, the heterologous fertilizing agent can be embedded on or conjugated to the surface of the PMP.

Examples of heterologous fertilizing agents include plant nutrients or plant growth regulators, such as those well known in the art. Alternatively, or additionally, the fertilizing agent can be a peptide, a polypeptide, a nucleic acid, or a polynucleotide that can increase the fitness of a plant symbiont. The fertilizing agent may be an agent that can increase the fitness of a variety of plants or plant symbionts or can be one that targets one or more specific target plants or plant symbionts (e.g., a specific species or genera of plants or plant symbionts).

In some instances, the heterologous fertilizing agent can be modified. For example, the modification can be a chemical modification, e.g., conjugation to a marker, e.g., fluorescent marker or a radioactive marker. In other examples, the modification can include conjugation or operational linkage to a moiety that enhances the stability, delivery, targeting, bioavailability, or half-life of the agent, e.g., a lipid, a glycan, a polymer (e.g., PEG), a cation moiety.

Examples of heterologous fertilizing agents that can be used in the presently disclosed PMP compositions and methods are outlined below.

In some instances, the heterologous fertilizing agent includes any material of natural or synthetic origin that is applied to soils or to plant tissues to supply one or more plant nutrients essential to the growth of plants. The plant nutrient may include a macronutrient, micronutrient, or a combination thereof. Plant macronutrients include nitrogen, phosphorus, potassium, calcium, magnesium, and/or sulfur. Plant micronutrients include copper, iron, manganese, molybdenum, zinc, boron, silicon, cobalt, and/or vanadium. Examples of plant nutrient fertilizers include a nitrogen fertilizer including, but not limited to urea, ammonium nitrate, ammonium sulfate, non-pressure nitrogen solutions, aqua ammonia, anhydrous ammonia, ammonium thiosulfate, sulfur-coated urea, urea-formaldehydes, IBDU, polymer-coated urea, calcium nitrate, ureaform, or methylene urea, phosphorous fertilizers such as diammonium phosphate, monoammonium phosphate, ammonium polyphosphate, concentrated superphosphate and triple superphosphate, or potassium fertilizers such as potassium chloride, potassium sulfate, potassium-magnesium sulfate, potassium nitrate. Such compositions can exist as free salts or ions within the composition. Fertilizers may be designated by the content of one or more of its components, such as nitrogen, phosphorous, or potassium. The content of these elements in a fertilizer may be indicated by the N—P—K value (where N=nitrogen content by weight percentage, P=phosphorous content by weight percentage, and K=potassium content by weight percentage).

Inorganic fertilizers, on the other hand, are manufactured from non-living materials and include, for example, ammonium nitrate, ammonium sulfate, urea, potassium chloride, potash, ammonium phosphate, anhydrous ammonia, and other phosphate salts. Inorganic fertilizers are readily commercially available and contain nutrients in soluble form that are immediately available to the plant. Inorganic fertilizers are generally inexpensive, having a low unit cost for the desired element. One skilled in the art will appreciate that the exact amount of a given element in a fertilizing agent may be calculated and administered to the plant or soil.

Fertilizers may be further classified as either organic fertilizers or inorganic fertilizers. Organic fertilizers include fertilizers having a molecular skeleton with a carbon backbone, such as in compositions derived from living matter. Organic fertilizers are made from materials derived from living things. Animal manures, compost, bonemeal, feather meal, and blood meal are examples of common organic fertilizers. Organic fertilizers, on the other hand, are typically not immediately available to plants and require soil microorganisms to break the fertilizer components down into simpler structures prior to use by the plants. In addition, organic fertilizers may not only elicit a plant growth response as observed with common inorganic fertilizers, but natural organic fertilizers may also stimulate soil microbial population growth and activities. Increased soil microbial population (e.g., plant symbionts) may have significant beneficial effects on the physical and chemical properties of the soil, as well as increasing disease and pest resistance.

In one aspect, a PMP composition including a plant nutrient as described herein can be contacted with the plant in an amount and for a time sufficient to: (a) reach a target level (e.g., a predetermined or threshold level) of plant nutrient concentration inside or on the plant, and (b) increase the fitness of the plant relative to an untreated plant.

In another aspect, a PMP composition including a plant nutrient as described herein can be contacted with the plant symbiont in an amount and for a time sufficient to: (a) reach a target level (e.g., a predetermined or threshold level) of plant nutrient concentration inside or on the plant symbiont (e.g., a bacteria or fungal endosymbiont), and (b) increase the fitness of the plant symbiont relative to an untreated plant symbiont.

The heterologous fertilizing agent may include a plant growth regulator. Exemplary plant growth regulators include auxins, cytokinins, gibberellins, and abscisic acid. In some instances, the plant growth regulator is abscisic cacid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole. Other plant growth regulators that can be incorporated seed coating compositions are described in US 2012/0108431, which is incorporated by reference in its entirety.

x. Plant-Modifying Agents

The PMP compositions described herein include one or more heterologous plant-modifying agents. For example, the PMPs may encapsulate the heterologous plant-modifying agent. Alternatively or additionally, the heterologous plant-modifying agent can be embedded on or conjugated to the surface of the PMP.

In some instances, the plant-modifying agent can include a peptide or a nucleic acid. The plant-modifying agent may be an agent that increases the fitness of a variety of plants or can be one that targets one or more specific plants (e.g., a specific species or genera of plants). Additionally, in some instances, the PMP compositions include two or more (e.g., 2, 3, 4, 5, 6, 7, 8, 9, 10, or more than 10) different plant-modifying agents.

Further, in some instances, the heterologous plant-modifying agent (e.g., an agent including a nucleic acid molecule or peptide) can be modified. For example, the modification can be a chemical modification, e.g., conjugation to a marker, e.g., fluorescent marker or a radioactive marker. In other examples, the modification can include conjugation or operational linkage to a moiety that enhances the stability, delivery, targeting, bioavailability, or half-life of the agent, e.g., a lipid, a glycan, a polymer (e.g., PEG), a cation moiety.

Examples of heterologous plant-modifying agents (e.g., peptides or nucleic acids) that can be used in the presently disclosed PMP compositions and methods are outlined below.

B. Polypeptides

The PMP composition (e.g., PMPs) described herein may include a heterologous polypeptide. In some instances, the PMP composition described herein includes a polypeptide or functional fragments or derivative thereof that modifies a plant (e.g., e.g., increases the fitness of the plant). For example, the polypeptide can increase the fitness of a plant. A PMP composition including a polypeptide as described herein can be contacted with a plant in an amount and for a time sufficient to: (a) reach a target level (e.g., a predetermined or threshold level) of polypeptide concentration; and (b) modify the plant (e.g., increase the fitness of the plant).

Examples of polypeptides that can be used herein can include an enzyme (e.g., a metabolic recombinase, a helicase, an integrase, a RNAse, a DNAse, or an ubiquitination protein), a pore-forming protein, a signaling ligand, a cell penetrating peptide, a transcription factor, a receptor, an antibody, a nanobody, a gene editing protein (e.g., CRISPR-Cas system, TALEN, or zinc finger), riboprotein, a protein aptamer, or a chaperone.

Polypeptides included herein may include naturally occurring polypeptides or recombinantly produced variants. In some instances, the polypeptide may be a functional fragments or variants thereof (e.g., an enzymatically active fragment or variant thereof). For example, the polypeptide may be a functionally active variant of any of the polypeptides described herein with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a polypeptide described herein or a naturally occurring polypeptide. In some instances, the polypeptide may have at least 50% (e.g., at least 50%, 60%, 70%, 80%, 90%, 95%, 97%, 99%, or greater) identity to a protein of interest.

The polypeptides described herein may be formulated in a composition for any of the uses described herein. The compositions disclosed herein may include any number or type (e.g., classes) of polypeptides, such as at least about any one of 1 polypeptide, 2, 3, 4, 5, 10, 15, 20, or more polypeptides. A suitable concentration of each polypeptide in the composition depends on factors such as efficacy, stability of the polypeptide, number of distinct polypeptides in the composition, the formulation, and methods of application of the composition. In some instances, each polypeptide in a liquid composition is from about 0.1 ng/mL to about 100 mg/mL. In some instances, each polypeptide in a solid composition is from about 0.1 ng/g to about 100 mg/g.

Methods of making a polypeptide are routine in the art. See, in general, Smales & James (Eds.), Therapeutic Proteins: Methods and Protocols (Methods in Molecular Biology), Humana Press (2005); and Crommelin, Sindelar & Meibohm (Eds.), Pharmaceutical Biotechnology: Fundamentals and Applications, Springer (2013).

Methods for producing a polypeptide involve expression in plant cells, although recombinant proteins can also be produced using insect cells, yeast, bacteria, mammalian cells, or other cells under the control of appropriate promoters. Mammalian expression vectors may comprise nontranscribed elements such as an origin of replication, a suitable promoter and enhancer, and other 5' or 3' flanking nontranscribed sequences, and 5' or 3' nontranslated sequences such as necessary ribosome binding sites, a polyadenylation site, splice donor and acceptor sites, and termination sequences. DNA sequences derived from the SV40 viral genome, for example, SV40 origin, early promoter, enhancer, splice, and polyadenylation sites may be used to provide the other genetic elements required for expression of a heterologous DNA sequence. Appropriate cloning and expression vectors for use with bacterial, fungal, yeast, and mammalian cellular hosts are described in Green & Sambrook, Molecular Cloning: A Laboratory Manual (Fourth Edition), Cold Spring Harbor Laboratory Press (2012).

Various mammalian cell culture systems can be employed to express and manufacture a recombinant polypeptide agent. Examples of mammalian expression systems include CHO cells, COS cells, HeLA and BHK cell lines. Processes of host cell culture for production of protein therapeutics are described in, e.g., Zhou and Kantardjieff (Eds.), Mammalian Cell Cultures for Biologics Manufacturing (Advances in Biochemical Engineering/Biotechnology), Springer (2014). Purification of proteins is described in Franks, Protein Biotechnology: Isolation, Characterization, and Stabilization, Humana Press (2013); and in Cutler, Protein Purification Protocols (Methods in Molecular Biology), Humana Press (2010). Formulation of protein therapeutics is described in Meyer (Ed.), Therapeutic Protein Drug Products: Practical Approaches to formulation in the Laboratory, Manufacturing, and the Clinic, Woodhead Publishing Series (2012).

In some instances, the PMP composition includes an antibody or antigen binding fragment thereof. For example, an agent described herein may be an antibody that blocks or potentiates activity and/or function of a component of the plant. The antibody may act as an antagonist or agonist of a polypeptide (e.g., enzyme or cell receptor) in the plant. The making and use of antibodies against a target antigen is known in the art. See, for example, Zhiqiang An (Ed.), Therapeutic Monoclonal Antibodies: From Bench to Clinic, 1st Edition, Wiley, 2009 and also Greenfield (Ed.), Antibodies: A Laboratory Manual, 2nd Edition, Cold Spring Harbor Laboratory Press, 2013, for methods of making recombinant antibodies, including antibody engineering, use of degenerate oligonucleotides, 5'-RACE, phage display, and mutagenesis; antibody testing and characterization; antibody pharmacokinetics and pharmacodynamics; antibody purification and storage; and screening and labeling techniques.

C. Nucleic Acids

In some instances, the PMPs described herein include a heterologous nucleic acid (heterologous polynucleotide). Numerous nucleic acids are useful in the PMP compositions and methods described herein. The PMPs disclosed herein may include any number or type (e.g., classes) of heterologous nucleic acids (e.g., DNA molecule (e.g., plasmid) or RNA molecule, e.g., mRNA, guide RNA (gRNA), or inhibitory RNA molecule or precursor thereof (e.g., siRNA, shRNA, or miRNA or a precursor of any of these), or a hybrid DNA-RNA molecule), such as at least about 1 class or variant of a nucleic acid, or 2, 3, 4, 5, 10, 15, 20, or more classes or variants of nucleic acids. A suitable concentration of each nucleic acid in the composition depends on factors such as efficacy, stability of the nucleic acid, number of distinct nucleic acids, the formulation, and methods of application of the composition. Examples of nucleic acids useful herein include a DNA molecule (e.g., a plasmid), an mRNA, an siRNA, a Dicer substrate small interfering RNA (dsiRNA), an antisense RNA, a short interfering RNA (siRNA) or siRNA precursor (e.g., one or more strands of RNA that hybridize inter- or intra-molecularly to form at least partially double-stranded RNA having at least about 20 contiguous base-pairs), a short hairpin (shRNA), a microRNA (miRNA) or miRNA precursor, an asymmetric interfering RNA (aiRNA), a peptide nucleic acid (PNA), a morpholino, a locked nucleic acid (LNA), a piwi-interacting RNA (piRNA), a ribozyme, a deoxyribozymes (DNAzyme), an aptamer (DNA, RNA), a circular RNA (circRNA), a guide RNA (gRNA), or a DNA molecule encoding any of these RNAs.

A PMP composition including a nucleic acid as described herein can be contacted with a plant in an amount and for a time sufficient to: (a) reach a target level (e.g., a predetermined or threshold level) of nucleic acid concentration; and (b) modify the plant (e.g., increase the fitness of the plant).

(a) Nucleic Acids Encoding Peptides

In some instances, the PMPs include a heterologous nucleic acid encoding a polypeptide. Nucleic acids encoding a polypeptide may have a length from about 10 to about 50,000 nucleotides (nts), about 25 to about 100 nts, about 50 to about 150 nts, about 100 to about 200 nts, about 150 to about 250 nts, about 200 to about 300 nts, about 250 to about 350 nts, about 300 to about 500 nts, about 10 to about 1000 nts, about 50 to about 1000 nts, about 100 to about 1000 nts, about 1000 to about 2000 nts, about 2000 to about 3000 nts, about 3000 to about 4000 nts, about 4000 to about 5000 nts, about 5000 to about 6000 nts, about 6000 to about 7000 nts, about 7000 to about 8000 nts, about 8000 to about 9000 nts, about 9000 to about 10,000 nts, about 10,000 to about 15,000 nts, about 10,000 to about 20,000 nts, about 10,000 to about 25,000 nts, about 10,000 to about 30,000 nts, about 10,000 to about 40,000 nts, about 10,000 to about 45,000 nts, about 10,000 to about 50,000 nts, or any range therebetween.

The PMP composition may also include active variants of a nucleic acid sequence of interest. In some instances, the variant of the nucleic acids has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a nucleic acid of interest. In some instances, the invention includes an active polypeptide encoded by a nucleic acid variant as described herein. In some instances, the active polypeptide encoded by the nucleic acid variant has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire amino acid sequence, to a sequence of a polypeptide of interest or the naturally derived polypeptide sequence.

Certain methods for expressing a nucleic acid encoding a protein may involve expression in cells, including insect, yeast, plant, bacteria, or other cells under the control of appropriate promoters. Expression vectors may include non-transcribed elements, such as an origin of replication, a suitable promoter and enhancer, and other 5' or 3' flanking nontranscribed sequences, and 5' or 3' nontranslated sequences such as necessary ribosome binding sites, a polyadenylation site, splice donor and acceptor sites, and termination sequences. DNA sequences derived from the SV40 viral genome, for example, SV40 origin, early promoter, enhancer, splice, and polyadenylation sites may be used to provide the other genetic elements required for expression of a heterologous DNA sequence. Appropriate cloning and expression vectors for use with bacterial, fungal, yeast, and mammalian cellular hosts are described in Green et al., Molecular Cloning: A Laboratory Manual, Fourth Edition, Cold Spring Harbor Laboratory Press, 2012.

Genetic modification using recombinant methods is generally known in the art. A nucleic acid sequence coding for a desired gene can be obtained using recombinant methods known in the art, such as, for example by screening libraries from cells expressing the gene, by deriving the gene from a vector known to include the same, or by isolating directly from cells and tissues containing the same, using standard techniques. Alternatively, a gene of interest can be produced synthetically, rather than cloned.

Expression of natural or synthetic nucleic acids is typically achieved by operably linking a nucleic acid encoding the gene of interest to a promoter, and incorporating the construct into an expression vector. Expression vectors can be suitable for replication and expression in bacteria. Expression vectors can also be suitable for replication and integration in eukaryotes. Typical cloning vectors contain transcription and translation terminators, initiation sequences, and promoters useful for expression of the desired nucleic acid sequence.

Additional promoter elements, e.g., enhancers, regulate the frequency of transcriptional initiation. Typically, these are located in the region 30-110 basepairs (bp) upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter.

Alternatively, the promoter may be an inducible promoter. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

The expression vector to be introduced can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes may be used for identifying potentially transformed cells and for evaluating the functionality of regulatory sequences. In general, a reporter gene is a gene that is not present in or expressed by the recipient source and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., FEBS Letters 479:79-82, 2000). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some instances, an organism may be genetically modified to alter expression of one or more proteins. Expression of the one or more proteins may be modified fora specific time, e.g., development or differentiation state of the organism. In one instances, the invention includes a composition to alter expression of one or more proteins, e.g., proteins that affect activity, structure, or function. Expression of the one or more proteins may be restricted to a specific location(s) or widespread throughout the organism.

(b) Synthetic mRNA

The PMP composition may include a synthetic mRNA molecule, e.g., a synthetic mRNA molecule encoding a polypeptide. The synthetic mRNA molecule can be modified, e.g., chemically. The mRNA molecule can be chemically synthesized or transcribed in vitro. The mRNA molecule can be disposed on a plasmid, e.g., a viral vector, bacterial vector, or eukaryotic expression vector. In some examples, the mRNA molecule can be delivered to cells by transfection, electroporation, or transduction (e.g., adenoviral or lentiviral transduction).

In some instances, the modified RNA agent of interest described herein has modified nucleosides or nucleotides. Such modifications are known and are described, e.g., in WO 2012/019168. Additional modifications are described, e.g., in WO 2015/038892; WO 2015/038892; WO 2015/089511; WO 2015/196130; WO 2015/196118 and WO 2015/196128 A2.

In some instances, the modified RNA encoding a polypeptide of interest has one or more terminal modification, e.g., a 5' cap structure and/or a poly-A tail (e.g., of between 100-200 nucleotides in length). The 5' cap structure may be selected from the group consisting of CapO, CapI, ARCA, inosine, NI-methyl-guanosine, 2'fluoro-guanosine, 7-deaza-guanosine, 8-oxo-guanosine, 2-amino-guanosine, LNA-guanosine, and 2-azido-guanosine. In some cases, the modified RNAs also contain a 5' UTR including at least one Kozak sequence, and a 3 UTR. Such modifications are known and are described, e.g., in WO 2012/135805 and WO 2013/052523. Additional terminal modifications are described, e.g., in WO 2014/164253 and WO 2016/011306, WO 2012/045075, and WO 2014/093924. Chimeric enzymes for synthesizing capped RNA molecules (e.g., modified mRNA) which may include at least one chemical modification are described in WO 2014/028429.

In some instances, a modified mRNA may be cyclized, or concatemerized, to generate a translation competent molecule to assist interactions between poly-A binding proteins and 5'-end binding proteins. The mechanism of cyclization or concatemerization may occur through at least 3 different routes: 1) chemical, 2) enzymatic, and 3) ribozyme catalyzed. The newly formed 5'-13'-linkage may be intramolecular or intermolecular. Such modifications are described, e.g., in WO 2013/151736.

Methods of making and purifying modified RNAs are known and disclosed in the art. For example, modified RNAs are made using only in vitro transcription (IVT) enzymatic synthesis. Methods of making IVT polynucleotides are known in the art and are described in WO 2013/151666, WO 2013/151668, WO 2013/151663, WO 2013/151669, WO 2013/151670, WO 2013/151664, WO 2013/151665, WO 2013/151671, WO 2013/151672, WO 2013/151667 and WO 2013/151736. Methods of purification include purifying an RNA transcript including a polyA tail by contacting the sample with a surface linked to a plurality of thymidines or derivatives thereof and/or a plurality of uracils or derivatives thereof (polyT/U) under conditions such that the RNA transcript binds to the surface and eluting the purified RNA transcript from the surface (WO 2014/152031); using ion (e.g., anion) exchange chromatography that allows for separation of longer RNAs up to 10,000 nucleotides in length via a scalable method (WO 2014/144767); and subjecting a modified mRNA sample to DNAse treatment (WO 2014/152030).

Formulations of modified RNAs are known and are described, e.g., in WO 2013/090648. For example, the formulation may be, but is not limited to, nanoparticles, poly(lactic-co-glycolic acid)(PLGA) microspheres, lipidoids, lipoplex, liposome, polymers, carbohydrates (including simple sugars), cationic lipids, fibrin gel, fibrin hydrogel, fibrin glue, fibrin sealant, fibrinogen, thrombin, rapidly eliminated lipid nanoparticles (reLNPs) and combinations thereof.

Modified RNAs encoding polypeptides in the fields of human disease, antibodies, viruses, and a variety of in vivo settings are known and are disclosed in for example, Table 6 of International Publication Nos. WO 2013/151666, WO 2013/151668, WO 2013/151663, WO 2013/151669, WO 2013/151670, WO 2013/151664, WO 2013/151665, WO 2013/151736; Tables 6 and 7 International Publication No. WO 2013/151672; Tables 6, 178 and 179 of International Publication No. WO 2013/151671; Tables 6, 185 and 186 of International Publication No WO 2013/151667. Any of the foregoing may be synthesized as an IVT polynucleotide, chimeric polynucleotide or a circular polynucleotide, and each may include one or more modified nucleotides or terminal modifications.

(c) Inhibitory RNA

In some instances, the PMP composition includes an inhibitory RNA molecule, e.g., that acts via the RNA interference (RNAi) pathway. In some instances, the inhibitory RNA molecule decreases the level of gene expression in a plant and/or decreases the level of a protein in the plant. In some instances, the inhibitory RNA molecule inhibits expression of a plant gene. For example, an inhibitory RNA molecule may include a short interfering RNA or its precursor, short hairpin RNA, and/or a microRNA or its precursor that targets a gene in the plant. Certain RNA molecules can inhibit gene expression through the biological process of RNA interference (RNAi). RNAi molecules include RNA or RNA-like structures typically containing 15-50 base pairs (such as about 18-25 base pairs) and having a nucleobase sequence identical (or complementary) or nearly identical (or substantially complementary) to a coding sequence in an expressed target gene within the cell. RNAi molecules include, but are not limited to: short interfering RNAs (siRNAs), double-strand RNAs (dsRNA), short hairpin RNAs (shRNA), meroduplexes, dicer substrates, and multivalent RNA interference (U.S. Pat. Nos. 8,084,599 8,349,809, 8,513,207 and 9,200,276). A shRNA is a RNA molecule including a hairpin turn that decreases expression of target genes via RNAi. shRNAs can be delivered to cells in the form of plasmids, e.g., viral or bacterial vectors, e.g., by transfection, electroporation, or transduction). A microRNA is a non-coding RNA molecule that typically has a length of about 21 or 22 nucleotides. MiRNAs bind to target sites on mRNA molecules and silence the mRNA, e.g., by causing cleavage of the mRNA, destabilization of the mRNA, or inhibition of translation of the mRNA. In some instances, the inhibitory RNA molecule decreases the level and/or activity of a negative regulator of function. In other instances, the inhibitor RNA molecule decreases the level and/or activity of an inhibitor of a positive regulator of function. The inhibitory RNA molecule can be chemically synthesized or transcribed in vitro.

In some instances, the nucleic acid is a DNA, a RNA, or a PNA. In some instances, the RNA is an inhibitory RNA. In some instances, the inhibitory RNA inhibits gene expression in a plant. In some instances, the nucleic acid is an mRNA, a modified mRNA, or a DNA molecule that, in the plant, increases expression of an enzyme (e.g., a metabolic recombinase, a helicase, an integrase, a RNAse, a DNAse, or an ubiquitination protein), a pore-forming protein, a signaling ligand, a cell penetrating peptide, a transcription factor, a receptor, an antibody, a nanobody, a gene editing protein (e.g., CRISPR-Cas system, TALEN, or zinc finger), riboprotein, a protein aptamer, or a chaperone. In some instances, the nucleic acid is an mRNA, a modified mRNA, or a DNA molecule that increases the expression of an enzyme (e.g., a metabolic enzyme, a recombinase enzyme, a helicase enzyme, an integrase enzyme, a RNAse enzyme, a DNAse enzyme, or an ubiquitination protein), a pore-forming protein, a signaling ligand, a cell penetrating peptide, a transcription factor, a receptor, an antibody, a nanobody, a gene editing protein (e.g., a CRISPR-Cas system, a TALEN, or a zinc finger), a riboprotein, a protein aptamer, or a chaperone. In some aspects, the nucleic acid encodes the enzyme, pore-forming protein, signaling ligand, cell penetrating peptide, transcription factor, receptor, antibody, nanobody, gene editing protein, riboprotein, protein aptamer, or chaperone. In some instances, the increase in expression in the plant is an increase in expression of about 5%, 10%, 15%, 20%, 30%, 40%, 50%, 60%, 70%, 80%, 90%, 100%, or more than 100% relative to a reference level (e.g., the expression in an untreated plant). In some instances, the increase in expression in the plant is an increase in expression of about 2× fold, about 4× fold, about 5× fold, about 10× fold, about 20× fold, about 25× fold, about 50× fold, about 75× fold, or about 100× fold or more, relative to a reference level (e.g., the expression in an untreated plant).

In some instances, the nucleic acid is an antisense RNA, a dsiRNA, a siRNA, a shRNA, a miRNA, an aiRNA, a PNA, a morpholino, a LNA, a piRNA, a ribozyme, a DNAzyme, an aptamer (DNA, RNA), a circRNA, a gRNA, or a DNA molecules (e.g., a plasmid) that acts to reduce, in the plant, expression of, e.g., an enzyme (a metabolic enzyme, a recombinase enzyme, a helicase enzyme, an integrase enzyme, a RNAse enzyme, a DNAse enzyme, a polymerase enzyme, a ubiquitination protein, a superoxide management enzyme, or an energy production enzyme), a transcription factor, a secretory protein, a structural factor (actin, kinesin, or tubulin), a riboprotein, a protein aptamer, a chaperone, a receptor, a signaling ligand, or a transporter. In some instances, the decrease in expression in the plant is a decrease in expression of about 5%, 10%, 15%, 20%, 30%, 40%, 50%, 60%, 70%, 80%, 90%, 100%, or more than 100% relative to a reference level (e.g., the expression in an untreated plant). In some instances, the decrease in expression in the plant is a decrease in expression of about 2× fold, about 4× fold, about 5× fold, about 10× fold, about 20× fold, about 25× fold, about 50× fold, about 75× fold, or about 100× fold or more, relative to a reference level (e.g., the expression in an untreated plant).

RNAi molecules include a sequence substantially complementary, or fully complementary, to all or a fragment of a target gene. RNAi molecules may complement sequences at the boundary between introns and exons to prevent the maturation of newly-generated nuclear RNA transcripts of specific genes into mRNA for transcription. RNAi molecules complementary to specific genes can hybridize with the mRNA for a target gene and prevent its translation. The antisense molecule can be DNA, RNA, or a derivative or hybrid thereof. Examples of such derivative molecules include, but are not limited to, peptide nucleic acid (PNA) and phosphorothioate-based molecules such as deoxyribonucleic guanidine (DNG) or ribonucleic guanidine (RNG).

RNAi molecules can be provided as ready-to-use RNA synthesized in vitro or as sense and antisense RNA sequences (or DNA encoding sense and antisense RNA sequences) transfected into cells which will yield RNAi molecules upon transcription. Hybridization of the RNA molecule with, e.g., the target mRNA results in degradation of the hybridized complex by RNAse H and/or inhibition of the formation of translation complexes. Both result in a failure to produce the product of the original gene.

The length of the RNAi molecule that hybridizes to the transcript of interest may be around 10 nucleotides, between about 15 or 30 nucleotides, or about 15, 16, 17, 18, 19, 20, 21, 22, 23, 24, 25, 26, 27, 28, 29, 30 or more nucleotides. In embodiments, the RNAi molecule hybridizes to the transcript of interest to form a perfectly or near-perfectly double-stranded region of at least about 17 base pairs; in embodiments the double-stranded region includes at least about 10 contiguous base pairs. The degree of identity of the antisense sequence to the targeted transcript may be at least 75%, at least 80%, at least 85%, at least 90%, or at least 95.

RNAi molecules may also include overhangs, i.e., typically unpaired, overhanging nucleotides which are not directly involved in the double helical structure normally formed by the core sequences of the herein defined pair of sense strand and antisense strand. RNAi molecules may contain 3' and/or 5' overhangs of about 1-5 bases independently on each of the sense strands and antisense strands. In some instances, both the sense strand and the antisense strand contain 3' and 5' overhangs. In some instances, one or more of the 3' overhang nucleotides of one strand base pairs with one or more 5' overhang nucleotides of the other strand. In other instances, the one or more of the 3' overhang nucleotides of one strand base do not pair with the one or more 5' overhang nucleotides of the other strand. The sense and antisense strands of an RNAi molecule may or may not contain the same number of nucleotide bases. The antisense and sense strands may form a duplex wherein the 5' end only has a blunt end, the 3' end only has a blunt end, both the 5' and 3' ends are blunt ended, or neither the 5' end nor the 3' end are blunt ended. In another instance, one or more of the nucleotides in the overhang contains a thiophosphate, phosphorothioate, deoxynucleotide inverted (3' to 3' linked) nucleotide or is a modified ribonucleotide or deoxynucleotide.

Small interfering RNA (siRNA) molecules include a nucleotide sequence that is identical to about 15 to about 25 contiguous nucleotides of the target mRNA. In some instances, the siRNA sequence commences with the dinucleotide AA, includes a GC-content of about 30-70% (about 30-60%, about 40-60%, or about 45%-55%), and does not have a high percentage identity to any nucleotide sequence other than the target in the genome in which it is to be introduced, for example as determined by standard BLAST search.

siRNAs and shRNAs resemble intermediates in the processing pathway of the endogenous microRNA (miRNA) genes (Bartel, Cell 116:281-297, 2004). In some instances, siRNAs can function as miRNAs and vice versa (Zeng et al., Mol. Cell 9:1327-1333, 2002; Doench et al., Genes Dev. 17:438-442, 2003). Exogenous siRNAs downregulate mRNAs with seed complementarity to the siRNA (Birmingham et al., Nat. Methods 3:199-204, 2006). Multiple target sites within a 3' UTR give stronger downregulation (Doench et al., Genes Dev. 17:438-442, 2003).

Known effective siRNA sequences and cognate binding sites are also well represented in the relevant literature. RNAi molecules are readily designed and produced by technologies known in the art. In addition, there are computational tools that increase the chance of finding effective and specific sequence motifs (Pei et al., Nat. Methods 3(9):670-676, 2006; Reynolds et al., Nat. Biotechnol. 22(3): 326-330, 2004; Khvorova et al., Nat. Struct. Biol. 10(9): 708-712, 2003; Schwarz et al., Cell 115(2):199-208, 2003; Ui-Tei et al., Nucleic Acids Res. 32(3):936-948, 2004; Heale et al., Nucleic Acids Res. 33(3):e30, 2005; Chalk et al., Biochem. Biophys. Res. Commun. 319(1):264-274, 2004; and Amarzguioui et al., Biochem. Biophys. Res. Commun. 316(4):1050-1058, 2004).

The RNAi molecule modulates expression of RNA encoded by a gene. Because multiple genes can share some degree of sequence homology with each other, in some instances, the RNAi molecule can be designed to target a class of genes with sufficient sequence homology. In some instances, the RNAi molecule can contain a sequence that has complementarity to sequences that are shared amongst different gene targets or are unique for a specific gene target. In some instances, the RNAi molecule can be designed to target conserved regions of an RNA sequence having homology between several genes thereby targeting several genes in a gene family (e.g., different gene isoforms, splice variants, mutant genes, etc.). In some instances, the RNAi molecule can be designed to target a sequence that is unique to a specific RNA sequence of a single gene.

An inhibitory RNA molecule can be modified, e.g., to contain modified nucleotides, e.g., 2'-fluoro, 2'-o-methyl, 2'-deoxy, unlocked nucleic acid, 2'-hydroxy, phosphorothioate, 2'-thiouridine, 4'-thiouridine, 2'-deoxyuridine. Without being bound by theory, it is believed that such modifications can increase nuclease resistance and/or serum stability, or decrease immunogenicity.

In some instances, the RNAi molecule or its precursor is linked to a delivery polymer via a physiologically labile bond or linker. The physiologically labile linker is selected such that it undergoes a chemical transformation (e.g., cleavage) when present in certain physiological conditions, (e.g., disulfide bond cleaved in the reducing environment of the cell cytoplasm). Release of the molecule from the polymer, by cleavage of the physiologically labile linkage, facilitates interaction of the molecule with the appropriate cellular components for activity.

The RNAi molecule-polymer conjugate may be formed by covalently linking the molecule to the polymer. The polymer is polymerized or modified such that it contains a reactive group A. The RNAi molecule is also polymerized or modified such that it contains a reactive group B. Reactive groups A and B are chosen such that they can be linked via a reversible covalent linkage using methods known in the art.

Conjugation of the RNAi molecule to the polymer can be performed in the presence of an excess of polymer. Because the RNAi molecule and the polymer may be of opposite charge during conjugation, the presence of excess polymer can reduce or eliminate aggregation of the conjugate. Alternatively, an excess of a carrier polymer, such as a polycation, can be used. The excess polymer can be removed from the conjugated polymer prior to administration of the conjugate. Alternatively, the excess polymer can be co-administered with the conjugate.

The making and use of inhibitory agents based on non-coding RNA such as ribozymes, RNAse P, siRNAs, and miRNAs are also known in the art, for example, as described in Sioud, RNA Therapeutics: Function, Design, and Delivery (Methods in Molecular Biology). Humana Press (2010).

(d) Gene Editing

The PMP compositions described herein may include a component of a gene editing system. For example, the agent may introduce an alteration (e.g., insertion, deletion (e.g., knockout), translocation, inversion, single point mutation, or other mutation) in a gene in the plant. Exemplary gene editing systems include the zinc finger nucleases (ZFNs), Transcription Activator-Like Effector-based Nucleases (TALEN), and the clustered regulatory interspaced short palindromic repeat (CRISPR) system. ZFNs, TALENs, and CRISPR-based methods are described, e.g., in Gaj et al., Trends Biotechnol. 31(7):397-405, 2013.

In a typical CRISPR/Cas system, an endonuclease is directed to a target nucleotide sequence (e.g., a site in the genome that is to be sequence-edited) by sequence-specific, non-coding guide RNAs that target single- or double-stranded DNA sequences. Three classes (I-III) of CRISPR systems have been identified. The class II CRISPR systems use a single Cas endonuclease (rather than multiple Cas proteins). One class II CRISPR system includes a type II Cas endonuclease such as Cas9, a CRISPR RNA (crRNA), and a trans-activating crRNA (tracrRNA). The crRNA contains a guide RNA, i.e., typically an about 20-nucleotide RNA sequence that corresponds to a target DNA sequence. The crRNA also contains a region that binds to the tracrRNA to form a partially double-stranded structure which is cleaved by RNase III, resulting in a crRNA/tracrRNA hybrid. The RNAs serve as guides to direct Cas proteins to silence specific DNA/RNA sequences, depending on the spacer sequence. See, e.g., Horvath et al., Science 327:167-170, 2010; Makarova et al., Biology Direct 1:7, 2006; Pennisi, Science 341:833-836, 2013. The target DNA sequence must generally be adjacent to a protospacer adjacent motif (PAM) that is specific for a given Cas endonuclease; however, PAM sequences appear throughout a given genome. CRISPR endonucleases identified from various prokaryotic species have unique PAM sequence requirements; examples of PAM sequences include 5'-NGG (SEQ ID NO: 1) (*Streptococcus pyogenes*), 5'-NNAGAA (SEQ ID NO: 2) (*Streptococcus thermophilus* CRISPR1), 5'-NGGNG (SEQ ID NO: 3) (*Streptococcus thermophilus* CRISPR3), and 5'-NNNGATT (SEQ ID NO: 4) (*Neisseria meningiditis*). Some endonucleases, e.g., Cas9 endonucleases, are associated with G-rich PAM sites, e.g., 5'-NGG (SEQ ID NO: 1), and perform blunt-end cleaving of the target DNA at a location 3 nucleotides upstream from (5' from) the PAM site. Another class II CRISPR system includes the type V endonuclease Cpf1, which is smaller than Cas9; examples include AsCpf1 (from *Acidaminococcus* sp.) and LbCpf1 (from Lachnospiraceae sp.). Cpf1-associated CRISPR arrays are processed into mature crRNAs without the requirement of a tracrRNA; in other words a Cpf1 system requires only the Cpf1 nuclease and a crRNA to cleave the target DNA sequence. Cpf1 endonucleases, are associated with T-rich PAM sites, e.g., 5'-TTN (SEQ ID NO: 5). Cpf1 can also recognize a 5'-CTA (SEQ ID NO: 6) PAM motif. Cpf1 cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) from the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e.g., Zetsche et al., Cell 163:759-771, 2015.

For the purposes of gene editing, CRISPR arrays can be designed to contain one or multiple guide RNA sequences corresponding to a desired target DNA sequence; see, for example, Cong et al., Science 339:819-823, 2013; Ran et al., Nature Protocols 8:2281-2308, 2013. At least about 16 or 17 nucleotides of gRNA sequence are required by Cas9 for DNA cleavage to occur; for Cpf1 at least about 16 nucleotides of gRNA sequence is needed to achieve detectable DNA cleavage. In practice, guide RNA sequences are generally designed to have a length of between 17-24 nucleotides (e.g., 19, 20, or 21 nucleotides) and complementarity to the targeted gene or nucleic acid sequence. Custom gRNA generators and algorithms are available commercially for use in the design of effective guide RNAs. Gene editing has also been achieved using a chimeric single guide RNA (sgRNA), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing). Chemically modified sgRNAs have also been demonstrated to be effective in genome editing; see, for example, Hendel et al., Nature Biotechnol. 985-991, 2015.

Whereas wild-type Cas9 generates double-strand breaks (DSBs) at specific DNA sequences targeted by a gRNA, a number of CRISPR endonucleases having modified functionalities are available, for example: a nickase version of Cas9 generates only a single-strand break; a catalytically inactive Cas9 (dCas9) does not cut the target DNA but interferes with transcription by steric hindrance. dCas9 can further be fused with an effector to repress (CRISPRi) or activate (CRISPRa) expression of a target gene. For example, Cas9 can be fused to a transcriptional repressor (e.g., a KRAB domain) or a transcriptional activator (e.g., a dCas9-VP64 fusion). A catalytically inactive Cas9 (dCas9) fused to FokI nuclease (dCas9-FokI) can be used to generate DSBs at target sequences homologous to two gRNAs. See, e.g., the numerous CRISPR/Cas9 plasmids disclosed in and publicly available from the Addgene repository (Addgene, 75 Sidney St., Suite 550A, Cambridge, MA 02139). A double nickase Cas9 that introduces two separate double-strand breaks, each directed by a separate guide RNA, is described as achieving more accurate genome editing by Ran et al., Cell 154:1380-1389, 2013.

CRISPR technology for editing the genes of eukaryotes is disclosed in US Patent Application Publications US 2016/0138008 A1 and US 2015/0344912 A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1.

In some instances, the desired genome modification involves homologous recombination, wherein one or more double-stranded DNA breaks in the target nucleotide sequence is generated by the RNA-guided nuclease and guide RNA(s), followed by repair of the break(s) using a homologous recombination mechanism (homology-directed repair). In such instances, a donor template that encodes the desired nucleotide sequence to be inserted or knocked-in at the double-stranded break is provided to the cell or subject; examples of suitable templates include single-stranded DNA templates and double-stranded DNA templates (e.g., linked to the polypeptide described herein). In general, a donor template encoding a nucleotide change over a region of less than about 50 nucleotides is provided in the form of single-stranded DNA; larger donor templates (e.g., more than 100 nucleotides) are often provided as double-stranded DNA plasmids. In some instances, the donor template is provided to the cell or subject in a quantity that is sufficient to achieve the desired homology-directed repair but that does not persist in the cell or subject after a given period of time (e.g., after one or more cell division cycles). In some instances, a donor template has a core nucleotide sequence that differs from the target nucleotide sequence (e.g., a homologous endogenous genomic region) by at least 1, at least 5, at least 10, at least 20, at least 30, at least 40, at least 50, or more nucleotides. This core sequence is flanked by homology arms or regions of high sequence identity with the targeted nucleotide sequence; in some instances, the regions of high identity include at least 10, at least 50, at least 100, at least 150, at least 200, at least 300, at least 400, at least 500, at least 600, at least 750, or at least 1000 nucleotides on each side of the core sequence. In some instances where the donor template is in the form of a single-stranded DNA, the core sequence is flanked by homology arms including at least 10, at least 20, at least 30, at least 40, at least 50, at least 60, at least 70, at least 80, or at least 100 nucleotides on each side of the core sequence. In instances, where the donor template is in the form of a double-stranded DNA, the core sequence is flanked by homology arms including at least 500, at least 600, at least 700, at least 800, at least 900, or at least 1000 nucleotides on each side of the core sequence. In one instance, two separate double-strand breaks are introduced into the cell or subject's target nucleotide sequence with a double nickase Cas9 (see Ran et al., Cell 154:1380-1389, 2013), followed by delivery of the donor template.

In some instances, the composition includes a gRNA and a targeted nuclease, e.g., a Cas9, e.g., a wild type Cas9, a nickase Cas9 (e.g., Cas9 D10A), a dead Cas9 (dCas9), eSpCas9, Cpf1, C2C1, or C2C3, or a nucleic acid encoding such a nuclease. The choice of nuclease and gRNA(s) is determined by whether the targeted mutation is a deletion, substitution, or addition of nucleotides, e.g., a deletion, substitution, or addition of nucleotides to a targeted sequence. Fusions of a catalytically inactive endonuclease e.g., a dead Cas9 (dCas9, e.g., D10A; H840A) tethered with all or a portion of (e.g., biologically active portion of) an (one or more) effector domain create chimeric proteins that can be linked to the polypeptide to guide the composition to specific DNA sites by one or more RNA sequences (sgRNA) to modulate activity and/or expression of one or more target nucleic acids sequences.

In instances, the agent includes a guide RNA (gRNA) for use in a CRISPR system for gene editing. In some instances, the agent includes a zinc finger nuclease (ZFN), or a mRNA encoding a ZFN, that targets (e.g., cleaves) a nucleic acid sequence (e.g., DNA sequence) of a gene in the plant. In some instances, the agent includes a TALEN, or an mRNA encoding a TALEN, that targets (e.g., cleaves) a nucleic acid sequence (e.g., DNA sequence) in a gene in the plant.

For example, the gRNA can be used in a CRISPR system to engineer an alteration in a gene in the plant. In other examples, the ZFN and/or TALEN can be used to engineer an alteration in a gene in the plant. Exemplary alterations include insertions, deletions (e.g., knockouts), translocations, inversions, single point mutations, or other mutations. The alteration can be introduced in the gene in a cell, e.g., in vitro, ex vivo, or in vivo. In some examples, the alteration increases the level and/or activity of a gene in the plant. In other examples, the alteration decreases the level and/or activity of (e.g., knocks down or knocks out) a gene in the plant. In yet another example, the alteration corrects a defect (e.g., a mutation causing a defect), in a gene in the plant.

In some instances, the CRISPR system is used to edit (e.g., to add or delete a base pair) a target gene in the plant. In other instances, the CRISPR system is used to introduce a premature stop codon, e.g., thereby decreasing the expression of a target gene. In yet other instances, the CRISPR system is used to turn off a target gene in a reversible manner, e.g., similarly to RNA interference. In some instances, the CRISPR system is used to direct Cas to a promoter of a gene, thereby blocking an RNA polymerase sterically.

In some instances, a CRISPR system can be generated to edit a gene in the plant, using technology described in, e.g., U.S. Publication No. 20140068797, Cong, Science 339: 819-823, 2013; Tsai, Nature Biotechnol. 32:6 569-576, 2014; U.S. Pat. Nos. 8,871,445; 8,865,406; 8,795,965; 8,771,945; and 8,697,359.

In some instances, the CRISPR interference (CRISPRi) technique can be used for transcriptional repression of specific genes in the plant. In CRISPRi, an engineered Cas9 protein (e.g., nuclease-null dCas9, or dCas9 fusion protein, e.g., dCas9-KRAB or dCas9-SID4X fusion) can pair with a sequence specific guide RNA (sgRNA). The Cas9-gRNA complex can block RNA polymerase, thereby interfering with transcription elongation. The complex can also block transcription initiation by interfering with transcription factor binding. The CRISPRi method is specific with minimal off-target effects and is multiplexable, e.g., can simultaneously repress more than one gene (e.g., using multiple gRNAs). Also, the CRISPRi method permits reversible gene repression.

In some instances, CRISPR-mediated gene activation (CRISPRa) can be used for transcriptional activation of a gene in the plant. In the CRISPRa technique, dCas9 fusion proteins recruit transcriptional activators. For example, dCas9 can be fused to polypeptides (e.g., activation domains) such as VP64 or the p65 activation domain (p65D) and used with sgRNA (e.g., a single sgRNA or multiple sgRNAs), to activate a gene or genes in the plant. Multiple activators can be recruited by using multiple sgRNAs—this can increase activation efficiency. A variety of activation domains and single or multiple activation domains can be used. In addition to engineering dCas9 to recruit activators, sgRNAs can also be engineered to recruit activators. For example, RNA aptamers can be incorporated into a sgRNA to recruit proteins (e.g., activation domains) such as VP64. In some examples, the synergistic activation mediator (SAM) system can be used for transcriptional activation. In SAM, MS2 aptamers are added to the sgRNA. MS2 recruits the MS2 coat protein (MCP) fused to p65AD and heat shock factor 1 (HSF1).

The CRISPRi and CRISPRa techniques are described in greater detail, e.g., in Dominguez et al., Nat. Rev. Mol. Cell Biol. 17:5-15, 2016, incorporated herein by reference. In addition, dCas9-mediated epigenetic modifications and simultaneous activation and repression using CRISPR systems, as described in Dominguez et al., can be used to modulate a gene in the plant.

D. Heterologous Therapeutic Agents

The PMPs manufactured herein can include a heterologous therapeutic agent (e.g., an agent that affects an animal (e.g., a mammal, e.g., a human), an animal pathogen, or a pathogen vector thereof, and can be loaded into a PMP), such as a therapeutic peptide, a therapeutic nucleic acid (e.g., a therapeutic RNA), a therapeutic small molecule, or a pathogen control agent (e.g., antifungal agent, an antibacterial agent, a virucidal agent, an anti-viral agent, an insecticidal agent, a nematicidal agent, an antiparasitic agent, or an insect repellent). PMPs loaded with such agents can be formulated with a pharmaceutically acceptable carrier for delivery to an animal, an animal pathogen, or a pathogen vector thereof.

i. Antibacterial Agents

The PMP compositions described herein can further include an antibacterial agent. For example, a PMP composition including an antibiotic as described herein can be administered to an animal in an amount and for a time sufficient to: reach a target level (e.g., a predetermined or threshold level) of antibiotic concentration inside or on the animal; and/or treat or prevent a bacterial infection in the animal. The antibacterials described herein may be formulated in a PMP composition for any of the methods described herein, and in certain instances, may be associated with the PMP thereof. In some instances, the PMP compositions includes two or more (e.g., 2, 3, 4, 5, 6, 7, 8, 9, 10, or more than 10) different antibacterial agents.

As used herein, the term "antibacterial agent" refers to a material that kills or inhibits the growth, proliferation, division, reproduction, or spread of bacteria, such as phytopathogenic bacteria, and includes bactericidal (e.g., disinfectant compounds, antiseptic compounds, or antibiotics) or bacteriostatic agents (e.g., compounds or antibiotics). Bactericidal antibiotics kill bacteria, while bacteriostatic antibiotics only slow their growth or reproduction.

Bactericides can include disinfectants, antiseptics, or antibiotics. The most used disinfectants can comprise: active chlorine (i.e., hypochlorites (e.g., sodium hypochlorite), chloramines, dichloroisocyanurate and trichloroisocyanurate, wet chlorine, chlorine dioxide etc.), active oxygen (peroxides, such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols are used), phenolic substances (such as phenol (also called carbolic acid), cresols (called Lysole in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants, such as some quaternary ammonium cations (such as benzalkonium chloride, cetyl trimethylammonium bromide or chloride, didecyldimethylammonium chloride, cetylpyridinium chloride, benzethonium chloride) and others, non-quaternary compounds, such as chlorhexidine, glucoprotamine, octenidine dihydrochloride etc.), strong oxidizers, such as ozone and permanganate solutions; heavy metals and their salts, such as colloidal silver, silver nitrate, mercury chloride, phenylmercury salts, copper sulfate, copper oxide-chloride, copper hydroxide, copper octanoate, copper oxychloride sulfate, copper sulfate, copper sulfate pentahydrate, etc. Heavy metals and their salts are the most toxic, and environment-hazardous bactericides and therefore, their use is strongly oppressed or canceled; further, also properly concentrated strong acids (phosphoric, nitric, sulfuric, amidosulfuric, toluenesulfonic acids) and alkalis (sodium, potassium, calcium hydroxides). As antiseptics (i.e., germicide agents that can be used on human or animal body, skin, mucoses, wounds and the like), few of the above mentioned disinfectants can be used, under proper conditions (mainly concentration, pH, temperature and toxicity toward man/animal). Among them, important are: properly diluted chlorine preparations (i.e., Daquin's solution, 0.5% sodium or potassium hypochlorite solution, pH-adjusted to pH 7-8, or 0.5-1% solution of sodium benzenesulfochloramide (chloramine B)), some iodine preparations, such as iodopovidone in various galenics (ointment, solutions, wound plasters), in the past also Lugol's solution, peroxides as urea perhydrate solutions and pH-buffered 0.1-0.25% peracetic acid solutions, alcohols with or without antiseptic additives, used mainly for skin antisepsis, weak organic acids such as sorbic acid, benzoic acid, lactic acid and salicylic acid some phenolic compounds, such as hexachlorophene, triclosan and Dibromol, and cation-active compounds, such as 0.05-0.5% benzalkonium, 0.5-4% chlorhexidine, 0.1-2% octenidine solutions.

The PMP composition described herein may include an antibiotic. Any antibiotic known in the art may be used. Antibiotics are commonly classified based on their mechanism of action, chemical structure, or spectrum of activity.

The antibiotic described herein may target any bacterial function or growth processes and may be either bacteriostatic (e.g., slow or prevent bacterial growth) or bactericidal (e.g., kill bacteria). In some instances, the antibiotic is a bactericidal antibiotic. In some instances, the bactericidal antibiotic is one that targets the bacterial cell wall (e.g., penicillins and cephalosporins); one that targets the cell membrane (e.g., polymyxins); or one that inhibits essential bacterial enzymes (e.g., rifamycins, lipiarmycins, quinolones, and sulfonamides). In some instances, the bactericidal antibiotic is an aminoglycoside (e.g., kasugamycin). In some instances, the antibiotic is a bacteriostatic antibiotic. In some instances the bacteriostatic antibiotic targets protein synthesis (e.g., macrolides, lincosamides, and tetracyclines). Additional classes of antibiotics that may be used herein include cyclic lipopeptides (such as daptomycin), glycylcyclines (such as tigecycline), oxazolidinones (such as linezolid), or lipiarmycins (such as fidaxomicin). Examples of antibiotics include rifampicin, ciprofloxacin, doxycycline, ampicillin, and polymyxin B. The antibiotic described herein may have any level of target specificity (e.g., narrow- or broad-spectrum). In some instances, the antibiotic is a narrow-spectrum antibiotic, and thus targets specific types of bacteria, such as gram-negative or gram-positive bacteria. Alternatively, the antibiotic may be a broad-spectrum antibiotic that targets a wide range of bacteria.

Examples of antibacterial agents suitable for the treatment of animals include Penicillins (Amoxicillin, Ampicillin, Bacampicillin, Carbenicillin, Cloxacillin, Dicloxacillin, Flucloxacillin, Mezlocillin, Nafcillin, Oxacillin, Penicillin G, Crysticillin 300 A.S., Pentids, Permapen, Pfizerpen, Pfizerpen-AS, Wycillin, Penicillin V, Piperacillin, Pivampicillin, Pivmecillinam, Ticarcillin), Cephalosporins (Cefacetrile (cephacetrile), Cefadroxil (cefadroxyl), Cefalexin (cephalexin), Cefaloglycin (cephaloglycin), Cefalonium (cephalonium), Cefaloridine (cephaloradine), Cefalotin (cephalothin), Cefapirin (cephapirin), Cefatrizine, Cefazaflur, Cefazedone, Cefazolin (cephazolin), Cefradine (cephradine), Cefroxadine, Ceftezole, Cefaclor, Cefamandole, Cefmetazole, Cefonicid, Cefotetan, Cefoxitin, Cefprozil (cefproxil), Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Ceftobiprole, Ceftaroline, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Cefuracetime, Ceftioxide, Combinations, Ceftazidime/Avibactam, Ceftolozane/Tazobactam), Monobactams (Aztreonam), Carbapenems (Imipenem, Imipenem/cilastatin, Doripenem, Ertapenem, Meropenem, Meropenem/vaborbactam), Macrolide (Azithromycin, Erythromycin, Clarithromycin, Dirithromycin, Roxithromycin, Telithromycin), Lincosamides (Clindamycin, Lincomycin), Streptogramins (Pristinamycin, Quinupristin/dalfopristin), Aminoglycoside (Amikacin, Gentamicin, Kanamycin, Neomycin, Netilmicin, Paromomycin, Streptomycin, Tobramycin), Quinolone (Flumequine, Nalidixic acid, Oxolinic acid, Piromidic acid, Pipemidic acid, Rosoxacin, Second Generation, Ciprofloxacin, Enoxacin, Lomefloxacin, Nadifloxacin, Norfloxacin, Ofloxacin, Pefloxacin, Rufloxacin, Balofloxacin, Gatifloxacin, Grepafloxacin, Levofloxacin, Moxifloxacin, Pazufloxacin, Sparfloxacin, Temafloxacin, Tosufloxacin, Besifloxacin, Delafloxacin, Clinafloxacin, Gemifloxacin, Prulifloxacin, Sitafloxacin, Trovafloxacin), Sulfonamides (Sulfamethizole, Sulfamethoxazole, Sulfisoxazole, Trimethoprim-Sulfamethoxazole), Tetracycline (Demeclocycline, Doxycycline, Minocycline, Oxytetracycline, Tetracycline, Tigecycline), Other (Lipopeptides, Fluoroquinolone, Lipoglycopeptides, Cephalosporin, Macrocyclics, Chloramphenicol, Metronidazole, Tinidazole, Nitrofurantoin, Glycopeptides, Vancomycin, Teicoplanin, Lipoglycopeptides, Telavancin, Oxazolidinones, Linezolid, Cycloserine 2, Rifamycins, Rifampin, Rifabutin, Rifapentine, Rifalazil, Polypeptides, Bacitracin, Polymyxin B, Tuberactinomycins, Viomycin, Capreomycin).

One skilled in the art will appreciate that a suitable concentration of each antibiotic in the composition depends on factors such as efficacy, stability of the antibiotic, number of distinct antibiotics, the formulation, and methods of application of the composition.

ii. Antifungal Agents

The PMP compositions described herein can further include an antifungal agent. For example, a PMP composition including an antifungal as described herein can be administered to an animal in an amount and for a time sufficient to reach a target level (e.g., a predetermined or threshold level) of antifungal concentration inside or on the animal; and/or treat or prevent a fungal infection in the animal. The antifungals described herein may be formulated in a PMP composition for any of the methods described herein, and in certain instances, may be associated with the PMP thereof. In some instances, the PMP compositions includes two or more (e.g., 2, 3, 4, 5, 6, 7, 8, 9, 10, or more than 10) different antifungal agents.

As used herein, the term "fungicide" or "antifungal agent" refers to a substance that kills or inhibits the growth, proliferation, division, reproduction, or spread of fungi, such as fungi that are pathogenic to animals. Many different types of antifungal agent have been produced commercially. Non limiting examples of antifungal agents include: Allylamines (Amorolfin, Butenafine, Naftifine, Terbinafine), Imidazoles ((Bifonazole, Butoconazole, Clotrimazole, Econazole, Fenticonazole, Ketoconazole, Isoconazole, Luliconazole, Miconazole, Omoconazole, Oxiconazole, Sertaconazole, Sulconazole, Tioconazole, Terconazole); Triazoles (Albaconazole, Efinaconazole, Fluconazole, Isavuconazole, Itraconazole, Posaconazole, Ravuconazole, Terconazole, Voriconazole), Thiazoles (Abafungin), Polyenes (Amphotericin B, Nystatin, Natamycin, Trichomycin), Echinocandins (Anidulafungin, Caspofungin, Micafungin), Other (Tolnaftate, Flucytosine, Butenafine, Griseofulvin, Ciclopirox, Selenium sulfide, Tavaborole). One skilled in the art will appreciate that a suitable concentration of each antifungal in the composition depends on factors such as efficacy, stability of the antifungal, number of distinct antifungals, the formulation, and methods of application of the composition.

iii. Insecticides

The PMP compositions described herein can further include an insecticide. For example, the insecticide can decrease the fitness of (e.g., decrease growth or kill) an insect vector of an animal pathogen. A PMP composition including an insecticide as described herein can be contacted with an insect, in an amount and for a time sufficient to: (a) reach a target level (e.g., a predetermined or threshold level) of insecticide concentration inside or on the insect; and (b) decrease fitness of the insect. In some instances, the insecticide can decrease the fitness of (e.g., decrease growth or kill) a parasitic insect. A PMP composition including an insecticide as described herein can be contacted with a parasitic insect, or an animal infected therewith, in an amount and for a time sufficient to: (a) reach a target level (e.g., a predetermined or threshold level) of insecticide concentration inside or on the parasitic insect; and (b) decrease the fitness of the parasitic insect. The insecticides described herein may be formulated in a PMP composition for any of the methods described herein, and in certain instances, may be associated with the PMP thereof. In some instances, the PMP compositions include two or more (e.g., 2, 3, 4, 5, 6, 7, 8, 9, 10, or more than 10) different insecticide agents.

As used herein, the term "insecticide" or "insecticidal agent" refers to a substance that kills or inhibits the growth, proliferation, reproduction, or spread of insects, such as insect vectors of animal pathogens or parasitic insects. Non limiting examples of insecticides are shown in Table 4. Additional non-limiting examples of suitable insecticides include biologics, hormones or pheromones such as azadirachtin, *Bacillus* species (e.g., *Bacillus thuringiensis*), *Beauveria* species, codlemone, *Metarrhizium* species, *Paecilomyces* species, *Saccharopolyspora* species, and *Verticillium* species, and active compounds having unknown or non-specified mechanisms of action such as fumigants (such as aluminium phosphide, methyl bromide and sulphuryl fluoride) and selective feeding inhibitors (such as cryolite, flonicamid and pymetrozine). One skilled in the art will appreciate that a suitable concentration of each insecticide in the composition depends on factors such as efficacy, stability of the insecticide, number of distinct insecticides, the formulation, and methods of application of the composition.

TABLE 4

Examples of insecticides

| Class | Compounds |
|---|---|
| chloronicotinyls/ neonicotinoids | acetamiprid, clothianidin, dinotefuran, imidacloprid, nitenpyram, nithiazine, thiacloprid, thiamethoxam, imidaclothiz, (2E)-1-[(2-chloro-1,3-thiazol-5-yl)methyl]-3,5-dimethyl-N-nitro-1,3,5-tri-azinan-2-imine, acetylcholinesterase (AChE) inhibitors (such as carbamates and organophosphates) |
| carbamates | alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, chloethocarb, dimetilan, ethiofencarb, fenobucarb, fenothiocarb, formetanate, furathiocarb, isoprocarb, metam-sodium, methiocarb, methomyl, metolcarb, oxamyl, phosphocarb, pirimicarb, promecarb, propoxur, thiodicarb, thiofanox, triazamate, trimethacarb, XMC, xylylcarb |
| organophosphates | acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, |

TABLE 4-continued

Examples of insecticides

| Class | Compounds |
|---|---|
|  | fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion |
| pyrethroids | acrinathrin, allethrin (d-cis-trans, d-trans), cypermethrin (alpha-, beta-, theta-, zeta-), permethrin (cis-, trans-), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda, cyhalothrin, metofluthrin, phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralocythrin, tralomethrin, transfluthrin, ZXI 8901, pyrethrins (pyrethrum) |
| oxadiazines | indoxacarb, acetylcholine receptor modulators (such as spinosyns) |
| spinosyns | spinosad |
| cyclodiene | camphechlor, chlordane, endosulfan, gamma-HCH, HCH, heptachlor, |
| organochlorines | lindane, methoxychlor |
| fiproles | acetoprole, ethiprole, vaniliprole, fipronil |
| mectins | abamectin, avermectin, emamectin, emamectin-benzoate, fenoxycarb, hydroprene, kinoprene, methoprene, ivermectin, lepimectin, epofenonane, pyriproxifen, milbemectin, milbemycin, triprene |
| diacylhydrazines | chromafenozide, halofenozide, methoxyfenozide, tebufenozide |
| benzoylureas | bistrifluoron, chlorfluazuron, diflubenzuron, fluazuron, flucycloxuron, flufenoxuron, hexaflumuron, lufenuron, novaluron, noviflumuron, penfluoron, teflubenzuron, triflumuron |
| organotins | azocyclotin, cyhexatin, fenbutatin oxide |
| pyrroles | chlorfenapyr |
| dinitrophenols | binapacyrl, dinobuton, dinocap, DNOC |
| METIs | fenazaquin, fenpyroximate, pyrimidifen, pyridaben, tebufenpyrad, tolfenpyrad, rotenone, acequinocyl, fluacrypyrim, microbial disrupters of the intestinal membrane of insects (such as *Bacillus thuringiensis* strains), inhibitors of lipid synthesis (such as tetronic acids and tetramic acids) |
| tetronic acids | spirodiclofen, spiromesifen, spirotetramat |
| tetramic acids | cis-3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester; CAS Reg. No.: 382608-10-8), carboxamides (such as flonicamid), octopaminergic agonists (such as amitraz), inhibitors of the magnesium-stimulated ATPase (such as propargite), ryanodin receptor agonists (such as phthalamides or rynaxapyr) |
| phthalamides | N2-[1,1-dimethyl-2-(methylsulphonyl)ethyl]-3-iodo-N1-[2-methyl--4-[1,2,2,2-tetrafluoro-1-(trifluoromethyl)ethyl]phenyl]-1,2-benzenedi-carboxamide (i.e., flubendiamide; CAS reg. No.: 272451-65-7) | iv. Nematicides

The PMP compositions described herein can further include a nematicide. In some instances, the PMP composition includes two or more (e.g., 2, 3, 4, 5, 6, 7, 8, 9, 10, or more than 10) different nematicides. For example, the nematicide can decrease the fitness of (e.g., decrease growth or kill) a parasitic nematode. A PMP composition including a nematicide as described herein can be contacted with a parasitic nematode, or an animal infected therewith, in an amount and for a time sufficient to: (a) reach a target level (e.g., a predetermined or threshold level) of nematicide concentration inside or on the target nematode; and (b) decrease fitness of the parasitic nematode. The nematicides described herein may be formulated in a PMP composition for any of the methods described herein, and in certain instances, may be associated with the PMP thereof.

As used herein, the term "nematicide" or "nematicidal agent" refers to a substance that kills or inhibits the growth, proliferation, reproduction, or spread of nematodes, such as a parasitic nematode. Non limiting examples of nematicides are shown in Table 5. One skilled in the art will appreciate that a suitable concentration of each nematicide in the composition depends on factors such as efficacy, stability of the nematicide, number of distinct nematicides, the formulation, and methods of application of the composition.

TABLE 5

Examples of Nematicides

| | |
|---|---|
| FUMIGANTS | D-D, 1,3-Dichloropropene, Ethylene Dibromide, 1,2-Dibromo-3-Chloropropane, Methyl Bromide, Chloropicrin, Metam Sodium, Dazomet, Methyl Isothiocyanate (MITC), Sodium Tetrathiocarbonate, Chloropicrin, |
| CARBAMATES | Aldicarb, Aldoxycarb, Carbofuran, Oxamyl, Cleothocarb |
| ORGANOPHOSPHATES | Ethoprophos, Fenamiphos, Cadusafos, Fosthiazate, Fensulfothion, Thionazin, Isazofos, |
| BIOCHEMICALS | DITERA ®, CLANDOSAN ®, SINCOCIN ® | v. Antiparasitic Agent

The PMP compositions described herein can further include an antiparasitic agent. For example, the antiparasitic can decrease the fitness of (e.g., decrease growth or kill) a parasitic protozoan. A PMP composition including an antiparasitic as described herein can be contacted with a protozoan in an amount and for a time sufficient to: (a) reach a target level (e.g., a predetermined or threshold level) of antiparasitic concentration inside or on the protozoan, or animal infected therewith; and (b) decrease fitness of the protozoan. This can be useful in the treatment or prevention of parasites in animals. For example, a PMP composition including an antiparasitic agent as described herein can be administered to an animal in an amount and for a time sufficient to: reach a target level (e.g., a predetermined or threshold level) of antiparasitic concentration inside or on the animal; and/or treat or prevent a parasite (e.g., parasitic nematode, parasitic insect, or protozoan) infection in the animal. The antiparasitic described herein may be formulated in a PMP composition for any of the methods described herein, and in certain instances, may be associated with the PMP thereof. In some instances, the PMP composition includes two or more (e.g., 2, 3, 4, 5, 6, 7, 8, 9, 10, or more than 10) different antiparasitic agents.

As used herein, the term "antiparasitic" or "antiparasitic agent" refers to a substance that kills or inhibits the growth, proliferation, reproduction, or spread of parasites, such as parasitic protozoa, parasitic nematodes, or parasitic insects. Examples of antiparasitic agents include Antihelmintics (Bephenium, Diethylcarbamazine, Ivermectin, Niclosamide, Piperazine, Praziquantel, Pyrantel, Pyrvinium, Benzimidazoles, Albendazole, Flubendazole, Mebendazole, Thiabendazole, Levamisole, Nitazoxanide, Monopantel, Emodepside, Spiroindoles), Scabicides (Benzyl benzoate, Benzyl benzoate/disulfiram, Lindane, Malathion, Permethrin), Pediculicides (Piperonyl butoxide/pyrethrins, Spinosad, Moxidectin), Scabicides (Crotamiton), Anticestodes (Niclosamide, Pranziquantel, Albendazole), Antiamoebics (Rifampin, Apmphotericin B); or Antiprotozoals (Melarsoprol, Eflornithine, Metronidazole, Tinidazole, Miltefosine, Artemisinin). In certain instances, the antiparasitic agent may be use for treating or preventing infections in livestock animals, e.g., Levamisole, Fenbendazole, Oxfendazole, Albendazole, Moxidectin, Eprinomectin, Doramectin, Ivermectin, or Clorsulon. One skilled in the art will appreciate that a suitable concentration of each antiparasitic in the composition depends on factors such as efficacy, stability of the antiparasitic, number of distinct antiparasitics, the formulation, and methods of application of the composition.

vi. Antiviral Agent

The PMP compositions described herein can further include an antiviral agent. A PMP composition including an antiviral agent as described herein can be administered to an animal in an amount and for a time sufficient to reach a target level (e.g., a predetermined or threshold level) of antiviral concentration inside or on the animal; and/or to treat or prevent a viral infection in the animal. The antivirals described herein may be formulated in a PMP composition for any of the methods described herein, and in certain instances, may be associated with the PMP thereof. In some instances, the PMP composition includes two or more (e.g., 2, 3, 4, 5, 6, 7, 8, 9, 10, or more than 10) different antivirals.

As used herein, the term "antiviral" or "virucide" refers to a substance that kills or inhibits the growth, proliferation, reproduction, development, or spread of viruses, such as viral pathogens that infect animals. A number of agents can be employed as an antiviral, including chemicals or biological agents (e.g., nucleic acids, e.g., dsRNA). Examples of antiviral agents useful herein include Abacavir, Acyclovir (Aciclovir), Adefovir, Amantadine, Amprenavir (Agenerase), Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nitazoxanide, Nucleoside analogues, Norvir, Oseltamivir (Tamiflu), Peginterferon alfa-2a, Penciclovir, Peramivir, Pleconaril, Podophyllotoxin, Raltegravir, Ribavirin, Rimantadine, Ritonavir, Pyramidine, Saquinavir, Sofosbuvir, Stavudine, Synergistic enhancer (antiretroviral), Telaprevir, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), or Zidovudine. One skilled in the art will appreciate that a suitable concentration of each antiviral in the composition depends on factors such as efficacy, stability of the antivirals, number of distinct antivirals, the formulation, and methods of application of the composition.

vii. Repellents

The PMP compositions described herein can further include a repellent. For example, the repellent can repel a vector of animal pathogens, such as insects. The repellent described herein may be formulated in a PMP composition for any of the methods described herein, and in certain instances, may be associated with the PMP thereof. In some instances, the PMP composition includes two or more (e.g., 2, 3, 4, 5, 6, 7, 8, 9, 10, or more than 10) different repellents.

For example, a PMP composition including a repellent as described herein can be contacted with an insect vector or a habitat of the vector in an amount and for a time sufficient to: (a) reach a target level (e.g., a predetermined or threshold level) of repellent concentration; and/or (b) decrease the levels of the insect near or on nearby animals relative to a control. Alternatively, a PMP composition including a repellent as described herein can be contacted with an animal in an amount and for a time sufficient to: (a) reach a target level (e.g., a predetermined or threshold level) of repellent concentration; and/or (b) decrease the levels of the insect near or on the animal relative to an untreated animal.

Some examples of well-known insect repellents include: benzil; benzyl benzoate; 2,3,4,5-bis(butyl-2-ene)tetrahydrofurfural (MGK Repellent 11); butoxypolypropylene glycol; N-butylacetanilide; normal-butyl-6,6-dimethyl-5,6-dihydro-1,4-pyrone-2-carboxylate (Indalone); dibutyl adipate; dibutyl phthalate; di-normal-butyl succinate (Tabatrex); N,N-diethyl-meta-toluamide (DEET); dimethyl carbate (endo,endo)-dimethyl bicyclo[2.2.1] hept-5-ene-2,3-dicarboxylate); dimethyl phthalate; 2-ethyl-2-butyl-1,3-propanediol; 2-ethyl-1,3-hexanediol (Rutgers 612); di-normal-propyl isocinchomeronate (MGK Repellent 326); 2-phenylcyclohexanol; p-methane-3,8-diol, and normal-propyl N,N-diethylsuccinamate. Other repellents include citronella oil, dimethyl phthalate, normal-butylmesityl oxide oxalate and 2-ethyl hexanediol-1,3 (See, Kirk-Othmer Encyclopedia of Chemical Technology, 2nd Ed., Vol. 11: 724-728; and The Condensed Chemical Dictionary, 8th Ed., p 756).

In some instances, the repellent is an insect repellent, including synthetic or nonsynthetic insect repellents. Examples of synthetic insect repellents include methyl anthranilate and other anthranilate-based insect repellents, benzaldehyde, DEET (N,N-diethyl-m-toluamide), dimethyl carbate, dimethyl phthalate, icaridin (i.e., picaridin, Bayrepel, and KBR 3023), indalone (e.g., as used in a "6-2-2" mixture (60% Dimethyl phthalate, 20% Indalone, 20% Ethylhexanediol), IR3535 (3-[N-Butyl-N-acetyl]-aminopropionic acid, ethyl ester), metofluthrin, permethrin, SS220, or tricyclodecenyl allyl ether. Examples of natural insect repellents include beautyberry (*Callicarpa*) leaves, birch tree bark, bog myrtle (*Myrica gale*), catnip oil (e.g., nepetalactone), citronella oil, essential oil of the lemon eucalyptus (*Corymbia citriodora*; e.g., p-menthane-3,8-diol (PMD)), neem oil, lemongrass, tea tree oil from the leaves of *Melaleuca alternifolia*, tobacco, or extracts thereof.

III. Methods of Use

The PMPs herein are useful in a variety of agricultural or therapeutic methods. Examples of methods of using PMPs (e.g., including modified PMPs described herein) are described further below.

A. Delivery to a Plant

Provided herein are methods of delivering a PMP composition (e.g., including modified PMPs described herein) to a plant, e.g., by contacting the plant, or part thereof, with the PMP composition. In some instances, plants may be treated with PMPs not including a heterologous functional agent. In other instances, the PMPs include a heterologous functional agent, e.g., pesticidal agents (e.g., antibacterial agents, antifungal agents, nematicides, molluscicides, virucides, herbicides), pest control agents (e.g., repellents), fertilizing agents, or plant-modifying agents.

In one aspect, provided herein is a method of increasing the fitness of a plant, the method including delivering to the plant the PMP composition described herein (e.g., in an effective amount and duration) to increase the fitness of the plant relative to an untreated plant (e.g., a plant that has not been delivered the PMP composition).

An increase in the fitness of the plant as a consequence of delivery of a PMP composition can manifest in a number of ways, e.g., thereby resulting in a better production of the plant, for example, an improved yield, improved vigor of the plant (e.g., improved tolerance of abiotic or biotic stress or improved resistance to pests) or improved quality of the harvested product from the plant. An improved yield of a plant relates to an increase in the yield of a product (e.g., as measured by plant biomass, grain, seed or fruit yield, protein content, carbohydrate or oil content or leaf area) of the plant by a measurable amount over the yield of the same product of the plant produced under the same conditions, but without the application of the instant compositions or compared with application of conventional agricultural agents. For example, yield can be increased by at least about 0.5%, about 1%, about 2%, about 3%, about 4%, about 5%, about 10%, about 20%, about 30%, about 40%, about 50%, about 60%, about 70%, about 80%, about 90%, about 100%, or more than 100%. Yield can be expressed in terms of an amount by weight or volume of the plant or a product of the plant on some basis. The basis can be expressed in terms of time, growing area, weight of plants produced, or amount of a raw material used. For example, such methods may increase the yield of plant tissues including, but not limited to: seeds, fruits, kernels, bolls, tubers, roots, and leaves.

An increase in the fitness of a plant as a consequence of delivery of a PMP composition can also be measured by other methods, such as an increase or improvement of the vigor rating, the stand (the number of plants per unit of area), plant height, stalk circumference, stalk length, leaf number, leaf size, plant canopy, visual appearance (such as greener leaf color), root rating, emergence, protein content, increased tillering, bigger leaves, more leaves, less dead basal leaves, stronger tillers, less fertilizer needed, less seeds needed, more productive tillers, earlier flowering, early grain or seed maturity, less plant verse (lodging), increased shoot growth, earlier germination, or any combination of these factors, by a measurable or noticeable amount over the same factor of the plant produced under the same conditions, but without the administration of the instant compositions or with application of conventional agricultural agents.

Provided herein is a method of modifying or increasing the fitness of a plant, the method including delivering to the plant an effective amount of a PMP composition provided herein, wherein the method modifies the plant and thereby introduces or increases a beneficial trait in the plant (e.g., by about 1%, 2%, 5%, 10%, 20%, 30%, 40%, 50%, 60%, 70%, 80%, 90%, 100%, or more than 100%) relative to an untreated plant. In particular, the method may increase the fitness of the plant (e.g., by about 1%, 2%, 5%, 10%, 20%, 30%, 40%, 50%, 60%, 70%, 80%, 90%, 100%, or more than 100%) relative to an untreated plant.

In some instances, the increase in plant fitness is an increase (e.g., by about 1%, 2%, 5%, 10%, 20%, 30%, 40%, 50%, 60%, 70%, 80%, 90%, 100%, or more than 100%) in disease resistance, drought tolerance, heat tolerance, cold tolerance, salt tolerance, metal tolerance, herbicide tolerance, chemical tolerance, water use efficiency, nitrogen utilization, resistance to nitrogen stress, nitrogen fixation, pest resistance, herbivore resistance, pathogen resistance, yield, yield under water-limited conditions, vigor, growth, photosynthetic capability, nutrition, protein content, carbohydrate content, oil content, biomass, shoot length, root length, root architecture, seed weight, or amount of harvestable produce.

In some instances, the increase in fitness is an increase (e.g., by about 1%, 2%, 5%, 10%, 20%, 30%, 40%, 50%, 60%, 70%, 80%, 90%, 100%, or more than 100%) in development, growth, yield, resistance to abiotic stressors, or resistance to biotic stressors. An abiotic stress refers to an environmental stress condition that a plant or a plant part is subjected to that includes, e.g., drought stress, salt stress, heat stress, cold stress, and low nutrient stress. A biotic stress refers to an environmental stress condition that a plant or plant part is subjected to that includes, e.g. nematode stress, insect herbivory stress, fungal pathogen stress, bacterial pathogen stress, or viral pathogen stress. The stress may be temporary, e.g. several hours, several days, several months, or permanent, e.g. for the life of the plant.

In some instances, the increase in plant fitness is an increase (e.g., by about 1%, 2%, 5%, 10%, 20%, 30%, 40%, 50%, 60%, 70%, 80%, 90%, 100%, or more than 100%) in quality of products harvested from the plant. For example, the increase in plant fitness may be an improvement in commercially favorable features (e.g., taste or appearance) of a product harvested from the plant. In other instances, the increase in plant fitness is an increase in shelf-life of a product harvested from the plant (e.g., by about 1%, 2%, 5%, 10%, 20%, 30%, 40%, 50%, 60%, 70%, 80%, 90%, 100%, or more than 100%).

Alternatively, the increase in fitness may be an alteration of a trait that is beneficial to human or animal health, such as a reduction in allergen production. For example, the increase in fitness may be a decrease (e.g., by about 1%, 2%, 5%, 10%, 20%, 30%, 40%, 50%, 60%, 70%, 80%, 90%, 100%, or more than 100%) in production of an allergen (e.g., pollen) that stimulates an immune response in an animal (e.g., human).

The modification of the plant (e.g., increase in fitness) may arise from modification of one or more plant parts. For example, the plant can be modified by contacting leaf, seed, pollen, root, fruit, shoot, flower, cells, protoplasts, or tissue (e.g., meristematic tissue) of the plant. As such, in another aspect, provided herein is a method of increasing the fitness of a plant, the method including contacting pollen of the plant with an effective amount of a PMP composition herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In yet another aspect, provided herein is a method of increasing the fitness of a plant, the method including contacting a seed of the plant with an effective amount of a PMP composition disclosed herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In another aspect, provided herein is a method including contacting a protoplast of the plant with an effective amount of a PMP composition herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In a further aspect, provided herein is a method of increasing the fitness of a plant, the method including contacting a plant cell of the plant with an effective amount of a PMP composition herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In another aspect, provided herein is a method of increasing the fitness of a plant, the method including contacting meristematic tissue of the plant with an effective amount of a PMP composition herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In another aspect, provided herein is a method of increasing the fitness of a plant, the method including contacting an embryo of the plant with an effective amount of a PMP composition herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In cases where an herbicide is included in the PMP, or compositions thereof, the methods may be further used to decrease the fitness of or kill weeds. In such instances, the method may be effective to decrease the fitness of the weed by about 2%, 5%, 10%, 20%, 30%, 40%, 50%, 60%, 70%, 80%, 90%, 100%, or more in comparison to an untreated weed (e.g., a weed to which the PMP composition has not been administered). For example, the method may be effective to kill the weed, thereby decreasing a population of the weed by about 2%, 5%, 10%, 20%, 30%, 40%, 50%, 60%, 70%, 80%, 90%, 100%, or more in comparison to an untreated weed. In some instances, the method substantially eliminates the weed. Examples of weeds that can be treated in accordance with the present methods are further described herein.

i. Plants

A variety of plants can be delivered or treated with a PMP composition described herein. Plants that can be delivered a PMP composition (i.e., "treated") in accordance with the present methods include whole plants and parts thereof, including, but not limited to, shoot vegetative organs/structures (e.g., leaves, stems and tubers), roots, flowers and floral organs/structures (e.g., bracts, sepals, petals, stamens, carpels, anthers and ovules), seed (including embryo, endosperm, cotyledons, and seed coat) and fruit (the mature ovary), plant tissue (e.g., meristematic tissue, vascular tissue, ground tissue, and the like) and cells (e.g., guard cells, egg cells, and the like), and progeny of same. Plant parts can further refer parts of the plant such as the shoot, root, stem, seeds, stipules, leaves, petals, flowers, ovules, bracts, branches, petioles, internodes, bark, pubescence, tillers, rhizomes, fronds, blades, pollen, stamen, and the like.

The class of plants that can be treated in a method disclosed herein includes the class of higher and lower plants, including angiosperms (monocotyledonous and dicotyledonous plants), gymnosperms, ferns, horsetails, psilophytes, lycophytes, bryophytes, and algae (e.g., multicellular or unicellular algae). Plants that can be treated in accordance with the present methods further include any vascular plant, for example monocotyledons or dicotyledons or gymnosperms, including, but not limited to alfalfa, apple, *Arabidopsis*, banana, barley, canola, castor bean, *chrysanthemum*, clover, cocoa, coffee, cotton, cottonseed, corn, *crambe*, cranberry, crucifers, cucumber, dendrobium, *dioscorea, eucalyptus*, fescue, flax, *gladiolus*, liliacea, linseed, millet, muskmelon, mustard, oat, oil palm, canola or oilseed rape, *papaya*, peanut, pineapple, ornamental plants, *Phaseolus*, potato, rapeseed, rice, rye, ryegrass, safflower, sesame, sorghum, soybean, sugarbeet, sugarcane, sunflower, strawberry, tobacco, tomato, turfgrass, wheat, and vegetable crops such as lettuce, celery, broccoli, cauliflower, cucurbits; fruit and nut trees, such as apple, pear, peach, orange, grapefruit, lemon, lime, almond, pecan, walnut, hazel; vines, such as grapes (e.g., a vineyard), kiwi, hops; *cannabis*, fruit shrubs and brambles, such as raspberry, blackberry, gooseberry; forest trees, such as ash, pine, fir, maple, oak, chestnut, popular; with alfalfa, canola, castor bean, corn, cotton, *crambe*, flax, linseed, mustard, oil palm, oilseed rape, peanut, potato, rice, safflower, sesame, soybean, sugarbeet, sunflower, tobacco, tomato, and wheat. Plants that can be treated in accordance with the methods of the present invention include any crop plant, for example, forage crop, oilseed crop, grain crop, fruit crop, vegetable crop, fiber crop, spice crop, nut crop, turf crop, sugar crop, beverage crop, and forest crop. In certain instances, the crop plant that is treated in the method is a soybean plant. In other certain instances, the crop plant is wheat. In certain instances, the crop plant is corn. In certain instances, the crop plant is cotton. In certain instances, the crop plant is alfalfa. In certain instances, the crop plant is sugarbeet. In certain instances, the crop plant is rice. In certain instances, the crop plant is potato. In certain instances, the crop plant is tomato.

In certain instances, the plant is a crop. Examples of such crop plants include, but are not limited to, monocotyledonous and dicotyledonous plants including, but not limited to, fodder or forage legumes, ornamental plants, food crops, trees, or shrubs selected from Acer spp., *Allium* spp., *Amaranthus* spp., *Ananas comosus*, *Apium graveolens*, *Arachis* spp, *Asparagus officinalis*, *Beta vulgaris*, *Brassica* spp. (e.g., *Brassica napus*, *Brassica rapa* ssp. (canola, oilseed rape, turnip rape), *Camellia sinensis*, *Canna indica*, *Cannabis sativa*, *Capsicum* spp., *Castanea* spp., *Cichorium endivia*, *Citrullus lanatus*, *Citrus* spp., *Cocos* spp., *Coffea* spp., *Coriandrum sativum*, *Corylus* spp., *Crataegus* spp., *Cucurbita* spp., *Cucumis* spp., *Daucus carota*, *Fagus* spp., *Ficus carica*, *Fragaria* spp., *Ginkgo biloba*, *Glycine* spp. (e.g., *Glycine max*, *Soja hispida* or *Soja max*), *Gossypium hirsutum*, *Helianthus* spp. (e.g., *Helianthus annuus*), *Hibiscus* spp., *Hordeum* spp. (e.g., *Hordeum vulgare*), *Ipomoea batatas*, *Juglans* spp., *Lactuca sativa*, *Linum usitatissimum*, *Litchi chinensis*, *Lotus* spp., *Luffa acutangula*, *Lupinus* spp., *Lycopersicon* spp. (e.g., *Lycopersicon esculenturn*, *Lycopersicon lycopersicum*, *Lycopersicon pyriforme*), *Malus* spp., *Medicago sativa*, *Mentha* spp., *Miscanthus sinensis*, *Morus nigra*, *Musa* spp., *Nicotiana* spp., *Olea* spp., *Oryza* spp. (e.g., *Oryza sativa*, *Oryza latifolia*), *Panicum miliaceum*, *Panicum virgatum*, *Passiflora edulis*, *Petroselinum crispum*, *Phaseolus* spp., *Pinus* spp., *Pistacia vera*, *Pisum* spp., *Poa* spp., *Populus* spp., *Prunus* spp., *Pyrus communis*, *Quercus* spp., *Raphanus sativus*, *Rheum rhabarbarum*, *Ribes* spp., *Ricinus communis*, *Rubus* spp., *Saccharum* spp., *Salix* sp., *Sambucus* spp., *Secale cereale*, *Sesamum* spp., *Sinapis* spp., *Solanum* spp. (e.g., *Solanum tuberosum*, *Solanum integrifolium* or *Solanum lycopersicum*), *Sorghum bicolor*, *Sorghum halepense*, *Spinacia* spp., *Tamarindus indica*, *Theobroma cacao*, *Trifolium* spp., *Triticosecale rimpaui*, *Triticum* spp. (e.g., *Triticum aestivum*, *Triticum durum*, *Triticum turgidum*, *Triticum hybernum*, *Triticum macha*, *Triticum sativum* or *Triticum vulgare*), *Vaccinium* spp., *Vicia* spp., *Vigna* spp., *Viola odorata*, *Vitis* spp., and *Zea mays*. In certain embodiments, the crop plant is rice, oilseed rape, canola, soybean, corn (maize), cotton, sugarcane, alfalfa, sorghum, or wheat.

In certain instance, the compositions and methods can be used to treat post-harvest plants or plant parts, food, or feed products. In some instances, the food or feed product is a non-plant food or feed product (e.g., a product edible for humans, veterinary animals, or livestock (e.g., mushrooms)).

The plant or plant part for use in the present invention include plants of any stage of plant development. In certain instances, the delivery can occur during the stages of germination, seedling growth, vegetative growth, and reproductive growth. In certain instances, delivery to the plant occurs during vegetative and reproductive growth stages. Alternatively, the delivery can occur to a seed. The stages of vegetative and reproductive growth are also referred to herein as "adult" or "mature" plants.

ii. Weeds

In cases where an herbicide is included in the PMP, or compositions thereof, the methods may be further used to decrease the fitness of or kill weeds. In such instances, the method may be effective to decrease the fitness of the weed by about 2%, 5%, 10%, 20%, 30%, 40%, 50%, 60%, 70%, 80%, 90%, 100%, or more in comparison to an untreated weed (e.g., a weed to which the PMP composition has not been administered). For example, the method may be effective to kill the weed, thereby decreasing a population of the weed by about 2%, 5%, 10%, 20%, 30%, 40%, 50%, 60%, 70%, 80%, 90%, 100%, or more in comparison to an untreated weed. In some instances, the method substantially eliminates the weed. Examples of weeds that can be treated in accordance with the present methods are further described herein.

As used herein, the term weed refers to a plant that grows where it is not wanted. Such plants are typically invasive and, at times, harmful, or have the risk of becoming so. Weeds may be treated with the present PMP compositions to reduce or eliminate the presence, viability, or reproduction of the plant. For example, and without being limited thereto, the methods can be used to target weeds known to damage plants. For example, and without being limited thereto, the weeds can be any member of the following group of families: Gramineae, Umbelliferae, Papilionaceae, Cruciferae, Malvaceae, Eufhorbiaceae, Compositae, Chenopodiaceae, Fumariaceae, Charyophyllaceae, Primulaceae, Geraniaceae, Polygonaceae, Juncaceae, Cyperaceae, Aizoaceae, Asteraceae, Convolvulaceae, Cucurbitaceae, Euphorbiaceae, Polygonaceae, Portulaceae, Solanaceae, Rosaceae, Simaroubaceae, Lardizabalaceae, Liliaceae, Amaranthaceae, Vitaceae, Fabaceae, Primulaceae, Apocynaceae, Araliaceae, Caryophyllaceae, Asclepiadaceae, Celastraceae, Papaveraceae, Onagraceae, Ranunculaceae, Lamiaceae, Commelinaceae, Scrophulariaceae, Dipsacaceae, Boraginaceae, Equisetaceae, Geraniaceae, Rubiaceae, Cannabaceae, Hyperiacaceae, Balsaminaceae, Lobeliaceae, Caprifoliaceae, Nyctaginaceae, Oxalidaceae, Vitaceae, Urticaceae, Polypodiaceae, Anacardiaceae, Smilacaceae, Araceae, Campanulaceae, Typhaceae, Valerianaceae, Verbenaceae, Violaceae. For example, and without being limited thereto, the weeds can be any member of the group consisting of *Lolium rigidum*, *Amaramthus palmeri*, *Abutilon theopratsi*, *Sorghum halepense*, *Conyza Canadensis*, *Setaria verticillata*, *Capsella pastoris*, and *Cyperus rotundas*. Additional weeds include, for example, Mimosapigra, salvinia, hyptis, senna, noogoora, burr, *Jatropha gossypifolia*, *Parkinsonia aculeate*, *Chromolaena odorata*, *Cryptoslegia grandiflora*, or *Andropogon gayanus*. Weeds can include monocotyledonous plants (e.g., *Agrostis*, *Alopecurus*, *Avena*, *Bromus*, *Cyperus*, *Digitaria*, *Echinochloa*, *Lolium*, *Monochoria*, *Rottboellia*, *Sagittaria*, *Scirpus*, *Setaria*, *Sida* or *Sorghum*) or dicotyledonous plants (*Abutilon*, *Amaranthus*, *Chenopodium*, *Chrysanthemum*, *Conyza*, *Galium*, *Ipomoea*, *Nasturtium*, *Sinapis*, *Solanum*, *Stellaria*, *Veronica*, *Viola* or *Xanthium*).

The compositions and related methods can be used to prevent infestation by or reduce the numbers of pathogens or pathogen vectors in any habitats in which they reside (e.g., outside of animals, e.g., on plants, plant parts (e.g., roots, fruits and seeds), in or on soil, water, or on another pathogen or pathogen vector habitat. Accordingly, the compositions and methods can reduce the damaging effect of pathogen vectors by for example, killing, injuring, or slowing the activity of the vector, and can thereby control the spread of the pathogen to animals. Compositions disclosed herein can be used to control, kill, injure, paralyze, or reduce the activity of one or more of any pathogens or pathogen vectors in any developmental stage, e.g., their egg, nymph, instar, larvae, adult, juvenile, or desiccated forms. The details of each of these methods are described further below.

B. Delivery to a Plant Pest

Provided herein are methods of delivering a PMP composition (e.g., including modified PMPs described herein) to a plant pest, e.g., by contacting the plant pest with the PMP composition. In some instances, the plant pests may be treated with PMPs not including a heterologous functional agent. In other instances, the PMPs include a heterologous functional agent, e.g., pesticidal agents (e.g., antibacterial agents, antifungal agents, nematicides, molluscicides, virucides, or herbicides) or pest control agents (e.g., repellents). For example, the methods can be useful for decreasing the fitness of a pest, e.g., to prevent or treat a pest infestation as a consequence of delivery of a PMP composition.

In one aspect, provided herein is a method of decreasing the fitness of a pest, the method including delivering to the pest the PMP composition described herein (e.g., in an effective amount and for an effective duration) to decrease the fitness of the pest relative to an untreated pest (e.g., a pest that has not been delivered the PMP composition).

In one aspect, provided herein is a method of decreasing a fungal infection in (e.g., treating) a plant having a fungal infection, wherein the method includes delivering to the plant pest a PMP composition including a plurality of PMPs (e.g., a PMP composition described herein).

In another aspect, provided herein is a method of decreasing a fungal infection in (e.g., treating) a plant having a fungal infection, wherein the method includes delivering to the plant pest a PMP composition including a plurality of PMPs (e.g., a PMP composition described herein), and wherein the plurality of PMPs include an antifungal agent. In some instances, the antifungal agent is a nucleic acid that inhibits expression of a gene (e.g., dcl1 and dcl2 dcl1/2) in a fungus that causes the fungal infection. In some instances, the fungal infection is caused be a fungus belonging to a *Sclerotinia* spp. (e.g., *Sclerotinia sclerotiorum*), a *Botrytis* spp. (e.g., *Botrytis cinerea*), an *Aspergillus* spp., a *Fusarium* spp., or a *Penicillium* spp. In some instances, the composition includes a PMP produced from an *Arabidopsis* apoplast EV. In some instances, the method decreases or substantially eliminates the fungal infection.

In another aspect, provided herein is a method of decreasing a bacterial infection in (e.g., treating) a plant having a bacterial infection, wherein the method includes delivering to the plant pest a PMP composition including a plurality of PMPs (e.g., a PMP composition described herein).

In another aspect, provided herein is a method of decreasing a bacterial infection in (e.g., treating) a plant having a bacterial infection, wherein the method includes delivering to the plant pest a PMP composition including a plurality of PMPs, and wherein the plurality of PMPs include an antibacterial agent. In some instances, the antibacterial agent is streptomycin. In some instances, the bacterial infection is caused by a bacterium belonging to a *Pseudomonas* spp (e.g., *Pseudomonas syringae*). In some instances, the composition includes a PMP produced from an *Arabidopsis* apoplast EV. In some instances, the method decreases or substantially eliminates the bacterial infection.

In another aspect, provided herein is a method of decreasing the fitness of an insect plant pest, wherein the method includes delivering to the insect plant pest a PMP composition including a plurality of PMPs (e.g., a PMP composition described herein).

In another aspect, provided herein is a method of decreasing the fitness of an insect plant pest, wherein the method includes delivering to the insect plant pest a PMP composition including a plurality of PMPs (e.g., a PMP composition described herein), and wherein the plurality of PMPs includes an insecticidal agent. In some instances, the insecticidal agent is a peptide nucleic acid. In some instances, the insect plant pest is an aphid. In some instances, the insect plant pest is a lepidopteran (e.g., *Spodoptera frugiperda*). In some instances, the insect plant pest is an arachnid, e.g., a mite. In some instances, the method decreases the fitness of the insect plant pest relative to an untreated insect plant pest In another aspect, provided herein is a method of decreasing the fitness of a nematode plant pest, wherein the method includes delivering to the nematode plant pest a PMP composition including a plurality of PMPs (e.g., a PMP composition described herein).

In another aspect, provided herein is a method of decreasing the fitness of a nematode plant pest, wherein the method includes delivering to the nematode plant pest a PMP composition including a plurality of PMPs (e.g., a PMP composition described herein), and wherein the plurality of PMPs include a nematicidal agent. In some instances, the nematicidal agent is a neuropeptide (e.g., Mi-NLP-15b). In some instances, the nematode plant pest is a root-knot nematode. In some instances, the method decreases the fitness of the nematode plant pest relative to an untreated nematode plant pest.

In another aspect, provided herein is a method of decreasing the fitness of a weed, wherein the method includes delivering to the weed a PMP composition including a plurality of PMPs (e.g., a PMP composition described herein).

In another aspect, provided herein is a method of decreasing the fitness of a weed, wherein the method includes delivering to the weed a PMP composition including a plurality of PMPs (e.g., a PMP composition described herein), and wherein the plurality of PMPs include an herbicidal agent (e.g. Glufosinate). In some instances, the weed is an Indian goosegrass (*Eleusine indica*). In some instances, the method decreases the fitness of the weed relative to an untreated weed.

A decrease in the fitness of the pest as a consequence of delivery of a PMP composition can manifest in a number of ways. In some instances, the decrease in fitness of the pest may manifest as a deterioration or decline in the physiology of the pest (e.g., reduced health or survival) as a consequence of delivery of the PMP composition. In some instances, the fitness of an organism may be measured by one or more parameters, including, but not limited to, reproductive rate, fertility, lifespan, viability, mobility, fecundity, pest development, body weight, metabolic rate or activity, or survival in comparison to a pest to which the PMP composition has not been administered. For example, the methods or compositions provided herein may be effective to decrease the overall health of the pest or to decrease the overall survival of the pest. In some instances, the decreased survival of the pest is about 2%, 5%, 10%, 20%, 30%, 40%, 50%, 60%, 70%, 80%, 90%, 100%, or greater than 100% greater relative to a reference level (e.g., a level found in a pest that does not receive a PMP composition). In some instances, the methods and compositions are effective to decrease pest reproduction (e.g., reproductive rate, fertility) in comparison to a pest to which the PMP composition has not been administered. In some instances, the methods and compositions are effective to decrease other physiological parameters, such as mobility, body weight, life span, fecundity, or metabolic rate, by about 2%, 5%, 10%, 20%, 30%, 40%, 50%, 60%, 70%, 80%, 90%, 100%, or greater than 100% relative to a reference level (e.g., a level found in a pest that does not receive a PMP composition).

In some instances, the decrease in pest fitness may manifest as a decrease in the production of one or more nutrients in the pest (e.g., vitamins, carbohydrates, amino acids, or polypeptides) in comparison to a pest to which the PMP composition has not been administered. In some instances, the methods or compositions provided herein may be effective to decrease the production of nutrients in the pest (e.g., vitamins, carbohydrates, amino acids, or polypeptides) by about 2%, 5%, 10%, 20%, 30%, 40%, 50%, 60%, 70%, 80%, 90%, 100%, or greater than 100% relative to a reference level (e.g., a level found in a pest that does not receive a PMP composition).

In some instances, the decrease in pest fitness may manifest as an increase in the pest's sensitivity to a pesticidal agent and/or a decrease in the pest's resistance to a pesticidal agent in comparison to a pest to which the PMP composition has not been administered. In some instances, the methods or compositions provided herein may be effective to increase the pest's sensitivity to a pesticidal agent by about 2%, 5%, 10%, 20%, 30%, 40%, 50%, 60%, 70%, 80%, 90%, 100%, or greater than 100% relative to a reference level (e.g., a level found in a pest that does not receive a PMP composition). The pesticidal agent may be any pesticidal agent known in the art, including insecticidal agents. In some instances, the methods or compositions provided herein may increase the pest's sensitivity to a pesticidal agent by decreasing the pest's ability to metabolize or degrade the pesticidal agent into usable substrates in comparison to a pest to which the PMP composition has not been administered.

In some instances, the decrease in pest fitness may manifest as an increase in the pest's sensitivity to an allelochemical agent and/or a decrease in the pest's resistance to an allelochemical agent in comparison to a pest to which the PMP composition has not been administered. In some instances, the methods or compositions provided herein may be effective to decrease the pest's resistance to an allelochemical agent by about 2%, 5%, 10%, 20%, 30%, 40%, 50%, 60%, 70%, 80%, 90%, 100%, or greater than 100% relative to a reference level (e.g., a level found in a pest that does not receive a PMP composition). In some instances, the allelochemical agent is caffeine, soyacystatin, fenitrothion, monoterpenes, diterpene acids, or phenolic compounds (e.g., tannins, flavonoids). In some instances, the methods or compositions provided herein may increase the pest's sensitivity to an allelochemical agent by decreasing the pest's ability to metabolize or degrade the allelochemical agent into usable substrates in comparison to a pest to which the PMP composition has not been administered.

In some instances, the methods or compositions provided herein may be effective to decease the pest's resistance to parasites or pathogens (e.g., fungal, bacterial, or viral pathogens or parasites) in comparison to a pest to which the PMP composition has not been administered. In some instances, the methods or compositions provided herein may be effective to decrease the pest's resistance to a pathogen or parasite (e.g., fungal, bacterial, or viral pathogens; or parasitic mites) by about 2%, 5%, 10%, 20%, 30%, 40%, 50%, 60%, 70%, 80%, 90%, 100%, or greater than 100% relative to a reference level (e.g., a level found in a pest that does not receive a PMP composition).

In some instances, the methods or compositions provided herein may be effective to decrease the pest's ability to carry or transmit a plant pathogen (e.g., plant virus (e.g., TYLCV) or a plant bacterium (e.g., *Agrobacterium* spp.)) in compari-son to a pest to which the PMP composition has not been administered. For example, the methods or compositions provided herein may be effective to decrease the pest's ability to carry or transmit a plant pathogen (e.g., a plant virus (e.g., TYLCV) or plant bacterium (e.g., *Agrobacterium* spp.)) by about 2%, 5%, 10%, 20%, 30%, 40%, 50%, 60%, 70%, 80%, 90%, 100%, or greater than 100% relative to a reference level (e.g., a level found in a pest that does not receive a PMP composition).

Additionally or alternatively, in cases where an herbicide is included in the PMP, or compositions thereof, the methods may be further used to decrease the fitness of or kill weeds. In such instances, the method may be effective to decrease the fitness of the weed by about 2%, 5%, 10%, 20%, 30%, 40%, 50%, 60%, 70%, 80%, 90%, 100%, or more in comparison to an untreated weed (e.g., a weed to which the PMP composition has not been administered). For example, the method may be effective to kill the weed, thereby decreasing a population of the weed by about 2%, 5%, 10%, 20%, 30%, 40%, 50%, 60%, 70%, 80%, 90%, 100%, or more in comparison to an untreated weed. In some instances, the method substantially eliminates the weed. Examples of weeds that can be treated in accordance with the present methods are further described herein.

In some instances, the decrease in pest fitness may manifest as other fitness disadvantages, such as a decreased tolerance to certain environmental factors (e.g., a high or low temperature tolerance), a decreased ability to survive in certain habitats, or a decreased ability to sustain a certain diet in comparison to a pest to which the PMP composition has not been administered. In some instances, the methods or compositions provided herein may be effective to decrease pest fitness in any plurality of ways described herein. Further, the PMP composition may decrease pest fitness in any number of pest classes, orders, families, genera, or species (e.g., 1 pest species, 2, 3, 4, 5, 6, 7, 8, 9, 10, 15, 20, 30, 40, 50, 60, 70, 80, 90, 100, 150, 200, 200, 250, 500, or more pest species). In some instances, the PMP composition acts on a single pest class, order, family, genus, or species.

Pest fitness may be evaluated using any standard methods in the art. In some instances, pest fitness may be evaluated by assessing an individual pest. Alternatively, pest fitness may be evaluated by assessing a pest population. For example, a decrease in pest fitness may manifest as a decrease in successful competition against other insects, thereby leading to a decrease in the size of the pest population.

i. Fungi

The PMP compositions and related methods can be useful for decreasing the fitness of a fungus, e.g., to prevent or treat a fungal infection in a plant. Included are methods for delivering a PMP composition to a fungus by contacting the fungus with the PMP composition. Additionally or alternatively, the methods include delivering the PMP composition to a plant at risk of or having a fungal infection, by contacting the plant with the PMP composition.

The PMP compositions and related methods are suitable for delivery to fungi that cause fungal diseases in plants, including diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*; diseases caused by rust disease pathogens, for example *Gymnosporangium* species, for example *Gymnosporangium sabinae*; *Hemileia* species, for example *Hemil-* eia vastatrix; Phakopsora species, for example Phakopsora pachyrhizi and Phakopsora meibomiae; Puccinia species, for example Puccinia recondite, P. triticina, P. graminis or P. striiformis or P. hordei; Uromyces species, for example Uromyces appendiculatus; diseases caused by pathogens from the group of the Oomycetes, for example Albugo species, for example Algubo candida; Bremia species, for example Bremia lactucae; Peronospora species, for example Peronospora pisi, P. parasitica or P. brassicae; Phytophthora species, for example Phytophthora infestans; Plasmopara species, for example Plasmopara viticola; Pseudoperonospora species, for example Pseudoperonospora humuli or Pseudoperonospora cubensis; Pythium species, for example Pythium ultimum; leaf blotch diseases and leaf wilt diseases caused, for example, by Alternaria species, for example Alternaria solani; Cercospora species, for example Cercospora beticola; Cladiosporium species, for example Cladiosporium cucumerinum; Cochliobolus species, for example Cochliobolus sativus (conidia form: Drechslera, Syn: Helminthosporium), Cochliobolus miyabeanus; Colletotrichum species, for example Colletotrichum lindemuthanium; Cycloconium species, for example Cycloconium oleaginum; Diaporthe species, for example Diaporthe citri; Elsinoe species, for example Elsinoe fawcettii; Gloeosporium species, for example Gloeosporium laeticolor; Glomerella species, for example Glomerella cingulata; Guignardia species, for example Guignardia bidwelli; Leptosphaeria species, for example Leptosphaeria maculans, Leptosphaeria nodorum; Magnaporthe species, for example Magnaporthe grisea; Microdochium species, for example Microdochium nivale; Mycosphaerella species, for example Mycosphaerella graminicola, M. arachidicola and M. fifiensis; Phaeosphaeria species, for example Phaeosphaeria nodorum; Pyrenophora species, for example Pyrenophora teres, Pyrenophora tritici repentis; Ramularia species, for example Ramularia collo-cygni, Ramularia areola; Rhynchosporium species, for example Rhynchosporium secalis; Septoria species, for example Septoria apii, Septoria lycopersii; Typhula species, for example Typhula incarnata; Venturia species, for example Venturia inaequalis; root and stem diseases caused, for example, by Corticium species, for example Corticium graminearum; Fusarium species, for example Fusarium oxysporum; Gaeumannomyces species, for example Gaeumannomyces graminis; Rhizoctonia species, such as, for example Rhizoctonia solani; Sarocladium diseases caused for example by Sarocladium oryzae; Sclerotium diseases caused for example by Sclerotium oryzae; Tapesia species, for example Tapesia acuformis; Thielaviopsis species, for example Thielaviopsis basicola; ear and panicle diseases (including corn cobs) caused, for example, by Alternaria species, for example Alternaria spp.; Aspergillus species, for example Aspergillus flavus; Cladosporium species, for example Cladosporium cladosporioides; Claviceps species, for example Claviceps purpurea; Fusarium species, for example Fusarium culmorum; Gibberella species, for example Gibberella zeae; Monographella species, for example Monographella nivalis; Septoria species, for example Septoria nodorum; diseases caused by smut fungi, for example Sphacelotheca species, for example Sphacelotheca reiliana; Tilletia species, for example Tilletia caries, T. controversa; Urocystis species, for example Urocystis occulta; Ustilago species, for example Ustilago nuda, U. nuda tritici; fruit rot caused, for example, by Aspergillus species, for example Aspergillus flavus; Botrytis species, for example Botrytis cinerea; Penicillium species, for example Penicillium expansum and P. purpurogenum; Sclerotinia species, for example Sclerotinia sclerotiorum; Verticilium species, for example Verticilium alboatrum; seed and soilborne decay, mould, wilt, rot and damping-off diseases caused, for example, by Alternaria species, caused for example by Alternaria brassicicola; Aphanomyces species, caused for example by Aphanomyces euteiches; Ascochyta species, caused for example by Ascochyta lentis; Aspergillus species, caused for example by Aspergillus flavus; Cladosporium species, caused for example by Cladosporium herbarum; Cochliobolus species, caused for example by Cochliobolus sativus; (Conidiaform: Drechslera, Bipolaris Syn: Helminthosporium); Colletotrichum species, caused for example by Colletotrichum coccodes; Fusarium species, caused for example by Fusarium culmorum; Gibberella species, caused for example by Gibberella zeae; Macrophomina species, caused for example by Macrophomina phaseolina; Monographella species, caused for example by Monographella nivalis; Penicillium species, caused for example by Penicillium expansum; Phoma species, caused for example by Phoma lingam; Phomopsis species, caused for example by Phomopsis sojae; Phytophthora species, caused for example by Phytophthora cactorum; Pyrenophora species, caused for example by Pyrenophora graminea; Pyricularia species, caused for example by Pyricularia oryzae; Pythium species, caused for example by Pythium ultimum; Rhizoctonia species, caused for example by Rhizoctonia solani; Rhizopus species, caused for example by Rhizopus oryzae; Sclerotium species, caused for example by Sclerotium rolfsii; Septoria species, caused for example by Septoria nodorum; Typhula species, caused for example by Typhula incarnata; Verticillium species, caused for example by Verticillium dahliae; cancers, galls and witches' broom caused, for example, by Nectria species, for example Nectria galligena; wilt diseases caused, for example, by Monilinia species, for example Monilinia laxa; leaf blister or leaf curl diseases caused, for example, by Exobasidium species, for example Exobasidium vexans; Taphrina species, for example Taphrina deformans; decline diseases of wooden plants caused, for example, by Esca disease, caused for example by Phaemoniella clamydospora, Phaeoacremonium aleophilum and Fomitiporia mediterranea; Eutypa dyeback, caused for example by Eutypa lata; Ganoderma diseases caused for example by Ganoderma boninense; Rigidoporus diseases caused for example by Rigidoporus lignosus; diseases of flowers and seeds caused, for example, by Botrytis species, for example Botrytis cinerea; diseases of plant tubers caused, for example, by Rhizoctonia species, for example Rhizoctonia solani; Helminthosporium species, for example Helminthosporium solani; Club root caused, for example, by Plasmodiophora species, for example Plamodiophora brassicae; diseases caused by bacterial pathogens, for example Xanthomonas species, for example Xanthomonas campestris pv. oryzae; Pseudomonas species, for example Pseudomonas syringae pv. lachrymans; Erwinia species, for example Erwinia amylovora.

Fungal diseases on leaves, stems, pods and seeds caused, for example, by Alternaria leaf spot (Alternaria spec. atrans tenuissima), Anthracnose (Colletotrichum gloeosporoides dematium var. truncatum), brown spot (Septoria glycines), cercospora leaf spot and blight (Cercospora kikuchii), choanephora leaf blight (Choanephora infundibulifera trispora (Syn.)), dactuliophora leaf spot (Dactuliophora glycines), downy mildew (Peronospora manshurica), drechslera blight (Drechslera glycini), frogeye leaf spot (Cercospora sojina), leptosphaerulina leaf spot (Leptosphaerulina trifoli), phyllostica leaf spot (Phyllosticta sojaecola), pod and stem blight (Phomopsis sojae), powdery mildew (Mi-

*crosphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

In certain instances, the fungus is a *Sclerotinia* spp (*Sclerotinia sclerotiorum*). In certain instances, the fungus is a *Botrytis* spp (e.g., *Botrytis cinerea*). In certain instances, the fungus is an *Aspergillus* spp. In certain instances, the fungus is a *Fusarium* spp. In certain instances, the fungus is a *Penicillium* spp.

Compositions of the present invention are useful in various fungal control applications. The above-described compositions may be used to control fungal phytopathogens prior to harvest or post-harvest fungal pathogens. In one embodiment, any of the above-described compositions are used to control target pathogens such as *Fusarium* species, *Botrytis* species, *Verticillium* species, *Rhizoctonia* species, *Trichoderma* species, or *Pythium* species by applying the composition to plants, the area surrounding plants, or edible cultivated mushrooms, mushroom spawn, or mushroom compost. In another embodiment, compositions of the present invention are used to control post-harvest pathogens such as *Penicillium, Geotrichum, Aspergillus niger*, or *Colletotrichum* species.

Table 6 provides further examples of fungi, and plant diseases associated therewith, that can be treated or prevented using the PMP composition and related methods described herein.

TABLE 6

Fungal pests

| Disease | Causative Agent |
|---|---|
| *Alternaria* leaf blight of wheat | *Alternaria triticina* |
| *Alternaria* leaf spot of cole crops | *Alternaria japonica* |
| American soybean rust | *Phakopsora meibomiae* |
| Ampelopsis rust | *Phakopsora ampelopsidis* |
| Anemone | *Ochropsora ariae* |
| Angular leaf spot of Citrus | *Pseudocercospora angolensis* |
| Arctic Rubus rust | *Phragmidium arcticum* |
| Ascochyta blight of broad beans | *Didymella fabae* |
| Ash dieback | *Chalara fraxinea* |
| Asia mountain Rosa rust | *Phragmidium butleri* |
| Asian filbert rust | *Pucciniastrum coryli* |
| Asian *Kuehneola* rose rust | *Kuehneola japonica* |
| Asian Mountain Rubus rust | *Phragmidium assamense* |
| Asian *Phragmidium* Rubus rust | *Phragmidium arisanense* |
| Asian pistacio rust | *Pileolaria pistaciae* |
| Asian rose rust | *Gerwasia rosae* |
| Asian Rubus rust | *Hamaspora hashiokai* |
| Asian soybean rust | *Phakopsora pachyrhizi* |
| Asian sugarcane smut | *Sporisorium sacchari* |
| Asian Wart bark, blister canker, ring rot, Physalospora canker of pear and apple | *Botryosphaeria berengeriana* f. sp. *pyricola* |
| Asian/European brown rot of rosaceae | *Monilinia fructigena* |
| Asiatic brown fruit rot | *Monilia polystroma* |
| Barclay's Asian Rubus rust | *Phragmidium barclayi* |
| Black leaf blight of soybean | *Arkoola nigra* |
| Blister blight of tea | *Exobasidium vexans* |
| Blue stain of Mongolian oak | *Ophiostoma longicollum* |
| Box Rust or Boxwood Rust | *Puccinia buxi* |
| Brown rust of sugarcane | *Puccinia melanocephala* |
| Cherry leaf scorch | *Apiognomonia erythrostoma* |
| Chocolate spot of Ya Li pears | *Alternaria yaliinficiens* |
| Chrysanthemum White Rust | *Puccinia horiana* |
| Coffee Leaf Rust | *Hemileia vastatrix* |
| Common Asian Rubus Rust | *Hamaspora acutissima* |
| Common larch | *Melampsora capraearum* |
| Common potato and tomato rust | *Puccinia pittieriana* |
| *Crumenulopsis* pine dieback | *Crumenulopsis sororia* |
| Daylily Rust | *Puccinia hemerocallidis* |
| Digitalis Downy Mildew | *Peronospora digitalis* |
| Downy mildew (*Plasmopara*) of Impatiens | *Plasmopara obducens* |
| Eggplant | *Puccinia substriata* var. *substriata* |
| Ergot of pearl millet | *Claviceps fusiformis* |

TABLE 6-continued

Fungal pests

| Disease | Causative Agent |
|---|---|
| European Larch canker | *Lachnellula willkommii* |
| Few-loculed Asian Rubus rust | *Phragmidium pauciloculare* |
| Flag smut of wheat | *Urocystis agropyri* |
| Gladiolus Rust | *Uromyces transversalis* |
| *Goplana dioscoreae* | *Goplana dioscoreae* |
| Grape leaf rust | *Phakopsora euvitis* |
| Gray Rubus rust | *Phragmidium griseum* |
| Himalayan rhododendron spruce rust | *Chrysomyxa himalensis* |
| Hiratsuka Rubus rust | *Phragmidium hiratsukanum* |
| Horse's tooth or ergot of maize | *Claviceps gigantea* |
| Japanese apple rust | *Gymnosporangium yamadae* |
| Japanese Chamaecyparis | *Gymnosporangium miyabei* |
| Japanese ergot of *sorghum* | *Claviceps sorghicola* |
| Kamtschatka rose rust | *Phragmidium kamtschatkae* |
| Late wilt of maize | *Harpophora maydis* |
| Long-Spored Asian Rubus rust | *Hamaspora longissima* |
| Mal secco disease of Citrus | *Phoma tracheiphila* |
| Miscanthus | *Puccinia miscanthi* |
| Mulberry rust | *Aecidium mori* |
| Nambu Rubus rust | *Phragmidium nambuanum* |
| Neck rot of onion | *Ciborinia allii* |
| New Zealand Rubus Rust | *Hamaspora australis* |
| Northern blue stain of pine | *Leptographium wingfieldii* |
| Northern spruce | *Chrysomyxa rhododendri* |
| Oak Wilt | *Ceratocystis fagacearum* |
| Orange rust of sugarcane | *Puccinia kuehnii* |
| *Peronospora radii* | *Peronospora radii* |
| Pistachio Rust | *Pileolaria terebinthi* |
| Poinsettia scab | *Sphaceloma poinsettiae* |
| Potato smut | *Thecaphora solani* |
| *Puccinia gladioli* on Gladiolus | *Puccinia gladioli* |
| *Puccinia glyceriae* (anam. *Aecidium hydrangea* | *Puccinia glyceriae* |
| *Puccinia mccleanii* on Gladiolus | *Puccinia mccleanii* |
| *Puccinia psidii* | *Puccinia psidii* |
| *Pucciniastrum actinidiae* on *Actinidia* spp. | *Pucciniastrum actinidiae* |
| Red Miscanthus rust | *Puccinia erythropus* |
| Rust of European blackberry | *Phragmidium bulbosum* |
| Rust of Rubus saxitilis | *Phragmidium acuminatum* |
| Rust on Asian Rubus | *Gerwasia rubi* |
| Rust on South American Rubus | *Gerwasia imperialis* |
| Scots stem pine rust | *Cronartium flaccidum* |
| Shoot blight of boxwood | *Calonectria pseudonaviculata* |
| Sirex wasp fungus | *Amylostereum areolatum* |
| Solanum | *Puccinia agrophila* |
| South American Rubus rust | *Gerwasia mayorii* |
| *Sporisorium* smut of wild *Saccharum* | *Sporisorium pulverulentum* |
| Spruce needle rust | *Chrysomyxa abietis* |
| Stackburn, seedling blight, leaf spot of rice | *Alternaria padwickii* |
| Sudden needle drop of Spruce (SNEED) | *Setomelanomma holmii* |
| Sugary disease or Asian ergot of *sorghum* | *Claviceps sorghi* |
| Sweet potato rust | *Endophyllum kaernbachii* |
| Taiwan Rubus rust | *Phragmidium formosanum* |
| Tar spot of corn | *Phyllachora maydis* |
| Teak Rust | *Olivea tectonae* |
| *Thekopsora areolate* | *Thekopsora areolata* |
| Tip over disease of eggplant | *Diaporthe vexans* |
| Tropical American *Kuehneola* rust of Rubus | *Kuehneola loeseneriana* |
| Tropical American *Mainsia* Rubus rust | *Mainsia rubi* |
| Tropical Soybean Rust | *Aecidium glycines* |
| *Uromyces gladioli* on Gladiolus | *Uromyces gladioli* |
| *Uromyces nyikensis* on Gladiolus | *Uromyces nyikensis* |
| *Uromycladium tepperianum* on *Acacia* spp. | *Uromycladium tepperianum* |
| Variable Rubus | *Gerwasia variabilis* |
| Wineberry Rubus rust | *Hamaspora sinica* var. *sinica* |
| Yamada Rubusrust | *Phragmidium yamadanum* |

TABLE 6-continued

Fungal pests

| Disease | Causative Agent |
|---|---|
| Anthracnose leaf blight and stalk rot | *Colletotrichum graminicola anthracnose* (teleomorph: *Glomerella graminicola*), *Glomerella tucumanensis* (anamorph: *Glomerella falcatum*) |
| *Aspergillus* ear and kernel rot | *Aspergillus flavus* |
| Banded leaf and sheath spot | *Rhizoctonia solani* = *Rhizoctonia microsclerotia* (teleomorph: *Thanatephorus cucumeris*) |
| Bean rust | *Uromyces appendiculatus* |
| Black bundle disease | *Acremonium strictum* = *Cephalosporium acremonium* |
| Black kernel rot | *Lasiodiplodia theobromae* = *Botryodiplodia theobromae* |
| Borde bianco | *Marasmiellus* sp. |
| Brown spot (black spot, stalk rot) | *Physoderma maydis* |
| Brown stripe downy mildew | *Sclerophthora rayssiae* var. *zeae* |
| *Cephalosporium* kernel rot | *Acremonium strictum* = *Cephalosporium acremonium* |
| Charcoal rot | *Macrophomina phaseolina* |
| Corn common rust | *Puccinia sorghi* |
| Corn southern rust | *Puccinia polysora* |
| Corn tropical rust | *Physopella pallescens, P. zeae* = *Angiospora zeae* |
| *Corticium* ear rot | *Thanatephorus cucumeris* = *Corticium sasakii* |
| Cotton rust | *Puccinia schedonnardi* |
| Cotton southwestern rust | *Puccinia cacabata* |
| Cotton tropical rust | *Phakopsora gossypii* |
| Crazy top downy mildew | *Sclerophthora macrospora* = *S. macrospora* |
| *Curvularia* leaf spot | *Curvularia clavata, C. eragrostidis,* = *C. maculans* (teleomorph: *Cochliobolus eragrostidis*), *Curvularia inaequalis, C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis, C. tuberculata* (teleomorph: *Cochliobolus tuberculatus*) |
| *Didymella* leaf spot | *Didymella exitialis* |
| *Diplodia* ear rot and stalk rot | *Diplodia frumenti* (teleomorph: *Botryosphaeria festucae*) |
| *Diplodia* ear rot, stalk rot, seed rot and seedling blight | *Diplodia maydis* = *Stenocarpella maydis* |
| *Diplodia* leaf spot or leaf streak | *Stenocarpella macrospora* = *Diplodia macrospore* |
| Grape leaf Downey mildew | *Plasmopara viticola* |
| Dry ear rot (cob, kernel and stalk rot) | *Nigrospora oryzae* (teleomorph: *Khuskia oryzae*) |
| Ear rots, minor | *Aspergillus glaucus, A. niger, Aspergillus* spp., *Cunninghamella* sp., *Curvularia pallescens, Doratomyces stemonitis* = *Cephalotrichum stemonitis, Fusarium culmorum, Gonatobotrys simplex, Pithomyces maydicus, Rhizopus microsporus, R. stolonifer* = *R. nigricans, Scopulariopsis brumptii* |
| epitea | *Melampsora larici* |
| Ergot (horse's tooth, diente del caballo) | *Claviceps gigantea* (anamorph: *Sphacelia* sp.) |
| Eyespot | *Aureobasidium zeae* = *Kabatiella zeae* |
| *Fusarium* ear and stalk rot | *Fusarium subglutinans* = *F. moniliforme* var. *subglutinans* |
| *Fusarium* kernel, root and stalk rot, seed rot and seedling blight | *Fusarium moniliforme* (teleomorph: *Gibberella fujikuroi*) |
| *Fusarium* stalk rot, seedling root rot | *Fusarium avenaceum* (teleomorph: *Gibberella avenacea*) |
| *Gibberella* ear and stalk rot | *Gibberella zeae* (anamorph: *Fusarium graminearum*) |
| Gray ear rot | *Botryosphaeria zeae* = *Physalospora zeae* (anamorph: *Macrophoma zeae*) |
| Gray leaf spot (*Cercospora*) | *Cercospora sorghi* = *C. sorghi* var. *maydis, C. zeae-maydis* leaf spot) |
| Green ear downy mildew | *Sclerospora graminicola* |
| *Helminthosporium* ear rot (race 1) | *Bipolaris zeicola* = *Helminthosporium carbonum* |
| *Helminthosporium* root rot | *Exserohilum pedicellatum* = *Helminthosporium pedicellatum* (teleomorph: *Setosphaeria*) |
| *Hormodendrum* ear rot (*Cladosporium* rot) | *Cladosporium cladosporioides* = *Hormodendrum cladosporioides, C. herbarum* (teleomorph: *Mycosphaerella tassiana*) |
| *Hyalothyridium* leaf spot | *Hyalothyridium maydis* |
| Java downy mildew | *Peronosclerospora maydis* = *Sclerospora maydis* |
| Late wilt | *Cephalosporium maydis* |
| Leaf (brown) rust | *Puccinia recondita* (anamorph: *Aecidium clematitis*) |
| Leaf spots, minor | *Alternaria alternata, Ascochyta maydis, A. tritici, A. zeicola, Bipolaris victoriae* = *Helminthosporium victoriae* (teleomorph: *Cochliobolus victoriae*), *C. sativus* (anamorph: *Bipolaris sorokiniana* = *H. Exserohilum maydis, Leptothyrium zeae, Ophiosphaerella herpotricha, Setosphaeria prolata*) *Graphium penicillioides, Leptosphaeria prolatum* = *Drechslera prolata* (teleomorph: *sorokinianum* = *H. sativum*), *Epicoccum nigrum*, (anamorph: *Scolecosporiella* sp.), *Paraphaeosphaeria michotii, Phoma* sp., *Septoria zeae, S. zeicola, S. zeina* |

TABLE 6-continued

Fungal pests

| Disease | Causative Agent |
| --- | --- |
| Rust fungi | *Puccinia veronicae-longifoliae* |
| Musk rose rust | *Phragmidium rosae-moschatae* |
| Multiflora rose rust | *Phragmidium rosae-multiflorae* |
| Northern corn leaf blight | *Exaerohilum turcicum* = *Helminthosporium turcicum*, *Setosphaeria turcica* |
| Northern corn leaf spot | *Cochliobolus carbonum* |
| Oat crown rust | *Puccinia coronate* |
| Oat stem Rust | *Puccinia graminis* |
| Peanut rust | *Puccinia arachidis* |
| *Penicillium* ear rot (blue eye, blue mold) | *Penicillium* spp., *P. chrysogenum*, *P. expansum*, *P. oxalicum* |
| Bay willow-larch rust | *Melampsora larici-pentandrae* |
| *Phaeocytostroma* stalk rot and root rot | *Phaeocytostroma ambiguum*, *Phaeocytosporella zeae* |
| *Phaeosphaeria* leaf spot | *Phaeosphaeria maydis*, *Sphaerulina maydis* |
| Philippine downy mildew | *Peronosclerospora philippinensis* = *Sclerospora philippinensis* |
| *Physalospora* ear rot | *Botryosphaeria Botryosphaeria festucae* = *Physalospora zeicola*, (anamorph: *Diplodia frumenti*) |
| Potato common rust | *Puccinia pittierianap* |
| Potato deforming rust | *Aecidium cantensis* |
| Cereals and grasses Powdery mildew | *Erysiphe graminis* |
| Rose Powdery mildew | *Sphaerotheca pannosa* |
| Wheat Powdery mildew | *Blumeria graminis* f. sp. *tritici*, |
| Barley Powdery mildew | *Blumeria graminis* f. sp. *hordei* |
| Grape Powdery mildew | *Microsphaera diffusa* |
| Legume Powdery mildew | *Erysiphe necator* (or *Uncinula necator*) |
| Grape Powdery mildew | *Leveillula taurica*, or *Oidiopsis taurica* |
| Onion Powdery mildew | *Podosphaera leucotricha* |
| Apple Powdery mildew | *Podosphaera xanthii*, *Erysiphe cichoracearum*, *Podosphaera fusca*, *Leveillula taurica* |
| Cucurbits Powdery mildew | *Microsphaera syringae* |
| Lilacs Powdery mildew | *Podosphaera aphanis*, *Geum rivale* |
| Strawberry Powdery mildew | *Erysiphe berberidis* |
| Hawthorn Powdery mildew | *Podosphaera oxyacanthae* |
| Gooseberry Powdery mildew | *Sphaerotheca mors-uvae* |
| Purple leaf sheath | Hemiparasitic bacteria and fungi |
| *Pyrenochaeta* stalk rot and root rot | *Phoma terrestris*, *Pyrenochaeta terrestris* |
| *Pythium* root rot | *Pythium* spp., *P. arrhenomanes*, *P. graminicola* |
| *Pythium* stalk rot | *Pythium aphanidermatum* = *P. butleri* L. |
| Red kernel disease (ear mold, leaf and seed rot) | *Epicoccum nigrum* |
| *Rhizoctonia* ear rot | *Rhizoctonia zeae* (teleomorph: *Waitea circinata*) |
| *Rhizoctonia* root rot and stalk rot | *Rhizoctonia solani*, *Rhizoctonia zeae* |
| Root rots, minor | *Alternaria alternata*, *Cercospora sorghi*, *Dictochaeta fertilis*, *Fusarium acuminatum* (teleomorph: *Gibberella acuminate*), *F. equiseti* (teleomorph: *G. intricans*), *F. oxysporum*, *F. pallidoroseum*, *F. poae*, *F. roseum*, *F. cyanogena*, (anamorph: *F. sulphureum*), *Microdochium bolleyi*, *Mucor* sp., *Periconia circinata*, *Phytophthora cactorum*, *P. drechsleri*, *P. nicotianae* var. *parasitica*, *Rhizopus arrhizus* |
| *Rostratum* leaf spot (leaf disease, ear and, stalk rot) | *Setosphaeria rostrata*, *Helminthosporium* (anamorph: *Exserohilum rostratum* = *Helminthosporium rostratum*) |
| rugosae | *Phragmidium rosae* |
| Rust, common corn | *Puccinia sorghi* |
| Rust, southern corn | *Puccinia polysora* |
| Rust, tropical corn | *Physopella pallescens*, *P. zeae* = *Angiospora zeae* |
| sativae | *Balansia oryzae* |
| *Sclerotium* ear rot (southern blight) | *Sclerotium rolfsii* (teleomorph: *Athelia rolfsii*) |
| Seed rot-seedling blight | *Bipolaris sorokiniana*, *B. zeicola* = *Helminthosporium carbonum*, *Diplodia maydis*, *Exserohilum pedicellatum*, *Exserohilum turcicum* = *Helminthosporium turcicum*, *Fusarium avenaceum*, *F. culmorum*, *F. moniliforme*, *Gibberella zeae* (anamorph: *F. graminearum*), *Macrophomina phaseolina*, *Penicillium* spp., *Phomopsis* sp., *Pythium* spp., *Rhizoctonia solani*, *R. zeae*, *Sclerotium rolfsii*, *Spicaria* sp. |
| *Selenophoma* leaf spot | *Selenophoma* sp. |
| Sheath rot | *Gaeumannomyces graminis* |
| Shuck rot | *Myrothecium gramineum* |
| sieboldii | *Hamaspora rubi* |
| Silage mold | *Monascus purpureus*, *M. rubber* |
| Smut, common | *Ustilago zeae* = *U. maydis* |
| Smut, false | *Ustilaginoidea virens* |

TABLE 6-continued

Fungal pests

| Disease | Causative Agent |
| --- | --- |
| Smut, head | *Sphacelotheca reiliana* = *Sporisorium holci-sorghi* |
| *Sorghum* downy mildew | *Peronosclerospora sorghi* = *Sclerospora sorghi* |
| Southern corn leaf blight and stalk rot | *Cochliobolus heterostrophus* (anamorph: *Bipolaris maydis* = *Helminthosporium maydis*) |
| Southern leaf spot | *Stenocarpella macrospora* = *Diplodia macrospora* |
| Soybean rust | *Phakopsora pachyrhizi* |
| *Spontaneum* downy mildew | *Peronosclerospora spontanea* = *Sclerospora spontanea* |
| Stalk rots, minor | *Cercospora sorghi*, *Fusarium episphaeria*, *F. merismoides*, *F. oxysportum*, *F. poae*, *F. roseum*, *F. solani* (teleomorph: *Nectria haematococca*), *F. tricinctum*, *Mariannaea elegans*, *Mucor* sp., *Rhopographus zeae*, *Spicaria* sp. |
| Stem rust | *Puccinia graminis* = *P. graminis* f. sp. *secalis* |
| Storage rots | *Aspergillus* spp., *Penicillium* spp. and other fungi |
| Sugarcane common rust | *Puccinia melanocephala* = *P. eriantha* |
| Sugarcane downy mildew | *Peronosclerospora sacchari* = *Sclerospora sacchari* |
| Tar spot | *Phyllachora maydis* |
| thunbergii | *Phragmidium rubi* |
| *Trichoderma* ear rot and root rot | *Trichoderma viride* = *T. lignorum* (teleomorph: *Hypocrea* sp.) |
| Wheat leaf (brown) rust | *Puccinia triticina* = *P. Recondita* f. Sp. *tritici* = *P. tritici-duri* |
| Wheat stem (black) rust | *Puccinia graminis* = *P. graminis* f. sp. *tritici* |
| Wheat stripe (yellow) rust | *Puccinia striiformis* (anamorph: *P. uredoglumarum*) |
| White ear rot, root and stalk rot | *Stenocarpella maydis* = *Diplodia zeae* |
| Yellow leaf blight | *Ascochyta ischaemi*, *Phyllosticta maydis* (teleomorph: *Mycosphaerella zeae-maydis*) |
| Zonate leaf spot | *Gloeocercospora sorghi* | ii. Bacteria

The PMP compositions and related methods can be useful for decreasing the fitness of a bacterium, e.g., to prevent or treat a bacterial infection in a plant. Included are methods for delivering a PMP composition to a bacterium by contacting the bacteria with the PMP composition. Additionally or alternatively, the methods include delivering the biopesticide to a plant at risk of or having a bacterial infection, by contacting the plant with the PMP composition.

The PMP compositions and related methods are suitable for delivery to bacteria, or a plant infected therewith, including any bacteria described further below. For example, the bacteria may be one belonging to Actinobacteria or Proteobacteria, such as bacteria in the families of the Burkholderiaceae, Xanthomonadaceae, Pseudomonadaceae, Enterobacteriaceae, Microbacteriaceae, and Rhizobiaceae.

In some instances the bacteria is a bacterial species capable of genetic transformation (e.g., *Agrobacterium tumefaciens* or other *Agrobacterium* spp., *Sinorhizobium* (=Ensifer) sp., *Mesorhizobium*, sp., *Bradyrhizobium* sp., *Azobacter* sp., *Phyllobacter* sp.), or capable of plant rhizosphere colonization or root nodulation (e.g., *Sinorhizobium* (=*Ensifer*) sp., *Mesorhizobium*, sp., *Azorhizobium* sp., *Bradyrhizobium* sp., *Rhizobium* sp.).

In some instances, the bacteria is an *Acidovorax avenae* subsp., including e.g., *Acidovorax avenae* subsp. *avenae* (=*Pseudomonas avenae* subsp. *avenae*), *Acidovorax avenae* subsp. *cattleyae* (=*Pseudomonas cattleyae*), or *Acidovorax avenae* subsp. *citrulli* (=*Pseudomonas pseudoalcaligenes* subsp. *citrulli, Pseudomonas avenae* subsp. *citrulli*)).

In some instances, the bacterium is a *Burkholderia* spp., including e.g., *Burkholderia andropogonis* (=*Pseudomonas andropogonis, Pseudomonas woodsii*), *Burkholderia caryophylli* (=*Pseudomonas caryophylli*), *Burkholderia cepacia* (=*Pseudomonas cepacia*), *Burkholderia gladioli* (=*Pseudomonas gladioli*), *Burkholderia gladioli* pv. *agaricicola* (=*Pseudomnas gladioli* pv. *agaricicola*), *Burkholderia gladioli* pv. *alliicola* (i.e., *Pseudomonas gladioli* pv. *alliicola*), *Burkholderia gladioli* pv. *gladioli* (i.e., *Pseudomonas gladioli, Pseudomonas gladioli* pv. *gladioli*), *Burkholderia glumae* (i.e., *Pseudomonas glumae*), *Burkholderia plantarii* (i.e., *Pseudomonas plantarii*), *Burkholderia solanacearum* (i.e., *Ralstonia solanacearum*), or *Ralstonia* spp.

In some instances, the bacterium is a *Liberibacter* spp., including Candidatus *Liberibacter* spec., including e.g., Candidatus *Liberibacter asiaticus, Liberibacter africanus* (Laf), *Liberibacter americanus* (Lam), *Liberibacter asiaticus* (Las), *Liberibacter europaeus* (Leu), *Liberibacter psyllaurous*, or *Liberibacter solanacearum* (Lso).

In some instances, the bacterium is a *Corynebacterium* spp. including e.g., *Corynebacterium fascians, Corynebacterium flaccumfaciens* pv. *flaccumfaciens, Corynebacterium michiganensis, Corynebacterium michiganense* pv. *tritici, Corynebacterium michiganense* pv. *nebraskense*, or *Corynebacterium sepedonicum.*

In some instances, the bacterium is a *Erwinia* spp. including e.g., *Erwinia amylovora, Erwinia ananas, Erwinia carotovora* (i.e., *Pectobacterium carotovorum*), *Erwinia carotovora* subsp. *atroseptica, Erwinia carotovora* subsp. *carotovora, Erwinia chrysanthemi, Erwinia chrysanthemi* pv. *zeae, Erwinia dissolvens, Erwinia herbicola, Erwinia rhapontic, Erwinia stewartiii, Erwinia tracheiphila*, or *Erwinia uredovora.*

In some instances, the bacterium is a *Pseudomonas syringae* subsp., including e.g., *Pseudomonas syringae* pv. *actinidiae* (Psa), *Pseudomonas syringae* pv. *atrofaciens, Pseudomonas syringae* pv. *coronafaciens, Pseudomonas syringae* pv. *glycinea, Pseudomonas syringae* pv. *lachrymans, Pseudomonas syringae* pv. *maculicola Pseudomonas syringae* pv. *papulans, Pseudomonas syringae* pv. *striafaciens, Pseudomonas syringae* pv. *syringae, Pseudomonas syringae* pv. tomato, or *Pseudomonas syringae* pv. *tabaci.*

In some instances, the bacterium is a *Streptomyces* spp., including e.g., *Streptomyces acidiscabies, Streptomyces albidoflavus, Streptomyces candidus* (i.e., *Actinomyces candidus*), *Streptomyces caviscabies, Streptomyces collinus, Streptomyces europaeiscabiei, Streptomyces intermedius,*

*Streptomyces ipomoeae, Streptomyces luridiscabiei, Streptomyces niveiscabiei, Streptomyces puniciscabiei, Streptomyces retuculiscabiei, Streptomyces scabiei, Streptomyces scabies, Streptomyces setonii, Streptomyces steliiscabiei, Streptomyces turgidiscabies,* or *Streptomyces wedmorensis.*

In some instances, the bacterium is a *Xanthomonas axonopodis* subsp., including e.g., *Xanthomonas axonopodis* pv. *alfalfae* (=*Xanthomonas alfalfae*), *Xanthomonas axonopodis* pv. *aurantifolii* (=*Xanthomonas fuscans* subsp. *aurantifolii*), *Xanthomonas axonopodis* pv. *allii* (=*Xanthomonas campestris* pv. *allii*), *Xanthomonas axonopodis* pv. *axonopodis, Xanthomonas axonopodis* pv. *bauhiniae* (=*Xanthomonas campestris* pv. *bauhiniae*), *Xanthomonas axonopodis* pv. *begoniae* (=*Xanthomonas campestris* pv. *begoniae*), *Xanthomonas axonopodis* pv. *betlicola* (=*Xanthomonas campestris* pv. *betlicola*), *Xanthomonas axonopodis* pv. *biophyti* (=*Xanthomonas campestris* pv. *biophyti*), *Xanthomonas axonopodis* pv. *cajani* (=*Xanthomonas campestris* pv. *cajani*), *Xanthomonas axonopodis* pv. *cassavae* (=*Xanthomonas cassavae, Xanthomonas campestris* pv. *cassavae*), *Xanthomonas axonopodis* pv. *cassiae* (=*Xanthomonas campestris* pv. *cassiae*), *Xanthomonas axonopodis* pv. *citri* (=*Xanthomonas citri*), *Xanthomonas axonopodis* pv. *citrumelo* (=*Xanthomonas alfalfae* subsp. *citrumelonis*), *Xanthomonas axonopodis* pv. *clitoriae* (=*Xanthomonas campestris* pv. *clitoriae*), *Xanthomonas axonopodis* pv. *coracanae* (=*Xanthomonas campestris* pv. *coracanae*), *Xanthomonas axonopodis* pv. *cyamopsidis* (=*Xanthomonas campestris* pv. *cyamopsidis*), *Xanthomonas axonopodis* pv. *desmodii* (=*Xanthomonas campestris* pv. *desmodii*), *Xanthomonas axonopodis* pv. *desmodiigangetici* (=*Xanthomonas campestris* pv. *desmodiigangetici*), *Xanthomonas axonopodis* pv. *desmodiilaxiflori* (=*Xanthomonas campestris* pv. *desmodiilaxiflon*), *Xanthomonas axonopodis* pv. *desmodiirotundifolii* (=*Xanthomonas campestris* pv. *desmodiirotundifolii*), *Xanthomonas axonopodis* pv. *dieffenbachiae* (=*Xanthomonas campestris* pv. *dieffenbachiae*), *Xanthomonas axonopodis* pv. *erythrinae* (=*Xanthomonas campestris* pv. *erythrinae*), *Xanthomonas axonopodis* pv. *fascicularis* (=*Xanthomonas campestris* pv. *fascicularis*), *Xanthomonas axonopodis* pv. *glycines* (=*Xanthomonas campestris* pv. *glycines*), *Xanthomonas axonopodis* pv. *khayae* (=*Xanthomonas campestris* pv. *khayae*), *Xanthomonas axonopodis* pv. *Iespedezae* (=*Xanthomonas campestris* pv. *Iespedezae*), *Xanthomonas axonopodis* pv. *maculifoliigardeniae* (=*Xanthomonas campestris* pv. *maculifoliigardeniae*), *Xanthomonas axonopodis* pv. *malvacearum* (=*Xanthomonas citri* subsp. *malvacearum*), *Xanthomonas axonopodis* pv. *manihotis* (=*Xanthomonas campestris* pv. *manihotis*), *Xanthomonas axonopodis* pv. *martyniicola* (=*Xanthomonas campestris* pv. *martyniicola*), *Xanthomonas axonopodis* pv. *melhusii* (=*Xanthomonas campestris* pv. *melhush*), *Xanthomonas axonopodis* pv. *nakataecorchori* (=*Xanthomonas campestris* pv. *nakataecorchon*), *Xanthomonas axonopodis* pv. *passiflorae* (=*Xanthomonas campestris* pv. *passiflorae*), *Xanthomonas axonopodis* pv. *patelii* (=*Xanthomonas campestris* pv. *pateli*), *Xanthomonas axonopodis* pv. *pedalii* (=*Xanthomonas campestris* pv. *pedalii*), *Xanthomonas axonopodis* pv. *phaseoli* (=*Xanthomonas campestris* pv. *phaseoli, Xanthomonas phaseoli*), *Xanthomonas axonopodis* pv. *phaseoli* var. *fuscans* (=*Xanthomonas fuscans*), *Xanthomonas axonopodis* pv. *phyllanthi* (=*Xanthomonas campestris* pv. *phyllanthi*), *Xanthomonas axonopodis* pv. *physalidicola* (=*Xanthomonas campestris* pv. *physalidicola*), *Xanthomonas axonopodis* pv. *poinsettiicola* (=*Xanthomonas campestris* pv. *poinsettiicola*), *Xanthomonas axonopodis* pv. *punicae* (=*Xanthomonas campestris* pv. *punicae*), *Xanthomonas axonopodis* pv. *rhynchosiae* (=*Xanthomonas campestris* pv. *rhynchosiae*), *Xanthomonas axonopodis* pv. *ricini* (=*Xanthomonas campestris* pv. *ricini*), *Xanthomonas axonopodis* pv. *sesbaniae* (=*Xanthomonas campestris* pv. *sesbaniae*), *Xanthomonas axonopodis* pv. *tamarindi* (=*Xanthomonas campestris* pv. *tamarindi*), *Xanthomonas axonopodis* pv. *vasculorum* (=*Xanthomonas campestris* pv. *vasculorum*), *Xanthomonas axonopodis* pv. *vesicatoria* (=*Xanthomonas campestris* pv. *vesicatoria, Xanthomonas vesicatoria*), *Xanthomonas axonopodis* pv. *vignaeradiatae* (=*Xanthomonas campestris* pv. *vignaeradiatae*), *Xanthomonas axonopodis* pv. *vignicola* (=*Xanthomonas campestris* pv. *vignicola*), or *Xanthomonas axonopodis* pv. *vitians* (=*Xanthomonas campestris* pv. *vitians*).

In some instances, the bacterium is *Xanthomonas campestris* pv. *musacearum, Xanthomonas campestris* pv. *pruni* (=*Xanthomonas arboricola* pv. *pruni*), or Xanthomonas *fragariae.*

In some instances, the bacteria is a *Xanthomonas translucens* supsp. (=*Xanthomonas campestris* pv. *hordei*) including e.g., *Xanthomonas translucens* pv. *arrhenatheri* (=*Xanthomonas campestris* pv. *arrhenathen*), *Xanthomonas translucens* pv. *cerealis* (=*Xanthomonas campestris* pv. *cerealis*), *Xanthomonas translucens* pv. *graminis* (=*Xanthomonas campestris* pv. *graminis*), *Xanthomonas translucens* pv. *phlei* (=*Xanthomonas campestris* pv. *phlei*), *Xanthomonas translucens* pv. *phleipratensis* (=*Xanthomonas campestris* pv. *phleipratensis*), *Xanthomonas translucens* pv. *poae* (=*Xanthomonas campestris* pv. *poae*), *Xanthomonas translucens* pv. *secalis* (=*Xanthomonas campestris* pv. *secalis*), *Xanthomonas translucens* pv. *translucens* (=*Xanthomonas campestris* pv. *translucens*), or *Xanthomonas translucens* pv. *undulosa* (=*Xanthomonas campestris* pv. *undulosa*).

In some instances, the bacterium is a *Xanthomonas oryzae* supsp., *Xanthomonas oryzae* pv. *oryzae* (=*Xanthomonas campestris* pv. *oryzae*), or Xanthomonas *oryzae* pv. *oryzicola* (=*Xanthomonas campestris* pv. *oryzicola*).

In some instances, the bacterium is a *Xylella fastidiosa* from the family of Xanthomonadaceae.

Table 7 shows further examples of bacteria, and diseases associated therewith, that can be treated or prevented using the PMP composition and related methods described herein.

TABLE 7

| Disease | Causative Agent |
| --- | --- |
| Bacterial leaf blight and stalk rot | *Pseudomonas avenae* subsp. *avenae* |
| Bacterial leaf spot | *Xanthomonas campestris* pv. *holcicola* |
| Bacterial stalk rot | *Enterobacter dissolvens* = *Erwinia dissolvens* |
| Bacterial stalk and top rot | *Erwinia carotovora* subsp. *carotovora, Erwinia chrysanthemi* pv. *Zeae* |

TABLE 7-continued

| Bacterial pests | |
|---|---|
| Disease | Causative Agent |
| Bacterial stripe | *Pseudomonas andropogonis* |
| Chocolate spot | *Pseudomonas syringae* pv. *Coronafaciens* |
| Goss's bacterial wilt blight (leaf freckles and wilt) | *Clavibacter michiganensis* subsp. *nebraskensis* = *Cornebacterium michiganense* pv. *Nebraskense* |
| *Holcus* spot | *Pseudomonas syringae* pv. *Syringae* |
| Purple leaf sheath | Hemiparasitic bacteria |
| Seed rot-seedling blight | *Bacillus subtilis* |
| Stewart's disease (bacterial wilt) | *Pantoea stewartii* = *Erwinia stewartii* |
| Corn stunt (Mesa Central or Rio Grande stunt) | Achapparramiento, stunt, *Spiroplasma kunkelii* |
| Soft rot | *Dickeya dianthicola* |
| Soft rot | *Dickeya solani* |
| Fire blight | *Erwinia amylovora* |
| Soft rot | *P. atrosepticum* |
| Soft rot | *Pectobacterium carotovorum* ssp. *carotovorum* |
| Soft rot | *Pectobacterium wasabiae* |
| Bacterial blight | *Pseudomonas syringae* pv. *Porri* and pv. *Tomato* |
| Brown blotch Disease | *Pseudomonas tolaasii* |
| Bacterial wilt | *Ralstonia solanacearum* |
| Bacteria wilt | *Ralstonia solanacearum* |
| Common scab | *Streptomyces scabies* |
| Common scab | *Streptomyces scabies* |
| *Xanthomonas*leaf blight of onion | *Xanthomonas axonopodis* pv. *allii* |
| Asiatic citrus canker | *Xanthomonas axonopodis* pv. *citri* |
| *Citrus* bacterial spot | *Xanthomonas axonopodis* pv. *citrumelo* |
| Bacterial spot | *Xanthomonas campestris* pv. *vesicatoria* |
| Pierce's Disease | *Xylella fastidiosa* | iii. Arthropods

The PMP compositions and related methods can be useful for decreasing the fitness of an insect, e.g., to prevent or treat an insect infestation in a plant. The term "insect" includes any organism belonging to the phylum Arthropoda and to the class Insecta or the class Arachnida, in any stage of development, i.e., immature and adult insects. Included are methods for delivering a PMP composition to an insect by contacting the insect with the PMP composition. Additionally or alternatively, the methods include delivering the biopesticide to a plant at risk of or having an insect infestation, by contacting the plant with the PMP composition.

The PMP compositions and related methods are suitable for preventing or treating infestation by an insect, or a plant infested therewith, including insects belonging to the following orders: Acari, Araneae, Anoplura, Coleoptera, Collembola, Dermaptera, Dictyoptera, Diplura, Diptera (e.g., spotted-wing *Drosophila*), Embioptera, Ephemeroptera, Grylloblatodea, Hemiptera (e.g., aphids, Greenhous whitefly), Homoptera, Hymenoptera, Isoptera, Lepidoptera, Mallophaga, Mecoptera, Neuroptera, Odonata, Orthoptera, Phasmida, Plecoptera, Protura, Psocoptera, Siphonaptera, Siphunculata, Thysanura, Strepsiptera, Thysanoptera, Trichoptera, or Zoraptera.

In some instances, the insect is from the class Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia graminum*, *Bryobia praetiosa*, *Centruroides* spp., *Chorioptes* spp., *Dermanyssus gallinae*, *Dermatophagoides pteronyssinus*, *Dermatophagoides farinae*, *Dermacentor* spp., *Eotetranychus* spp., *Epitrimerus pyri*, *Eutetranychus* spp., *Eriophyes* spp., *Glycyphagus domesticus*, *Halotydeus destructor*, *Hemitarsonemus* spp., *Hyalomma* spp., *Ixodes* spp., *Latrodectus* spp., *Loxosceles* spp., *Metatetranychus* spp., *Neutrombicula autumnalis*, *Nuphersa* spp., *Oligonychus* spp., *Ornithodorus* spp., *Ornithonyssus* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Steneotarsonemus* spp., *Steneotarsonemus spinki*, *Tarsonemus* spp., *Tetranychus* spp., *Trombicula alfreddugesi*, *Vaejovis* spp., or *Vasates lycopersici*.

In some instances, the insect is from the class Chilopoda, for example, *Geophilus* spp. or *Scutigera* spp.

In some instances, the insect is from the order Collembola, for example, *Onychiurus armatus*.

In some instances, the insect is from the class Diplopoda, for example, *Blaniulus guttulatus*; from the class Insecta, e.g. from the order Blattodea, for example, *Blattella asahinai*, *Blattella germanica*, *Blatta orientalis*, *Leucophaea maderae*, *Panchlora* spp., *Parcoblatta* spp., *Periplaneta* spp., or *Supella longipalpa*.

In some instances, the insect is from the order Coleoptera, for example, *Acalymma vittatum*, *Acanthoscelides obtectus*, *Adoretus* spp., *Agelastica alni*, *Agriotes* spp., *Alphitobius diaperinus*, *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptolestes ferrugineus*, *Cryptorhynchus lapathi*, *Cylindrocopturus* spp., *Dermestes* spp., *Diabrotica* spp. (e.g., corn rootworm), *Dichocrocis* spp., *Dicladispa armigera*, *Diloboderus* spp., *Epilachna* spp., *Epitrix* spp., *Faustinus* spp., *Gibbium psylloides*, *Gnathocerus cornutus*, *Hellula undalis*, *Heteronychus arator*, *Heteronyx* spp., *Hylamorpha elegans*, *Hylotrupes bajulus*, *Hypera postica*, *Hypomeces squamosus*, *Hypothenemus* spp., *Lachnosterna consanguinea*, *Lasioderma serricorne*, *Latheticus oryzae*, *Lathridius* spp., *Lema* spp., *Leptinotarsa decemlineata*, *Leucoptera* spp., *Lissorhoptrus oryzophilus*, *Lixus* spp., *Luperodes* spp., *Lyc-* tus spp., *Megascelis* spp., *Melanotus* spp., *Meligethes aeneus*, *Melolontha* spp., *Migdolus* spp., *Monochamus* spp., *Naupactus xanthographus*, *Necrobia* spp., *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllophaga helleri*, *Phyllotreta* spp., *Popillia japonica*, *Premnotrypes* spp., *Prostephanus truncatus*, *Psylliodes* spp., *Ptinus* spp., *Rhizobius ventralis*, *Rhizopertha dominica*, *Sitophilus* spp., *Sitophilus oryzae*, *Sphenophorus* spp., *Stegobium paniceum*, *Sternechus* spp., *Symphyletes* spp., *Tanymecus* spp., *Tenebrio molitor*, *Tenebrioides mauretanicus*, *Tribolium* spp., *Trogoderma* spp., *Tychius* spp., *Xylotrechus* spp., or *Zabrus* spp.

In some instances, the insect is from the order Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Calliphora vicina*, *Ceratitis capitata*, *Chironomus* spp., *Chrysomyia* spp., *Chrysops* spp., *Chrysozona pluvialis*, *Cochliomyia* spp., *Contarinia* spp., *Cordylobia anthropophaga*, *Cricotopus sylvestris*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gasterophilus* spp., *Glossina* spp., *Haematopota* spp., *Hydrellia* spp., *Hydrellia griseola*, *Hylemya* spp., *Hippobosca* spp., *Hypoderma* spp., *Liriomyza* spp., *Lucilia* spp., *Lutzomyia* spp., *Mansonia* spp., *Musca* spp. (e.g., *Musca domestica*), *Oestrus* spp., *Oscinella frit*, *Paratanytarsus* spp., *Paralauterborniella subcincta*, *Pegomyia* spp., *Phlebotomus* spp., *Phorbia* spp., *Phormia* spp., *Piophila casei*, *Prodiplosis* spp., *Psila rosae*, *Rhagoletis* spp., *Sarcophaga* spp., *Simulium* spp., *Stomoxys* spp., *Tabanus* spp., *Tetanops* spp., or *Tipula* spp.

In some instances, the insect is from the order Heteroptera, for example, *Anasa tristis*, *Antestiopsis* spp., *Boisea* spp., *Blissus* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptocorisa varicornis*, *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., or *Triatoma* spp.

In some instances, the insect is from the order Homiptera, for example, *Acizzia acaciaebaileyanae*, *Acizzia dodonaeae*, *Acizzia uncatoides*, *Acrida turrita*, *Acyrthosipon* spp., *Acrogonia* spp., *Aeneolamia* spp., *Agonoscena* spp., *Aleyrodes proletella*, *Aleurolobus barodensis*, *Aleurothrixus floccosus*, *Allocaridara malayensis*, *Amrasca* spp., *Anuraphis cardui*, *Aonidiella* spp., *Aphanostigma pini*, *Aphis* spp. (e.g., *Apis gossypii*), *Arboridia apicalis*, *Arytainilla* spp., *Aspidiella* spp., *Aspidiotus* spp., *Atanus* spp., *Aulacorthum solani*, *Bemisia tabaci*, *Blastopsylla occidentalis*, *Boreioglycaspis melaleucae*, *Brachycaudus helichrysi*, *Brachycolus* spp., *Brevicoryne brassicae*, *Cacopsylla* spp., *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chondracris rosea*, *Chromaphis juglandicola*, *Chrysomphalus ficus*, *Cicadulina mbila*, *Coccomytilus halli*, *Coccus* spp., *Cryptomyzus ribis*, *Cryptoneossa* spp., *Ctenarytaina* spp., *Dalbulus* spp., *Dialeurodes citri*, *Diaphorina citri*, *Diaspis* spp., *Drosicha* spp., *Dysaphis* spp., *Dysmicoccus* spp., *Empoasca* spp., *Eriosoma* spp., *Erythroneura* spp., *Eucalyptolyma* spp., *Euphyllura* spp., *Euscelis bilobatus*, *Ferrisia* spp., *Geococcus coffeae*, *Glycaspis* spp., *Heteropsylla cubana*, *Heteropsylla spinulosa*, *Homalodisca coagulata*, *Homalodisca vitripennis*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Macrosteles facifrons*, *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nettigonicla spectra*, *Nilaparvata lugens*, *Oncometopia* spp., *Orthezia praelonga*, *Oxya chinensis*, *Pachypsylla* spp., *Parabemisia myricae*, *Paratrioza* spp., *Parlatoria* spp., *Pemphigus* spp., *Pentatomidae* spp. (e.g., *Halyomorpha halys*), *Peregrinus maidis*, *Phenacoccus* spp., *Phloeomyzus passerinii*, *Phorodon humuli*, *Phylloxera* spp., *Pinnaspis aspidistrae*, *Planococcus* spp., *Prosopidopsylla flava*, *Protopulvinaria pyriformis*, *Pseudaulacaspis pentagona*, *Pseudococcus* spp., *Psyllopsis* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoideus titanus*, *Schizaphis graminum*, *Selenaspidus articulatus*, *Sogata* spp., *Sogatella furcifera*, *Sogatodes* spp., *Stictocephala festina*, *Siphoninus phillyreae*, *Tenalaphara malayensis*, *Tetragonocephela* spp., *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*, *Zygina* spp.; from the order Hymenoptera, for example, *Acromyrmex* spp., *Athalia* spp., *Atta* spp., *Diprion* spp., *Hoplocampa* spp., *Lasius* spp., *Monomorium pharaonis*, *Sirex* spp., *Solenopsis invicta*, *Tapinoma* spp., *Urocerus* spp., *Vespa* spp., or *Xeris* spp.

In some instances, the insect is from the order Isopoda, for example, *Armadillidium vulgare*, *Oniscus asellus*, or *Porcellio scaber*.

In some instances, the insect is from the order Isoptera, for example, *Coptotermes* spp., *Cornitermes cumulans*, *Cryptotermes* spp., *Incisitermes* spp., *Microtermes obesi*, *Odontotermes* spp., or *Reticulitermes* spp.

In some instances, the insect is from the order Lepidoptera, for example, *Achroia grisella*, *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Cheimatobia brumata*, *Chilo* spp., *Choristoneura* spp., *Clysia ambiguella*, *Cnaphalocerus* spp., *Cnaphalocrocis medinalis*, *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia* spp., *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis* spp., *Lithophane antennata*, *Lobesia* spp., *Loxagrotis albicosta*, *Lymantria* spp., *Lyonetia* spp., *Malacosoma neustria*, *Maruca testulalis*, *Mamstra brassicae*, *Melanitis leda*, *Mocis* spp., *Monopis obviella*, *Mythimna separata*, *Nemapogon cloacellus*, *Nymphula* spp., *Oiketicus* spp., *Oria* spp., *Orthaga* spp., *Ostrinia* spp., *Oulema oryzae*, *Panolis flammea*, *Parnara* spp., *Pectino-*

*phora* spp., *Perileucoptera* spp., *Phthorimaea* spp., *Phyllocnistis citrella*, *Phyllonorycter* spp., *Pieris* spp., *Platynota stultana*, *Plodia interpunctella*, *Plusia* spp., *Plutella xylostella*, *Prays* spp., *Prodenia* spp., *Protoparce* spp., *Pseudaletia* spp., *Pseudaletia unipuncta*, *Pseudoplusia includens*, *Pyrausta nubilalis*, *Rachiplusia nu*, *Schoenobius* spp., *Scirpophaga* spp., *Scirpophaga innotata*, *Scotia segetum*, *Sesamia* spp., *Sesamia inferens*, *Sparganothis* spp., *Spodoptera* spp., *Spodoptera praefica*, *Stathmopoda* spp., *Stomopteryx subsecivella*, *Synanthedon* spp., *Tecia solanivora*, *Thermesia gemmatalis*, *Tinea cloacella*, *Tinea pellionella*, *Tineola bisselliella*, *Tortrix* spp., *Trichophaga tapetzella*, *Trichoplusia* spp., *Tryporyza incertulas*, *Tuta absoluta*, or *Virachola* spp.

In some instances, the insect is from the order Orthoptera or Saltatoria, for example, *Acheta domesticus*, *Dichroplus* spp., *Gryllotalpa* spp., *Hieroglyphus* spp., *Locusta* spp., *Melanoplus* spp., or *Schistocerca gregaria*.

In some instances, the insect is from the order Phthiraptera, for example, *Damalinia* spp., *Haematopinus* spp., *Linognathus* spp., *Pediculus* spp., *Ptirus pubis*, *Trichodectes* spp.

In some instances, the insect is from the order Psocoptera for example *Lepinatus* spp., or *Liposcelis* spp.

In some instances, the insect is from the order Siphonaptera, for example, *Ceratophyllus* spp., *Ctenocephalides* spp., *Pulex irritans*, *Tunga penetrans*, or *Xenopsylla cheopsis*.

In some instances, the insect is from the order Thysanoptera, for example, *Anaphothrips obscurus*, *Baliothrips biformis*, *Drepanothrips reuteri*, *Enneothrips flavens*, *Frankliniella* spp., *Heliothrips* spp., *Hercinothrips femoralis*, *Rhipiphorothrips cruentatus*, *Scirtothrips* spp., *Taeniothrips cardamomi*, or *Thrips* spp.

In some instances, the insect is from the order Zygentoma (=Thysanura), for example, *Ctenolepisma* spp., *Lepisma saccharina*, *Lepismodes inquilinus*, or *Thermobia domestica*.

In some instances, the insect is from the class Symphyla, for example, *Scutigerella* spp.

In some instances, the insect is a mite, including but not limited to, Tarsonemid mites, such as *Phytonemus pallidus*, *Polyphagotarsonemus latus*, *Tarsonemus bilobatus*, or the like; Eupodid mites, such as *Penthaleus erythrocephalus*, *Penthaleus major*, or the like; Spider mites, such as *Oligonychus shinkajii*, *Panonychus citri*, *Panonychus mori*, *Panonychus ulmi*, *Tetranychus kanzawai*, *Tetranychus urticae*, or the like; Eriophyid mites, such as *Acaphylla theavagrans*, *Aceria tulipae*, *Aculops lycopersici*, *Aculops pelekassi*, *Aculus schlechtendali*, *Eriophyes chibaensis*, *Phyllocoptruta oleivora*, or the like; Acarid mites, such as *Rhizoglyphus robini*, *Tyrophagus putrescentiae*, *Tyrophagus similis*, or the like; Bee brood mites, such as *Varroa jacobsoni*, *Varroa destructor* or the like; Ixodides, such as *Boophilus microplus*, *Rhipicephalus sanguineus*, *Haemaphysalis longicornis*, *Haemophysalis flava*, *Haemophysalis campanulata*, *Ixodes ovatus*, *Ixodes persulcatus*, *Amblyomma* spp., *Dermacentor* spp., or the like; Cheyletidae, such as *Cheyletiella yasguri*, *Cheyletiella blakei*, or the like; Demodicidae, such as *Demodex canis*, *Demodex cati*, or the like; Psoroptidae, such as *Psoroptes ovis*, or the like; Scarcoptidae, such as *Sarcoptes scabiei*, *Notoedres cati*, *Knemidocoptes* spp., or the like.

Table 8 shows further examples of insects that cause infestations that can be treated or prevented using the PMP compositions and related methods described herein.

TABLE 8

Insect pests

| Common Name | Latin name |
|---|---|
| European corn borer | *Ostrinia nubilalis* |
| Corn earworm | *Helicoverpa zea* |
| Beet armyworm | *Spodoptera exigua* |
| Fall armyworm | *Spodoptera frugiperda* |
| Southwestern corn borer | *Diatraea grandiosella* |
| Lesser cornstalk borer | *Elasmopalpus lignosellus* |
| Stalk borer | *Papaipema nebris* |
| Common armyworm | *Pseudaletia unipuncta* |
| Black cutworm | *Agrotis ipsilon* |
| Western bean cutworm | *Striacosta albicosta* |
| Yellowstriped armyworm | *Spodoptera ornithogalli* |
| Western yellowstriped armyworm | *Spodoptera praefica* |
| Southern armyworm | *Spodoptera eridania* |
| Southern armyworm | *Spodoptera eridania* |
| Variegated cutworm | *Peridroma saucia* |
| Stalk borer | *Papaipema nebris* |
| Cabbage looper | *Trichoplusia ni* |
| Tomato pinworm | *Keiferia lycopersicella* |
| Tobacco hornworm | *Manduca sexta* |
| Tomato hornworm | *Manduca quinquemaculata* |
| Imported cabbageworm | *Artogeia rapae* |
| Cabbage butterfly | *Pieris brassicae* |
| Cabbage looper | *Trichoplusia ni* |
| Diamondback moth | *Plutella xylostella* |
| Beet armyworm | *Spodoptera exigua* |
| Common cutworm | *Agrotis segetum* |
| Potato tuberworm | *Phthorimaea operculella* |
| Diamondback moth | *Plutella xylostella* |
| Sugarcane borer | *Diatraea saccharalis* |
| Glassy cutworm | *Crymodes devastator* |
| Dingy cutworm | *Feltia ducens* |
| Claybacked cutworm | *Agrotis gladiaria* |
| Green cloverworm | *Plathypena scabra* |
| Soybean looper | *Pseudoplusia includes* |
| Velvetbean caterpillar | *Anticarsia gemmatalis* |
| Northern corn rootworm | *Coleoptera Diabrotica barberi* |
| Southern corn rootworm | *Diabrotica undecimpunctata* |
| Western corn rootworm | *Diabrotica virgifera* |
| Maize weevil | *Sitophilus zeamais* |
| Colorado potato beetle | *Leptinotarsa decemlineata* |
| Tobacco flea beetle | *Epitrix hirtipennis* |
| Crucifer flea beetle | *Phyllotreta cruciferae* |
| Western black flea beetle | *Phyllotreta pusilia* |
| Pepper weevil | *Anthonomus eugenii* |
| Colorado potato beetle | *Leptinotarsa decemlineata* |
| Potato flea beetle | *Epitrix cucumeris* |
| Wireworms *Melanpotus* spp. | *Hemicrepidus memnonius* |
| Wireworms | *Ceutorhychus assimilis* |
| Cabbage seedpod weevil | *Phyllotreta Cruciferae* |
| Crucifer flea beetle | *Melanolus* spp. |
| Wireworm | *Aeolus mellillus* |
| Wheat wireworm | *Aeolus mancus* |
| Sand wireworm | *Horistonotus uhlerii* |
| Maize billbug | *Sphenophorus maidis* |
| Timothy bilibug | *Sphenophorus zeae* |
| Bluegrass billbug | *Sphenophorus parvulus* |
| Southern corn billbug | *Sphenophorus callosus* |
| White grubs | *Phyllophaga* spp. |
| Corn flea beetle | *Chaetocnema pulicaria* |
| Japanese beetle | *Popillia japonica* |
| Mexican bean beetle | *Epilachna varivestis* |
| Bean leaf beetle | *Cerotoma trifurcate* |
| Blister beetles | *Epicauta pestifera Epicauta lemniscata* |
| Corn leaf aphid | *Homoptera Rhopalosiphum maidis* |
| Corn root aphid | *Anuraphis maidiradicis* |
| Green peach aphid | *Myzus persicae* |
| Potato aphid | *Macrosiphum euphorbiae* |
| Greenhouse whitefly | *Trileurodes vaporariorum* |
| Sweetpotato whitefly | *Bemisia tabaci* |
| Silverleaf whitefly | *Bemisia argentifolii* |
| Cabbage aphid | *Brevicoryne brassicae* |
| Green peach aphid | *Myzus persicae* |
| Potato leafhopper | *Empoasca fabae* |
| Potato psyllid | *Paratrioza cockerelli* |
| Silverleaf whitefly | *Bemisia argentifolii* |

TABLE 8-continued

Insect pests

| Common Name | Latin name |
| --- | --- |
| Sweetpotato whitefly | Bemisia tabaci |
| Carrot aphid | Cavariella aegopodii |
| Cabbage aphid | Brevicoryne brassicae |
| West Indian canefly | Saccharosydne saccharivora |
| Yellow sugarcane aphid | Sipha flava |
| Threecornered alfalfa hopper | Spissistilus festinus |
| Lygus Hesperus | Hemiptera Lygus lineolaris |
| Lygus bug | Lygus rugulipennis |
| Green stink bug | Acrosternum hilare |
| Brown stick bug | Euschistus servus |
| Chinch bug | Blissus leucopterus leucopterus |
| Leafminer | Diptera Liriomyza trifolii |
| Vegetable leafminer | Liriomyza sativae |
| Tomato leafminer | Scrobipalpula absoluta |
| Seedcorn maggot | Delia platura |
| Cabbage maggot | Delia brassicae |
| Cabbage root fly | Delia radicum |
| Carrot rust fly | Psilia rosae |
| Sugarbeet root maggot | Tetanops myopaeformis |
| Differential grasshopper | Orthoptera Melanoplus differentialis |
| Redlegged grasshopper | Melanoplus femurrubrum |
| Twostriped grasshopper | Melanoplus bivittatus | iv. Mollusks

The PMP compositions and related methods can be useful for decreasing the fitness of a mollusk, e.g., to prevent or treat a mollusk infestation in a plant. The term "mollusk" includes any organism belonging to the phylum Mollusca. Included are methods for delivering a PMP composition to a mollusk by contacting the mollusk with the PMP composition. Additionally or alternatively, the methods include delivering the biopesticide to a plant at risk of or having a mollusk infestation, by contacting the plant with the PMP composition.

The PMP compositions and related methods are suitable for preventing or treating infestation by terrestrial Gastropods (e.g., slugs and snails) in agriculture and horticulture. They include all terrestrial slugs and snails which mostly occur as polyphagous pests on agricultural and horticultural crops. For example, the mollusk may belong to the family Achatinidae, Agriolimacidae, Ampullariidae, Arionidae, Bradybaenidae, Helicidae, Hydromiidae, Lymnaeidae, Milacidae, Urocyclidae, or Veronicellidae.

For example, in some instances, the mollusk is *Achatina* spp., *Archachatina* spp. (e.g., *Archachatina marginata*), *Agriolimax* spp., *Anon* spp. (e.g., *A. ater, A. circumscriptus, A. distinctus, A. fasciatus, A. hortensis, A. intermedius, A. rufus, A. subfuscus, A. silvaticus, A. lusitanicus*), *Arliomax* spp. (e.g., *Ariolimax columbianus*), *Biomphalaria* spp., *Bradybaena* spp. (e.g., *B. fruticum*), *Bulinus* spp., *Cantareus* spp. (e.g., *C. asperses*), *Cepaea* spp. (e.g., *C. hortensis, C. nemoralis, C. hortensis*), *Cernuella* spp., *Cochlicella* spp., *Cochlodina* spp. (e.g., *C. laminata*), *Deroceras* spp. (e.g., *D. agrestis, D. empiricorum, D. laeve, D. panornimatum, D. reticulatum*), *Discus* spp. (e.g., *D. rotundatus*), *Euomphalia* spp., *Galba* spp. (e.g., *G. trunculata*), *Helicella* spp. (e.g., *H. itala, H. obvia*), *Helicigona* spp. (e.g., *H. arbustorum*), *Helicodiscus* spp., *Helix* spp. (e.g., *H. aperta, H. aspersa, H. pomatia*), *Limax* spp. (e.g., *L. cinereoniger, L. flavus, L. marginatus, L. maximus, L. tenellus*), *Limicolaria* spp. (e.g., *Limicolaria aurora*), *Lymnaea* spp. (e.g., *L. stagnalis*), *Mesodon* spp. (e.g., *Meson thyroidus*), *Monadenia* spp. (e.g., *Monadenia fidelis*), *Milax* spp. (e.g., *M. gagates, M. marginatus, M. sowerbyi, M. budapestensis*), *Oncomelania* spp., *Neohelix* spp. (e.g., *Neohelix albolabris*), *Opeas* spp., *Otala* spp. (e.g., *Otala lacteal*), *Oxyloma* spp. (e.g., *O. pfeiffen*), *Pomacea* spp. (e.g., *P. canaliculata*), *Succinea* spp., *Tandonia* spp. (e.g., *T. budapestensis, T. sowerbyi*), *Theba* spp., *Vallonia* spp., or *Zonitoides* spp. (e.g., *Z. nitidus*).

v. Nematodes

The PMP compositions and related methods can be useful for decreasing the fitness of a nematode, e.g., to prevent or treat a nematode infestation in a plant. The term "nematode" includes any organism belonging to the phylum Nematoda. Included are methods for delivering a PMP composition to a nematode by contacting the nematode with the PMP composition. Additionally or alternatively, the methods include delivering the biopesticide to a plant at risk of or having a nematode infestation, by contacting the plant with the PMP composition.

The PMP compositions and related methods are suitable for preventing or treating infestation by nematodes that cause damage plants including, for example, *Meloidogyne* spp. (root-knot), *Heterodera* spp., *Globodera* spp., *Pratylenchus* spp., *Helicotylenchus* spp., *Radopholus similis*, *Ditylenchus dipsaci*, *Rotylenchulus reniformis*, *Xiphinema* spp., *Aphelenchoides* spp. and *Belonolaimus longicaudatus*. In some instances, the nematode is a plant parasitic nematodes or a nematode living in the soil. Plant parasitic nematodes include, but are not limited to, ectoparasites such as *Xiphinema* spp., *Longidorus* spp., and *Trichodorus* spp.; semiparasites such as *Tylenchulus* spp.; migratory endoparasites such as *Pratylenchus* spp., *Radopholus* spp., and *Scutellonema* spp.; sedentary parasites such as *Heterodera* spp., *Globodera* spp., and *Meloidogyne* spp., and stem and leaf endoparasites such as *Ditylenchus* spp., *Aphelenchoides* spp., and *Hirshmaniella* spp. Especially harmful root parasitic soil nematodes are such as cystforming nematodes of the genera *Heterodera* or *Globodera*, and/or root knot nematodes of the genus *Meloidogyne*. Harmful species of these genera are for example *Meloidogyne incognita*, *Heterodera glycines* (soybean cyst nematode), *Globodera pallida* and *Globodera rostochiensis* (potato cyst nematode), which species are effectively controlled with the PMP compositions described herein.

However, the use of the PMP compositions described herein is in no way restricted to these genera or species, but also extends in the same manner to other nematodes.

Other examples of nematodes that can be targeted by the methods and compositions described herein include but are not limited to e.g. *Aglenchus agricola*, *Anguina tritici*, *Aphelenchoides arachidis*, *Aphelenchoides fragaria* and the stem and leaf endoparasites *Aphelenchoides* spp. in general, *Belonolaimus gracilis*, *Belonolaimus longicaudatus*, *Belonolaimus nortoni*, *Bursaphelenchus cocophilus*, *Bursaphelenchus eremus*, *Bursaphelenchus xylophilus*, *Bursaphelenchus mucronatus*, and *Bursaphelenchus* spp. in general, *Cacopaurus pestis*, *Criconemella curvata*, *Criconemella onoensis*, *Criconemella ornata*, *Criconemella rusium*, *Criconemella xenoplax* (=*Mesocriconema xenoplax*) and *Criconemella* spp. in general, *Criconemoides femiae*, *Criconemoides onoense*, *Criconemoides ornatum* and *Criconemoides* spp. in general, *Ditylenchus destructor*, *Ditylenchus dipsaci*, *Ditylenchus myceliophagus* and the stem and leaf endoparasites *Ditylenchus* spp. in general, *Dolichodorus heterocephalus*, *Globodera pallida* (=*Heterodera pallida*), *Globodera rostochiensis* (potato cyst nematode), *Globodera solanacearum*, *Globodera tabacum*, *Globodera virginia* and the sedentary, cyst forming parasites *Globodera* spp. in general, *Helicotylenchus digonicus*, *Helicotylenchus dihystera*, *Helicotylenchus erythrine*, *Helicotylenchus multicinctus*, *Helicotylenchus nannus*, *Helicotylen-* chus pseudorobustus and Helicotylenchus spp. in general, Hemicriconemoides, Hemicycliophora arenaria, Hemicycliophora nudata, Hemicycliophora parvana, Heterodera avenae, Heterodera cruciferae, Heterodera glycines (soybean cyst nematode), Heterodera oryzae, Heterodera schachtii, Heterodera zeae and the sedentary, cyst forming parasites Heterodera spp. in general, Hirschmaniella gracilis, Hirschmaniella oryzae Hirschmaniella spinicaudata and the stem and leaf endoparasites Hirschmaniella spp. in general, Hoplolaimus aegyptii, Hoplolaimus califomicus, Hoplolaimus columbus, Hoplolaimus galeatus, Hoplolaimus indicus, Hoplolaimus magnistylus, Hoplolaimus pararobustus, Longidorus africanus, Longidorus breviannulatus, Longidorus elongatus, Longidorus laevicapitatus, Longidorus vineacola and the ectoparasites Longidorus spp. in general, Meloidogyne acronea, Meloidogyne africana, Meloidogyne arenaria, Meloidogyne arenaria thamesi, Meloidogyne artiella, Meloidogyne chitwoodi, Meloidogyne coffeicola, Meloidogyne ethiopica, Meloidogyne exigua, Meloidogyne fallax, Meloidogyne graminicola, Meloidogyne graminis, Meloidogyne hapla, Meloidogyne incognita, Meloidogyne incognita acrita, Meloidogyne javanica, Meloidogyne kikuyensis, Meloidogyne minor, Meloidogyne naasi, Meloidogyne paranaensis, Meloidogyne thamesi and the sedentary parasites Meloidogyne spp. in general, Meloinema spp., Nacobbus aberrans, Neotylenchus vigissi, Paraphelenchus pseudoparietinus, Paratrichodorus allius, Paratrichodorus lobatus, Paratrichodorus minor, Paratrichodorus nanus, Paratrichodorus porosus, Paratrichodorus teres and Paratrichodorus spp. in general, Paratylenchus hamatus, Paratylenchus minutus, Paratylenchus projectus and Paratylenchus spp. in general, Pratylenchus agilis, Pratylenchus alleni, Pratylenchus andinus, Pratylenchus brachyurus, Pratylenchus cerealis, Pratylenchus coffeae, Pratylenchus crenatus, Pratylenchus delattrei, Pratylenchus giibbicaudatus, Pratylenchus goodeyi, Pratylenchus hamatus, Pratylenchus hexincisus, Pratylenchus loosi, Pratylenchus neglectus, Pratylenchus penetrans, Pratylenchus pratensis, Pratylenchus scribneri, Pratylenchus teres, Pratylenchus thornei, Pratylenchus vulnus, Pratylenchus zeae and the migratory endoparasites Pratylenchus spp. in general, Pseudohalenchus minutus, Psilenchus magnidens, Psilenchus tumidus, Punctodera chalcoensis, Quinisulcius acutus, Radopholus citrophilus, Radopholus similis, the migratory endoparasites Radopholus spp. in general, Rotylenchulus borealis, Rotylenchulus parvus, Rotylenchulus reniformis and Rotylenchulus spp. in general, Rotylenchus laurentinus, Rotylenchus macrodoratus, Rotylenchus robustus, Rotylenchus uniformis and Rotylenchus spp. in general, Scutellonema brachyurum, Scutellonema bradys, Scutellonema clathricaudatum and the migratory endoparasites Scutellonema spp. in general, Subanguina radiciola, Tetylenchus nicotianae, Trichodorus cylindricus, Trichodorus minor, Trichodorus primitivus, Trichodorus proximus, Trichodorus similis, Trichodorus sparsus and the ectoparasites Trichodorus spp. in general, Tylenchorhynchus agri, Tylenchorhynchus brassicae, Tylenchorhynchus clarus, Tylenchorhynchus claytoni, Tylenchorhynchus digitatus, Tylenchorhynchus ebriensis, Tylenchorhynchus maximus, Tylenchorhynchus nudus, Tylenchorhynchus vulgaris and Tylenchorhynchus spp. in general, Tylenchulus semipenetrans and the semiparasites Tylenchulus spp. in general, Xiphinema americanum, Xiphinema brevicolle, Xiphinema dimorphicaudatum, Xiphinema index and the ectoparasites Xiphinema spp. in general.

Other examples of nematode pests include species belonging to the family Criconematidae, Belonolaimidae, Hoploaimidae, Heteroderidae, Longidoridae, Pratylenchidae, Trichodoridae, or Anguinidae.

Table 9 shows further examples of nematodes, and diseases associated therewith, that can be treated or prevented using the PMP compositions and related methods described herein.

TABLE 9

Nematode Pests

| Disease | Causative Agent |
| --- | --- |
| Awl | Dolichoderus spp., D. heterocephalus |
| Bulb and stem (Europe) | Ditylenchus dipsaci |
| Burrowing | Radopholus similes R. similis |
| Cyst | Heterodera avenae, H. zeae, H. schachti; Globodera rostochiensis, G. pallida, and G. tabacum; Heterodera trifolii, H. medicaginis, H. ciceri, H. mediterranea, H. cyperi, H. salixophila, H. zeae, H. goettingiana, H. riparia, H. humuli, H. latipons, H. sorghi, H. fici, H. litoralis, and H. turcomanica; Punctodera chalcoensis |
| Dagger | Xiphinema spp., X. americanum, X. Mediterraneum |
| False root-knot | Nacobbus dorsalis |
| Lance | Hoplolaimus spp., H. galeatus |
| Lance, Columbia | Hoplolaimus Columbus |
| Lesion | Pratylenchus spp., P. brachyurus, P. coffeae P. crenatus, P. hexincisus, P. neglectus, P. penetrans, P. scribneri, P. magnica, P. neglectus, P. thornei, P. vulnus, P. zeae |
| Needle | Longidorus spp., L. breviannulatus |
| Others | Hirschmanniella species, Pratylenchoid magnicauda |
| Ring | Criconemella spp., C. ornata |
| Root-knot | Meloidogyne spp., M. arenaria, M. chitwoodi, M. artiellia, M. fallax, M. hapla, M. javanica, M. incognita, M. microtyla, M. partityla, M. panyuensis, M, paranaensis |
| Spiral | Helicotylenchus spp. |
| Sting | Belonolaimus spp., B. longicaudatus |
| Stubby-root | Paratrichodorus spp., P. christiei, P. minor, Quinisulcius acutus, Trichodorus spp. |
| Stunt | Tylenchorhynchus dubius | vi. Viruses

The PMP compositions and related methods can be useful for decreasing the fitness of a virus, e.g., to prevent or treat a viral infection in a plant. Included are methods for delivering a PMP composition to a virus by contacting the virus with the PMP composition. Additionally or alternatively, the methods include delivering the PMP composition to a plant at risk of or having a viral infection, by contacting the plant with the PMP composition.

The PMP compositions and related methods are suitable for delivery to a virus that causes viral diseases in plants, including the viruses and diseases listed in Table 10.

TABLE 10

Viral Plant Pathogens

| Disease | Causative Agent |
|---|---|
| Alfamoviruses: Bromoviridae | Alfalfa mosaic alfamovirus |
| Alphacryptoviruses: Partitiviridae | Alfalfa 1 alphacryptovirus, Beet 1 alphacryptovirus, Beet 2 alphacryptovirus, Beet 3 alphacryptovirus, Carnation 1 alphacryptovirus, Carrot temperate 1 alphacryptovirus, Carrot temperate 3 alphacryptovirus, Carrot temperate 4 alphacryptovirus, Cocksfoot alphacryptovirus, Hop trefoil 1 alphacryptovirus, Hop trefoil 3 alphacryptovirus, Radish yellow edge alphacryptovirus, Ryegrass alphacryptovirus, Spinach temperate alphacryptovirus, *Vicia* alphacryptovirus, White clover 1 alphacryptovirus, White clover 3 alphacryptovirus |
| Badnaviruses | Banana streak badnavirus, *Cacao* swollen shoot badnavirus, *Canna* yellow mottle badnavirus, *Commelina* yellow mottle badnavirus, *Dioscorea* bacilliform badnavirus, Kalanchoe top-spotting badnavirus, Rice tungro bacilliform badnavirus, *Schefflera* ringspot badnavirus, Sugarcane bacilliform badnavirus |
| Betacryptoviruses: Partitiviridae | Carrot temperate 2 betacryptovirus, Hop trefoil 2 betacryptovirus, Red clover 2 betacryptovirus, White clover 2 betacryptovirus |
| Bigeminiviruses: Geminiviridae | *Abutilon* mosaic bigeminivirus, *Ageratum* yellow vein bigeminivirus, Bean calico mosaic bigeminivirus, Bean golden mosaic bigeminivirus, Bhendi yellow vein mosaic bigeminivirus, Cassava African mosaic bigeminivirus, Cassava Indian mosaic bigeminivirus, Chino del tomate bigeminivirus, Cotton leaf crumple bigeminivirus, Cotton leaf curl bigeminivirus, Croton yellow vein mosaic bigeminivirus, *Dolichos* yellow mosaic bigeminivirus, *Euphorbia* mosaic bigeminivirus, Horsegram yellow mosaic bigeminivirus, *Jatropha* mosaic bigeminivirus, Lima bean golden mosaic bigeminivirus, Melon leaf curl bigeminivirus, Mung bean yellow mosaic bigeminivirus, Okra leaf-curl bigeminivirus, Pepper hausteco bigeminivirus, Pepper Texas bigeminivirus, Potato yellow mosaic bigeminivirus, *Rhynchosia* mosaic bigeminivirus, Serrano golden mosaic bigeminivirus, Squash leaf curl bigeminivirus, Tobacco leaf curl bigeminivirus, Tomato Australian leafcurl bigeminivirus, Tomato golden mosaic bigeminivirus, Tomato Indian leafcurl bigeminivirus, Tomato leaf crumple bigeminivirus, Tomato mottle bigeminivirus, Tomato yellow leaf curl bigeminivirus, Tomato yellow mosaic bigeminivirus, Watermelon chlorotic stunt bigeminivirus, Watermelon curly mottle bigeminivirus |
| Bromoviruses: Bromoviridae | Broad bean mottle bromovirus, Brome mosaic bromovirus, *Cassia* yellow blotch bromovirus, Cowpea chlorotic mottle bromovirus, *Melandrium* yellow fleck bromovirus, Spring beauty latent bromovirus |
| Bymoviruses: Potyviridae | Barley mild mosaic bymovirus, Barley yellow mosaic bymovirus, Oat mosaic bymovirus, Rice necrosis mosaic bymovirus, Wheat spindle streak mosaic bymovirus, Wheat yellow mosaic bymovirus |
| Capilloviruses | Apple stem grooving capillovirus, Cherry A capillovirus, *Citrus* tatter leaf capillovirus, Lilac chlorotic leafspot capillovirus |
| Carlaviruses | Blueberry scorch carlavirus, Cactus 2 carlavirus, Caper latent carlavirus, Carnation latent carlavirus, *Chrysanthemum* B carlavirus, Dandelion latent carlavirus, Elderberry carlavirus, Fig S carlavirus, *Helenium* S carlavirus, Honeysuckle latent carlavirus, Hop American latent carlavirus, Hop latent carlavirus, Hop mosaic carlavirus, *Kalanchoe* latent carlavirus, Lilac mottle carlavirus, Lily symptomless carlavirus, Mulberry latent carlavirus, Muskmelon vein necrosis carlavirus, *Nerine* latent carlavirus, *Passiflora* latent carlavirus, Pea streak carlavirus, Poplar mosaic carlavirus, Potato M carlavirus, Potato S carlavirus, Red clover vein mosaic carlavirus, Shallot latent carlavirus, Strawberry pseudo mild yellow edge carlavirus |
| Carmoviruses: Tombusviridae | Bean mild mosaic carmovirus, *Cardamine* chlorotic fleck carmovirus, Carnation mottle carmovirus, Cucumber leaf spot carmovirus, Cucumber soil-borne carmovirus, *Galinsoga* mosaic carmovirus, *Hibiscus* chlorotic ringspot carmovirus, Melon necrotic spot carmovirus, *Pelargonium* flower break carmovirus, Turnip crinkle carmovirus |
| Caulimoviruses | Blueberry red ringspot caulimovirus, Carnation etched ring caulimovirus, Cauliflower mosaic caulimovirus, *Dahlia* mosaic caulimovirus, Figwort mosaic caulimovirus, Horseradish latent caulimovirus, *Mirabilis* mosaic caulimovirus, Peanut chlorotic streak caulimovirus, Soybean chlorotic mottle caulimovirus, Sweet potato caulimovirus, Thistle mottle caulimovirus |

TABLE 10-continued

Viral Plant Pathogens

| Disease | Causative Agent |
| --- | --- |
| Closteroviruses | Beet yellow stunt closterovirus, Beet yellows closterovirus, Broad bean severe chlorosis closterovirus, Burdock yellows closterovirus, Carnation necrotic fleck closterovirus, *Citrus* tristeza closterovirus, Clover yellows closterovirus, Grapevine stem pitting associated closterovirus, Wheat yellow leaf closterovirus |
| Comoviruses: Comoviridae | Bean pod mottle comovirus, Bean rugose mosaic comovirus, Broad bean stain comovirus, Broad bean true mosaic comovirus, Cowpea mosaic comovirus, Cowpea severe mosaic comovirus, Glycine mosaic comovirus, Pea mild mosaic comovirus, Potato Andean mottle comovirus, Quail pea mosaic comovirus, Radish mosaic comovirus, Red clover mottle comovirus, Squash mosaic comovirus, *Ullucus* C comovirus |
| Cucumoviruses: Bromoviridae | Cucumber mosaic cucuamovirus, Peanut stunt cucumovirus, Tomato aspermy cucumovirus |
| Cytorhabdoviruses: Rhabdoviridae | Barley yellow striate mosaic cytorhabdovirus, Broad bean yellow vein cytorhabdovirus, Broccoli necrotic yellows cytorhabdovirus, Cereal northern mosaic cytorhabdovirus, *Festuca* leaf streak cytorhabdovirus, Lettuce necrotic yellows cytorhabdovirus, *Sonchus* cytorhabdovirus, Strawberry crinkle cytorhabdovirus |
| Dianthoviruses | Carnation ringspot dianthovirus, Red clover necrotic mosaic dianthovirus, Sweet clover necrotic mosaic dianthovirus |
| Enamoviruses | Pea enation mosaic enamovirus |
| Fijiviruses: Reoviridae | Maize rough dwarf fijivirus, Oat sterile dwarf fijivirus, Pangola stunt fijivirus, Rice black-streaked dwarf fijivirus, Sugarcane Fiji disease fijivirus |
| Furoviruses | Beet necrotic yellow vein furovirus, Beet soil-borne furovirus, Broad bean necrosis furovirus, Oat golden stripe furovirus, Peanut clump furovirus, Potato mop-top furovirus, *Sorghum* chlorotic spot furovirus, Wheat soil-borne mosaic furovirus |
| Hordeiviruses | *Anthoxanthum* latent blanching hordeivirus, Barley stripe mosaic hordeivirus, *Lychnis* ringspot hordeivirus, *Poa* semilatent Hordeivirus |
| Hybrigeminiviruses: Geminiviridae | Beet curly top hybrigeminivirus, Tomato pseudo curly top hybrigeminivirus |
| Idaeoviruses | Raspberry bushy dwarf idaeovirus |
| Ilarviruses: Bromoviridae | Apple mosaic ilarvirus, Asparagus 2 ilarvirus, Blueberry necrotic shock ilarvirus, *Citrus* leaf rugose ilarvirus, *Citrus* variegation ilarvirus, Elm mottle ilarvirus, *Humulus japonicus* ilarvirus, *Hydrangea* mosaic ilarvirus, Lilac ring mottle ilarvirus, *Parietaria* mottle ilarvirus, Plum American line pattern ilarvirus, Prune dwarf ilarvirus, *Prunus* necrotic ringspot ilarvirus, Spinach latent ilarvirus, Tobacco streak ilarvirus, Tulare apple mosaic ilarvirus |
| Ipomoviruses: Potyviridae | Sweet potato mild mottle ipomovirus, Sweet potato yellow dwarf ipomovirus |
| Luteoviruses | Barley yellow dwarf luteovirus, Bean leaf roll luteovirus, Beet mild yellowing luteovirus, Beet western yellows luteovirus, Carrot red leaf luteovirus, Groundnut rosette assistor luteovirus, Potato leafroll luteovirus, *Solanum* yellows luteovirus, Soybean dwarf luteovirus, Soybean Indonesian dwarf luteovirus, Strawberry mild yellow edge luteovirus, Subterranean clover red leaf luteovirus, Tobacco necrotic dwarf luteovirus |
| Machlomoviruses | Maize chlorotic mottle machlomovirus |
| Macluraviruses | *Maclura* mosaic macluravirus, *Narcissus* latent macluravirus |
| Marafiviruses | Bermuda grass etched-line marafivirus, Maize rayado fino marafivirus, Oat blue dwarf marafivirus |
| Monogeminiviruses: Geminiviridae | *Chloris* striate mosaic monogeminivirus, *Digitaria* striate mosaic monogeminivirus, *Digitaria* streak monogeminivirus, Maize streak monogeminivirus, *Miscanthus* streak monogeminivirus, *Panicum* streak monogeminivirus, *Paspalum* striate mosaic monogeminivirus, Sugarcane streak monogeminivirus, Tobacco yellow dwarf monogeminivirus, Wheat dwarf monogeminivirus |
| Nanaviruses | Banana bunchy top nanavirus, Coconut foliar decay nanavirus, Faba bean necrotic yellows nanavirus, Milk vetch dwarf nanavirus, Subterranean clover stunt nanavirus |
| Necroviruses | Tobacco necrosis necrovirus, Carnation yellow stripe necrovirus, *Lisianthus* necrosis necrovirus |
| Nepoviruses: Comoviridae | *Arabis* mosaic nepovirus, Arracacha A nepovirus, Artichoke Italian latent nepovirus, Artichoke yellow ringspot nepovirus, Blueberry leaf mottle nepovirus, *Cacao* necrosis nepovirus, Cassava green mottle nepovirus, Cherry leaf roll nepovirus, Cherry rasp leaf nepovirus, Chicory yellow mottle nepovirus, Crimson clover latent nepovirus, *Cycas* necrotic stunt nepovirus, Grapevine Bulgarian latent nepovirus, Grapevine chrome mosaic nepovirus, Grapevine fanleaf nepovirus, *Hibiscus* latent ringspot nepovirus, Lucerne Australian latent nepovirus, Mulberry ringspot nepovirus, Myrobalan latent ringspot nepovirus, Olive latent ringspot |

TABLE 10-continued

Viral Plant Pathogens

| Disease | Causative Agent |
| --- | --- |
|  | nepovirus, Peach rosette mosaic nepovirus, Potato black ringspot nepovirus, Potato U nepovirus, Raspberry ringspot nepovirus, Tobacco ringspot nepovirus, Tomato black ring nepovirus, Tomato ringspot nepovirus |
| Nucleorhabdoviruses: Rhabdoviridae | Carrot latent nucleorhabdovirus, Coriander feathery red vein nucleorhabdovirus, Cow parsnip mosaic nucleorhabdovirus, *Cynodon* chlorotic streak nucleorhabdovirus, *Datura* yellow vein nucleorhabdovirus, Eggplant mottled dwarf nucleorhabdovirus, Maize mosaic nucleorhabdovirus, *Pittosporum* vein yellowing nucleorhabdovirus, Potato yellow dwarf nucleorhabdovirus, *Sonchus* yellow net nucleorhabdovirus, Sowthistle yellow vein nucleorhabdovirus, Tomato vein clearing nucleorhabdovirus, Wheat American striate mosaic nucleorhabdovirus |
| Oryzaviruses: Reoviridae | *Echinochloa* ragged stunt oryzavirus, Rice ragged stunt oryzavirus |
| Ourmiaviruses | Cassava Ivorian bacilliform ourmiavirus, Epirus cherry ourmiavirus, Melon Ourmia ourmiavirus, *Pelargonium* zonate spot ourmiavirus |
| Phytoreoviruses: Reoviridae | Clover wound tumor phytoreovirus, Rice dwarf phytoreovirus, Rice gall dwarf phytoreovirus, Rice bunchy stunt phytoreovirus, Sweet potato phytoreovirus |
| Potexviruses | *Asparagus* 3 potexvirus, Cactus × potexvirus, Cassava × potexvirus, Chicory × potexvirus, Clover yellow mosaic potexvirus, *Commelina* × potexvirus, *Cymbidium* mosaic potexvirus, *Daphne* × potexvirus, Foxtail mosaic potexvirus, *Hydrangea* ringspot potexvirus, Lily × potexvirus, *Narcissus* mosaic potexvirus, *Nerine* × potexvirus, Papaya mosaic potexvirus, Pepino mosaic potexvirus, *Plantago asiatica* mosaic potexvirus, Plantain × potexvirus, Potato *aucuba* mosaic potexvirus, Potato × potexvirus, Tulip × potexvirus, *Viola* mottle potexvirus, White clover mosaic potexvirus |
| Potyviruses: Potyviridae | *Alstroemeria* mosaic potyvirus, *Amaranthus* leaf mottle potyvirus, *Araujia* mosaic potyvirus, Arracacha Y potyvirus, Artichoke latent potyvirus, *Asparagus* 1 potyvirus, Banana bract mosaic potyvirus, Bean common mosaic necrosis potyvirus, Bean common mosaic potyvirus, Bean yellow mosaic potyvirus, Beet mosaic potyvirus, *Bidens* mosaic potyvirus, *Bidens* mottle potyvirus, Cardamom mosaic potyvirus, Carnation vein mottle potyvirus, Carrot thin leaf potyvirus, Cassava brown streak potyvirus, *Cassia* yellow spot potyvirus, Celery mosaic potyvirus, Chickpea bushy dwarf potyvirus, Chickpea distortion mosaic potyvirus, Clover yellow vein potyvirus, *Commelina diffusa* potyvirus, *Commelina* mosaic potyvirus, Cowpea green vein-banding potyvirus, Cowpea Moroccan aphid-borne mosaic potyvirus, Cowpea rugose mosaic potyvirus, *Crinum* mosaic potyvirus, *Daphne* Y potyvirus, Dasheen mosaic potyvirus, *Datura* Colombian potyvirus, *Datura* distortion mosaic potyvirus, *Datura* necrosis potyvirus, *Datura* shoestring potyvirus, *Dendrobium* mosaic potyvirus, *Desmodium* mosaic potyvirus, *Dioscorea alata* potyvirus, *Dioscorea* green banding mosaic potyvirus, Eggplant green mosaic potyvirus, *Euphorbia* ringspot potyvirus, *Freesia* mosaic potyvirus, Groundnut eyespot potyvirus, Guar symptomless potyvirus, Guinea grass mosaic potyvirus, *Helenium* Y potyvirus, Henbane mosaic potyvirus, *Hippeastrum* mosaic potyvirus, Hyacinth mosaic potyvirus, *Iris fulva* mosaic potyvirus, *Iris* mild mosaic potyvirus, *Iris* severe mosaic potyvirus, Johnsongrass mosaic potyvirus, *Kennedya* Y potyvirus, Leek yellow stripe potyvirus, Lettuce mosaic potyvirus, Lily mottle potyvirus, Maize dwarf mosaic potyvirus, *Malva* vein clearing potyvirus, Marigold mottle potyvirus, *Narcissus* yellow stripe potyvirus, *Nerine* potyvirus, Onion yellow dwarf potyvirus, *Ornithogalum* mosaic potyvirus, Papaya ringspot potyvirus, Parsnip mosaic potyvirus, *Passiflora* ringspot potyvirus, *Passiflora* South African potyvirus, Passionfruit woodiness potyvirus, Patchouli mosaic potyvirus, Pea mosaic potyvirus, Pea seed-borne mosaic potyvirus, Peanut green mosaic potyvirus, Peanut mottle potyvirus, Pepper Indian mottle potyvirus, Pepper mottle potyvirus, Pepper severe mosaic potyvirus, Pepper veinal mottle potyvirus, Plum pox potyvirus, Pokeweed mosaic potyvirus, Potato A potyvirus, Potato V potyvirus, Potato Y potyvirus, *Primula* mosaic potyvirus, *Ranunculus* mottle potyvirus, *Sorghum* mosaic potyvirus, Soybean mosaic potyvirus, Statice Y potyvirus, Sugarcane mosaic potyvirus, Sweet potato feathery mottle potyvirus, Sweet potato G potyvirus, Swordbean distortion mosaic potyvirus, Tamarillo mosaic potyvirus, *Telfairia* mosaic potyvirus, Tobacco etch potyvirus, Tobacco vein-banding mosaic potyvirus, Tobacco vein mottling potyvirus, Tobacco wilt potyvirus, Tomato Peru potyvirus, |

TABLE 10-continued

Viral Plant Pathogens

| Disease | Causative Agent |
|---|---|
| | Tradescantia-Zebrina potyvirus, *Tropaeolum* 1 potyvirus, *Tropaeolum* 2 potyvirus, Tuberose potyvirus, Tulip band-breaking potyvirus, Tulip breaking potyvirus, Tulip chlorotic blotch potyvirus, Turnip mosaic potyvirus, *Ullucus* mosaic potyvirus, *Vallota* mosaic potyvirus, Vanilla mosaic potyvirus, Vanilla necrosis potyvirus, *Voandzeia* distortion mosaic potyvirus, Watermelon mosaic 1 potyvirus, Watermelon mosaic 2 potyvirus, Wild potato mosaic potyvirus, *Wisteria* vein mosaic potyvirus, Yam mosaic potyvirus, Zucchini yellow fleck potyvirus, Zucchini yellow mosaic potyvirus |
| Rymoviruses: Potyviridae Agropyron mosaic rymovirus | *Hordeum* mosaic rymovirus, Oat necrotic mottle rymovirus, Ryegrass mosaic rymovirus, Wheat streak mosaic rymovirus |
| Satellite RNAs | *Arabis* mosaic satellite RNA, Chicory yellow mottle satellite RNA, Cucumber mosaic satellite RNA, Grapevine fanleaf satellite RNA, Strawberry latent ringspot satellite RNA, Tobacco ringspot satellite RNA, Tomato black ring satellite RNA, Velvet tobacco mottle satellite RNA |
| Satelliviruses | Maize white line mosaic satellivirus, *Panicum* mosaic satellivirus, Tobacco mosaic satellivirus, Tobacco necrosis satellivirus |
| Sequiviruses: Sequiviridae | Dandelion yellow mosaic sequivirus, Parsnip yellow fleck sequivirus |
| Sobemoviruses | Bean southern mosaic sobemovirus, Blueberry shoestring sobemovirus, Cocksfoot mottle sobemovirus, Lucerne transient streak sobemovirus, Rice yellow mottle sobemovirus, *Rottboellia* yellow mottle sobemovirus, *Solanum nodiflorum* mottle sobemovirus, Sowbane mosaic sobemovirus, Subterranean clover mottle sobemovirus, Turnip rosette sobemovirus, Velvet tobacco mottle, sobemovirus |
| Tenuiviruses | Maize stripe tenuivirus, Rice grassy stunt tenuivirus, Rice hoja blanca tenuivirus, Rice stripe tenuivirus |
| Tobamoviruses | Cucumber green mottle mosaic tobamovirus, Frangipani mosaic tobamovirus, Kyuri green mottle mosaic tobamovirus, *Odontoglossum* ringspot tobamovirus, Paprika mild mottle tobamovirus, Pepper mild mottle tobamovirus, Ribgrass mosaic tobamovirus, *Opuntia* Sammons' tobamovirus, Sunn-hemp mosaic tobamovirus, Tobacco mild green mosaic tobamovirus, Tobacco mosaic tobamovirus, Tomato mosaic tobamovirus, *Ullucus* mild mottle tobamovirus |
| Tobraviruses | Pea early browning tobravirus, Pepper ringspot tobravirus, Tobacco rattle tobravirus |
| Tombusviruses: Tombusviridae | Artichoke mottled crinkle tombusvirus, Carnation Italian ringspot tombusvirus, Cucumber necrosis tombusvirus, *Cymbidium* ringspot tombusvirus, Eggplant mottled crinkle tombusvirus, Grapevine Algerian latent tombusvirus, Lato River tombusvirus, Neckar River tombusvirus, *Pelargonium* leaf curl tombusvirus, Pepper Moroccan tombusvirus, *Petunia* asteroid mosaic tombusvirus, Tomato bushy stunt tombusvirus |
| Tospoviruses: Bunyaviridae | *Impatiens* necrotic spot tospovirus, Peanut yellow spot tospovirus, Tomato spotted wilt tospovirus |
| Trichoviruses | Apple chlorotic leaf spot trichovirus, *Heracleum* latent trichovirus, Potato T trichovirus |
| Tymoviruses | *Abelia* latent tymovirus, *Belladonna* mottle tymovirus, *Cacao* yellow mosaic tymovirus, *Clitoria* yellow vein tymovirus, *Desmodium* yellow mottle tymovirus, *Dulcamara* mottle tymovirus, Eggplant mosaic tymovirus, *Erysimum* latent tymovirus, *Kennedya* yellow mosaic tymovirus, Melon rugose mosaic tymovirus, Okra mosaic tymovirus, *Ononis* yellow mosaic tymovirus, Passionfruit yellow mosaic tymovirus, *Physalis* mosaic tymovirus, *Plantago* mottle tymovirus, Potato Andean latent tymovirus, *Scrophularia* mottle tymovirus, Turnip yellow mosaic, tymovirus, *Voandzeia* necrotic mosaic tymovirus, Wild cucumber mosaic tymovirus |
| Umbraviruses | Bean yellow vein banding umbravirus, Carrot mottle mimic umbravirus, Carrot mottle umbravirus, Carrot mottle mimic umbravirus, Groundnut rosette umbravirus, Lettuce speckles mottle umbravirus, Tobacco mottle umbravirus |
| Varicosaviruses | *Freesia* leaf necrosis varicosavirus, Lettuce big-vein varicosavirus, Tobacco stunt varicosavirus |
| Waikaviruses: Sequiviridae | *Anthriscus* yellows waikavirus, Maize chlorotic dwarf waikavirus, Rice tungro spherical waikavirus |
| Putative Ungrouped Viruses | Alsike clover vein mosaic virus, *Alstroemeria* streak potyvirus, *Amaranthus* mosaic potyvirus, Amazon lily mosaic potyvirus, *Anthoxanthum* mosaic potyvirus, Apple stem pitting virus, *Aquilegia* potyvirus, *Asclepias* rhabdovirus, *Atropa belladonna* |

TABLE 10-continued

Viral Plant Pathogens

| Disease | Causative Agent |
|---|---|
| | rhabdovirus, Barley mosaic virus, Barley yellow streak mosaic virus, Beet distortion mosaic virus, Beet leaf curl rhabdovirus, Beet western yellows ST9-associated RNA virus, Black raspberry necrosis virus, Bramble yellow mosaic potyvirus, Brinjal mild mosaic potyvirus, Broad bean B virus, Broad bean V potyvirus, Broad bean yellow ringspot virus, *Bryonia* mottle potyvirus, Burdock mosaic virus, Burdock mottle virus, *Callistephus chinensis* chlorosis rhabdovirus, Canary reed mosaic potyvirus, *Canavalia maritima* mosaic potyvirus, Carnation rhabdovirus, Carrot mosaic potyvirus, Cassava symptomless rhabdovirus, *Cassia* mosaic virus, *Cassia* ringspot virus, Celery yellow mosaic potyvirus, Celery yellow net virus, Cereal flame chlorosis virus, Chickpea filiform potyvirus, Chilli veinal mottle potyvirus, *Chrysanthemum* spot potyvirus, *Chrysanthemum* vein chlorosis rhabdovirus, *Citrus* leprosis rhabdovirus, *Citrus* ringspot virus, Clover mild mosaic virus, Cocksfoot streak potyvirus, *Colocasia* bobone disease rhabdovirus, Cucumber toad-skin rhabdovirus, Cucumber vein yellowing virus, *Cypripedium* calceolus potyvirus, *Datura innoxia* Hungarian mosaic potyvirus, *Dioscorea trifida* potyvirus, Dock mottling mosaic potyvirus, *Dodonaea* yellows-associated virus, Eggplant severe mottle potyvirus, *Euonymus* fasciation rhabdovirus, *Euonymus* rhabdovirus, Fern potyvirus, Fig potyvirus, *Gerbera* symptomless rhabdovirus, Grapevine fleck virus, Grapevine stunt virus, Guar top necrosis virus, *Habenaria* mosaic potyvirus, *Holcus lanatus* yellowing rhabdovirus, *Holcus* streak potyvirus, *Iris germanica* leaf stripe rhabdovirus, *Iris* Japanese necrotic ring virus, *Isachne* mosaic potyvirus, *Kalanchoe* isometric virus, Kenaf vein-clearing rhabdovirus, *Launaea* mosaic potyvirus, Lupin yellow vein rhabdovirus, Maize eyespot virus, Maize line virus, Maize mottle/chlorotic stunt virus, Maize white line mosaic virus, *Malvastrum* mottle virus, *Melilotus* mosaic potyvirus, Melon vein-banding mosaic potyvirus, *Melothria* mottle potyvirus, *Mimosa* mosaic virus, Mung bean mottle potyvirus, *Narcissus* degeneration potyvirus, *Narcissus* late season yellows potyvirus, *Nerine* Y potyvirus, *Nothoscordum* mosaic potyvirus, Oak ringspot virus, Orchid fleck rhabdovirus, Palm mosaic potyvirus, Parsley green mottle potyvirus, Parsley rhabdovirus, Parsnip leafcurl virus, Passionfruit Sri Lankan mottle potyvirus, Passionfruit vein-clearing rhabdovirus, Patchouli mottle rhabdovirus, Pea stem necrosis virus, Peanut top paralysis potyvirus, Peanut veinal chlorosis rhabdovirus, *Pecteilis* mosaic potyvirus, Pepper mild mosaic potyvirus, *Perilla* mottle potyvirus, Pigeonpea proliferation rhabdovirus, Pigeonpea sterility mosaic virus, Plantain 7 potyvirus, Plantain mottle rhabdovirus, *Pleioblastus* chino potyvirus, Poplar decline potyvirus, *Primula* mottle potyvirus, Purple granadilla mosaic virus, *Ranunculus repens* symptomless rhabdovirus, Rice yellow stunt virus, *Saintpaulia* leaf necrosis rhabdovirus, *Sambucus* vein clearing rhabdovirus, *Sarracenia purpurea* rhabdovirus, Shamrock chlorotic ringspot potyvirus, Soybean mild mosaic virus, Soybean rhabdovirus, Soybean spherical virus, Soybean yellow vein virus, Soybean Z potyvirus, Strawberry latent C rhabdovirus, Strawberry mottle virus, Strawberry pallidosis virus, Sunflower mosaic potyvirus, Sweet potato latent potyvirus, Teasel mosaic potyvirus, Thimbleberry ringspot virus, Tomato mild mottle potyvirus, *Trichosanthes* mottle potyvirus, Tulip halo necrosis virus, Tulip mosaic virus, Turnip vein-clearing virus, Urd bean leaf crinkle virus, *Vigna sinensis* mosaic rhabdovirus, Watercress yellow spot virus, Watermelon Moroccan mosaic potyvirus, Wheat chlorotic spot rhabdovirus, White bryony potyvirus, Wineberry latent virus, *Zinnia* mild mottle potyvirus, *Zoysia* mosaic potyvirus |

C. Delivery to a Plant Symbiont

Provided herein are methods of delivering to a plant symbiont a PMP composition (e.g., including modified PMPs described herein) disclosed herein. Included are methods for delivering a PMP composition to a symbiont (e.g., a bacterial endosymbiont, a fungal endosymbiont, or an insect) by contacting the symbiont with a PMP composition. The methods can be useful for increasing the fitness of plant symbiont, e.g., a symbiont that is beneficial to the fitness of a plant. In some instances, plant symbionts may be treated with PMPs not including a heterologous functional agent. In other instances, the PMPs include a heterologous functional agent, e.g., fertilizing agents.

As such, the methods can be used to increase the fitness of a plant symbiont. In one aspect, provided herein is a method of increasing the fitness of a symbiont, the method including delivering to the symbiont the PMP composition described herein (e.g., in an effective amount and for an effective duration) to increase the fitness of the symbiont relative to an untreated symbiont (e.g., a symbiont that has not been delivered the PMP composition).

In one aspect, provided herein is a method of increasing the fitness of a fungus (e.g., a fungal endosymbiont of a plant), wherein the method includes delivering to the endosymbiont a PMP composition including a plurality of PMPs (e.g., a PMP composition described herein). For example, the plant symbiont may be an endosymbiotic fungus, such as a fungus of the genus Aspergillaceae, Ceratobasidiaceae, Coniochaetaceae, Cordycipitaceae, Corticiaceae, Cystofilobasidiaceae, Davidiellaceae, Debaryomycetaceae, Dothioraceae, Erysiphaceae, Filobasidiaceae, Glomerellaceae, Hydnaceae, Hypocreaceae, Leptosphaeriaceae, Montagnulaceae, Mortierellaceae, Mycosphaerellaceae, Nectriaceae, Orbiliaceae, Phaeosphaeriaceae, Pleosporaceae, Pseudeurotiaceae, Rhizopodaceae, Sclerotiniaceae, Stereaceae, or Trichocomacea.

In another aspect, provided herein is a method of increasing the fitness of a bacterium (e.g., a bacterial endosymbiont of a plant), wherein the method includes delivering to the bacteria a PMP composition including a plurality of PMPs (e.g., a PMP composition described herein). For example, the plant symbiont may be an endosymbiotic bacteria, such as a bacteria of the genus Acetobacteraceae, Acidobacteriaceae, Acidothermaceae, Aerococcaceae, Alcaligenaceae, Alicyclobacillaceae, Alteromonadaceae, Anaerolineaceae, Aurantimonadaceae, Bacillaceae, Bacteriovoracaceae, Bdellovibrionaceae, Bradyrhizobiaceae, Brevibacteriaceae, Brucellaceae, Burkholderiaceae, Carboxydocellaceae, Caulobacteraceae, Cellulomonadaceae, Chitinophagaceae, Chromatiaceae, Chthoniobacteraceae, Chthonomonadaceae, Clostridiaceae, Comamonadaceae, Corynebacteriaceae, Coxiellaceae, Cryomorphaceae, Cyclobacteriaceae, Cytophagaceae, Deinococcaceae, Dermabacteraceae, Dermacoccaceae, Enterobacteriaceae, Enterococcaceae, Erythrobacteraceae, Fibrobacteraceae, Flammeovirgaceae, Flavobacteriaceae, Frankiaceae, Fusobacteriaceae, Gaiellaceae, Gemmatimonadaceae, Geodermatophilaceae, Gly corny cetaceae, Haliangiaceae, Halomonadaceae, Holosporaceae, Hyphomicrobiaceae, lamiaceae, Intrasporangiaceae, Kineosporiaceae, Koribacteraceae, Lachnospiraceae, Lactobacillaceae, Legionellaceae, Leptospiraceae, Leuconostocaceae, Methylobacteriaceae, Methylocystaceae, Methylophilaceae, Microbacteriaceae, Micrococcaceae, Micromonosporaceae, Moraxellaceae, Mycobacteriaceae, Mycoplasmataceae, Myxococcaceae, Nakamurellaceae, Neisseriaceae, Nitrosomonadaceae, Nocardiaceae, Nocardioidaceae, Oceanospirillaceae, Opitutaceae, Oxalobacteraceae, Paenibacillaceae, Parachlamydiaceae, Pasteurellaceae, Patulibacteraceae, Peptostreptococcaceae, Phyllobacteriaceae, Piscirickettsiaceae, Planctomycetaceae, Planococcaceae, Polyangiaceae, Porphyromonadaceae, Prevotellaceae, Promicromonosporaceae, Pseudomonadaceae, Pseudonocardiaceae, Rhizobiaceae, Rhodobacteraceae, Rhodospirillaceae, Roseiflexaceae, Rubrobacteriaceae, Sandaracinaceae, Sanguibacteraceae, Saprospiraceae, Segniliparaceae, Shewanellaceae, Sinobacteraceae, Solibacteraceae, Solimonadaceae, Solirubrobacteraceae, Sphingobacteriaceae, Sphingomonadaceae, Spiroplasmataceae, Sporichthyaceae, Sporolactobacillaceae, Staphylococcaceae, Streptococcaceae, Streptomycetaceae, Syntrophobacteraceae, Veillonellaceae, Verrucomicrobiaceae, Weeksellaceae, Xanthobacteraceae, or Xanthomonadaceae.

In yet another aspect, provided herein is a method of increasing the fitness of an insect (e.g., an insect symbiont of a plant), wherein the method includes delivering to the insect a PMP composition including a plurality of PMPs (e.g., a PMP composition described herein). In some instances, the insect is a plant pollinator. For example, the insect may be of the genus Hymenoptera or Diptera. In some instances, the insect of the genus Hymenoptera is a bee. In other instances, the insect of the genus Diptera is a fly.

In some instances, the increase in symbiont fitness may manifest as an improvement in the physiology of the symbiont (e.g., improved health or survival) as a consequence of administration of the PMP composition. In some instances, the fitness of an organism may be measured by one or more parameters, including, but not limited to, reproductive rate, lifespan, mobility, fecundity, body weight, metabolic rate or activity, or survival in comparison to a symbiont to which the PMP composition has not been delivered. For example, the methods or compositions provided herein may be effective to improve the overall health of the symbiont or to improve the overall survival of the symbiont in comparison to a symbiont organism to which the PMP composition has not been administered. In some instances, the improved survival of the symbiont is about 2%, 5%, 10%, 20%, 30%, 40%, 50%, 60%, 70%, 80%, 90%, 100%, or greater than 100% greater relative to a reference level (e.g., a level found in a symbiont that does not receive a PMP composition). In some instances, the methods and compositions are effective to increase symbiont reproduction (e.g., reproductive rate) in comparison to a symbiont organism to which the PMP composition has not been administered. In some instances, the methods and compositions are effective to increase other physiological parameters, such as mobility, body weight, life span, fecundity, or metabolic rate, by about 2%, 5%, 10%, 20%, 30%, 40%, 50%, 60%, 70%, 80%, 90%, 100%, or greater than 100% relative to a reference level (e.g., a level found in a symbiont that does not receive a PMP composition).

In some instances, the increase in symbiont fitness may manifest as an increase in the frequency or efficacy of a desired activity carried out by the symbiont (e.g., pollination, predation on pests, seed spreading, or breakdown of waste or organic material) in comparison to a symbiont organism to which the PMP composition has not been administered. In some instances, the methods or compositions provided herein may be effective to increase the frequency or efficacy of a desired activity carried out by the symbiont (e.g., pollination, predation on pests, seed spreading, or breakdown of waste or organic material) by about 2%, 5%, 10%, 20%, 30%, 40%, 50%, 60%, 70%, 80%, 90%, 100%, or greater than 100% relative to a reference level (e.g., a level found in a symbiont that does not receive a PMP composition).

In some instances, the increase in symbiont fitness may manifest as an increase in the production of one or more nutrients in the symbiont (e.g., vitamins, carbohydrates, amino acids, or polypeptides) in comparison to a symbiont organism to which the PMP composition has not been administered. In some instances, the methods or compositions provided herein may be effective to increase the production of nutrients in the symbiont (e.g., vitamins, carbohydrates, amino acids, or polypeptides) by about 2%, 5%, 10%, 20%, 30%, 40%, 50%, 60%, 70%, 80%, 90%, 100%, or greater than 100% relative to a reference level (e.g., a level found in a symbiont that does not receive a PMP composition). In some instances, the methods or compositions provided herein may increase nutrients in an associated plant by increasing the production or metabolism of nutrients by one or more microorganisms (e.g., endosymbiont) in the symbiont.

In some instances, the increase in symbiont fitness may manifest as a decrease in the symbiont's sensitivity to a pesticidal agent and/or an increase in the symbiont's resistance to a pesticidal agent in comparison to a symbiont organism to which the PMP composition has not been administered. In some instances, the methods or compositions provided herein may be effective to decrease the symbiont's sensitivity to a pesticidal agent by about 2%, 5%, 10%, 20%, 30%, 40%, 50%, 60%, 70%, 80%, 90%, 100%, or greater than 100% relative to a reference level (e.g., a level found in a symbiont that does not receive a PMP composition).

In some instances, the increase in symbiont fitness may manifest as a decrease in the symbiont's sensitivity to an allelochemical agent and/or an increase in the symbiont's resistance to an allelochemical agent in comparison to a symbiont organism to which the PMP composition has not been administered. In some instances, the methods or compositions provided herein may be effective to increase the symbiont's resistance to an allelochemical agent by about 2%, 5%, 10%, 20%, 30%, 40%, 50%, 60%, 70%, 80%, 90%, 100%, or greater than 100% relative to a reference level (e.g., a level found in a symbiont that does not receive a PMP composition). In some instances, the allelochemical agent is caffeine, soyacystatin N, monoterpenes, diterpene acids, or phenolic compounds. In some instances, the methods or compositions provided herein may decrease the symbiont's sensitivity to an allelochemical agent by increasing the symbiont's ability to metabolize or degrade the allelochemical agent into usable substrates.

In some instances, the methods or compositions provided herein may be effective to increase the symbiont's resistance to parasites or pathogens (e.g., fungal, bacterial, or viral pathogens; or parasitic mites (e.g., *Varroa destructor* mite in honeybees)) in comparison to a symbiont organism to which the PMP composition has not been administered. In some instances, the methods or compositions provided herein may be effective to increase the symbiont's resistance to a pathogen or parasite (e.g., fungal, bacterial, or viral pathogens; or parasitic mites (e.g., *Varroa destructor* mite in honeybees)) by about 2%, 5%, 10%, 20%, 30%, 40%, 50%, 60%, 70%, 80%, 90%, 100%, or greater than 100% relative to a reference level (e.g., a level found in a symbiont that does not receive a PMP composition).

In some instances, the increase in symbiont fitness may manifest as other fitness advantages, such as improved tolerance to certain environmental factors (e.g., a high or low temperature tolerance), improved ability to survive in certain habitats, or an improved ability to sustain a certain diet (e.g., an improved ability to metabolize soy vs corn) in comparison to a symbiont organism to which the PMP composition has not been administered. In some instances, the methods or compositions provided herein may be effective to increase symbiont fitness in any plurality of ways described herein. Further, the PMP composition may increase symbiont fitness in any number of symbiont classes, orders, families, genera, or species (e.g., 1 symbiont species, 2, 3, 4, 5, 6, 7, 8, 9, 10, 15, 20, 30, 40, 50, 60, 70, 80, 90, 100, 150, 200, 200, 250, 500, or more symbiont species). In some instances, the PMP composition acts on a single symbiont class, order, family, genus, or species.

Symbiont fitness may be evaluated using any standard methods in the art. In some instances, symbiont fitness may be evaluated by assessing an individual symbiont. Alternatively, symbiont fitness may be evaluated by assessing a symbiont population. For example, an increase in symbiont fitness may manifest as an increase in successful competition against other insects, thereby leading to an increase in the size of the symbiont population.

Examples of plant symbionts that can be treated with the present compositions or related methods are further described herein.

i. Fungi

The PMP compositions and related methods can be useful for increasing the fitness of a fungus, e.g., a fungus that is an endosymbiont of a plant (e.g., mycorrhizal fungus).

In some instances, the fungus is of the family Aspergillaceae, Ceratobasidiaceae, Coniochaetaceae, Cordycipitaceae, Corticiaceae, Cystofilobasidiaceae, Davidiellaceae, Debaryomycetaceae, Dothioraceae, Erysiphaceae, Filobasidiaceae, Glomerellaceae, Hydnaceae, Hypocreaceae, Leptosphaeriaceae, Montagnulaceae, Mortierellaceae, Mycosphaerellaceae, Nectriaceae, Orbiliaceae, Phaeosphaeriaceae, Pleosporaceae, Pseudeurotiaceae, Rhizopodaceae, Sclerotiniaceae, Stereaceae, or Trichocomacea.

In some instances, the fungus is a fungus having a mychorrhizal (e.g., ectomycorrhizal or endomycorrhizal) association with the roots of a plant, including fungi belonging to Glomeromycota, Basidiomycota, Ascomycota, or Zygomycota.

ii. Bacteria

The PMP compositions and related methods can be useful for increasing the fitness of a bacterium, e.g., a bacterium that is an endosymbiont of a plant (e.g., nitrogen-fixing bacteria).

For example, the bacterium may be of the genus *Acidovorax, Agrobacterium, Bacillus, Burkholderia, Chryseobacterium, Curtobacterium, Enterobacter, Escherichia, Methylobacterium, Paenibacillus, Pantoea, Pseudomonas, Ralstonia, Rhizobium, Saccharibacillus, Sphingomonas,* or *Stenotrophomonas*.

In some instances, the bacteria is of the family: Acetobacteraceae, Acidobacteriaceae, Acidothermaceae, Aerococcaceae, Alcaligenaceae, Alicyclobacillaceae, Alteromonadaceae, Anaerolineaceae, Aurantimonadaceae, Bacillaceae, Bacteriovoracaceae, Bdellovibrionaceae, Bradyrhizobiaceae, Brevibacteriaceae, Brucellaceae, Burkholderiaceae, Carboxydocellaceae, Caulobacteraceae, Cellulomonadaceae, Chitinophagaceae, Chromatiaceae, Chthoniobacteraceae, Chthonomonadaceae, Clostridiaceae, Comamonadaceae, Corynebacteriaceae, Coxiellaceae, Cryomorphaceae, Cyclobacteriaceae, Cytophagaceae, Deinococcaceae, Dermabacteraceae, Dermacoccaceae, Enterobacteriaceae, Enterococcaceae, Erythrobacteraceae, Fibrobacteraceae, Flammeovirgaceae, Flavobacteriaceae, Frankiaceae, Fusobacteriaceae, Gaiellaceae, Gemmatimonadaceae, Geodermatophilaceae, Gly corny cetaceae, Haliangiaceae, Halomonadaceae, Holosporaceae, Hyphomicrobiaceae, Iamiaceae, Intrasporangiaceae, Kineosporiaceae, Koribacteraceae, Lachnospiraceae, Lactobacillaceae, Legionellaceae, Leptospiraceae, Leuconostocaceae, Methylobacteriaceae, Methylocystaceae, Methylophilaceae, Microbacteriaceae, Micrococcaceae, Micromonosporaceae, Moraxellaceae, Mycobacteriaceae, Mycoplasmataceae, Myxococcaceae, Nakamurellaceae, Neisseriaceae, Nitrosomonadaceae, Nocardiaceae, Nocardioidaceae, Oceanospirillaceae, Opitutaceae, Oxalobacteraceae, Paenibacillaceae, Parachlamydiaceae, Pasteurellaceae, Patulibacteraceae, Peptostreptococcaceae, Phyllobacteriaceae, Piscirickettsiaceae, Planctomycetaceae, Planococcaceae, Polyangiaceae, Porphyromonadaceae, Prevotellaceae, Promicromonosporaceae, Pseudomonadaceae, Pseudonocardiaceae, Rhizobiaceae, Rhodobacteraceae, Rhodospirillaceae, Roseiflexaceae, Rubrobacteriaceae, Sandaracinaceae, Sanguibacteraceae, Saprospiraceae, Segniliparaceae, Shewanellaceae, Sinobacteraceae, Solibacteraceae, Solimonadaceae, Solirubrobacteraceae, Sphingobacteriaceae, Sphingomonadaceae, Spiroplasmataceae, Sporichthyaceae, Sporolactobacillaceae, Staphylococcaceae, Streptococcaceae, Streptomycetaceae, Syntrophobacteraceae, Veillonellaceae, Verrucomicrobiaceae, Weeksellaceae, Xanthobacteraceae, or Xanthomonadaceae.

In some instances, the endosymbiotic bacterium is of a family selected from the group consisting of: Bacillaceae, Burkholderiaceae, Comamonadaceae, Enterobacteriaceae, Flavobacteriaceae, Methylobacteriaceae, Microbacteriaceae, Paenibacillileae, Pseudomonnaceae, Rhizobiaceae, Sphingomonadaceae, and Xanthomonadaceae.

In some instances, the endosymbiotic bacterium is of a genus selected from the group consisting of: *Acidovorax, Agrobacterium, Bacillus, Burkholderia, Chryseobacterium, Curtobacterium, Enterobacter, Escherichia, Methylobacterium, Paenibacillus, Pantoea, Pseudomonas, Ralstonia, Saccharibacillus, Sphingomonas*, and *Stenotrophomonas*.

iii. Insects

The PMP compositions and related methods can be useful for increasing the fitness of an insect, e.g., an insect that is beneficial to plant. The term insect includes any organism belonging to the phylum Arthropoda and to the class Insecta or the class Arachnida, in any stage of development, i.e., immature and adult insects. For example, the host may include insects that are used in agricultural applications, including insects that aid in the pollination of crops, spreading seeds, or pest control.

In some instances, the host aids in pollination of a plant (e.g., bees, beetles, wasps, flies, butterflies, or moths). In some instances, the host aiding in pollination of a plant is a bee. In some instances, the bee is in the family Andrenidae, Apidae, Colletidae, Halictidae, or Megachilidae. In some examples, the host aiding in pollination of a plant is beetle. In particular instances, the PMP composition may be used to increase the fitness of a honeybee.

In some instances, the host aiding in pollination of a plant is a beetle, e.g., a species in the family Buprestidae, Cantharidae, Cerambycidae, Chrysomelidae, Cleridae, Coccinellidae, Elateridae, Melandryidae, Meloidae, Melyridae, Mordellidae, Nitidulidae, Oedemeridae, Scarabaeidae, or Staphyllinidae.

In some instances, the host aiding in pollination of a plant is a butterfly or moth (e.g., Lepidoptera). In some instances, the butterfly or moth is a species in the family Geometridae, Hesperiidae, Lycaenidae, Noctuidae, Nymphalidae, Papilionidae, Pieridae, or Sphingidae.

In some instances, the host aiding in pollination of a plant is a fly (e.g., Diptera). In some instances, the fly is in the family Anthomyiidae, Bibionidae, Bombyliidae, Calliphoridae, Cecidomiidae, Certopogonidae, Chrionomidae, Conopidae, Culicidae, Dolichopodidae, Empididae, Ephydridae, Lonchopteridae, Muscidae, Mycetophilidae, Phoridae, Simuliidae, Stratiomyidae, or Syrphidae.

In some instances, the host aiding in pollination is an ant (e.g., Formicidae), sawfly (e.g., Tenthredinidae), or wasp (e.g., Sphecidae or Vespidae).

D. Delivery to an Animal Pathogen

Provided herein are methods of delivering a PMP composition (e.g., including modified PMPs described herein) to an animal (e.g., human) pathogen, such as one disclosed herein, by contacting the pathogen with a PMP composition. As used herein the term "pathogen" refers to an organism, such as a microorganism or an invertebrate, which causes disease or disease symptoms in an animal by, e.g., (i) directly infecting the animal, (ii) by producing agents that causes disease or disease symptoms in an animal (e.g., bacteria that produce pathogenic toxins and the like), and/or (iii) that elicit an immune (e.g., inflammatory response) in animals (e.g., biting insects, e.g., bedbugs). As used herein, pathogens include, but are not limited to bacteria, protozoa, parasites, fungi, nematodes, insects, viroids and viruses, or any combination thereof, wherein each pathogen is capable, either by itself or in concert with another pathogen, of eliciting disease or symptoms in animals, such as humans.

In some instances, animal (e.g., human) pathogen may be treated with PMPs not including a heterologous functional agent. In other instances, the PMPs include a heterologous functional agent, e.g., a heterologous therapeutic agent (e.g., antibacterial agent, antifungal agent, insecticide, nematicide, antiparasitic agent, antiviral agent, or a repellent). The methods can be useful for decreasing the fitness of an animal pathogen, e.g., to prevent or treat a pathogen infection or control the spread of a pathogen as a consequence of delivery of the PMP composition.

Examples of pathogens that can be targeted in accordance with the methods described herein include bacteria (e.g., *Streptococcus* spp., Pneumococcus spp., *Pseudomonas* spp., *Shigella* spp, *Salmonella* spp., *Campylobacter* spp., or an *Escherichia* spp), fungi (*Saccharomyces* spp. or a *Candida* spp), parasitic insects (e.g., *Cimex* spp), parasitic nematodes (e.g., *Heligmosomoides* spp), or parasitic protozoa (e.g., *Trichomoniasis* spp).

For example, provided herein is a method of decreasing the fitness of a pathogen, the method including delivering to the pathogen a PMP composition described herein, wherein the method decreases the fitness of the pathogen relative to an untreated pathogen. In some embodiments, the method includes delivering the composition to at least one habitat where the pathogen grows, lives, reproduces, feeds, or infests. In some instances of the methods described herein, the composition is delivered as a pathogen comestible composition for ingestion by the pathogen. In some instances of the methods described herein, the composition is delivered (e.g., to a pathogen) as a liquid, a solid, an aerosol, a paste, a gel, or a gas.

Also provided herein is a method of decreasing the fitness of a parasitic insect, wherein the method includes delivering to the parasitic insect a PMP composition including a plurality of PMPs. In some instances, the method includes delivering to the parasitic insect a PMP composition including a plurality of PMPs, wherein the plurality of PMPs includes an insecticidal agent. For example, the parasitic insect may be a bedbug. Other non-limiting examples of parasitic insects are provided herein. In some instances, the method decreases the fitness of the parasitic insect relative to an untreated parasitic insect Additionally provided herein is a method of decreasing the fitness of a parasitic nematode, wherein the method includes delivering to the parasitic nematode a PMP composition including a plurality of PMPs. In some instances, the method includes delivering to the parasitic nematode a PMP composition including a plurality of PMPs, wherein the plurality of PMPs includes a nematicidal agent. For example, the parasitic nematode is *Heligmosomoides polygyrus*. Other non-limiting examples of parasitic nematodes are provided herein. In some instances, the method decreases the fitness of the parasitic nematode relative to an untreated parasitic nematode.

Further provided herein is a method of decreasing the fitness of a parasitic protozoan, wherein the method includes delivering to the parasitic protozoan a PMP composition including a plurality of PMPs. In some instances, the method includes delivering to the parasitic protozoan a PMP composition including a plurality of PMPs, wherein the plurality of PMPs includes an antiparasitic agent. For example, the parasitic protozoan may be *T. vaginalis*. Other non-limiting examples of parasitic protozoans are provided herein. In some instances, the method decreases the fitness of the parasitic protozoan relative to an untreated parasitic protozoan.

A decrease in the fitness of the pathogen as a consequence of delivery of a PMP composition can manifest in a number of ways. In some instances, the decrease in fitness of the pathogen may manifest as a deterioration or decline in the physiology of the pathogen (e.g., reduced health or survival) as a consequence of delivery of the PMP composition. In some instances, the fitness of an organism may be measured by one or more parameters, including, but not limited to, reproductive rate, fertility, lifespan, viability, mobility, fecundity, pathogen development, body weight, metabolic rate or activity, or survival in comparison to a pathogen to which the PMP composition has not been administered. For example, the methods or compositions provided herein may be effective to decrease the overall health of the pathogen or to decrease the overall survival of the pathogen. In some instances, the decreased survival of the pathogen is about 2%, 5%, 10%, 20%, 30%, 40%, 50%, 60%, 70%, 80%, 90%, 100%, or greater than 100% greater relative to a reference level (e.g., a level found in a pathogen that does not receive a PMP composition. In some instances, the methods and compositions are effective to decrease pathogen reproduction (e.g., reproductive rate, fertility) in comparison to a pathogen to which the PMP composition has not been administered. In some instances, the methods and compositions are effective to decrease other physiological parameters, such as mobility, body weight, life span, fecundity, or metabolic rate, by about 2%, 5%, 10%, 20%, 30%, 40%, 50%, 60%, 70%, 80%, 90%, 100%, or greater than 100% relative to a reference level (e.g., a level found in a pathogen that does not receive a PMP composition).

In some instances, the decrease in pest fitness may manifest as an increase in the pathogen's sensitivity to an antipathogen agent and/or a decrease in the pathogen's resistance to an antipathogen agent in comparison to a pathogen to which the PMP composition has not been delivered. In some instances, the methods or compositions provided herein may be effective to increase the pathogen's sensitivity to a pesticidal agent by about 2%, 5%, 10%, 20%, 30%, 40%, 50%, 60%, 70%, 80%, 90%, 100%, or greater than 100% relative to a reference level (e.g., a level found in a pest that does not receive a PMP composition).

In some instances, the decrease in pathogen fitness may manifest as other fitness disadvantages, such as a decreased tolerance to certain environmental factors (e.g., a high or low temperature tolerance), a decreased ability to survive in certain habitats, or a decreased ability to sustain a certain diet in comparison to a pathogen to which the PMP composition has not been delivered. In some instances, the methods or compositions provided herein may be effective to decrease pathogen fitness in any plurality of ways described herein. Further, the PMP composition may decrease pathogen fitness in any number of pathogen classes, orders, families, genera, or species (e.g., 1 pathogen species, 2, 3, 4, 5, 6, 7, 8, 9, 10, 15, 20, 30, 40, 50, 60, 70, 80, 90, 100, 150, 200, 200, 250, 500, or more pathogen species). In some instances, the PMP composition acts on a single pest class, order, family, genus, or species.

Pathogen fitness may be evaluated using any standard methods in the art. In some instances, pest fitness may be evaluated by assessing an individual pathogen. Alternatively, pest fitness may be evaluated by assessing a pathogen population. For example, a decrease in pathogen fitness may manifest as a decrease in successful competition against other pathogens, thereby leading to a decrease in the size of the pathogen population.

The PMP compositions and related methods described herein are useful to decrease the fitness of an animal pathogen and thereby treat or prevent infections in animals. Examples of animal pathogens, or vectors thereof, that can be treated with the present compositions or related methods are further described herein.

i. Fungi

The PMP compositions and related methods can be useful for decreasing the fitness of a fungus, e.g., to prevent or treat a fungal infection in an animal. Included are methods for delivering a PMP composition to a fungus by contacting the fungus with the PMP composition. Additionally or alternatively, the methods include preventing or treating a fungal infection (e.g., caused by a fungus described herein) in an animal at risk of or in need thereof, by administering to the animal a PMP composition.

The PMP compositions and related methods are suitable for treatment or preventing of fungal infections in animals, including infections caused by fungi belonging to Ascomycota (*Fusarium oxysporum, Pneumocystis jirovecii, Aspergillus* spp., *Coccidioides immitis/posadasii, Candida albicans*), Basidiomycota (*Filobasidiella neoformans, Trichosporon*), Microsporidia (*Encephalitozoon cuniculi, Enterocytozoon bieneusi*), Mucoromycotina (*Mucor circinelloides, Rhizopus oryzae, Lichtheimia corymbifera*).

In some instances, the fungal infection is one caused by a belonging to the phylum Ascomycota, Basidiomycota, Chytridiomycota, Microsporidia, or Zygomycota. The fungal infection or overgrowth can include one or more fungal species, e.g., *Candida albicans, C. tropicalis, C. parapsilosis, C. glabrata, C. auris, C. krusei, Saccharomyces cerevisiae, Malassezia globose, M. restricta*, or *Debaryomyces hansenii, Gibberella moniliformis, Alternaria brassicicola, Cryptococcus neoformans, Pneumocystis carinii, P. jirovecii, P. murina, P. oryctolagi, P. wakefieldiae*, and *Aspergillus clavatus*. The fungal species may be considered a pathogen or an opportunistic pathogen.

In some instances, the fungal infection is caused by a fungus in the genus *Candida* (i.e., a *Candida* infection). For example, a *Candida* infection can be caused by a fungus in the genus *Candida* that is selected from the group consisting of *C. albicans, C. glabrata, C. dubliniensis, C. krusei, C. auris, C. parapsilosis, C. tropicalis, C. orthopsilosis, C. guilliermondii, C. rugose*, and *C. lusitaniae*. *Candida* infections that can be treated by the methods disclosed herein include, but are not limited to candidemia, oropharyngeal candidiasis, esophageal candidiasis, mucosal candidiasis, genital candidiasis, vulvovaginal candidiasis, rectal candidiasis, hepatic candidiasis, renal candidiasis, pulmonary candidiasis, splenic candidiasis, otomycosis, osteomyelitis, septic arthritis, cardiovascular candidiasis (e.g., endocarditis), and invasive candidiasis.

ii. Bacteria

The PMP compositions and related methods can be useful for decreasing the fitness of a bacterium, e.g., to prevent or treat a bacterial infection in an animal. Included are methods for administering a PMP composition to a bacterium by contacting the bacteria with the PMP composition. Additionally or alternatively, the methods include preventing or treating a bacterial infection (e.g., caused by a bacteria described herein) in an animal at risk of or in need thereof, by administering to the animal a PMP composition.

The PMP compositions and related methods are suitable for preventing or treating a bacterial infection in animals caused by any bacteria described further below. For example, the bacteria may be one belonging to Bacillales (*B. anthracis, B. cereus, S. aureus, L. monocytogenes*), Lactobacillales (*S. pneumoniae, S. pyogenes*), Clostridiales (*C. botulinum, C. difficile, C. perfringens, C. tetani*), Spirochaetales (*Borrelia burgdorferi, Treponema pallidum*), Chlamydiales (*Chlamydia trachomatis, Chlamydophila psittaci*), Actinomycetales (*C. diphtheriae, Mycobacterium tuberculosis, M. avium*), Rickettsiales (*R. prowazekii, R. rickettsii, R. typhi, A. phagocytophilum, E. chaffeensis*), Rhizobiales (*Brucella melitensis*), Burkholderiales (*Bordetella pertussis, Burkholderia mallei, B. pseudomallei*), Neisseriales (*Neisseria gonorrhoeae, N. meningitidis*), Campylobacterales (*Campylobacter jejuni, Helicobacter pylori*), Legionellales (*Legionella pneumophila*), Pseudomonadales (*A. baumannii, Moraxella catarrhalis, P. aeruginosa*), Aeromonadales (*Aeromonas* sp.), Vibrionales (*Vibrio cholerae, V. parahaemolyticus*), Thiotrichales, Pasteurellales (*Haemophilus influenzae*), Enterobacteriales (*Klebsiella pneumoniae, Proteus mirabilis, Yersinia pestis, Y. enterocolitica, Shigella flexneri, Salmonella enterica, E. coli*).

iii. Parasitic Insects

The PMP compositions and related methods can be useful for decreasing the fitness of a parasitic insect, e.g., to prevent or treat a parasitic insect infection in an animal. The term "insect" includes any organism belonging to the phylum Arthropoda and to the class Insecta or the class Arachnida, in any stage of development, i.e., immature and adult insects. Included are methods for delivering a PMP composition to an insect by contacting the insect with the PMP composition. Additionally or alternatively, the methods include preventing or treating a parasitic insect infection (e.g., caused by a parasitic insect described herein) in an animal at risk of or in need thereof, by administering to the animal a PMP composition.

The PMP compositions and related methods are suitable for preventing or treating infection in animals by a parasitic insect, including infections by insects belonging to Phthiraptera: *Anoplura* (Sucking lice), *Ischnocera* (Chewing lice), *Amblycera* (Chewing lice). Siphonaptera: Pulicidae (Cat fleas), Ceratophyllidae (Chicken-fleas). Diptera: Culicidae (Mosquitoes), Ceratopogonidae (Midges), Psychodidae (Sandflies), Simuliidae (Blackflies), Tabanidae (Horseflies), Muscidae (House-flies, etc.), Calliphoridae (Blowflies), Glossinidae (Tsetse-flies), Oestridae (Bot-flies), Hippoboscidae (Louse-flies). Hemiptera: Reduviidae (Assassin-bugs), Cimicidae (Bed-bugs). Arachnida: Sarcoptidae (Sarcoptic mites), Psoroptidae (Psoroptic mites), Cytoditidae (Air-sac mites), Laminosioptes (Cyst-mites), Analgidae (Feather-mites), Acaridae (Grain-mites), Demodicidae (Hair-follicle mites), Cheyletiellidae (Fur-mites), Trombiculidae (Trombiculids), Dermanyssidae (Bird mites), Macronyssidae (Bird mites), Argasidae (Soft-ticks), Ixodidae (Hard-ticks).

iv. Protozoa

The PMP compositions and related methods can be useful for decreasing the fitness of a parasitic protozoa, e.g., to prevent or treat a parasitic protozoa infection in an animal. The term "protozoa" includes any organism belonging to the phylum Protozoa. Included are methods for delivering a PMP composition to a parasitic protozoan by contacting the parasitic protozoa with the PMP composition. Additionally or alternatively, the methods include preventing or treating a protozoal infection (e.g., caused by a protozoan described herein) in an animal at risk of or in need thereof, by administering to the animal a PMP composition.

The PMP compositions and related methods are suitable for preventing or treating infection by parasitic protozoa in animals, including protozoa belonging to Euglenozoa (*Trypanosoma cruzi, Trypanosoma brucei, Leishmania* spp.), Heterolobosea (*Naegleria fowleri*), Diplomonadida (*Giardia intestinalis*), Amoebozoa (*Acanthamoeba castellanii, Balamuthia mandrillaris, Entamoeba histolytica*), Blastocystis (*Blastocystis hominis*), Apicomplexa (*Babesia microti, Cryptosporidium parvum, Cyclospora cayetanensis, Plasmodium* spp., *Toxoplasma gondii*).

v. Nematodes

The PMP compositions and related methods can be useful for decreasing the fitness of a parasitic nematode, e.g., to prevent or treat a parasitic nematode infection in an animal. Included are methods for delivering a PMP composition to a parasitic nematode by contacting the parasitic nematode with the PMP composition. Additionally or alternatively, the methods include preventing or treating a parasitic nematode infection (e.g., caused by a parasitic nematode described herein) in an animal at risk of or in need thereof, by administering to the animal a PMP composition.

The PMP compositions and related methods are suitable for preventing or treating infection by parasitic nematodes in animals, including nematodes belonging to Nematoda (roundworms): *Angiostrongylus cantonensis* (rat lungworm), *Ascaris lumbricoides* (human roundworm), *Baylisascaris procyonis* (raccoon roundworm), *Trichuris trichiura* (human whipworm), *Trichinella spiralis, Strongyloides stercoralis, Wuchereria bancrofti, Brugia malayi, Ancylostoma duodenale* and *Necator americanus* (human hookworms), Cestoda (tapeworms): *Echinococcus granulosus, Echinococcus multilocularis, Taenia solium* (pork tapeworm).

vi. Viruses

The PMP compositions and related methods can be useful for decreasing the fitness of a virus, e.g., to prevent or treat a viral infection in an animal. Included are methods for delivering a PMP composition to a virus by contacting the virus with the PMP composition. Additionally or alternatively, the methods include preventing or treating a viral infection (e.g., caused by a virus described herein) in an animal at risk of or in need thereof, by administering to the animal a PMP composition.

The PMP compositions and related methods are suitable for preventing or treating a viral infection in animals, including infections by viruses belonging to DNA viruses: Parvoviridae, Papillomaviridae, Polyomaviridae, Poxviridae, Herpesviridae; Single-stranded negative strand RNA viruses: Arenaviridae, Paramyxoviridae (Rubulavirus, Respirovirus, Pneumovirus, Moribillivirus), Filoviridae (Marburgvirus, Ebolavirus), Bornaviridae, Rhabdoviridae, Orthomyxoviridae, Bunyaviridae, Nairovirus, Hantaviruses, Orthobunyavirus, Phlebovirus. Single-stranded positive strand RNA viruses: Astroviridae, Coronaviridae, Caliciviridae, Togaviridae (Rubivirus, Alphavirus), Flaviviridae (Hepacivirus, Flavivirus), Picornaviridae (Hepatovirus, Rhinovirus, Enterovirus); or dsRNA and Retro-transcribed Viruses: Reoviridae (Rotavirus, Coltivirus, Seadornavirus), Retroviridae (Deltaretrovirus, Lentivirus), Hepadnaviridae (Orthohepadnavirus).

E. Delivery to a Pathogen Vector

Provided herein are methods of delivering a PMP composition (e.g., including modified PMPs described herein) to pathogen vector, such as one disclosed herein, by contacting the pathogen vector with a PMP composition. As used herein, the term "vector" refers to an insect that can carry or transmit an animal pathogen from a reservoir to an animal. Exemplary vectors include insects, such as those with piercing-sucking mouthparts, as found in Hemiptera and some Hymenoptera and Diptera such as mosquitoes, bees, wasps, midges, lice, tsetse fly, fleas and ants, as well as members of the Arachnidae such as ticks and mites.

In some instances, the vector of the animal (e.g., human) pathogen may be treated with PMPs not including a heterologous functional agent. In other instances, the PMPs include a heterologous functional agent, e.g., a heterologous therapeutic agent (e.g., antibacterial agent, antifungal agent, insecticide, nematicide, antiparasitic agent, antiviral agent, or a repellent). The methods can be useful for decreasing the fitness of a pathogen vector, e.g., to control the spread of a pathogen as a consequence of delivery of the PMP composition. Examples of pathogen vectors that can be targeted in accordance with the present methods include insects, such as those described herein.

For example, provided herein is a method of decreasing the fitness of an animal pathogen vector, the method including delivering to the vector an effective amount of the PMP compositions described herein, wherein the method decreases the fitness of the vector relative to an untreated vector. In some instances, the method includes delivering the composition to at least one habitat where the vector grows, lives, reproduces, feeds, or infests. In some instances, the composition is delivered as a comestible composition for ingestion by the vector. In some instances, the vector is an insect. In some instances, the insect is a mosquito, a tick, a mite, or a louse. In some instances, the composition is delivered (e.g., to the pathogen vector) as a liquid, a solid, an aerosol, a paste, a gel, or a gas.

For example, provided herein is a method of decreasing the fitness of an insect vector of an animal pathogen, wherein the method includes delivering to the vector a PMP composition including a plurality of PMPs. In some instances, the method includes delivering to the vector a PMP composition including a plurality of PMPs, wherein the plurality of PMPs includes an insecticidal agent. For example, the insect vector may be a mosquito, tick, mite, or louse. Other non-limiting examples of pathogen vectors are provided herein. In some instances, the method decreases the fitness of the vector relative to an untreated vector.

In some instances, the decrease in vector fitness may manifest as a deterioration or decline in the physiology of the vector (e.g., reduced health or survival) as a consequence of administration of a composition. In some instances, the fitness of an organism may be measured by one or more parameters, including, but not limited to, reproductive rate, lifespan, mobility, fecundity, body weight, metabolic rate or activity, or survival in comparison to a vector organism to which the composition has not been delivered. For example, the methods or compositions provided herein may be effective to decrease the overall health of the vector or to decrease the overall survival of the vector. In some instances, the decreased survival of the vector is about 2%, 5%, 10%, 20%, 30%, 40%, 50%, 60%, 70%, 80%, 90%, 100%, or greater than 100% greater relative to a reference level (e.g., a level found in a vector that does not receive a composition). In some instances, the methods and compositions are effective to decrease vector reproduction (e.g., reproductive rate) in comparison to a vector organism to which the composition has not been delivered. In some instances, the methods and compositions are effective to decrease other physiological parameters, such as mobility, body weight, life span, fecundity, or metabolic rate, by about 2%, 5%, 10%, 20%, 30%, 40%, 50%, 60%, 70%, 80%, 90%, 100%, or greater than 100% relative to a reference level (e.g., a level found in a vector that is not delivered the composition).

In some instances, the decrease in vector fitness may manifest as an increase in the vector's sensitivity to a pesticidal agent and/or a decrease in the vector's resistance to a pesticidal agent in comparison to a vector organism to which the composition has not been delivered. In some instances, the methods or compositions provided herein may be effective to increase the vector's sensitivity to a pesticidal agent by about 2%, 5%, 10%, 20%, 30%, 40%, 50%, 60%, 70%, 80%, 90%, 100%, or greater than 100% relative to a reference level (e.g., a level found in a vector that does not receive a composition). The pesticidal agent may be any pesticidal agent known in the art, including insecticidal agents. In some instances, the methods or compositions provided herein may increase the vector's sensitivity to a pesticidal agent by decreasing the vector's ability to metabolize or degrade the pesticidal agent into usable substrates in comparison to a vector to which the composition has not been delivered.

In some instances, the decrease in vector fitness may manifest as other fitness disadvantages, such as decreased tolerance to certain environmental factors (e.g., a high or low temperature tolerance), decreased ability to survive in certain habitats, or a decreased ability to sustain a certain diet in comparison to a vector organism to which the composition has not been delivered. In some instances, the methods or compositions provided herein may be effective to decrease vector fitness in any plurality of ways described herein. Further, the composition may decrease vector fitness in any number of vector classes, orders, families, genera, or species (e.g., 1 vector species, 2, 3, 4, 5, 6, 7, 8, 9, 10, 15, 20, 30, 40, 50, 60, 70, 80, 90, 100, 150, 200, 200, 250, 500, or more vector species). In some instances, the composition acts on a single vector class, order, family, genus, or species.

Vector fitness may be evaluated using any standard methods in the art. In some instances, vector fitness may be evaluated by assessing an individual vector. Alternatively, vector fitness may be evaluated by assessing a vector population. For example, a decrease in vector fitness may manifest as a decrease in successful competition against other vectors, thereby leading to a decrease in the size of the vector population.

By decreasing the fitness of vectors that carry animal pathogens, the compositions provided herein are effective to reduce the spread of vector-borne diseases. The composition may be delivered to the insects using any of the formulations and delivery methods described herein, in an amount and for a duration effective to reduce transmission of the disease, e.g., reduce vertical or horizontal transmission between vectors and/or reduce transmission to animals. For example, the composition described herein may reduce vertical or horizontal transmission of a vector-borne pathogen by about 2%, 5%, 10%, 20%, 30%, 40%, 50%, 60%, 70%, 80%, 90%, 100%, or more in comparison to a vector organism to which the composition has not been delivered. As another example, the composition described herein may reduce vectorial competence of an insect vector by about 2%, 5%, 10%, 20%, 30%, 40%, 50%, 60%, 70%, 80%, 90%, 100%, or more in comparison to a vector organism to which the composition has not been delivered.

Non-limiting examples of diseases that may be controlled by the compositions and methods provided herein include diseases caused by Togaviridae viruses (e.g., Chikungunya, Ross River fever, Mayaro, Onyon-nyong fever, Sindbis fever, Eastern equine enchephalomyeltis, Wesetern equine encephalomyelitis, Venezualan equine encephalomyelitis, or Barmah forest); diseases caused by Flavivirdae viruses (e.g., Dengue fever, Yellow fever, Kyasanur Forest disease, Omsk haemorrhagic fever, Japaenese encephalitis, Murray Valley encephalitis, Rocio, St. Louis encephalitis, West Nile encephalitis, or Tick-borne encephalitis); diseases caused by Bunyaviridae viruses (e.g., Sandly fever, Rift Valley fever, La Crosse encephalitis, California encephalitis, Crimean-Congo haemorrhagic fever, or Oropouche fever); disease caused by Rhabdoviridae viruses (e.g., Vesicular stomatitis); disease caused by Orbiviridae (e.g., Bluetongue); diseases caused by bacteria (e.g., Plague, Tularaemia, Q fever, Rocky Mountain spotted fever, Murine typhus, Boutonneuse fever, Queensland tick typhus, Siberian tick typhus, Scrub typhus, Relapsing fever, or Lyme disease); or diseases caused by protozoa (e.g., Malaria, African trypanosomiasis, Nagana, Chagas disease, Leishmaniasis, Piroplasmosis, Bancroftian filariasis, or Brugian filariasis).

i. Pathogen Vectors

The methods and compositions provided herein may be useful for decreasing the fitness of a vector for an animal pathogen. In some instances, the vector may be an insect. For example, the insect vector may include, but is not limited to those with piercing-sucking mouthparts, as found in Hemiptera and some Hymenoptera and Diptera such as mosquitoes, bees, wasps, midges, lice, tsetse fly, fleas and ants, as well as members of the Arachnidae such as ticks and mites; order, class or family of *Acarina* (ticks and mites) e.g. representatives of the families Argasidae, Dermanyssidae, Ixodidae, Psoroptidae or Sarcoptidae and representatives of the species *Amblyomma* spp., *Anocenton* spp., *Argas* spp., *Boophilus* spp., *Cheyletiella* spp., *Chorioptes* spp., *Demodex* spp., *Dermacentor* spp., *Denmanyssus* spp., *Haemophysalis* spp., *Hyalomma* spp., *Ixodes* spp., *Lynxacarus* spp., *Mesostigmata* spp., *Notoednes* spp., *Ornithodoros* spp., *Ornithonyssus* spp., *Otobius* spp., *otodectes* spp., *Pneumonyssus* spp., *Psoroptes* spp., *Rhipicephalus* spp., *Sancoptes* spp., or *Trombicula* spp.; *Anoplura* (sucking and biting lice) e.g. representatives of the species *Bovicola* spp., *Haematopinus* spp., *Linognathus* spp., *Menopon* spp., *Pediculus* spp., *Pemphigus* spp., *Phylloxera* spp., or *Solenopotes* spp.; Diptera (flies) e.g. representatives of the species *Aedes* spp., *Anopheles* spp., *Calliphora* spp., *Chrysomyia* spp., *Chrysops* spp., *Cochliomyia* spp., *Cw/ex* spp., *Culicoides* spp., *Cuterebra* spp., *Dermatobia* spp., *Gastrophilus* spp., *Glossina* spp., *Haematobia* spp., *Haematopota* spp., *Hippobosca* spp., *Hypoderma* spp., *Lucilia* spp., *Lyperosia* spp., *Melophagus* spp., *Oestrus* spp., *Phaenicia* spp., *Phlebotomus* spp., *Phormia* spp., *Acari* (sarcoptic mange) e.g., *Sarcoptidae* spp., *Sarcophaga* spp., *Simulium* spp., *Stomoxys* spp., *Tabanus* spp., *Tannia* spp. or *Zzpu/alpha* spp.; Mallophaga (biting lice) e.g. representatives of the species *Damalina* spp., *Felicola* spp., *Heterodoxus* spp. or *Trichodectes* spp.; or Siphonaptera (wingless insects) e.g. representatives of the species *Ceratophyllus* spp., *Xenopsylla* spp; Cimicidae (true bugs) e.g. representatives of the species *Cimex* spp., *Tritominae* spp., *Rhodinius* spp., or *Triatoma* spp.

In some instances, the insect is a blood-sucking insect from the order Diptera (e.g., suborder Nematocera, e.g., family Colicidae). In some instances, the insect is from the subfamilies Culicinae, Corethrinae, Ceratopogonidae, or Simuliidae. In some instances, the insect is of a *Culex* spp., *Theobaldia* spp., *Aedes* spp., *Anopheles* spp., *Aedes* spp., *Forciponiyia* spp., *Culicoides* spp., or *Helea* spp.

In certain instances, the insect is a mosquito. In certain instances, the insect is a tick. In certain instances, the insect is a mite. In certain instances, the insect is a biting louse.

F. Delivery to an Animal

Provided herein are methods of delivering a PMP composition (e.g., including modified PMPs described herein) to an animal cell, tissue or subject (e.g., a mammal, e.g., a human), e.g., by contacting the animal cell, tissue, subject, or a part thereof, with the PMP composition. In some instances, animals may be treated with PMPs not including a heterologous functional agent. In other instances, the PMPs include a heterologous functional agent, e.g., a heterologous therapeutic agent (e.g., a therapeutic protein or peptide nucleic acid, or small molecule, an antibacterial agent, antifungal agent, insecticide, nematicide, antiparasitic agent, antiviral agent, or a repellent).

In one aspect, provided herein is a method of increasing the fitness of an animal (e.g., a human), the method including delivering to the animal the PMP composition described herein (e.g., in an effective amount and duration) to increase the fitness of the animal relative to an untreated animal (e.g., an animal that has not been delivered the PMP composition).

An increase in the fitness of the animal as a consequence of delivery of a PMP composition can be determined by any method of assessing animal fitness (e.g., fitness of a mammal, e.g., fitness (e.g., health) of a human).

Provided herein is a method of modifying or increasing the fitness of an animal (e.g., a human), the method including delivering to the animal an effective amount of a PMP composition provided herein, wherein the method modifies the animal and thereby introduces or increases a beneficial trait in the animal (e.g., by about 1%, 2%, 5%, 10%, 20%, 30%, 40%, 50%, 60%, 70%, 80%, 90%, 100%, or more than 100%) relative to an untreated animal. In particular, the method may increase the fitness of the animal, e.g., a mammal, e.g., a human (e.g., by about 1%, 2%, 5%, 10%, 20%, 30%, 40%, 50%, 60%, 70%, 80%, 90%, 100%, or more than 100%) relative to an untreated animal.

In a further aspect, provided herein is a method of increasing the fitness of an animal (e.g., a human), the method including contacting a cell of the animal with an effective amount of a PMP composition herein, wherein the method increases the fitness of the animal, e.g., mammal, e.g., human (e.g., by about 1%, 2%, 5%, 10%, 20%, 30%, 40%, 50%, 60%, 70%, 80%, 90%, 100%, or more than 100%) relative to an untreated animal.

In certain instances, the animal is a mammal, e.g., a human. In certain instances, the animal is a livestock animal or a veterinary animal. In certain instances, the animal is a mouse.

G. Application Methods

A plant described herein can be exposed to a PMP composition (e.g., including modified PMPs described herein) in any suitable manner that permits delivering or administering the composition to the plant. The PMP composition may be delivered either alone or in combination with other active (e.g., fertilizing agents) or inactive substances and may be applied by, for example, spraying, injection (e.g., microinjection), through plants, pouring, dipping, in the form of concentrated liquids, gels, solutions, suspensions, sprays, powders, pellets, briquettes, bricks and the like, formulated to deliver an effective concentration of the PMP composition. Amounts and locations for application of the compositions described herein are generally determined by the habitat of the plant, the lifecycle stage at which the plant can be targeted by the PMP composition, the site where the application is to be made, and the physical and functional characteristics of the PMP composition.

In some instances, the composition is sprayed directly onto a plant e.g., crops, by e.g., backpack spraying, aerial spraying, crop spraying/dusting etc. In instances where the PMP composition is delivered to a plant, the plant receiving the PMP composition may be at any stage of plant growth. For example, formulated PMP compositions can be applied as a seed-coating or root treatment in early stages of plant growth or as a total plant treatment at later stages of the crop cycle. In some instances, the PMP composition may be applied as a topical agent to a plant.

Further, the PMP composition may be applied (e.g., in the soil in which a plant grows, or in the water that is used to water the plant) as a systemic agent that is absorbed and distributed through the tissues of a plant. In some instances, plants or food organisms may be genetically transformed to express the PMP composition.

Delayed or continuous release can also be accomplished by coating the PMP composition or a composition with the PMP composition(s) with a dissolvable or bioerodable coating layer, such as gelatin, which coating dissolves or erodes in the environment of use, to then make the PMP composition available, or by dispersing the agent in a dissolvable or erodable matrix. Such continuous release and/or dispensing devices may be advantageously employed to consistently maintain an effective concentration of one or more of the PMP compositions described herein.

In some instances, the PMP composition is delivered to a part of the plant, e.g., a leaf, seed, pollen, root, fruit, shoot, or flower, or a tissue, cell, or protoplast thereof. In some instances, the PMP composition is delivered to a cell of the plant. In some instances, the PMP composition is delivered to a protoplast of the plant. In some instances, the PMP composition is delivered to a tissue of the plant. For example, the composition may be delivered to meristematic tissue of the plant (e.g., apical meristem, lateral meristem, or intercalary meristem). In some instances, the composition is delivered to permanent tissue of the plant (e.g., simple tissues (e.g., parenchyma, collenchyma, or sclerenchyma) or complex permanent tissue (e.g., xylem or phloem)). In some instances, the composition is delivered to a plant embryo.

In some instances, the PMP composition may be recommended for field application as an amount of PMPs per hectare (g/ha or kg/ha) or the amount of active ingredient (e.g., PMP with or without a heterologous functional agent) or acid equivalent per hectare (kg a.i./ha or g a.i./ha). In some instances, a lower amount of heterologous functional agent in the present compositions may be required to be applied to soil, plant media, seeds plant tissue, or plants to achieve the same results as where the heterologous functional agent is applied in a composition lacking PMPs. For example, the amount of heterologous functional agent may be applied at levels about 2, 3, 4, 5, 6, 7, 8, 9, 10, 15, 20, 30, 50, or 100-fold (or any range between about 2 and about 100-fold, for example about 2- to 10-fold; about 5- to 15-fold, about 10- to 20-fold; about 10- to 50-fold) less than the same heterologous functional agent applied in a non-PMP composition, e.g., direct application of the same heterologous functional agent without PMPs. PMP compositions of the invention can be applied at a variety of amounts per hectare, for example at about 0.0001, 0.001, 0.005, 0.01, 0.1, 1, 2, 10, 100, 1,000, 2,000, 5,000 (or any range between about 0.0001 and 5,000) kg/ha. For example, about 0.0001 to about 0.01, about 0.01 to about 10, about 10 to about 1,000, about 1,000 to about 5,000 kg/ha.

H. Therapeutic Methods

The PMP compositions (e.g., including modified PMPs described herein) can also be useful in a variety of therapeutic methods. For example, the methods and composition may be used for the prevention or treatment of pathogen infections in animals (e.g., humans). As used herein, the term "treatment" refers to administering a pharmaceutical composition to an animal for prophylactic and/or therapeutic purposes. To "prevent an infection" refers to prophylactic treatment of an animal who is not yet ill, but who is susceptible to, or otherwise at risk of, a particular disease. To "treat an infection" refers to administering treatment to an animal already suffering from a disease to improve or stabilize the animal's condition. The present methods involve delivering the PMP compositions described herein to an animal, such as a human.

For example, provided herein is a method of treating an animal having a fungal infection, wherein the method includes administering to the animal an effective amount of a PMP composition including a plurality of PMPs. In some instances, the method includes administering to the animal an effective amount of a PMP composition including a plurality of PMPs, wherein the plurality of PMPs includes an antifungal agent. In some instances, the antifungal agent is a nucleic acid that inhibits expression of a gene in a fungus that causes the fungal infection (e.g., Enhanced Filamentous Growth Protein (EFG1)). In some instances, the fungal infection is caused by *Candida albicans*. In some instances, composition includes a PMP produced from an *Arabidopsis* apoplast EV. In some instances, the method decreases or substantially eliminates the fungal infection.

In another aspect, provided herein is a method of treating an animal having a bacterial infection, wherein the method includes administering to the animal an effective amount of a PMP composition including a plurality of PMPs. In some instances, the method includes administering to the animal an effective amount of a PMP composition including a plurality of PMPs, and wherein the plurality of PMPs includes an antibacterial agent (e.g., Amphotericin B). In some instances, the bacterium is a *Streptococcus* spp., *Pneumococcus* spp., *Pseudamonas* spp., *Shigella* spp, *Salmonella* spp., *Campylobacter* spp., or an *Escherichia* spp. In some instances, the composition includes a PMP produced from an *Arabidopsis* apoplast EV. In some instances, the method decreases or substantially eliminates the bacterial infection. In some instances, the animal is a human, a veterinary animal, or a livestock animal.

The present methods are useful to treat an infection (e.g., as caused by an animal pathogen) in an animal, which refers to administering treatment to an animal already suffering from a disease to improve or stabilize the animal's condition. This may involve reducing colonization of a pathogen in, on, or around an animal by one or more pathogens (e.g., by about 1%, 2%, 5%, 10%, 20%, 30%, 40%, 50%, 60%, 70%, 80%, 90%, or 100%) relative to a starting amount and/or allow benefit to the individual (e.g., reducing colonization in an amount sufficient to resolve symptoms). In such instances, a treated infection may manifest as a decrease in symptoms (e.g., by about 1%, 2%, 5%, 10%, 20%, 30%, 40%, 50%, 60%, 70%, 80%, 90%, or 100%). In some instances, a treated infection is effective to increase the likelihood of survival of an individual (e.g., an increase in likelihood of survival by about 1%, 2%, 5%, 10%, 20%, 30%, 40%, 50%, 60%, 70%, 80%, 90%, or 100%) or increase the overall survival of a population (e.g., an increase in likelihood of survival by about 1%, 2%, 5%, 10%, 20%, 30%, 40%, 50%, 60%, 70%, 80%, 90%, or 100%). For example, the compositions and methods may be effective to "substantially eliminate" an infection, which refers to a decrease in the infection in an amount sufficient to sustainably resolve symptoms (e.g., for at least 1, 2, 3, 4, 5, 6, 7, 8, 9, 10, 11, or 12 months) in the animal.

The present methods are useful to prevent an infection (e.g., as caused by an animal pathogen), which refers to preventing an increase in colonization in, on, or around an animal by one or more pathogens (e.g., by about 1%, 2%, 5%, 10%, 20%, 30%, 40%, 50%, 60%, 70%, 80%, 90%, 100%, or more than 100% relative to an untreated animal) in an amount sufficient to maintain an initial pathogen population (e.g., approximately the amount found in a healthy individual), prevent the onset of an infection, and/or prevent symptoms or conditions associated with infection. For example, individuals may receive prophylaxis treatment to prevent a fungal infection while being prepared for an invasive medical procedure (e.g., preparing for surgery, such as receiving a transplant, stem cell therapy, a graft, a prosthesis, receiving long-term or frequent intravenous catheterization, or receiving treatment in an intensive care unit), in immunocompromised individuals (e.g., individuals with cancer, with HIV/AIDS, or taking immunosuppressive agents), or in individuals undergoing long term antibiotic therapy.

The PMP composition can be formulated for administration or administered by any suitable method, including, for example, intravenously, intramuscularly, subcutaneously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subconjunctivally, intravesicularly, mucosally, intrapericardially, intraumbilically, intraocularly, intraorbitally, orally, topically, transdermally, intravitreally (e.g., by intravitreal injection), by eye drop, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated). In some instances, PMP composition is administered intravenously, intramuscularly, subcutaneously, topically, orally, transdermally, intraperitoneally, intraorbitally, by implantation, by inhalation, intrathecally, intraventricularly, or intranasally. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

For the prevention or treatment of an infection described herein (when used alone or in combination with one or more other additional therapeutic agents) will depend on the type of disease to be treated, the severity and course of the disease, whether the is administered for preventive or therapeutic purposes, previous therapy, the patient's clinical history and response to the PMP composition. The PMP composition can be, e.g., administered to the patient at one time or over a series of treatments. For repeated administrations over several days or longer, depending on the condition, the treatment would generally be sustained until a desired suppression of disease symptoms occurs or the infection is no longer detectable. Such doses may be administered intermittently, e.g., every week or every two weeks (e.g., such that the patient receives, for example, from about two to about twenty, doses of the PMP composition. An initial higher loading dose, followed by one or more lower doses may be administered. However, other dosage regimens may be useful. The progress of this therapy is easily monitored by conventional techniques and assays.

In some instances, the amount of the PMP composition administered to individual (e.g., human) may be in the range of about 0.01 mg/kg to about 5 g/kg (e.g., about 0.01 mg/kg-0.1 mg/kg, about 0.1 mg/kg-1 mg/kg, about 1 mg/kg-10 mg/kg, about 10 mg/kg-100 mg/kg, about 100 mg/kg-1 g/kg, or about 1 g/kg-5 g/kg), of the individual's body weight. In some instances, the amount of the PMP composition administered to individual (e.g., human) is at least 0.01 mg/kg (e.g., at least 0.01 mg/kg, at least 0.1 mg/kg, at least 1 mg/kg, at least 10 mg/kg, at least 100 mg/kg, at least 1 g/kg, or at least 5 g/kg), of the individual's body weight. The dose may be administered as a single dose or as multiple doses (e.g., 2, 3, 4, 5, 6, 7, or more than 7 doses). In some instances, the PMP composition administered to the animal may be administered alone or in combination with an additional therapeutic agent. The dose of the antibody administered in a combination treatment may be reduced as compared to a single treatment. The progress of this therapy is easily monitored by conventional techniques.

IV. Kits

The present invention also provides a kit including a container having a PMP composition described herein. The kit may further include instructional material for applying or delivering the PMP composition to a plant in accordance with a method of the present invention. The skilled artisan will appreciate that the instructions for applying the PMP composition in the methods of the present invention can be any form of instruction. Such instructions include, but are not limited to, written instruction material (such as, a label, a booklet, a pamphlet), oral instructional material (such as on an audio cassette or CD) or video instructions (such as on a video tape or DVD).

EXAMPLES

The following are examples of the methods of the invention. It is understood that various other embodiments may be practiced, given the general description provided above.

Table of Contents (Examples):

| | |
|---|---|
| Example 1. | Isolation of Plant Messenger Packs from plants |
| Example 2. | Production of purified Plant Messenger Packs (PMPs) |
| Example 3. | Plant Messenger Pack characterization |
| Example 4. | Characterization of Plant Messenger Pack stability |
| Example 5. | Loading PMPs with cargo |
| Example 6. | Increasing PMP cellular uptake by formulation of PMPs with ionic liquids |
| Example 7. | Modification of PMPs using ionizable lipids |
| Example 8. | Formulation of LPMPs with microfluidics |
| Example 9. | mRNA loading and delivery into lipid-reconstructed PMPs using ionizable lipids |
| Example 10. | Cellular uptake of natural and reconstructed PMPs, with and without ionizable lipid modifications |
| Example 11. | Increasing PMP cellular uptake by formulation of PMPs with cationic lipids |
| Example 12. | Modification of PMPs using cationic lipids |
| Example 13. | mRNA loading and delivery into lipid-reconstructed PMPs using cationic lipids |
| Example 14. | Cellular uptake of natural and reconstructed PMPs, with and without cationic lipid modifications |

| Table of Contents (Examples): |
| --- |
| Example 15. Imporved loading using the cationic lipids GL67 and Ethyl PC |
| Example 16. Optimization of lipid ratios for mRNA loading |
| Example 17. Optimization of lipid ratios for plasmid loading |

Example 1: Isolation of Plant Messenger Packs from Plants

This example describes the isolation of crude plant messenger packs (PMPs) from various plant sources, including the leaf apoplast, seed apoplast, root, fruit, vegetable, pollen, phloem, xylem sap and plant cell culture medium.

Experimental Design:

a) PMP Isolation from the Apoplast of *Arabidopsis thaliana* Leaves

*Arabidopsis* (*Arabidopsis thaliana* Col-0) seeds are surface sterilized with 50% bleach and plated on 0.53 Murashige and Skoog medium containing 0.8% agar. The seeds are vernalized for 2 d at 4° C. before being moved to short-day conditions (9-h days, 22° C., 150 $\mu Em^{-2}$). After 1 week, the seedlings are transferred to Pro-Mix PGX. Plants are grown for 4-6 weeks before harvest.

PMPs are isolated from the apoplastic wash of 4-6-week old *Arabidopsis* rosettes, as described by Rutter and Innes, *Plant Physiol.* 173(1): 728-741, 2017. Briefly, whole rosettes are harvested at the root and vacuum infiltrated with vesicle isolation buffer (20 mM MES, 2 mM CaCl2), and 0.1 M NaCl, pH6). Infiltrated plants are carefully blotted to remove excess fluid, placed inside 30-mL syringes, and centrifuged in 50 mL conical tubes at 700 g for 20 min at 2° C. to collect the apoplast extracellular fluid containing EVs. Next, the apoplast extracellular fluid is filtered through a 0.85 µm filter to remove large particles, and PMPs are purified as described in Example 2.

b) PMP Isolation from the Apoplast of Sunflower Seeds

Intact sunflower seeds (*H. annuus* L.), and are imbibed in water for 2 hours, peeled to remove the pericarp, and the apoplastic extracellular fluid is extracted by a modified vacuum infiltration-centrifugation procedure, adapted from Regente et al, *FEBS Letters*. 583: 3363-3366, 2009. Briefly, seeds are immersed in vesicle isolation buffer (20 mM MES, 2 mM CaCl2), and 0.1 M NaCl, pH6) and subjected to three vacuum pulses of 10 s, separated by 30 s intervals at a pressure of 45 kPa. The infiltrated seeds are recovered, dried on filter paper, placed in fritted glass filters and centrifuged for 20 min at 400 g at 4° C. The apoplast extracellular fluid is recovered, filtered through a 0.85 µm filter to remove large particles, and PMPs are purified as described in Example 2.

c) PMP Isolation from Ginger Roots

Fresh ginger (*Zingiber officinale*) rhizome roots are purchased from a local supplier and washed 3× with PBS. A total of 200 grams of washed roots is ground in a mixer (Osterizer 12-speed blender) at the highest speed for 10 min (pause 1 min for every 1 min of blending), and PMPs are isolated as described in Zhuang et al., *J Extracellular Vesicles.* 4(1):28713, 2015. Briefly, ginger juice is sequentially centrifuged at 1,000 g for 10 min, 3,000 g for 20 min and 10,000 g for 40 min to remove large particles from the PMP-containing supernatant. PMPs are purified as described in Example 2.

d) PMP Isolation from Grapefruit Juice

Fresh grapefruits (*Citrus×paradisi*) are purchased from a local supplier, their skins are removed, and the fruit is manually pressed, or ground in a mixer (Osterizer 12-speed blender) at the highest speed for 10 min (pause 1 min for every minute of blending) to collect the juice, as described by Wang et al., *Molecular Therapy.* 22(3): 522-534, 2014 with minor modifications. Briefly, juice/juice pulp is sequentially centrifuged at 1,000 g for 10 min, 3,000 g for 20 min, and 10,000 g for 40 min to remove large particles from the PMP-containing supernatant. PMPs are purified as described in Example 2.

e) PMP Isolation from Broccoli Heads

Broccoli (*Brassica oleracea* var. *italica*) PMPs are isolated as previously described (Deng et al., *Molecular Therapy,* 25(7): 1641-1654, 2017). Briefly, fresh broccoli is purchased from a local supplier, washed three times with PBS, and ground in a mixer (Osterizer 12-speed blender) at the highest speed for 10 min (pause 1 min for every minute of blending). Broccoli juice is then sequentially centrifuged at 1,000 g for 10 min, 3,000 g for 20 min, and 10,000 g for 40 min to remove large particles from the PMP-containing supernatant. PMPs are purified as described in Example 2.

f) PMP Isolation from Olive Pollen

Olive (*Olea europaea*) pollen PMPs are isolated as previously described in Prado et al., *Molecular Plant.* 7(3):573-577, 2014. Briefly, olive pollen (0.1 g) is hydrated in a humid chamber at room temperature for 30 min before transferring to petri dishes (15 cm in diameter) containing 20 ml germination medium: 10% sucrose, 0.03% $Ca(NO_3)_2$, 0.01% $KNO_3$, 0.02% $MgSO_4$, and 0.03% $H_3BO_3$. Pollen is germinated at 30° C. in the dark for 16 h. Pollen grains are considered germinated only when the tube is longer than the diameter of the pollen grain. Cultured medium containing PMPs is collected and cleared of pollen debris by two successive filtrations on 0.85 µm filters by centrifugation. PMPs are purified as described in Example 2.

g) PMP Isolation from *Arabidopsis* Phloem Sap

*Arabidopsis* (*Arabidopsis thaliana* Col-0) seeds are surface sterilized with 50% bleach and plated on 0.53 Murashige and Skoog medium containing 0.8% agar. The seeds are vernalized for 2 d at 4° C. before being moved to short-day conditions (9-h days, 22° C., 150 $\mu Em^{-2}$). After 1 week, the seedlings are transferred to Pro-Mix PGX. Plants are grown for 4-6 weeks before harvest.

Phloem sap from 4-6-week old *Arabidopsis* rosette leaves is collected as described by Tetyuk et al., *JoVE.* 80, 2013. Briefly, leaves are cut at the base of the petiole, stacked, and placed in a reaction tube containing 20 mM K2-EDTA for one hour in the dark to prevent sealing of the wound. Leaves are gently removed from the container, washed thoroughly with distilled water to remove all EDTA, put in a clean tube, and phloem sap is collected for 5-8 hours in the dark. Leaves are discarded, phloem sap is filtered through a 0.85 µm filter to remove large particles, and PMPs are purified as described in Example 2.

h) PMP Isolation from Tomato Plant Xylem Sap

Tomato (*Solanumlycopersicum*) seeds are planted in a single pot in an organic-rich soil, such as Sunshine Mix (Sun Gro Horticulture, Agawam, MA) and maintained in a greenhouse between 22° C. and 28° C. About two weeks after germination, at the two true-leaf stage, the seedlings are transplanted individually into pots (10 cm diameter and 17 cm deep) filled with sterile sandy soil containing 90% sand and 10% organic mix. Plants are maintained in a greenhouse at 22-28° C. for four weeks.

Xylem sap from 4-week old tomato plants is collected as described by Kohlen et al., *Plant Physiology.* 155(2):721-

734, 2011. Briefly, tomato plants are decapitated above the hypocotyl, and a plastic ring is placed around the stem. The accumulating xylem sap is collected for 90 min after decapitation. Xylem sap is filtered through a 0.85 μm filter to remove large particles, and PMPs are purified as described in Example 2.

i) PMP Isolation from Tobacco BY-2 Cell Culture Medium

Tobacco BY-2 (*Nicotiana tabacum* L cv. Bright Yellow 2) cells are cultured in the dark at 26° C., on a shaker at 180 rpm in MS (Murashige and Skoog, 1962) BY-2 cultivation medium (pH 5.8) comprised MS salts (Duchefa, Haarlem, Netherlands, at #M0221) supplemented with 30 g/L sucrose, 2.0 mg/L potassium dihydrogen phosphate, 0.1 g/L myo-inositol, 0.2 mg/L 2,4-dichlorophenoxyacetic acid, and 1 mg/L thiamine HCl. The BY-2 cells are subcultured weekly by transferring 5% (v/v) of a 7-day-old cell culture into 100 mL fresh liquid medium. After 72-96 hours, BY-2 cultured medium is collected and centrifuged at 300 g at 4° C. for 10 minutes to remove cells. The supernatant containing PMPs is collected and cleared of debris by filtration on 0.85 um filter. PMPs are purified as described in Example 2.

Example 2: Production of Purified Plant Messenger Packs (PMPs)

This example describes the production of purified PMPs from crude PMP fractions as described in Example 1, using ultrafiltration combined with size-exclusion chromatography, a density gradient (iodixanol or sucrose), and the removal of aggregates by precipitation or size-exclusion chromatography.

Experimental Design:

a) Production of Purified Grapefruit PMPs Using Ultrafiltration Combined with Size-Exclusion Chromatography The crude grapefruit PMP fraction from Example 1a is concentrated using 100-kDA molecular weight cut-off (MWCO) Amicon spin filter (Merck Millipore). Subsequently, the concentrated crude PMP solution is loaded onto a PURE-EV size exclusion chromatography column (HansaBioMed Life Sciences Ltd) and isolated according to the manufacturer's instructions. The purified PMP-containing fractions are pooled after elution. Optionally, PMPs can be further concentrated using a 100-kDa MWCO Amicon spin filter, or by Tangential Flow Filtration (TFF). The purified PMPs are analyzed as described in Example 3.

b) Production of Purified *Arabidopsis* Apoplast PMPs Using an Iodixanol Gradient Crude *Arabidopsis* leaf apoplast PMPs are isolated as described in Example 1a, and purified PMPs are produced by using an iodixanol gradient as described in Rutter and Innes, *Plant Physiol.* 173(1): 728-741, 2017. To prepare discontinuous iodixanol gradients (OptiPrep; Sigma-Aldrich), solutions of 40% (v/v), 20% (v/v), 10% (v/v), and 5% (v/v) iodixanol are created by diluting an aqueous 60% OptiPrep stock solution in vesicle isolation buffer (VIB; 20 mM MES, 2 mM CaCl2, and 0.1 M NaCl, pH6). The gradient is formed by layering 3 ml of 40% solution, 3 mL of 20% solution, 3 mL of 10% solution, and 2 mL of 5% solution. The crude apoplast PMP solution from Example 1a is centrifuged at 40,000 g for 60 min at 4° C. The pellet is resuspended in 0.5 ml of VIB and layered on top of the gradient. Centrifugation is performed at 100,000 g for 17 h at 4° C. The first 4.5 ml at the top of the gradient is discarded, and subsequently 3 volumes of 0.7 ml that contain the apoplast PMPs are collected, brought up to 3.5 mL with VIB and centrifuged at 100,000 g for 60 min at 4° C. The pellets are washed with 3.5 ml of VIB and repelleted using the same centrifugation conditions. The purified PMP pellets are combined for subsequent analysis, as described in Example 3.

c) Production of Purified Grapefruit PMPs Using a Sucrose Gradient

Crude grapefruit juice PMPs are isolated as described in Example 1d, centrifuged at 150,000 g for 90 min, and the PMP-containing pellet is resuspended in 1 ml PBS as described (Mu et al., *Molecular Nutrition & Food Research.* 58(7):1561-1573, 20141. The resuspended pellet is transferred to a sucrose step gradient (8%/15%/30%/45%/60%) and centrifuged at 150,000 g for 120 min to produce purified PMPs. Purified grapefruit PMPs are harvested from the 30%/45% interface, and subsequently analyzed, as described in Example 3.

d) Removal of Aggregates from Grapefruit PMPs

In order to remove protein aggregates from produced grapefruit PMPs as described in Example 1d or purified PMPs from Example 2a-c, an additional purification step can be included. The produced PMP solution is taken through a range of pHs to precipitate protein aggregates in solution. The pH is adjusted to 3, 5, 7, 9, or 11 with the addition of sodium hydroxide or hydrochloric acid. pH is measured using a calibrated pH probe. Once the solution is at the specified pH, it is filtered to remove particulates. Alternatively, the isolated PMP solution can be flocculated using the addition of charged polymers, such as Polymin-P or Praestol 2640. Briefly, 2-5 g per L of Polymin-P or Praestol 2640 is added to the solution and mixed with an impeller. The solution is then filtered to remove particulates. Alternatively, aggregates are solubilized by increasing salt concentration. NaCl is added to the PMP solution until it is at 1 mol/L. The solution is then filtered to purify the PMPs. Alternatively, aggregates are solubilized by increasing the temperature. The isolated PMP mixture is heated under mixing until it has reached a uniform temperature of 50° C. for 5 minutes. The PMP mixture is then filtered to isolate the PMPs. Alternatively, soluble contaminants from PMP solutions are separated by size-exclusion chromatography column according to standard procedures, where PMPs elute in the first fractions, whereas proteins and ribonucleoproteins and some lipoproteins are eluted later. The efficiency of protein aggregate removal is determined by measuring and comparing the protein concentration before and after removal of protein aggregates via BCA/Bradford protein quantification. The produced PMPs are analyzed as described in Example 3.

Example 3: Plant Messenger Pack Characterization

This example describes the characterization of PMPs produced as described in Example 1 or Example 2.

Experimental Design:

a) Determining PMP Concentration

PMP particle concentration is determined by Nanoparticle Tracking Analysis (NTA) using a Malvern NanoSight, or by Tunable Resistive Pulse Sensing (TRPS) using an iZon qNano, following the manufacturer's instructions. The protein concentration of purified PMPs is determined by using the DC Protein assay (Bio-Rad). The lipid concentration of purified PMPs is determined using a fluorescent lipophilic dye, such as DiOC6 (ICN Biomedicals) as described by Rutter and Innes, *Plant Physiol.* 173(1): 728-741, 2017. Briefly, purified PMP pellets from Example 2 are resuspended in 100 ml of 10 mM DiOC6 (ICN Biomedicals) diluted with MES buffer (20 mM MES, pH 6) plus 1% plant protease inhibitor cocktail (Sigma-Aldrich) and 2 mM 2,29- dipyridyl disulfide. The resuspended PMPs are incubated at 37° C. for 10 min, washed with 3 mL of MES buffer, repelleted (40,000 g, 60 min, at 4° C.), and resuspended in fresh MES buffer. DiOC6 fluorescence intensity is measured at 485 nm excitation and 535 nm emission.

b) Biophysical and Molecular Characterization of PMPs

PMPs are characterized by electron and cryo-electron microscopy on a JEOL 1010 transmission electron microscope, following the protocol from Wu et al., *Analyst.* 140(2):386-406, 2015. The size and zeta potential of the PMPs are also measured using a Malvern Zetasizer or iZon qNano, following the manufacturer's instructions. Lipids are isolated from PMPs using chloroform extraction and characterized with LC-MS/MS as demonstrated in Xiao et al. *Plant Cell.* 22(10): 3193-3205, 2010. Glycosyl inositol phosphorylceramides (GIPCs) lipids are extracted and purified as described by Cacas et al., *Plant Physiology.* 170: 367-384, 2016, and analyzed by LC-MS/MS as described above. Total RNA, DNA, and protein are characterized using Quant-It kits from Thermo Fisher according to instructions. Proteins on the PMPs are characterized by LC-MS/MS following the protocol in Rutter and Innes, *Plant Physiol.* 173(1): 728-741, 2017. RNA and DNA are extracted using Trizol, prepared into libraries with the TruSeq Total RNA with Ribo-Zero Plant kit and the Nextera Mate Pair Library Prep Kit from Illumina, and sequenced on an Illumina MiSeq following manufacturer's instructions.

Example 4: Characterization of Plant Messenger Pack Stability

This example describes measuring the stability of PMPs under a wide variety of storage and physiological conditions.

Experimental Design:

PMPs produced as described in Examples 1 and 2 are subjected to various conditions. PMPs are suspended in water, 5% sucrose, or PBS and left for 1, 7, 30, and 180 days at −20° C., 4° C., 20° C., and 37° C. PMPs are also suspended in water and dried using a rotary evaporator system and left for 1, 7, and 30, and 180 days at 4° C., 20° C., and 37° C. PMPs are also suspended in water or 5% sucrose solution, flash-frozen in liquid nitrogen and lyophilized. After 1, 7, 30, and 180 days, dried and lyophilized PMPs are then resuspended in water. The previous three experiments with conditions at temperatures above 0° C. are also exposed to an artificial sunlight simulator in order to determine content stability in simulated outdoor UV conditions. PMPs are also subjected to temperatures of 37° C., 40° C., 45° C., 50° C., and 55° C. for 1, 6, and 24 hours in buffered solutions with a pH of 1, 3, 5, 7, and 9 with or without the addition of 1 unit of trypsin or in other simulated gastric fluids.

After each of these treatments, PMPs are bought back to 20° C., neutralized to pH 7.4, and characterized using some or all of the methods described in Example 3.

Example 5. Loading PMPs with Cargo

This example describes methods of loading PMPs with small molecules, proteins, and nucleic acids to use as probes to determine PMP uptake efficiency in plants.

a) Loading Small Molecules into PMPs

PMPs are produced as described in Example 1 and Example 2. To load small molecules into PMPs, PMPs are placed in PBS solution with the small molecule either in solid form or solubilized. The solution is left for 1 hour at 22° C., according to the protocol in Sun, Mol. Ther., 2010. Alternatively, the solution is sonicated to induce poration and diffusion into the exosomes according to the protocol from Wang et al, Nature Comm., 4: Article number: 1867, 2013. Alternatively, PMPs are electroporated according to the protocol from Wahlgren et al, Nucl. Acids. Res., 40(17): e130, 2012.

Alternatively, PMP lipids are isolated by adding 3.75 ml 2:1 (v/v) MeOH:CHCl$_3$ to 1 ml of PMPs in PBS and are vortexed. CHCl$_3$ (1.25 ml) and ddH2O (1.25 ml) are added sequentially and vortexed. The mixture is then centrifuged at 2,000 r.p.m. for 10 min at 22° C. in glass tubes to separate the mixture into two phases (aqueous phase and organic phase). The organic phase sample containing the PMP lipids is dried by heating under nitrogen (2 psi). To produce small molecule-loaded PMPs, the isolated PMP lipids are mixed with the small molecule solution and passed through a lipid extruder according to the protocol from Haney et al, J Contr. Rel., 2015.

Before use, the loaded PMPs are purified using methods as described in Example 2 to remove unbound small molecules. Loaded PMPs are characterized as described in Example 3, and their stability is tested as described in Example 4.

b) Loading Proteins or Peptides into PMPs

PMPs are produced as described in Example 1 and Example 2. To load proteins or peptides into PMPs, PMPs are placed in solution with the protein or peptide in PBS. If the protein or peptide is insoluble, pH is adjusted until it is soluble. If the protein or peptide is still insoluble, the insoluble protein or peptide is used. The solution is then sonicated to induce poration and diffusion into the PMPs according to the protocol from Wang et al, Nature Comm., 4: Article number: 1867, 2013. Alternatively, PMPs are electroporated according to the protocol from Wahlgren et al, Nucl. Acids. Res., 40(17): e130, 2012.

Alternatively, PMP lipids are isolated by adding 3.75 ml 2:1 (v/v) MeOH:CHCl$_3$ to 1 ml of PMPs in PBS and are vortexed. CHCl$_3$ (1.25 ml) and ddH2O (1.25 ml) are added sequentially and vortexed. The mixture is then centrifuged at 2,000 r.p.m. for 10 min at 22° C. in glass tubes to separate the mixture into two phases (aqueous phase and organic phase). The organic phase sample containing the PMP lipids is dried by heating under nitrogen (2 psi). To produce small molecule-loaded PMPs, the isolated PMP lipids are mixed with the small molecule solution and passed through a lipid extruder according to the protocol from Haney et al, J Contr. Rel., 2015.

Before use, the loaded PMPs are purified using the methods as described in Example 2 to remove unbound peptides and protein. Loaded PMPs are characterized as described in Example 3, and their stability is tested as described in Example 4. To measure loading of the protein or peptide, the Pierce Quantitative Colorimetric Peptide Assay is used on a small sample of the loaded and unloaded PMPs.

c) Loading Nucleic Acids into PMPs

PMPs are produced as described in Example 1 and Example 2. To load nucleic acids into PMPs, PMPs are placed in solution with the nucleic acid in PBS. The solution is then sonicated to induce poration and diffusion into the PMPs according to the protocol from Wang et al, Nature Comm., 4: Article number: 1867, 2013. Alternatively, PMPs are electroporated according to the protocol from Wahlgren et al, Nucl. Acids. Res., 40(17): e130, 2012.

Alternatively, PMP lipids are isolated by adding 3.75 ml 2:1 (v/v) MeOH:CHCl$_3$ to 1 ml of PMPs in PBS and are vortexed. $CHCl_3$ (1.25 ml) and ddH2O (1.25 ml) are added sequentially and vortexed. The mixture is then centrifuged at 2,000 r.p.m. for 10 min at 22° C. in glass tubes to separate the mixture into two phases (aqueous phase and organic phase). The organic phase sample containing the PMP lipids is dried by heating under nitrogen (2 psi). To produce small molecule-loaded PMPs, the isolated PMP lipids are mixed with the small molecule solution and passed through a lipid extruder according to the protocol from Haney et al, J Contr. Rel., 2015.

Before use, the PMPs are purified using the methods as described in Example 2 to remove unbound nucleic acids. Loaded PMPs are characterized as described in Example 3, and their stability is tested as described in Example 4. Nucleic acids that are loaded in the PMPs are quantified using either a Quant-It assay from Thermo Fisher following manufacturer's instructions, or fluorescence is quantified with a plate reader if the nucleic acids are fluorescently labeled.

Example 6: Increasing PMP Cellular Uptake by Formulation of PMPs with Ionic Liquids This example describes formulation of PMPs with ionic liquids in order to improve PMP uptake through improved cell wall penetration. Ionic liquids have been described as potential agents of solubilizing cellulose, a major component of cell walls. In this example, EMIM Acetate is used as a model ionic liquid, grapefruit PMPs are used as a model PMP, cotton as a model plant, *Saccharomyces cerevisiae* as a model yeast, MDA-MB-231 as a model human cell line, *S. sclerotiorum* as a model fungus, and *Pseudomonas syringae* as a model bacterium.

Experimental Protocol:
a) Formulation of PMPs in Ionic Liquid

A concentrated solution of grapefruit PMPs are isolated as described in Example 1 and Example 2. PMPs are resuspended with vigorous mixing in 1%, 5%, 10%, 20%, 50%, or 100% solutions of EMIM Acetate. Alternatively, BMIM acetate, HMIM acetate, MMIM acetate, AllylMIM acetate are used. The concentration of PMPs is determined by assuming 100% recovery from the suspension and multiplying the concentration prior to formulation by the ratio of the volumes. PMP characteristics and stability in the ionic liquid is assessed as described in Example 3 and Example 4.

b) Increased PMP Uptake by *Saccharomyces cerevisiae* with EMIM Acetate-Formulated Grapefruit PMPs Loaded with GFP Protein PMPs are produced from grapefruit as described in Example 1 and Example 2, and are loaded with GFP protein as described in Example 5. GFP encapsulation by PMPs is measured by Western blot or fluorescence. All PMP formulations are next labeled with red PKH26 (Sigma) lipophilic membrane dye according to the manufacturer's protocol, with some modifications. Briefly, 50 mg PMPs in 1 mL dilute C of the PKH26 labelling kit are mixed with 2 ml of 1 mM PKH26 and incubated at 37° C. for 5 min. Labelling is stopped by adding 1 mL of 1% BSA. All unlabeled dye is washed away by methods described in Example 2, and labelled PMP pellets are resuspended in PBS (control) or EMIM Acetate solution as described in Example 6a. To determine the PMP uptake efficiency of GFP-loaded PKH26-labeled PMPs in PBS versus GFP-loaded EMIM Acetate-formulated PKH26-labeled PMPs, *Saccharomyces cerevisiae* fungal cells are treated.

*Saccharomyces cerevisiae* is obtained from the ATCC (#9763) and maintained at 30° C. in yeast extract peptone dextrose broth (YPD) as indicated by the manufacturer. To determine the PMP uptake by *S. cerevisiae*, yeast cells are grown to an $OD_{600}$ of 0.4-0.6 in selection media, and incubated with 0 (negative control), 1, 10, or 50, 100 and 250 μg/ml of PKH26-labeled GFP-loaded modified PMPs in PBS or EMIM Acetate, directly on glass slides. In addition to a PBS control, *S. cerevisiae* cells are incubated in the presence of PKH26 dye (final concentration 5 μg/ml). After incubation of 5 min, 30 min and 1 h at room temperature, images are acquired on a high-resolution fluorescence microscope. PMPs are taken up by yeast cells when red membrane and green GFP-loaded PMPs are observed in the cytoplasm, or if the cytoplasm of the yeast cell turns red and/or green, versus exclusive staining of the cell membrane by PKH26 dye. To assess the uptake efficiency of GFP-loaded EMIM Acetate-formulated PMPs compared to the PBS-formulated GFP-loaded PMPs, the percentage of yeast cells with a green cytoplasm/green PMPs in the cytoplasm, versus membrane only staining are compared between PMP-treated cells and the PBS and PKH26 dye only controls. The amount of uptake in each cell is quantified by measuring the median red and green fluorescence signal from the cell using ImageJ software, and the uptake efficiency of GFP-loaded EMIM Acetate-formulated PMPs is compared to the PBS-formulated GFP-loaded PMPs.

c) Increased PMP Uptake by *S. sclerotiorum* with EMIM Acetate-Formulated Grapefruit PMPs Loaded with GFP Protein PMPs are produced from grapefruit as described in Example 1 and Example 2, and are loaded with GFP protein as described in Example 5. GFP encapsulation by PMPs is measured by Western blot or fluorescence. All PMP formulations are next labeled with red PKH26 (Sigma) lipophilic membrane dye according to the manufacturer's protocol, with some modifications. Briefly, 50 mg PMPs in 1 mL dilute C are mixed with 2 ml of 1 mM PKH26 and incubated at 37° C. for 5 min. Labelling is stopped by adding 1 mL of 1% BSA. All unlabeled dye is washed away by methods described in Example 2, and labelled PMP pellets are resuspended in PBS. To determine the PMP uptake efficiency of GFP-loaded PKH26-labeled PMPs versus GFP-loaded with EMIM Acetate-formulated PKH26-labeled PMPs, *S. sclerotiorum* fungal cells are treated.

To determine the PMP uptake by *S. sclerotiorum* (ATCC, #18687) ascospores, 10,000 ascospores are incubated with and incubated with 0 (negative control), 1, 10, or 50, 100 and 250 μg/mL of PKH26-labeled GFP-loaded PMPs formulated in EMIM Acetate, or PMPs formulated in PBS directly on glass slides. In addition to a PBS control, *S. sclerotiorum* cells are incubated in the presence of PKH26 dye (final concentration 5 μg/mL). After incubation of 5 min, 30 min and 1 h at room temperature, images are acquired on a high-resolution fluorescence microscope. PMPs are taken up by yeast cells when red membrane and green GFP-loaded PMPs are observed in the cytoplasm, or if the cytoplasm of the yeast cell turns red and/or green, versus exclusive staining of the cell membrane by PKH26 dye. To assess the uptake efficiency of GFP-loaded EMIM Acetate-formulated PMPs compared to the GFP-loaded PMPs formulated in PBS, the percentage of *S. sclerotiorum* cells with a green cytoplasm/green PMPs in the cytoplasm, versus membrane only staining are compared between PMP-treated cells and the PBS and PKH26 dye only controls. The amount of uptake in each cell is quantified by measuring the median red and green fluorescence signal from the cell using ImageJ software, and the uptake efficiency of GFP-loaded PMPs formulated in EMIM Acetate-formulated PMPs is compared to the GFP-loaded PMPs formulated in PBS.

d) Increased PMP Uptake by MDA-MB-231 Cells with EMIM Acetate-Formulated Grapefruit PMPs Loaded with Calcein AM PMPs are produced from grapefruit as described in Example 1 and Example 2. Some of the PMPs are set aside as controls, and the rest are modified with cellulase as described in Example 6b. Modified and unmodified PMPs are loaded with Calcein AM (Sigma Aldrich) as described in Example 5 and Gray et al., *MethodsX*, 2: 360-367, 2015. Calcein AM is fluorescent only when encapsulated by PMPs, and encapsulation is measured by fluorescence. All PMP formulations are next labeled with red PKH26 (Sigma) lipophilic membrane dye according to the manufacturer's protocol, with some modifications. Briefly, 50 mg Calcein AM loaded PMPs in 1 mL dilute C are mixed with 2 mL of 1 mM PKH26 and incubated at 37° C. for 5 min. Labelling is stopped by adding 1 mL of 1% BSA. All unlabeled dye is washed away and PMPs are concentrated using a 100 kDa Amicon filter as described in Example 2. To determine the PMP uptake efficiency of Calcein AM-loaded PKH26-labeled PMPs formulated in PBS versus Calcein AM-loaded PKH26-labeled EMIM Acetate-formulated PMPs, human breast cancer cells are treated.

MDA-MB-231 breast cancer cell line is obtained from the ATCC (HTB-26) and grown and maintained according to the supplier's instructions. Cells at 70-80% confluency are harvested, counted and seeded in 96-well culture treated well plate at a seeding density of 10,000 cells per well in 200 uL cell culture medium. Cells are allowed to adhere for 3 hours, then the medium is removed, the cells are washed once with Dulbecco PBS, and medium without FCS is added to serum starve the cells for 3 hours prior to treatment. To determine the PMP uptake by breast cancer cells, the cells are incubated with 0 (negative control), 1, 10, or 50, 100 and 250 µg/mL of PKH26-labeled Calcein AM-loaded PMPs formulated in PBS and formulated in EMIM Acetate directly in the well. In addition to a PBS control, cells are incubated in the presence of Calcein AM (final concentration 5 µg/mL), PKH26 dye (final concentration 5 µg/mL), and unmodified PMPs. After incubation of 30 min, 1 h, 2 h and 4 h at 37 C, cell are washed 4×10' with PBS to remove PMPs in the medium. Images are next acquired on a high-resolution fluorescence microscope (EVOS2 FL) at 40× to determine uptake efficiency. PMPs are taken up by breast cancer cells when red membrane and green Calcein AM-loaded PMPs are observed in the cytoplasm, or if the cytoplasm of the cell turns red and/or green, versus exclusive staining of the cell membrane by PKH26 dye. To assess the uptake efficiency of Calcein-AM-loaded EMIM Acetate-formulated PMPs compared to the PBS-formulated Calcein AM-loaded PMPs, the percentage of cells with a green cytoplasm/green PMPs in the cytoplasm, versus membrane only staining are compared between PMP-treated cells and the PBS and PKH26 dye only controls. The amount of uptake in each cell is quantified by measuring the median red and green fluorescence signal from the cell using ImageJ software, and the uptake efficiency of GFP-loaded EMIM Acetate-formulated PMPs is compared to the GFP-loaded PBS-formulated PMPs.

e) Increased PMP Uptake by *Pseudomonas syringae* with EMIM Acetate-Formulated Grapefruit PMPs Loaded with Calcein AM PMPs are produced from grapefruit as described in Example 1 and Example 2. Modified and PBS-formulated PMPs are loaded with Calcein AM (Sigma Aldrich) as described in Example 5 and Gray et al., *MethodsX* 2015. Calcein AM is fluorescent only when encapsulated by PMPs, and encapsulation is measured by fluorescence. All PMP formulations are next labeled with red PKH26 (Sigma) lipophilic membrane dye according to the manufacturer's protocol, with some modifications. Briefly, 50 mg Calcein AM loaded PMPs in 1 mL dilute C of the PKH26 labelling kit are mixed with 2 ml of 1 mM PKH26 and incubated at 37° C. for 5 min. Labelling is stopped by adding 1 mL of 1% BSA. All unlabeled dye is washed away by methods described in Example 2, and labelled PMP pellets are resuspended in PBS (control) or EMIM Acetate solution as described in Example 6a. To determine the PMP uptake efficiency of Calcein AM-loaded PKH26-labeled PMPs formulated in PBS versus Calcein AM-loaded PKH26-labeled EMIM Acetate-formulated PMPs, *Pseudomonas syringae* bacterial cells are treated. *Pseudomonas syringae* bacteria are obtained from the ATCC (BAA-871) and grown on King's Medium B agar according to the manufacturer's instructions. To determine the PMP uptake by *P. syringae*, 10 µl of a 1 ml overnight bacterial suspension is incubated with 0 (negative control), 1, 10, or 50, 100 and 250 µg/ml of PBS-formulated PKH26-labeled Calcein AM-loaded PMPs and PKH26-labeled Calcein AM-loaded EMIM Acetate-formulated PMPs directly on a glass slide. In addition to a PBS control, *P. syringae* bacteria are incubated in the presence of Calcein AM (final concentration 5 µg/ml), PKH26 dye (final concentration 5 µg/ml). After incubation of 5 min, 30 min and 1 h at room temperature, images are acquired on a high-resolution fluorescence microscope. To assess the uptake efficiency of Calcein AM-loaded PKH26-labeled EMIM Acetate-formulated PMPs compared to the PBS-formulated Calcein AM-loaded PKH26-labeled PMPs, the percentage of bacterial cells with a green cytoplasm or green and red PMPs in the cytoplasm, versus membrane only staining are compared between PMP-treated cells and the PBS and PKH26 dye only controls. The amount of uptake in each cell is quantified by measuring the median red and green fluorescence signal from the cell using ImageJ software, and the uptake efficiency of Calcein AM-loaded PKH26-labeled EMIM Acetate-formulated PMPs is compared to the PBS-formulated Calcein AM-loaded PKH26-labeled PMPs. EMIM Acetate formulation of PMPs improves the cellular uptake efficiently compared to PBS-formulated PMPs.

f) Increased PMP Uptake of EMIM Acetate-Formulated Grapefruit PMPs Loaded with dsRNA Targeting CLA1 in Cotton Plants To demonstrate an increase in cellular uptake by EMIM Acetate-formulated PMPs, grapefruit PMPs are loaded with artificial miRNAs (amiRNAs, designed using Plant Small RNA Maker Site (P-SAMS; Fahlgren et al., *Bioinformatics*. 32(1):157-158, 2016)) or custom dicer substrate siRNA (DsiRNA, designed by IDT) targeting the cotton photosynthesis gene GrCLA1 (1-deoxy-D-xylulose-5-phosphate synthase). GrCLA1 is a homolog gene of *Arabidopsis* Cloroplastos alterados 1 gene (AtCLA1), which loss-of-function results in an albino phenotype on true leaves, providing a visual marker for silencing efficiency. Oligonucleotides are obtained from IDT.

PMPs are produced from grapefruit as described in Example 1 and Example 2. Grapefruit PMPs are loaded with GrCLA1-amiRNA or GrCLA1-DsiRNA duplexes, as described in Example 5. amiRNA or DsiRNA encapsulation by PMPs is measured using the Quant-iT™ RiboGreen® RNA assay kit, or using a control fluorescent dye labeled amiRNA or DsiRNA (IDT).

PMPs loaded with amiRNA or DsiRNA (collectively referred to as dsRNA) are formulated in water (ddH2O) to a concentration that delivers an equivalent of an effective dsRNA dose of 0, 1, 5, 10 and 20 ng/μl in sterile water.

To determine the PMP uptake efficiency of CLA1-amiRNA/DsiRNA-loaded PMPs versus CLA1-amiRNA/DsiRNA-loaded EMIM Acetate-formulated PMPs, cotton seedlings are treated and analyzed for CLA1 gene silencing.

Cotton seeds (*Gossypium hirsutum* and *Gossypium raimondii*) are obtained through the US National Plant Germplasm System. Sterilized seeds are wrapped in moist absorbent cotton, placed in Petri dishes and placed in a growth chamber at 25° C., 150 μE $m^{-2}$ $S^{-1}$ light intensity, with a 14 hour light/10 hour dark photoperiod for 3 days to germinate. The seedlings are grown in sterile culture vessels with Hoagland's nutrient solution (Sigma Aldrich) under long-day conditions (16/8 h light/dark photoperiod) with 26/20° C. day/night temperatures. After 4 days, seedlings with fully expanded cotyledons (before the first true leaf appeared) are used for PMP treatments.

Seven-day-old cotton seedlings are transferred onto 0.5× Murashige and Skoog (MS) mineral salts (Sigma Aldrich) with 1× MS vitamins (Sigma Aldrich) pH 5.6-5.8, with 0.8% (w/v) agarose and are treated with an effective dose of 0 (ddH2O), 1, 5, 10 and 20 ng/μl GrCLA1 dsRNA-loaded EMIM Acetate-formulated PMPs, and 0 (ddH2O), 1, 5, 10 and 20 ng/μl GrCLA1 dsRNA-loaded PBS-formulated PMPs by spraying the whole seedling, 1 ml solution per plant, with 3 plants per group. Alternatively, prior to PMP treatment the underside of cotyledons of cotton plant is punched with a 25 G needle without piercing through the cotyledons. The PMP solutions with an effective dose of 0 (ddH2O), 1, 5, 10 and 20 ng/μl GrCLA1 dsRNA-loaded EMIM Acetate-formulated PMPs, and 0 (ddH2O), 1, 5, 10 and 20 ng/μl GrCLA1 dsRNA-loaded VIB (Example 1)-formulated PMPs are hand infiltrated from the underside of cotyledons through the wounding sites using a 1 mL needleless syringe. Plants are transferred to a growth chamber and kept under long-day conditions (16 h/8 h light/dark photoperiod) with light intensity of 90 μmol $m^{-2}$ $s^{-1}$ and 26/20° C. day/night temperatures.

After 2, 5, 8 and 14 days, the gene silencing efficiency of the CLA1 dsRNA is examined by the expression level of endogenous CLA1 mRNA using quantitative reverse transcription polymerase chain reaction (qRT-PCR). Total RNA is extracted from 100 mg fresh cotton leaves using Trizol reagent according to the manufacturer's instructions (Invitrogen) and treated extensively with RNase-free DNase I (Promega). First-strand cDNA is synthesized from 2 μg total RNA with the SuperScript™ First-Strand Synthesis system (Invitrogen). To estimate the levels of CLA1 transcripts qRT-PCR is performed using SYBR Green Real-Time PCR Master Mix (Thermo Scientific) with primers: GrCLA1q1_F 5'-CCAGGTGGGGCTTATGCATC-3' (SEQ ID NO: 7), GrCLA1q1_R 5'-CCACACCAAGGCTTGAACCC-3' (SEQ ID NO: 8), and GrCLA1q2_F 5'-GGCCGGATTCACGAAACGGT-3' (SEQ ID NO: 9), GrCLA1q2_R 5'-CGTCGAGATTGGCAGTTGGC-3' (SEQ ID NO: 10), and 18s RNA_F 5'-TCTGCCCTATCAACTTTCGATGGTA-3' (SEQ ID NO: 11), 18s RNA_R 5'-AATTTGCGCGCCTGCTGCCTTCCTT-3' (SEQ ID NO: 12), using the following program: (a) 95° C. for 5 min; (b) 40 cycles of 94° C. for 30 s, 55° C. for 30 s; and 72° C. for 30 s. The 18S rRNA gene is used as internal control to normalize the results. The CLA1 knock down efficiency in cotton after treatment with CLA1-dsRNA-loaded EMIM Acetate-formulated and CLA1-dsRNA-loaded PBS-formulated PMPs is determined by calculating the ΔΔCt value, comparing the normalized CLA1 expression after treatment with EMIM Acetate-formulated PMPs, with normalized CLA1 expression after treatment with PBS-formulated PMPs.

Additionally, the gene silencing efficiency of CLA1 dsRNA is examined by phenotypic photobleaching analysis. Leaves of plants treated with EMIM Acetate-formulated PMPs and PBS-formulated PMPs are photographed and ImageJ software is used to determine the percentage gene silencing, which is reflected by white photobleaching on the leaf versus the control leaf green color. Three leaves per plant are assayed to quantify the effect of photobleaching, and the gene silencing efficiency of EMIM Acetate-formulated versus PBS-formulated CLA1-dsRNA-loaded PMPs are assessed.

EMIM Acetate-formulated PMPs are more efficiently uptaken by plant cells and induce greater CLA1 gene silencing compared to PBS-formulated PMPs.

Example 7: Modification of PMPs Using Ionizable Lipids

This example demonstrates the ability to modify surface charge in a pH-dependent manner, increasing the cargo loading capacity and cellular uptake of PMPs into plant cells, by modification of PMPs with ionizable lipids. In this example, C12-200 (1,1'-((2-(4-(2-((2-(bis(2-hydroxydodecyl)amino)ethyl) (2-hydroxydodecyl)amino)ethyl)piperazin-1-yl)ethyl)azanediyl)bis(dodecan-2-ol)) and MC3 ((6Z,9Z,28Z,31Z)-Heptatriaconta-6,9,28,31-tetraen-19-yl 4-(dimethylamino)butanoate, DLin-MC3-DMA) are used as model ionizable lipids, lemon PMPs are used as a model PMP, and Trans-activating CRISPR RNA (TracrRNA), single guide RNA (gRNA) as a model negatively charged payload. Black Mexican Sweet (BMS) maize cells are used as a model plant cell line.

a) Modification of PMPs with Ionizable Lipids

To prepare lipid-modified PMPs (LPMP), lipids were extracted using Bligh-Dyer method (Bligh and Dyer, 1959, *J Biolchem Physiol* 37:911-917) from a concentrated solution of lemon PMPs, isolated as described in Example 6. Ionizable lipids were added to PMP extracted lipid stock solution in Chloroform:Methanol (9:1) to amount to 25% or 40% (w/w) of total lipids, and lipids were resuspended by vigorous mixing. Dried lipid film and the reconstructed PMPs from extracted lipids were prepared as described in Example 6. Size of the LPMPs and number of particles were assessed by NanoFCM. The range of LPMP size and concentrations was 83±19 nm and $1.7\times10^{12}$ LPMPs/mL for LM LPMPs, 88±22 nm and $1.35\times10^{12}$ LPMPs/mL for MC3-modified LPMPs, and 86±16 nm and $1.19\times10^{12}$ LPMP/mL for C12-200-modified PMPs (FIG. 2). The surface charge (zeta potential) was measured by electrophoretic light scattering using a Zetasizer (Malvern Panalytical). Modification of lipid-reconstructed PMPs with the ionizable lipids C12-200 and MC3 enabled pH-dependent change in the surface charge of LPMPs: with decreasing pH, the surface charge of LPMP increased (FIG. 3A).

b) Loading of Ionizable Lipid-Modified PMPs with Negatively Charged Cargo

TracrRNA/gRNA dissolved in a nuclease-free water or Duplex Buffer (IDT®) was added to the dried lipid film at 1.5 nmol per 1 mg of PMP lipids and was left for 1 h at RT to hydrate. 0.1 M citrate buffer pH 3.2 (Teknova) was used to adjust the pH of the resuspended lipid solution to 4.5 to promote RNA entrapment. Lipid solution was then subjected to 5 freeze-thaw cycles. Subsequently, pH of the lipid solution was brought up to pH 9 using 0.1 M bicarbonate buffer (pH 10) and lipids were then subjected to an additional 5 freeze-thaw cycles. Formed lipid particles were extruded through 0.8 µm, 0.4 µm, and 0.2 µm polycarbonate filters using a Mini Extruder (Avanti® Polar Lipids). Loaded PMPs were dialyzed overnight against PBS in a dialysis device (Spectrum®) with a 100 kDa MWCO membrane and then sterilized using 0.2 µm Polyethersulfone (PES) filters. Additionally, samples were purified and concentrated using ultracentrifugation. Loaded PMPs were centrifuged for 30 min at 100,000×g at 4° C., supernatant was removed, and the pellet was resuspended in 1 mL PBS and concentrated at 100,000×g for 30 min. The resulting pellet was resuspended in water (for cellular uptake by plant cells). Size of the RNA-loaded LPMPs and number of particles were assessed by NanoFCM. The mean size and particle concentration were 89±15 nm and $1.54 \times 10^{12}$ LPMPs/mL for unmodified LPMP; 87±16 nm and $7.15 \times 10^{11}$ LPMPs/mL for C12-200-modified LPMPs; and 93±27 nm and $2.4 \times 10^{11}$ LPMP/mL for MC3-modified LPMPs. RNA loading was determined by RiboGreen™ assay or by measurement of fluorescent intensity of labeled cargo (TracrRNA ATTO 550). The RiboGreen™ assay was performed according to manufacturer's protocol in the presence of heparin (5 mg/mL) and 1% Triton™ X-100 to lyse PMPs and release encapsulated cargo. Modification of lipid-reconstructed PMPs with the ionizable lipids MC3 and C12-200 enabled pH-dependent change in the surface charge of LPMPs and increased loading of negatively charged cargo (e.g. RNA) in acidic pH, as compared to LPMPs without ionizable lipids (FIGS. 3B and 3C).

c) Increased Uptake of C12-200 Modified PMPs by Plant Cells (BMS)

Zea mays, Black Mexican sweet (BMS) cells were purchased from the Arabidopsis Biological Resource Center (ABRC). BMS cells were grown in Murashige and Skoog basal medium pH 5.8, containing 4.3 g/L Murashige and Skoog Basal Salt Mixture (Sigma M5524), 2% sucrose (S0389, Millipore Sigma), 2 mg/L 2,4-dichlorophenoxy-acetic acid (D7299, Millipore Sigma), 250 µg/L thiamine HCL (V-014, Millipore Sigma) and a 1×MS vitamin mix solution in ddH2O. The 1× vitamin mix solution contained niacin (N0761—100 G, Millipore Sigma), Pyroxidine hydrochloride (P6280—25 G, Millipore Sigma), D-pantothenic acid hemicalcium salt (P5155—100 G, Millipore Sigma), L-Asparagine (A4159—25 G, Millipore Sigma), and Myo-inositol (17508—100 G, Millipore Sigma) at respective final concentrations of 1.3 mg/L, 250 µg/L, 250 µg/L, 130 mg/L, and 200 mg/L. Cells were grown in 1 L vented conical sterile flasks, in dark conditions at 24° C. with agitation (110 rpm).

Figure 4:
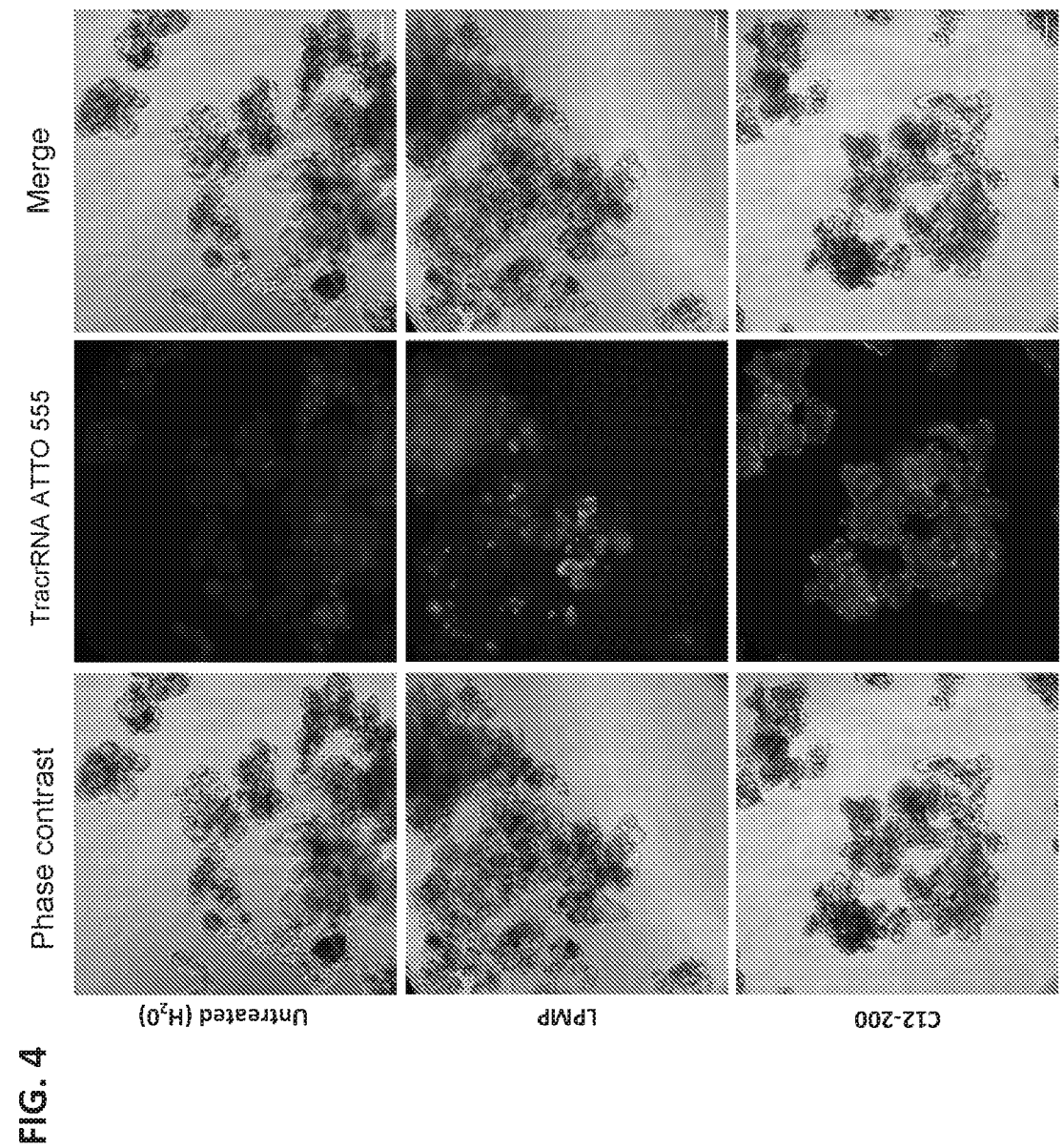
FIG. 4 is a set of photomicrographs showing phase contrast (left column), ATTO 550 fluorescence (center column), and merged views of maize Black Mexican Sweet (BMS) cells treated with LPMPs from lemon lipids not comprising added lipids (center row) and LPMPs comprising 25% C12-200 (bottom row). Cells that were treated with only H$_2$O are provided as a negative control (top row). Uptake of LPMPs or LPMPs modified with C12-200 by a cell is indicated by the presence of the TracrRNA ATTO 550 signal in the cell. Scale bar: 100 µm.

For BMS cell treatments, 10 mL of the cell suspensions were taken to determine the percent Pack Cell Volume (PCV). The PCV is defined as the volume of cells divided by the total volume of the cell culture aliquot and is expressed as a percentage. Cells were centrifuged for 5 min at 3900 rpm, and the volume of the cell pellet was determined. The % PCV for BMS was 20%. For the uptake experiment, the % PCV of the cultures was adjusted to 4% by diluting cells in the medium as described above. LPMPs and LPMPs modified with C12-200 were loaded with TracrRNA ATTO 550 as described above, sterilized, and resuspended in sterile water. In embodiments, the LPMPs and LPMPs modified with C12-200 are loaded with other polynucleotides of similar size, such as siRNA precursors (e.g., one or more strands of RNA that hybridize inter- or intra-molecularly to form at least partially double-stranded RNA having at least about 20 contiguous base-pairs), hairpin RNAs, miRNA precursors (e.g, pri-miRNAs or pre-miRNAs), small RNA aptamers (e.g., spinach, broccoli, or mango aptamers), or alternatively, DNA encoding such RNA molecules. The mean size and concentration of the particles analyzed by NanoFCM were 87±16 nm and $7.15 \times 10^{11}$ LPMPs/mL for C12-200-LPMPs and 89±15 nm and $7.15E \times 10^{12}$ LPMPs/mL for unmodified LPMPs. The amount of TracrRNA ATTO 550 (IDT) in samples was quantified by Quant-iT™ RiboGreen®. 50 µL of either LPMPs or LPMPs modified with C12-200 containing 433 ng of TracrRNA were added to an aliquot of 450 µL of plant cell suspension in a 24-well plate in duplicate. 50 µl of ultrapure sterile water was added to the cells and was used as a negative control. Cells were incubated for 3 hours at 24° C. in the dark, and were washed three times with 1 mL ultrapure sterile water to remove particles that had not been taken up by cells. Cells were resuspended in 500 µL of ultrapure sterile water for imaging on an epifluorescence microscope (Olympus IX83). Compared to the negative control (ultrapure sterile water), which had no detectable fluorescence, a variable fluorescent signal could be detected in plant cells treated with LPMPs and LPMPs modified with C12-200 (FIG. 4). LPMPs modified with C12-200 displayed the strongest fluorescence signal, indicating that this PMP modification had the highest delivery/association of TracrRNA with plant cells. Our data shows that modification of LPMPs with C12-200 ionizable lipid improved lemon LPMP uptake by plant cells in vitro.

Example 8: Formulation of LPMPs with Microfluidics

This example demonstrates the ability to formulate lipid-reconstructed PMPs (LPMPs) using microfluidics with optimized mixtures of solvents. In this example, LPMPs were prepared from grapefruit and lemon PMPs as model PMPs using a NanoAssemblr® IGNITE™ microfluidic instrument (Precision NanoSystems) as a model microfluidic system. This method allows formation of PMPs via self-assembly by mixing an aqueous phase and a miscible solvent or a combination of miscible solvents containing dissolved lipids extracted from grapefruit or lemon PMPs.

Experimental Protocol:

a) Production of Lemon/Grapefruit PMPs

Red organic grapefruits or yellow organic lemons were obtained from a local grocery store. Six liters of grapefruit juice was collected using a juice press, pH-adjusted to pH 4 with NaOH, incubated with 1 U/mL pectinase (Sigma, 17389) to remove pectin contaminants, and subsequently centrifuged at 3,000 g for 20 minutes, followed by centrifugation at 10,000 g for 40 minutes. Next, the processed juice was incubated with 500 mM EDTA pH 8.6, to a final concentration of 50 mM EDTA, pH 7.7 for 30 minutes to chelate calcium and prevent the formation of pectin macromolecules. Subsequently, the EDTA-treated juice was passed through an 11 µm, a 1 µm, and an 0.45 µm filter to remove large particles. Filtered juice was washed and concentrated by Tangential Flow Filtration (TFF) using a 300 kDa TFF. Juice was concentrated 10×, followed by diafiltration into 10 diavolumes of PBS, and further concentrated to a final concentration of 120 mL (50×). Next, we used size exclusion chromatography to elute the PMP-containing fractions, which were analyzed by 280 nm absorbance (SpectraMax®) and protein concentration (Pierce™ BCA Protein Assay) to verify the PMP-containing fractions and late fractions containing contaminants (Example 2). SEC fractions 3-7 contained purified PMPs (fractions 9-12 contained contaminants) and were pooled together, filter sterilized by sequential filtration using 0.8 µm, 0.45 µm and 0.22 µm syringe filters, and concentrated further by pelleting PMPs for 1.5 hrs at 40,000×g and resuspending the pellet in 4 ml UltraPure™ DNase/RNase-Free Distilled Water (ThermoFisher, 10977023). Final PMP concentration ($7.56 \times 10^{12}$ PMPs/ml) and PMP size (70.3 nm+/−12.4 nm SD) were determined by NanoFCM, using concentration and size standards provided by the manufacturer (Example 3).

b) Formulation of LPMP Using Microfluidics

To prepare lipid-modified PMPs (LPMPs), lipids from grapefruit or lemon were extracted using the Bligh-Dyer method (Bligh and Dyer, J Biolchem Physiol, 37: 911-917, 1959) from a concentrated solution of grapefruit (GF) or lemon (LM) PMPs, isolated as described above. PMP extracted lipid stock solution in chloroform:methanol (9:1) was dried by evaporation of the solvent with a stream of inert gas (e.g., nitrogen) to prepare a lipid film. In some embodiments, LPMPs were prepared by adding charged lipids (e.g., ionizable and/or cationic lipids) to PMP extracted lipid stock solution in chloroform:methanol (9:1) to amount to 25% or 40% (w/w) of the total lipid and resuspending by vigorous mixing before drying.

Combinations of water-miscible organic solvents with varying polarity were investigated to identify the optimal solvent to dissolve dried PMP lipids with or without additional charged lipids. The following organic solvents and solvent combinations were tested: acetonitrile, acetone, ethanol, methanol, dimethylformamide, tetrahydrofuran, 1-butanol, dimethyl sulfoxide, acetonitrile:ethanol (1:1), acetonitrile:methanol (3:1), acetone:methanol (3:1), methyl tert-butyl ether:propanol (3:2), tetrahydrofuran:methanol (3:2), dimethyl sulfoxide:methanol (3:1), and dimethylformamide:methanol (4:1).

In each assay, 275 µL of the organic solvent was added to 1 mg of dried PMP lipid film. Samples were sonicated for 10 min at 37° C. in a water bath sonicator. Turbidity of the lipid solution was assessed. Dimethylformamide:methanol (DMF:MeOH) (4:1) was identified as the most optimal solvent for dissolving dried PMP lipids among the tested organic solvents and solvent combinations.

PMP lipid solution (PMP lipids dissolved in an organic solvent or solvent combination; organic phase) was loaded into a 1 mL slip tip syringe (Becton Dickinson) and placed in a heating block set to 37° C. mounted to a NanoAssemblr® IGNITE™ microfluidic device (Precision Nanosystems). 825 µL of an aqueous phase (10 mM Citrate buffer, pH 3.2 for ionizable lipids or Milli-Q® H$_2$O or PBS for cationic lipids) was loaded into a 1 mL slip tip syringe (Becton Dickinson) and mounted to the microfluidic device. Aqueous and organic phases were mixed in the microfluidic device at a 3:1 volumetric ratio at a 12 mL/min flowrate. The resulting LPMP particles were dialyzed against PBS in a Slide-A-Lyzer™ G2 Cassette (20 kDa MWCO) for 4-24 h at RT. Hydrodynamic diameter and polydispersity of the LPMP particles was measured using a Zetasizer (Malvern Panalytical) (FIGS. 5A and 5B). LPMPs prepared in dimethylformamide:methanol (DMF:MeOH) (4:1) organic phase showed smaller size and lower polydispersity as compared to a suboptimal solvent, e.g., ethanol (FIGS. 5A and 5B). The final concentration of DMF:MeOH-formulated LPMPs (LM: $2.07 \times 10^{11}$ PMPs/mL, GF: $3.79 \times 10^{11}$ PMPs/mL) and LPMP size (LM: 91.7 nm+/−23.9 nm SD, GF: 75.6 nm+/−11.6 SD) were determined by NanoFCM, using concentration and size standards provided by the manufacturer.

Example 9: mRNA Loading and Delivery into Lipid-Reconstructed PMPs Using Ionizable Lipids This example demonstrates the ability to load messenger RNA (mRNA) into lipid-reconstructed PMPs (LPMPs) modified with ionizable lipids, and effectively deliver mRNA into human cells. In this example, C12-200 (2-hydroxydodecyl)amino)ethyl)piperazin-1-yl)ethyl)azanediyl) bis(dodecan-2-ol)] was used a model ionizable lipid, and lemon PMPs were used as a model PMP. mRNA encoding Firefly Luciferase (Fluc mRNA) was used as a model mRNA, and A549 (human lung epithelial carcinoma) cells as a model human cell line. LPMPs containing mRNA were formulated using extrusion and microfluidics.

Experimental Protocol:

a) Modification of PMPs with Ionizable Lipids

To prepare lipid-modified PMPs (LPMPs), lipids were extracted using the Bligh-Dyer method (Bligh and Dyer, J Biolchem Physiol, 37: 911-917, 1959) from a concentrated solution of lemon PMPs, isolated as described previously (Example 1 and Example 2), as described in Example 8. LPMPs were prepared by adding ionizable lipids to PMP extracted lipid stock solution in chloroform:methanol (9:1) to 25% or 40% (w/w) of the total lipid and resuspended by vigorous mixing before drying.

b) Loading of Lipid-Modified PMPs with mRNA

For the preparation of LPMPs with C12-200 via extrusion, mRNA dissolved in nuclease-free water was added to the dried lipid film at 35 ug of mRNA per 1 mg of PMP lipids and was left for 1 h at RT to hydrate. 0.1 M citrate buffer pH 3.2 (Teknova) was used to adjust the pH of the resuspended lipid solution to 4.5 to promote RNA entrapment. The lipid solution was then subjected to 5 freeze-thaw cycles. Subsequently, the pH of the lipid solution was brought up to pH 9 using 0.1 M bicarbonate buffer pH 10, and lipids were then subjected to 5 additional freeze-thaw cycles. LPMPs were dialyzed overnight against PBS in a dialysis device (Spectrum®) with a 100 kDa MWCO membrane. Free RNA was removed by ultracentrifugation. Modified PMPs were centrifuged for 30 min at 100,000 g at 4° C., supernatant was removed, and the pellet was washed with 1 mL PBS or water. Centrifugation was repeated as described above and the final PMP pellet was resuspended in a desired buffer (e.g. PBS). The size of the vesicles and final concentration was assessed by NanoFCM: C12-200 LPMPs (C12) were at a concentration of $2.4 \times 10^{10}$ PMPs/mL and had an average size of 105 nm+/−51 nm SD.

For the preparation of LPMPs via microfluidics, 1 mg of PMP lipids containing 25% (w/w) of C12-200 was dissolved in 275 µL of DMF:MeOH (4:1) and sonicated for 10 min at 37° C. in a water bath sonicator. The PMP lipid solution (organic phase) was loaded into a 1 mL slip tip syringe (Becton Dickinson) and placed in a heating block set to 37° C. mounted to a microfluidics device. 35 µg of firefly luciferase (Fluc) mRNA was dissolved in 825 µL of Milli-Q® H$_2$O or PBS pH 7.4 to formulate the aqueous phase. The aqueous phase was loaded into 1 mL slip tip syringe (Becton Dickinson) and mounted to the microfluidics device (NanoAssemblr® IGNITE™, Precision Nanosystems). The aqueous and organic phases were mixed in the microfluidic device at a 3:1 volumetric ratio and at a 12 mL/min flowrate. The resulting LPMP particles were dialyzed against PBS in a Slide-A-Lyzer™ G2 Cassette (20 kDa MWCO) for 4-24 h at RT. As a positive control, mRNA lipid nanoparticles (LNP) were prepared by solubilizing with ethanol a mixture of C12-200, 2-distearoyl-sn-glycero-3phosphocholine (DSPC, Avanti® Polar Lipids, Alabaster, AL), 1,2-distearoyl-sn-glycero-3-phosphoethanolamine (DSPE, Avanti® Polar Lipids), 1,2-dioleoyl-sn-glycero-3-phosphocholine (DOPC, Avanti® Polar Lipids), 1,2-dioleoyl-sn-glycero-3-phosphoethanolamine (DOPE, Avanti® Polar Lipids), cholesterol (Sigma), and/or 1,2-dimyristoylsn-glycero-3-phosphoethanolamine-N-[methoxy(polyethylene glycol)-2000] (ammonium salt) (C14-PEG 2000, Avanti® Polar Lipids) at predetermined molar ratios, as described by Kauffman et al., Nano Letters, 15(11), 7300-7306, 2015. LNPs were formulated using microfluidics with the same settings and dialyzed in the same conditions as the LPMPs. Size of the vesicles and final concentration was assessed by NanoFCM. C12-200 LPMPs (C12) were at a concentration of $1.8 \times 10^{11}$ PMPs/mL and had an average size of 87 nm+/−20 nm SD. C12-200 LNP (C12 LNP) were at a concentration of $2.8 \times 10^9$ PMPs/mL and had an average size of 84.7 nm+/−30 nm SD.

Figure 6A:
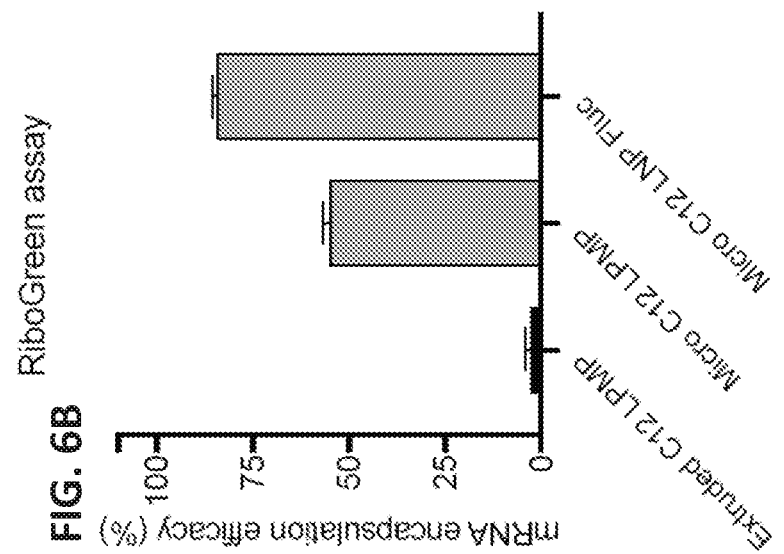
FIG. 6A is a bar graph showing total mRNA concentration (µg/mL) in LPMPs comprising C12-200 that have been formulated with 35 µg of firefly luciferase (Fluc) mRNA per 1 mg of PMP lipid using extrusion or microfluidics, as measured using a Quant-iT™ RiboGreen® analysis. Data are presented as Mean±SD.
Figure 6B:
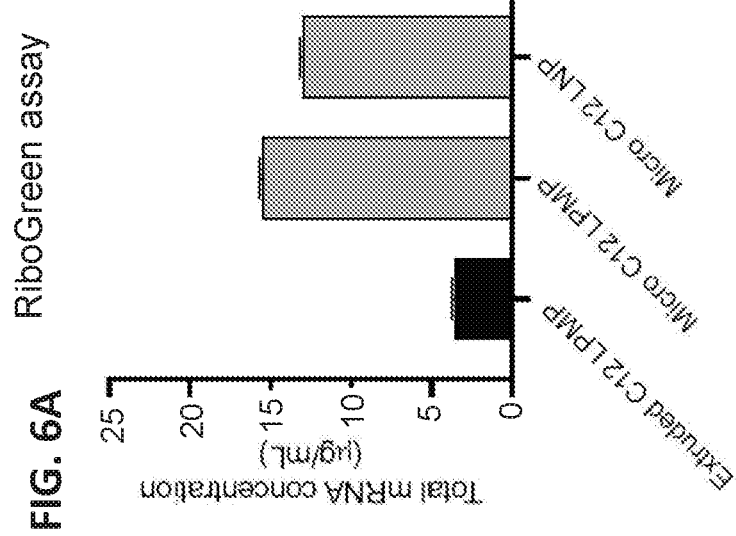
FIG. 6B is a bar graph showing the mRNA encapsulation efficacy (% difference in mRNA concentrations between intact and lysed (+Triton® X-100+Heparin) vesicles) for the LPMPs of FIG. 8A. Data are presented as Mean±SD.

RNA loading was determined by the Quant-iT™ RiboGreen® assay (Thermo Scientific). The RiboGreen® assay was performed according to the manufacturer's protocol in the presence of heparin (5 mg/mL) and 1% Triton™ X-100 to lyse LPMPs and release encapsulated cargo. C12-200 LPMPs prepared by the microfluidic method were able to efficiently load and encapsulate mRNA, as compared to a positive control C12-200 LNP formulation. LPMPs modified with ionizable lipids prepared by microfluidics showed more consistent loading and encapsulation, as compared to extrusion (FIGS. 6A and 6B).

c) Functional Delivery of Firefly Luciferase mRNA (Fluc) to Mammalian Cells (A549) by LPMP Modified with an Ionizable Lipid (C12-200)

Figure 6C:
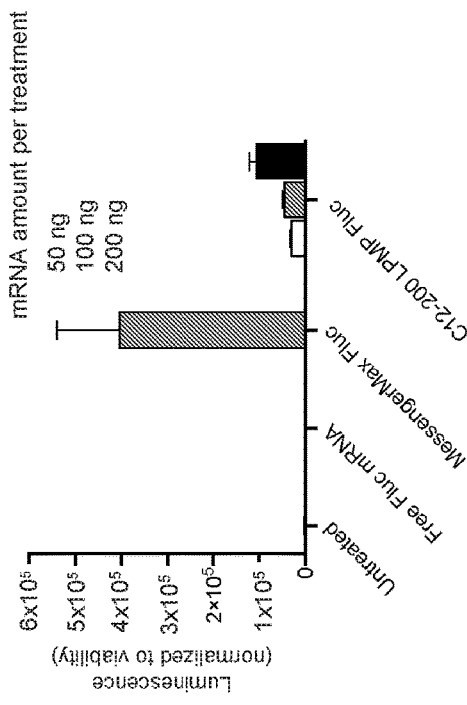
FIG. 6C is a bar graph showing the expression of firefly luciferase (Fluc) mRNA (mean luminescence normalized to viability ±SD; n=4) delivered to A549 cells by C12-200-modified LPMPs or a commercial transfection reagent (MessengerMax). Cells were transfected for 24 h with 50 ng, 100 ng, or 200 ng of FLuc mRNA
Figure 6D:
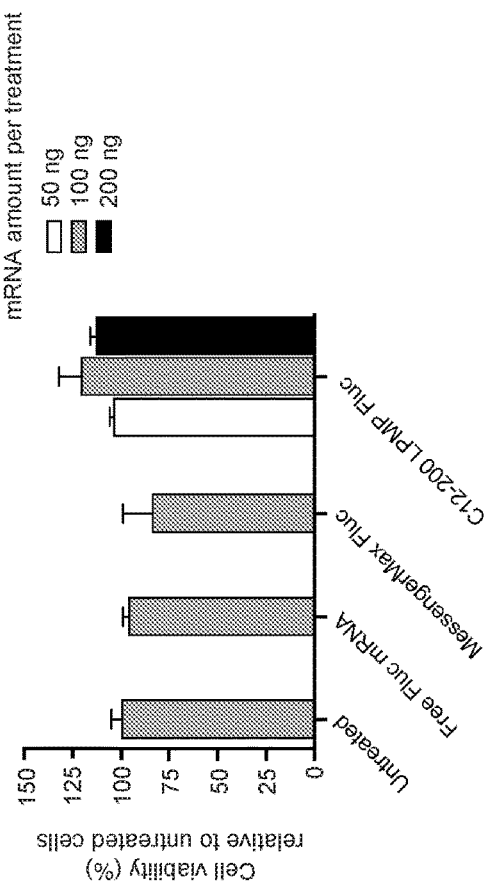
FIG. 6D is a bar graph showing cell viability (%) after transfection with C12-200-modified LPMPs or a commercial transfection reagent (MessengerMax) containing Fluc mRNA.

A549 cells (ATCC® CCL-184™) were cultured in Dulbecco's Modified Eagle's Medium (DMEM) (4500 mg/L glucose) supplemented with 10% heat-inactivated fetal bovine serum (hiFBS, Gibco) and penicillin/streptomycin at 37° C. and 5% $CO_2$. Cells were passaged every 3-4 days. For the experiments, 10,000 cells per well were seeded in a 96-well plate (Corning® Costar®) in 100 μL of medium one day before the experiment. C12-200-modified LPMPs containing mRNA were formulated with microfluidics (Nano-Assemblr® IGNITE™, Precision Nanosystems) and characterized as described above. C12-200 modified LPMPs containing 50, 100 and 200 ng of FLuc mRNA were added to each well and incubated for 24 h. As a positive control, cells were transfected with 100 ng of Fluc mRNA using Lipofectamine MessengerMax (Thermo Scientific), according to the manufacturer's protocol. 100 ng of free Fluc mRNA was used as negative control. Cell Viability and FLuc expression were analyzed with a CellTiter-Fluor™ Cell Viability Assay (Promega) and a Bright-Glo™ Luciferase Assay System (Promega), according to the manufacturer's protocols. Fluorescence and luminescence were quantified using a SYNERGY™ H1 plate reader (BioTek Instruments). C12-200-modified LPMPs showed functional delivery of mRNA to A549 cells, which resulted in the expression of Luciferase protein (FIG. 6C). No significant loss of cell viability upon transfection with mRNA LPMPs, as compared to untreated cells, was observed (FIG. 6D).

Example 10: Cellular Uptake of Natural and Reconstructed PMPs, with and without Ionizable Lipid Modifications This example demonstrates the ability to incorporate lipids of different origins into PMPs, thereby altering their uptake by human cells. This example also demonstrates the difference in cellular uptake between natural and reconstructed PMPs. In this example, C12-200 [1,1'-((2-(4-(2-((2-(bis(2-hydroxydodecyl)amino)ethyl)(2-hydroxydodecyl) amino)ethyl)piperazin-1-yl)ethyl)azanediyl)bis(dodecan-2-ol)] and MC3 [(6Z,9Z,28Z,31Z)-heptatriaconta-6,9,28,31-tetraen-19-yl 4-(dimethylamino)butanoate, DLin-MC3-DMA] are used as model ionizable lipids; lemon and grapefruit PMPs are used as model PMPs and lipids extracted from these PMPs are used for formation of reconstructed PMPs; and A549 cells are used as a model human cell line.

Experimental Protocol:

a) Reconstructed PMPs Demonstrate Higher Uptake than Natural PMPs

Lemon (LM) and grapefruit (GF) PMPs were produced and lipids were extracted as described in Example 8 and Example 9. Reconstructed lemon PMPs (recLM) and reconstructed grapefruit PMPs (recGF) were prepared using 2 mg of lemon lipids or 5.6 mg of grapefruit lipids at a final lipid concentration of 4 mg/mL and 9.3 mg/mL in UltaPure water, respectively. Dried lipid film was rehydrated in UltraPure™ DNase/RNase-Free Distilled Water (ThermoFisher, 10977023) for 2 h at RT in the dark. The resuspended lipid solution was subjected to sonication for 10 minutes at RT using a water bath sonicator, and extruded through 0.8 μm, 0.4 μm and 0.2 μm polycarbonate filters using a Mini Extruder (Avanti® Polar Lipids). All PMP formulations (i.e., reconstructed PMPs from extracted lipids and original PMPs from the same source) were labeled with green PKH67 lipophilic membrane dye (Sigma) according to the manufacturer's protocol, with some modifications. Briefly, PMPs ($5-7 \times 10^{13}$ particles/mL) resuspended in Dilute C (Dil.C) of the PKH26 labelling (1:1 ratio water:Dil.C) were mixed with PKH26 dye at a ratio of 1:500 (2 μl of 1 mM dye to 1 mL of solution) and incubated for 1.5 h at 37° C. in the dark. All unlabeled dye was washed away by ultracentrifugation (100,000 g, 1 h, UltraPure™ DNase/RNase-Free Distilled Water (ThermoFisher, 10977023), twice), and PKH67-labeled PMPs were sterilized using an 0.2 μm sterile filter. The final pellet was resuspended in sterile PBS and kept at 4° C. until further use. Fluorescent intensity and number of particles of PKH67-labeled PMPs were assessed by a SpectraMax® spectrophotometer (Ex/Em=485/510 nm) and by nano-flow cytometry (NanoFCM), respectively. Final PMP concentrations of PKH67-labeled PMPs (particles/mL) were determined by NanoFCM, using concentration standards provided by the manufacturer, and were as follows: $5.7 \times 10^{12}$ (recLM), $3.8 \times 10^{13}$ (LM), $1 \times 10^{13}$ (recGF), $1.8 \times 10^{13}$ (GF). The fluorescent intensity was 69183, 103529, 79465, 155459 fluorescent a.u./μL, respectively.

To determine the uptake efficiency of PKH26-labeled PMPs versus PKH26-labeled lipid-reconstructed PMPs, human A549 cells (ATCC® CCL-184™; adenocarcinomic human alveolar basal epithelial cells) were treated with the formulations for 2.5 h at 37° C. All formulations were normalized based on fluorescence intensity (180022 PKH67 fluorescent units/well). Free dye was used as a control. At the end of the incubation, cells were washed two times with ice cold PBS, detached by adding 50 μL Gibco TrypLE™ reagent per well (ThermoFisher), and incubated for 3 min. Then, 200 μL of ice cold FACS buffer (PBS containing 5% FBS) was added to neutralize the TrypLE™ reagent. Samples were collected and spun down at 1500 rpm (230 g) for 5 min at 4° C. To remove the supernatant, cells were washed with 1 mL of FACS buffer, and the centrifugation step was repeated one more time. Cells were resuspended in 150 µL of PBS supplemented with 0.5% of formaldehyde and incubated at least for 30 min at 4° C. prior to flow cytometry. The flow cytometry analysis was performed using a flow cytometer MACSQuant Analyzer 10 (Miltenyi Biotec). The analysis of PKH67-positive cells demonstrated increased association and uptake of lipid-reconstructed PMPs by cells compared to original PMPs for all sources (FIG. 7A).

b) PMPs Modified with Ionizable Lipids Demonstrate Higher Uptake

Lemon PMPs were produced and lipids were extracted as described in Example 8 and Example 9. Ionizable lipids were added to 1 mg of PMP extracted lipid stock solution in chloroform:methanol (9:1) to amount to 25% (C12-200) or 40% (w/w) (MC3) of the total lipid. The stock solution of DiI (a fluorescent lipophilic cationic indocarbocyanine dye from ThermoFisher) was prepared in anhydrous DMSO (10 mg/mL) and added to the lipid mixture at the final concentration of 1 mM (2.3 uL of DiI per 1 mg of lipids) upon vigorous mixing. Dried lipid film was prepared by evaporation of the solvent with a stream of inert gas (e.g., nitrogen) using a TurboVap® evaporator. Lipid-modified PMPs (LPMPs) without cargo were prepared by rehydration of the lipids in PBS followed by extrusion. Unincorporated dye was washed out twice with PBS using Nanosep® Centrifugal Devices (300 kDa MWCO, Pall Corporation), and DiI-labeled PMPs were concentrated by centrifugation at 15,000 g, 5 min, RT. Fluorescent intensity and number of particles of DiI-labeled lipid-modified LPMPs were assessed using a SpectraMax® spectrophotometer (Ex/Em=549/565 nm) and by nano-flow cytometry (NanoFCM), respectively. The final concentration and fluorescent intensity was $1.7 \times 10^{12}$ particles/mL with fluorescent intensity of 12902 fluorescent a.u./uL for DiI-labeled LPMPs; $1.35 \times 10^{12}$ particles/mL with 8268 a.u./µL for MC3-LPMPs; and $1.35 \times 10^{12}$ particles/mL with 13125 a.u./µL for C12-200-LPMPs.

Example 11: Increasing PMP Cellular Uptake by Formulation of PMPs with Cationic Lipids This example describes increasing the cellular uptake of PMPs into animal, plant, fungal or bacterial cells, by modification of the PMPs with cationic lipids to facilitate penetration of the cell wall and/or cell membrane. In this example, grapefruit PMPs are used as model PMPs, cotton as a model plant, *Saccharomyces cerevisiae* a model yeast, MDA-MB-231 as a model human cell line, *S. sclerotiorum* as a model fungus, and *Pseudomonas syringae* as a model bacterium Experimental Protocol:

a) Modification of PMPs with a Cationic Lipid

A concentrated solution of grapefruit PMPs are isolated as described in Example 1 and Example 2. PMPs are resuspended with vigorous mixing in 0.001%, 0.01% 0.1%, 0.5%, 1%, 2%, 3%, 4%, 5%, 10%, 15%, 20%, 30% w/v solutions of a cationic lipid (Avanti Polar Lipids). The concentration of PMPs is determined by assuming 100% recovery from the suspension and multiplying the concentration prior to formulation by the ratio of the volumes. Cationic lipid-modified PMP characteristics and stability are assessed as described in Example 3 and Example 4.

b) Increased PMP Uptake by *Saccharomyces cerevisiae* with Cationic Lipid-Modified Grapefruit PMPs Loaded with GFP Protein PMPs are produced from grapefruit as described in Example 1 and Example 2, and are loaded with GFP protein as described in Example 5. Some of the PMPs are set aside as controls, and the rest are modified with a cationic lipid as described in Example 11a. GFP encapsulation of PMPs is measured by Western blot or fluorescence. All PMP formulations are next labeled with red PKH26 (Sigma) lipophilic membrane dye according to the manufacturer's protocol, with some modifications. Briefly, 50 mg PMPs in 1 mL dilute C of the PKH26 labelling kit are mixed with 2 ml of 1 mM PKH26 and incubated at 37° C. for 5 min. Labelling is stopped by adding 1 mL of 1% BSA. All unlabeled dye is washed away by methods described in Example 2, and labelled PMP pellets are resuspended in PBS. To determine the PMP uptake efficiency of GFP-loaded PKH26-labeled PMPs versus GFP-loaded cationic lipid-modified PKH26-labeled PMPs, *Saccharomyces cerevisiae* fungal cells are treated.

*Saccharomyces cerevisiae* is obtained from the ATCC (#9763) and maintained at 30° C. in yeast extract peptone dextrose broth (YPD) as indicated by the manufacturer. To determine the PMP uptake by *S. cerevisiae*, yeast cells are grown to an $OD_{600}$ of 0.4-0.6 in selection media, and incubated with 0 (negative control), 1, 10, or 50, 100 and 250 µg/ml of PKH26-labeled GFP-loaded modified PMPs, or unmodified PMPs directly on glass slides. In addition to a PBS control, *S. cerevisiae* cells are incubated in the presence of PKH26 dye (final concentration 5 µg/ml). After incubation of 5 min, 30 min and 1 h at room temperature, images are acquired on a high-resolution fluorescence microscope. PMPs are taken up by yeast cells when red membrane and green GFP-loaded PMPs are observed in the cytoplasm, or if the cytoplasm of the yeast cell turns red and/or green, versus exclusive staining of the cell membrane by PKH26 dye. To assess the uptake efficiency of GFP-loaded cationic lipid-modified PMPs compared to the unmodified GFP-loaded PMPs, the percentage of yeast cells with a green cytoplasm/green PMPs in the cytoplasm, versus membrane only staining are compared between PMP-treated cells and the PBS and PKH26 dye only controls. The amount of uptake in each cell is quantified by measuring the median red and green fluorescence signal from the cell using ImageJ software, and the uptake efficiency of GFP-loaded cationic lipid-modified PMPs is compared to the unmodified GFP-loaded PMPs.

c) Increased PMP Uptake by *S. sclerotiorum* with Cationic Lipid-Modified Grapefruit PMPs Loaded with GFP Protein PMPs are produced from grapefruit as described in Example 1 and Example 2, and are loaded with GFP protein as described in Example 5. Some of the PMPs are set aside as controls, and the rest are modified with a cationic lipid as described in Example 11a. GFP encapsulation of PMPs is measured by Western blot or fluorescence. All PMP formulations are next labeled with red PKH26 (Sigma) lipophilic membrane dye according to the manufacturer's protocol, with some modifications. Briefly, 50 mg PMPs in 1 mL dilute C are mixed with 2 mL of 1 mM PKH26 and incubated at 37° C. for 5 min. Labelling is stopped by adding 1 mL of 1% BSA. All unlabeled dye is washed away by methods described in Example 2, and labelled PMP pellets are resuspended in PBS. To determine the PMP uptake efficiency of GFP-loaded PKH26-labeled PMPs versus GFP-loaded cationic lipid-modified PKH26-labeled PMPs, *S. sclerotiorum* fungal cells are treated.

To determine the PMP uptake by *S. sclerotiorum* (ATCC, #18687) ascospores, 10,000 ascospores are incubated with and incubated with 0 (negative control), 1, 10, or 50, 100 and 250 µg/mL of PKH26-labeled GFP-loaded modified PMPs, or unmodified PMPs directly on glass slides. In addition to a PBS control, *S. sclerotiorum* cells are incubated in the presence of PKH26 dye (final concentration 5 µg/ml). After incubation of 5 min, 30 min and 1 h at room temperature, images are acquired on a high-resolution fluorescence microscope. PMPs are taken up by yeast cells when red membrane and green GFP-loaded PMPs are observed in the cytoplasm, or if the cytoplasm of the yeast cell turns red and/or green, versus exclusive staining of the cell membrane by PKH26 dye. To assess the uptake efficiency of GFP-loaded cationic lipid-modified PMPs compared to the unmodified GFP-loaded PMPs, the percentage of *S. sclerotiorum* cells with a green cytoplasm/green PMPs in the cytoplasm, versus membrane only staining are compared between PMP-treated cells and the PBS and PKH26 dye only controls. The amount of uptake in each cell is quantified by measuring the median red and green fluorescence signal from the cell using ImageJ software, and the uptake efficiency of GFP-loaded cationic lipid-modified PMPs is compared to the unmodified GFP-loaded PMPs.

d) Increased PMP Uptake by MDA-MB-231 Cells with Cationic Lipid-Modified Grapefruit PMPs Loaded with Calcein AM PMPs are produced from grapefruit as described in Example 1 and Example 2. Some of the PMPs are set aside as controls, and the rest are modified with a cationic lipid as described in Example 11 b. Modified and unmodified PMPs are loaded with Calcein AM (Sigma Aldrich) as described in Example 5 and Gray et al., *MethodsX* 2015. Calcein AM is fluorescent only when encapsulated by PMPs, and encapsulation is measured by fluorescence. All PMP formulations are next labeled with red PKH26 (Sigma) lipophilic membrane dye according to the manufacturer's protocol, with some modifications. Briefly, 50 mg Calcein AM loaded PMPs in 1 mL dilute C are mixed with 2 ml of 1 mM PKH26 and incubated at 37° C. for 5 min. Labelling is stopped by adding 1 mL of 1% BSA. All unlabeled dye is washed away and PMPs are concentrated using a 100 kDa Amicon filter as described in Example 2. To determine the PMP uptake efficiency of Calcein AM-loaded PKH26-labeled PMPs versus Calcein AM-loaded PKH26-labeled cationic lipid-modified PMPs, human breast cancer cells are treated.

MDA-MB-231 breast cancer cell line is obtained from the ATCC (HTB-26) and grown and maintained according to the supplier's instructions. Cells at 70-80% confluency are harvested, counted and seeded in 96-well culture treated well plate at a seeding density of 10,000 cells per well in 200 μl cell culture medium. Cells are allowed to adhere for 3 hours, then the medium is removed, the cells are washed once with Dulbecco PBS, and medium without FCS is added to serum starve the cells for 3 hours prior to treatment. To determine the PMP uptake by breast cancer cells, the cells are incubated with 0 (negative control), 1, 10, or 50, 100 and 250 μg/ml of PKH26-labeled Calcein AM-loaded PKH26-labeled unmodified and cationic lipid modified PMPs directly in the well. In addition to a PBS control, cells are incubated in the presence of Calcein AM (final concentration 5 μg/ml), PKH26 dye (final concentration 5 μg/ml), and unmodified PMPs. After incubation of 30 min, 1 h, 2 h and 4 h at 37 C, cell are washed 4×10' with PBS to remove PMPs in the medium. Images are next acquired on a high-resolution fluorescence microscope (EVOS2 FL) at 40× to determine uptake efficiency. PMPs are taken up by breast cancer cells when red membrane and green Calcein AM-loaded PMPs are observed in the cytoplasm, or if the cytoplasm of the cell turns red and/or green, versus exclusive staining of the cell membrane by PKH26 dye. To assess the uptake efficiency of Calcein-AM-loaded cationic lipid-modified PMPs compared to the unmodified Calcein AM-loaded PMPs, the percentage of cells with a green cytoplasm/green PMPs in the cytoplasm, versus membrane only staining are compared between PMP-treated cells and the PBS and PKH26 dye only controls. The amount of uptake in each cell is quantified by measuring the median red and green fluorescence signal from the cell using ImageJ software, and the uptake efficiency of GFP-loaded cationic lipid-modified PMPs is compared to the unmodified GFP-loaded PMPs.

e) Increased PMP Uptake by *Pseudomonas syringae* with Cationic Lipid-Modified Grapefruit PMPs Loaded with Calcein AM PMPs are produced from grapefruit as described in Example 1 and Example 2. Some of the PMPs are set aside as controls, and the rest are modified with a cationic lipid as described in Example 12b. Modified and unmodified PMPs are loaded with Calcein AM (Sigma Aldrich) as described in Example 5 and Gray et al., *MethodsX* 2015. Calcein AM is fluorescent only when encapsulated by PMPs, and encapsulation is measured by fluorescence. All PMP formulations are next labeled with red PKH26 (Sigma) lipophilic membrane dye according to the manufacturer's protocol, with some modifications. Briefly, 50 mg Calcein AM loaded PMPs in 1 mL dilute C of the PKH26 labelling kit are mixed with 2 ml of 1 mM PKH26 and incubated at 37° C. for 5 min. Labelling is stopped by adding 1 mL of 1% BSA. All unlabeled dye is washed away and PMPs are concentrated using a 100 kDa Amicon filter as described in Example 2. To determine the PMP uptake efficiency of Calcein AM-loaded PKH26-labeled PMPs versus Calcein AM-loaded PKH26-labeled cationic lipid-modified PMPs, *Pseudomonas syringae* bacterial cells are treated.

*Pseudomonas syringae* bacteria are obtained from the ATCC (BAA-871) and grown on King's Medium B agar according to the manufacturer's instructions. To determine the PMP uptake by *P. syringae,* 10 ul of a 1 ml overnight bacterial suspension is incubated with 0 (negative control), 1, 10, or 50, 100 and 250 μg/ml of PKH26-labeled Calcein AM-loaded PKH26-labeled unmodified and cationic lipid-modified PMPs directly on a glass slide. In addition to a water control, *P. syringae* bacteria are incubated in the presence of Calcein AM (final concentration 5 μg/ml), PKH26 dye (final concentration 5 μg/ml), and unmodified PMPs. After incubation of 5 min, 30 min and 1 h at room temperature, images are acquired on a high-resolution fluorescence microscope. To assess the uptake efficiency of Calcein AM-loaded PKH26-labeled cationic lipid-modified PMPs compared to the unmodified Calcein AM-loaded PKH26-labeled PMPs, the percentage of bacterial cells with a green cytoplasm or green and red PMPs in the cytoplasm, versus membrane only staining are compared between PMP-treated cells and the PBS and PKH26 dye only controls. The amount of uptake in each cell is quantified by measuring the median red and green fluorescence signal from the cell using ImageJ software, and the uptake efficiency of Calcein AM-loaded PKH26-labeled cationic lipid-modified PMPs is compared to the unmodified Calcein AM-loaded PKH26-labeled PMPs. Cationic lipid modification of PMPs improve the cellular uptake efficiently compared to unmodified PMPs.

f) Increased PMP Uptake of Cationic Lipid-Modified Grapefruit PMPs Loaded with dsRNA Targeting CLA1 in Cotton Plants To demonstrate an increase in cellular uptake by cationic lipid-modified PMPs, grapefruit PMPs are loaded with artificial miRNAs (amiRNAs, designed using Plant Small RNA Maker Site (P-SAMS; Fahlgren et al., *Bioinformatics.* 32(1): 157-158, 2016)) or custom dicer substrate siRNA (DsiRNA, designed by IDT) targeting the cotton photosynthesis gene GrCLA1 (1-deoxy-D-xylulose-5-phosphate synthase). GrCLA1 is a homolog gene of *Arabidopsis* Cloroplastos alterados 1 gene (AtCLA1), which loss-of-function results in an albino phenotype on true leaves, providing a visual marker for silencing efficiency. Oligonucleotides are obtained from IDT.

PMPs are produced from grapefruit as described in Example 1 and Example 2. To determine the PMP uptake efficiency of cationic lipid-modified versus unmodified PMPs, grapefruit PMPs are loaded with GrCLA1-amiRNA or GrCLA1-DsiRNA duplexes, as described in Example 5. amiRNA or DsiRNA encapsulation of PMPs is measured using the Quant-iT™ RiboGreen™ assay kit, or using a control fluorescent dye labeled amiRNA or DsiRNA (IDT). Next, part of the loaded PMPs are set aside as controls, and the rest are modified with a cationic lipid as described in Example 6b. To determine the PMP uptake efficiency of CLA1-amiRNA/DsiRNA-loaded PMPs versus CLA1-amiRNA/DsiRNA-loaded cationic lipid-modified PMPs, cotton seedlings are treated and analyzed for CLA1 gene silencing. PMPs loaded with amiRNA or DsiRNA (collectively referred to as dsRNA) are formulated in water to a concentration that delivers an equivalent of effective dsRNA dose of 0, 1, 5, 10 and 20 ng/µl in sterile water.

Cotton seeds (*Gossypium hirsutum* and *Gossypium raimondii*) are obtained through the US National Plant Germplasm System. Sterilized seeds are wrapped in moist absorbent cotton, placed in Petri dishes and placed in a growth chamber at 25° C., 150 µE $m^{-2}$ $S^{-1}$ light intensity, with a 14 hour light/10 hour dark photoperiod for 3 days to germinate. The seedlings are grown in sterile culture vessels with Hoagland's nutrient solution (Sigma Aldrich) under long-day conditions (16/8 h light/dark photoperiod) with 26/20° C. day/night temperatures. After 4 days, seedlings with fully expanded cotyledons (before the first true leaf appeared) are used for PMP treatments.

Seven-day-old cotton seedlings are transferred onto 0.5× Murashige and Skoog (MS) mineral salts (Sigma Aldrich) with 1× MS vitamins (Sigma Aldrich) pH 5.6-5.8, with 0.8% (w/v) agarose and are treated with an effective dose of 0 (ddH2O), 1, 5, 10 and 20 ng/µl GrCLA1 dsRNA-loaded cationic lipid-modified PMPs and 0 (ddH2O), 1, 5, 10 and 20 ng/µl GrCLA1 dsRNA-loaded unmodified PMPs by spraying the whole seedling, 1 ml solution per plant, with 3 plants per group. Alternatively, prior to PMP treatment the underside of cotyledons of cotton plant is punched with a 25 G needle without piercing through the cotyledons. The PMP solutions are hand infiltrated from the underside of cotyledons through the wounding sites using a 1 mL needleless syringe. Plants are transferred to a growth chamber and kept under long-day conditions (16 h/8 h light/dark photoperiod) with light intensity of 90 µmol $m^{-2}$ $s^{-1}$ and 26/20° C. day/night temperatures.

After 2, 5, 8 and 14 days, the gene silencing efficiency of the CLA1 dsRNA is examined by the expression level of endogenous CLA1 mRNA using quantitative reverse transcription polymerase chain reaction (qRT-PCR). Total RNA is extracted from 100 mg fresh cotton leaves using Trizol reagent according to the manufacturer's instructions (Invitrogen) and treated extensively with RNase-free DNase I (Promega). First-strand cDNA is synthesized from 2 µg total RNA with the SuperScript™ First-Strand Synthesis system (Invitrogen). To estimate the levels of CLA1 transcripts qRT-PCR is performed using SYBR Green Real-Time PCR Master Mix (Thermo Scientific) with primers: GrCLA1q1_F 5'-CCAGGTGGGGCTTATGCATC-3' (SEQ ID NO: 7), GrCLA1q1_R 5'-CCACACCAAGGCTTGAACCC-3' (SEQ ID NO: 8), and GrCLA1q2_F 5'-GGCCGGATTCACGAAACGGT-3' (SEQ ID NO: 9), GrCLA1q2_R 5'-CGTCGAGATTGGCAGTTGGC-3' (SEQ ID NO: 10), and 18s RNA_F 5'-TCTGCCCTATCAACTTTC-GATGGTA-3' (SEQ ID NO: 11), 18s RNA_R 5'-AAT-TTGCGCGCCTGCTGCCTTCCTT-3' (SEQ ID NO: 12), using the following program: (a) 95° C. for 5 min; (b) 40 cycles of 94° C. for 30 s, 55° C. for 30 s; and 72° C. for 30 s. The 18S rRNA gene is used as internal control to normalize the results. The CLA1 knock down efficiency in cotton after treatment with CLA1-dsRNA-loaded cationic lipid-modified and CLA1-dsRNA-loaded unmodified PMPs is determined by calculating the ΔΔCt value, comparing the normalized CLA1 expression after treatment with cationic lipid-modified PMPs with normalized CLA1 expression after treatment with unmodified PMPs.

Additionally, the gene silencing efficiency of CLA1 dsRNA is examined by phenotypic photobleaching analysis. Leaves of treated and untreated cotton plants are photographed and ImageJ software is used to determine the percentage gene silencing, which is reflected by white photobleaching on the leaf versus the control leaf green color. Three leaves per plant are assayed to quantify the effect of photobleaching, and the gene silencing efficiency of cationic lipid-modified versus unmodified CLA1-dsRNA-loaded PMPs are assessed.

Cationic lipid-modified PMPs are more efficiently uptaken by plant cells and induce greater CLA1 gene silencing compared to unmodified PMPs.

Example 12: Modification of PMPs Using Cationic Lipids

This example demonstrates the ability to modify surface charge, increase the cargo loading capacity, and increase the cellular uptake of PMPs in human and plant cells, by modification of PMPs with cationic lipids. In this example, DOTAP (1,2-dioleoyl-3-trimethylammonium-propane) and DC-Cholesterol (3β[N—(N',N'-dimethylaminoethane)-carbamoyl]cholesterol) are used as model cationic lipids, grapefruit and lemon PMPs as model PMPs, siRNA/Transactivating CRISPR RNA (TracrRNA) as a model negatively charged payload, COLO679 as a model human cell line, and *Zea mays* (corn) Black Mexican sweet (BMS) as a model plant cell line.

Experimental Protocol:

a) Production of Lemon/Grapefruit PMPs

Red organic grapefruits or yellow organic lemons were obtained from a local grocery store. Six liters of grapefruit juice were collected using a juice press, pH adjusted to pH 4 with NaOH, incubated with 1 U/mL pectinase (Sigma, 17389) to remove pectin contaminants, and subsequently centrifuged at 3,000 g for 20 minutes, followed by 10,000 g for 40 minutes to remove large debris. Next, the processed juice was incubated with 500 mM EDTA pH 8.6 to a final concentration of 50 mM EDTA, pH 7.7 for 30 minutes to chelate calcium and prevent the formation of pectin macromolecules. Subsequently, the EDTA-treated juice was passed through an 11 µm, 1 µm and 0.45 µm filter to remove large particles. Filtered juice was washed and concentrated by Tangential Flow Filtration (TFF) using a 300 kDa TFF. Juice was concentrated 10×, followed by diafiltration into 10 diavolumes in of PBS, and further concentrated to a final concentration 120 mL (50×). Next, we used size exclusion chromatography (SEC) to elute the PMP-containing fractions, which were analyzed by absorbance at 280 (Spectra- Max®) and protein concentration (Pierce™ BCA Protein Assay) to verify the PMP-containing fractions and late fractions containing contaminants. SEC fractions 3-7 contained purified PMPs (fractions 9-12 contained contaminants) and were pooled together, filter sterilized by sequential filtration using 0.8 μm, 0.45 μm and 0.22 μm syringe filters, and concentrated further by pelleting PMPs for 1.5 hrs at 40,000× g and resuspending the pellet in 4 mL UltraPure™ DNase/RNase-Free Distilled Water (ThermoFisher, 10977023). Final PMP concentration ($7.56 \times 10^{12}$ PMPs/mL) and PMP size (70.3 nm+/−12.4 nm SD) were determined by NanoFCM, using concentration and size standards provided by the manufacturer. The produced grapefruit (GF) or lemon (LM) PMPs were used for lipid extraction using the Bligh-Dyer method, as described below.

b) Modification of PMPs with Cationic Lipids

Figure 12:
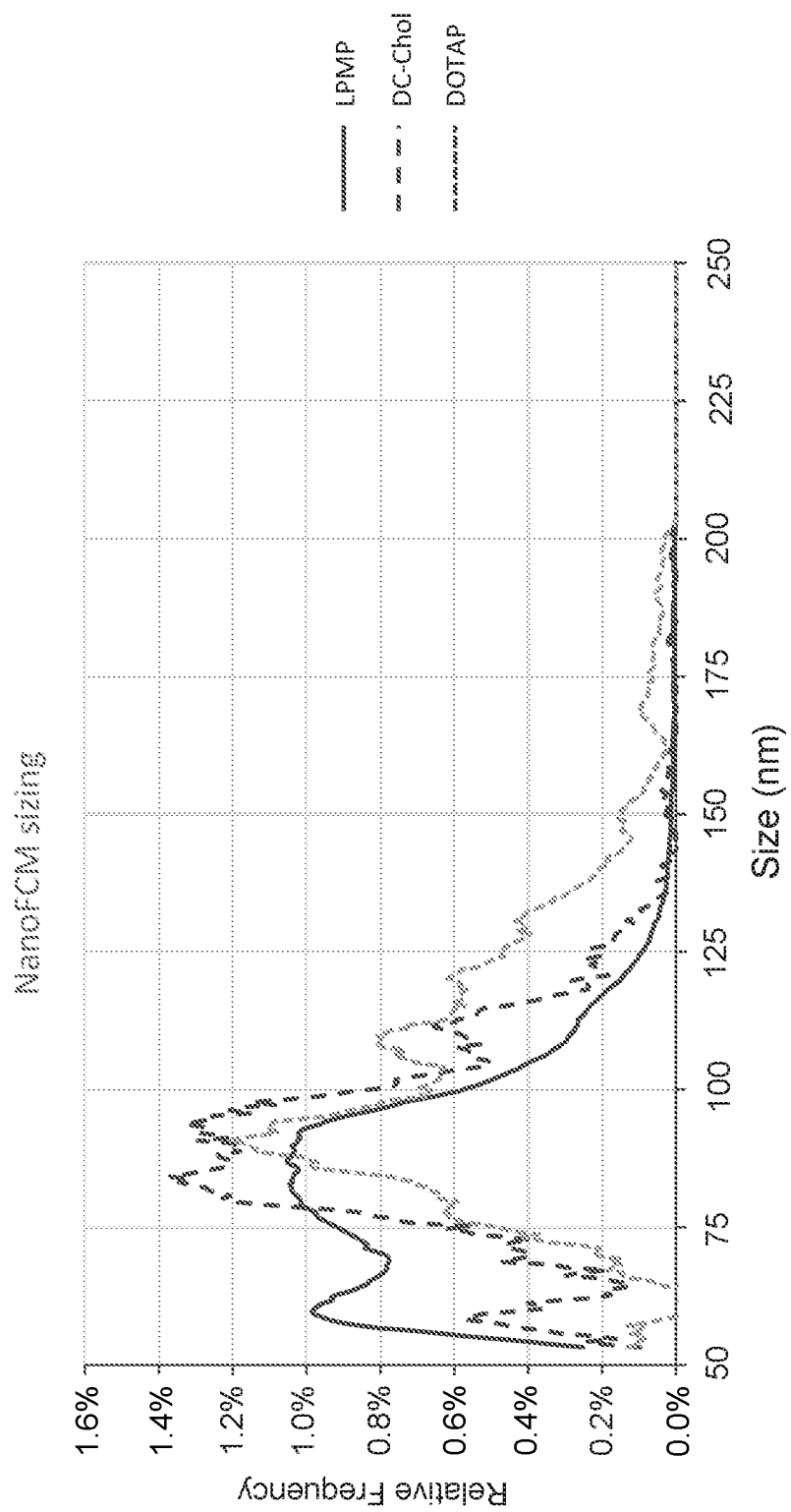
FIG. 12 is a graph showing the relative frequency of particles of a given size (nm) in LPMPs; LPMPs with added DC-cholesterol (DC-Chol); and LPMPs with added DOTAP (DOTAP). Data were acquired by NanoFCM using concentration and size standards provided by the manufacturer.
Figure 13A:
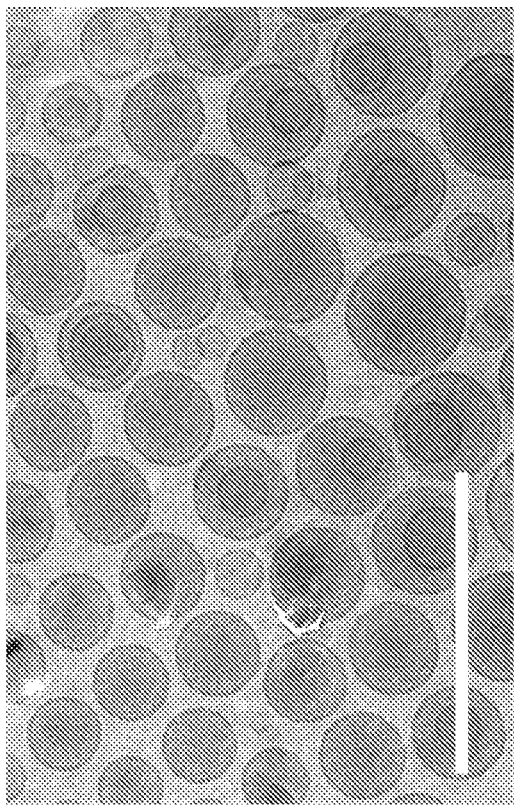
FIG. 13A is a cryo-electron micrograph showing LPMPs reconstructed from extracted lemon PMP lipids. Scale bar: 500 nm.
Figure 13B:
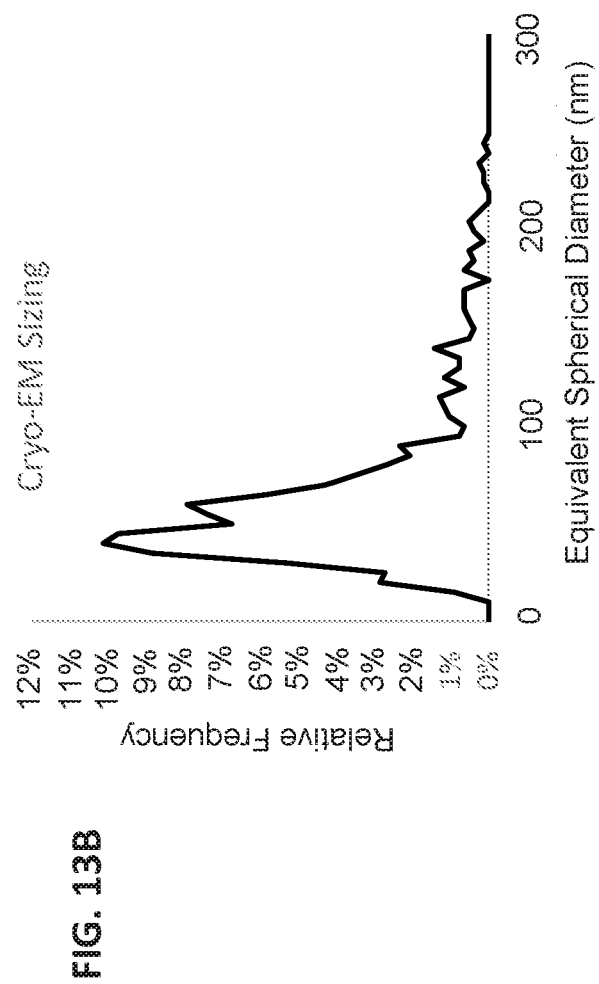
FIG. 13B is a graph showing the relative frequency of particles of a given equivalent spherical diameter (nm) in LPMPs reconstructed from extracted lemon lipids, as measured using cryo-electron microscopy.
Figure 14B:
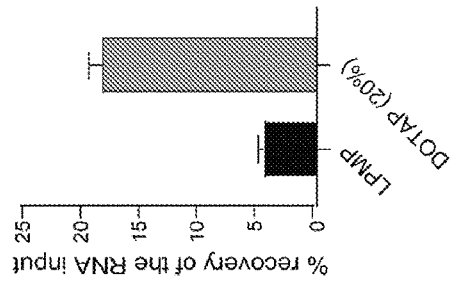
FIG. 14B is a bar graph showing the percent of Alexa Fluor 555-labeled siRNA input that was recovered from LPMPs following loading of LPMPs from grapefruit lipids not comprising added lipids (LPMPs) and LPMPs from grapefruit lipids comprising 20% DOTAP.
Figure 14A:
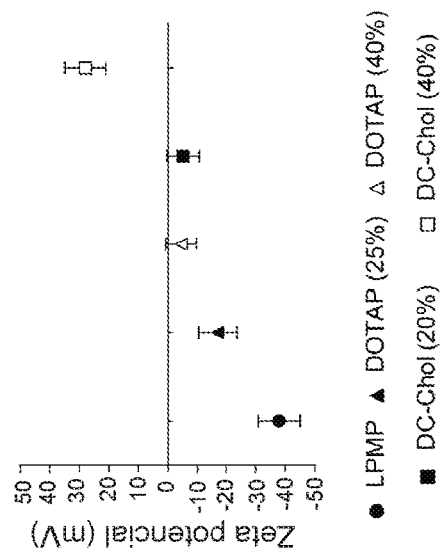
FIG. 14A is a graph showing the zeta potential (mV) of LPMPs not comprising added lipids (LPMPs) and LPMPs comprising 25% or 40% DOTAP or DC-cholesterol as measured using dynamic light scattering (DLS). Data are presented as Mean±SD.
Figure 14D:
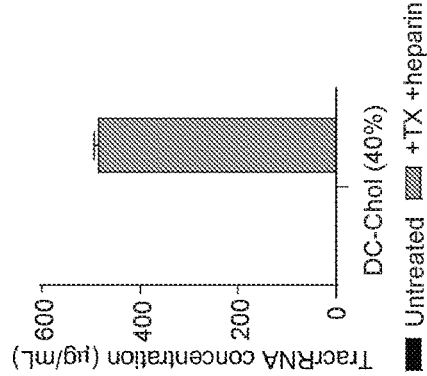
FIG. 14D is a bar graph showing TracrRNA concentration (µg/mL) in LPMPs comprising 40% DC-cholesterol that have not been treated or have been lysed using Triton™ X-100 and heparin (+TX+heparin), as measured using a Quant-iT™ RiboGreen® analysis.
Figure 14C:
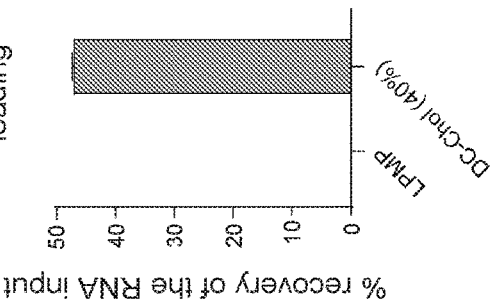
FIG. 14C is a bar graph showing the percent of ATTO-labeled TracrRNA input that was recovered from LPMPs following loading of LPMPs from lemon lipids not comprising added lipids (LPMPs) and LPMPs from lemon lipids comprising 40% DC-cholesterol (DC-Chol).

To prepare lipid reconstructed PMPs (LPMP), total lipid extraction from a concentrated solution of grapefruit or lemon PMPs was performed using the Bligh-Dyer method (Bligh and Dyer, *J Biolchem Physiol*, 37: 911-917, 1959). Briefly, 1 mL of concentrated PMPs ($10^{12}$-$10^{13}$ PMPs/mL) was mixed with a 3.5 mL chloroform:methanol mixture (1:2, v/v) and vortexed well. Then 1.25 mL chloroform was added and vortexed, followed by agitating with 1.25 mL sterile water. Finally, the mixture was centrifugated at 300 g for 5 minutes at RT. The bottom organic phase containing lipids was recovered and dried out using a TurboVap® system (Biotage®). To modify the lipid composition of natural LPMPs, synthetic cationic lipids (DOTAP, DC-Cholesterol) were dissolved in chloroform:methanol (9:1) and added to the PMP extracted lipids to amount to 25% or 40% (w/w) of the total lipid, followed by vigorous mixing. Dried lipid film was prepared by evaporation of the solvent with a stream of inert gas (e.g., nitrogen) or by evaporation using the TurboVap® system (FIG. 1). To prepare reconstructed PMPs from extracted lipids, water or buffer (e.g., PBS) was added to the dried lipid film and was left for 1 h at RT to hydrate. Formed lipid particles were subjected to 10 freeze-thaw cycles or sonication (Branson 2800 sonication bath, 10 min, RT). Then, to reduce the number of lipid bilayers and overall particle size, the lipid PMPs were extruded through 0.8 μm, 0.4 μm and 0.2 μm polycarbonate filters using a Mini Extruder (Avanti® Polar Lipids) (FIG. 1). If concentrated LPMP was required, the samples were concentrated by ultracentrifugation at 100,000×g for 30 min at 4° C. The final pellet was resuspended in sterile UltraPure water or PBS and kept at 4° C. until further use. Final LPMP concentration and median LPMP size (ranging from 89-104 nm) were determined by NanoFCM, using concentration and size standards provided by the manufacturer. The surface charge (zeta potential) was measured by laser doppler micro-electrophoresis using a Zetasizer (Malvern Panalytical) (FIG. 14A). The range of LPMP size and concentration was 83±19 nm and $1.7 \times 10^{12}$ LPMPs/mL for LM LPMPs, 106±25 nm and $6.54 \times 10^{10}$ LPMPs/mL for DOTAP-modified LPMPs, and 91±17 nm and $3.08 \times 10^{11}$ LPMPs/mL for DC-Cholesterol-modified PMPs (FIG. 12). Modification of LPMPs with the cationic lipids DOTAP and DC-Cholesterol changed the surface charge of LPMPs: with increasing cationic lipid content, the surface charge of LPMPs increased (FIG. 14A). Analysis of Cryo-EM images of LPMPs reconstructed from extracted lemon lipids confirmed the sphericity of LPMPs and particle size distribution (68.7±23 nm (SD)) (FIGS. 13A and 13B).

c) Loading of Cationic Lipid-Modified PMPs with Negatively Charged Cargo

To load siRNA/TracrRNA, GF or LM extracted lipids were supplemented with cationic lipids and dried out as described above. siRNA/TracrRNA dissolved in a nuclease free water or Duplex Buffer (IDT®) was added to the dried lipid film at 1.5 nmol per 1 mg of PMP lipids and was left for 1 h at RT to hydrate. Formed lipid particles were subjected to 10 freeze-thaw cycles and extruded through 0.8 μm, 0.4 μm and 0.2 μm polycarbonate filters using a Mini Extruder (Avanti® Polar Lipids) (FIG. 1). Loaded PMPs were dialyzed over night against PBS in a dialysis device (Spectrum®) with a 100 kDa MWCO membrane and then sterilized using 0.2 μm Polyethersulfone (PES) filters. Additionally, samples were purified and concentrated using ultracentrifugation. Loaded PMPs were centrifuged for 30 min at 100,000×g at 4° C., supernatant was removed, and the pellet was resuspended in 1 mL PBS and concentrated at 100,000×g for 30 min. The resulting pellet was resuspended either in PBS (for cellular uptake by human cells) or water (for cellular uptake by plant cells). Size of the RNA-loaded LPMPs and number of particles were assessed by NanoFCM: the mean size and particle concentration were 89±15 nm and $1.54 \times 10^{12}$ LPMPs/mL for unmodified LPMPs, 104±25 nm and $2.54 \times 10^{11}$ LPMPs/mL for DC-Chol, and 100±30 nm and $9.7 \times 10^{11}$ LPMPs/mL for DOTAP. RNA loading was determined by Quant-iT™ RiboGreen™ assay or by measurement of fluorescent intensity of labeled cargo (siRNA labeled with Alexa Fluor 555 or TracrRNA labeled with ATTO 550). The RiboGreen™ assay was performed according to the manufacturer's protocol in the presence of heparin (5 mg/mL) and 1% Triton™ X-100 to lyse PMPs and release encapsulated cargo. Modification of LPMPs with the cationic lipids DOTAP and DC-Cholesterol changed the surface charge of LPMPs and increased loading of negatively charged cargo (e.g. RNA), as compared to LPMPs without cationic lipids (FIGS. 14A-14D).

d) Increased Uptake of DOTAP Modified PMPs by Human Cells (COLO679)

Lipid modified PMPs (LPMP) from grapefruit supplemented with DOTAP (20%, w/w) were prepared as described above. PMP formulations were next labeled with green PKH67 lipophilic membrane dye (Sigma) according to the manufacturer's protocol, with some modifications. Briefly, 300 μL of LPMPs (approx. $1 \times 10^{12}$ PMPs/mL) were mixed 1:1 with diluent C, followed by mixing with PKH67 dye diluted in diluent C (final ratio of dye:sample was 1:500, v/v) and incubated at RT for 1 h with shaking at 100 rpm. Free dye was removed by purification of LPMPs on Zeba™ Spin Desalting Columns (40 kDa MWCO, Thermo Fisher Scientific) equilibrated with PBS. Labeled LPMPs were sterilized using 0.2 μm sterile filters, concentrated by ultracentrifugation (30 min, 100,000 g, 4° C.) and resuspended in sterile PBS. Final LPMP concentration and mean size ($1.1 \times 10^{12}$ LPMPs/mL and 83±19 nm for LPMP; $8.95 \times 10^{11}$ and 100±30 nm for DOTAP) were determined by NanoFCM. The fluorescent intensity was ascertained using a spectrophotometer (SpectraMax®) at Ex/Em=485/510 nm. Free PKH67 dye at the same concentration (1:500, v/v) was purified using the same approach.

Figure 15:
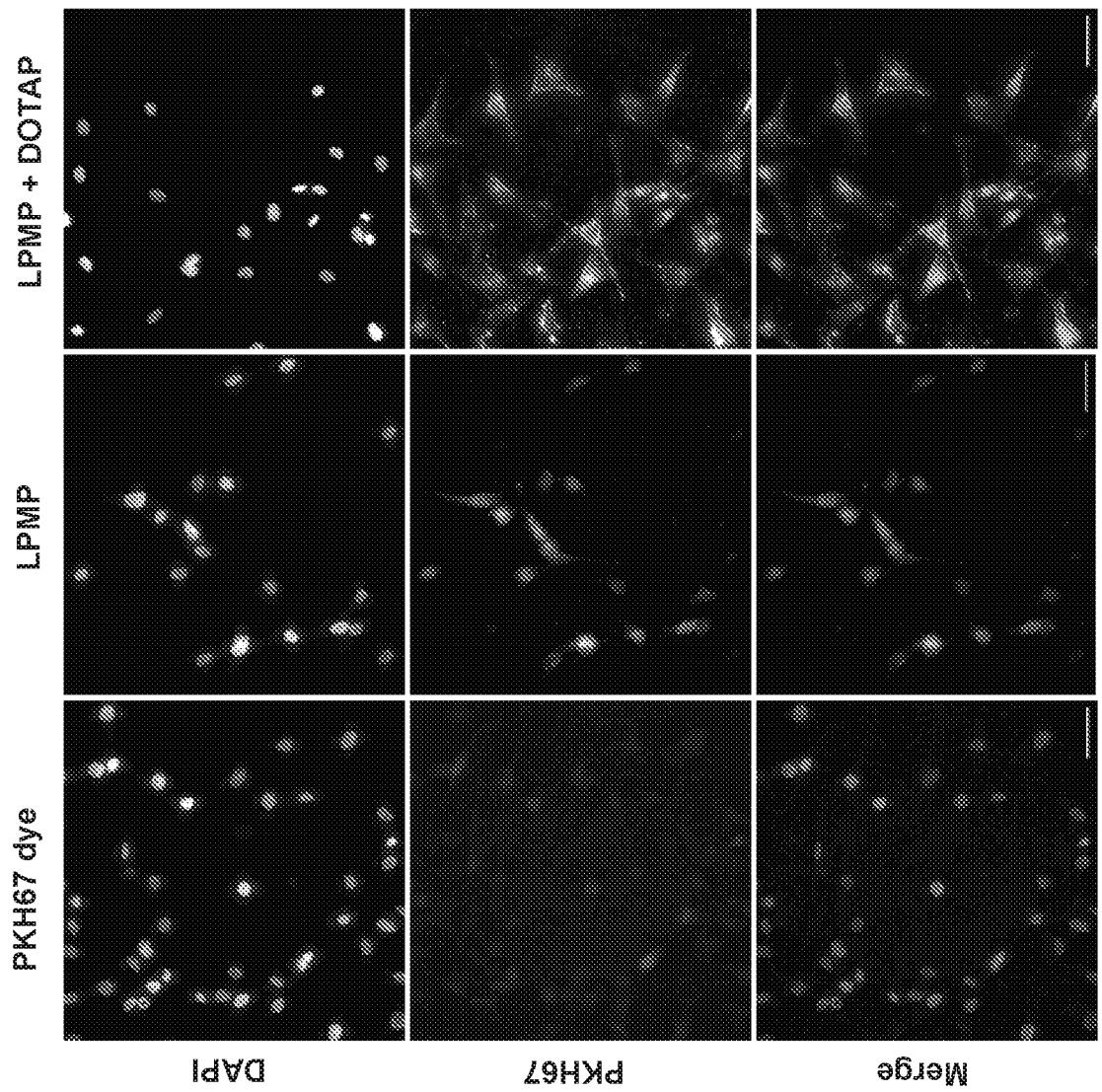
FIG. 15 is a set of photomicrographs showing DAPI (top row) and PKH67 (center row) fluorescence in COLO697 cells treated with PKH67-labeled LPMPs from grapefruit lipids not comprising added lipids (center column) and LPMPs containing 20% DOTAP (right column). A merged image comprising the DAPI and PKH67 signals is shown in the bottom row of panels. Cells treated with PKH67 dye are shown as a control. Scale bar: 50 µm.

COLO679 cells were cultured in RPMI 1640 medium (Thermo Fisher Scientific) with 10% of heat inactivated FBS (Gibco) and 1% Penicillin-Streptomycin (Gibco). Cells were seeded in a 96-well plate at 6000 cells/well one day prior to the experiment. To determine uptake of PKH67-labeled LPMPs, COLO679 cells were incubated with LPMPs at the concentration of $2 \times 10^{10}$ particles per well for 3 h at 37° C. Free PKH67 dye was used as a control. At the end of the incubation time, cells were washed two times with ice cold PBS 1× and fixed with 100 µL of 4% formaldehyde in PBS for 15-30 min. Cell nuclei were stained with DAPI (Thermo Fisher Scientific). Images were acquired using a fluorescence microscope (Olympus IX83) with a 40× objective lens. Modification with DOTAP increased the uptake/association of LPMPs with the COLO679 cells, as compared to LPMPs without cationic lipids (FIG. 15). Our data suggests that DOTAP-modified LPMPs enhanced uptake and/or association of vehicle with COLO679 cells compared to LPMPs without additional cationic lipids.

e) Increased Delivery of RNA to Plant Cells by DC-Cholesterol-Modified PMPs

*Zea mays*, Black Mexican sweet (BMS) cells were purchased from the *Arabidopsis* Biological Resource Center (ABRC). BMS cells were grown in Murashige and Skoog basal medium pH 5.8, containing 4.3 g/L Murashige and Skoog Basal Salt Mixture (Sigma M5524), 2% sucrose (S0389, Millipore Sigma), 2 mg/L 2,4-dichlorophenoxyacetic acid (D7299, Millipore Sigma), 250 µg/L thiamine HCL (V-014, Millipore Sigma) and a 1×MS vitamin mix solution in ddH2O. The 1× vitamin mix solution contained niacin (N0761—100 G, Millipore Sigma), Pyroxidine hydrochloride (P6280—25 G, Millipore Sigma), D-pantothenic acid hemicalcium salt (P5155—100 G, Millipore Sigma), L-Asparagine (A4159—25 G, Millipore Sigma), and Myo-inositol (17508—100 G, Millipore Sigma) at respective final concentrations of 1.3 mg/L, 250 µg/L, 250 µg/L, 130 mg/L, and 200 mg/L. Cells were grown in 1 L vented conical sterile flasks, in dark conditions at 24° C. with agitation (110 rpm).

Figure 16:
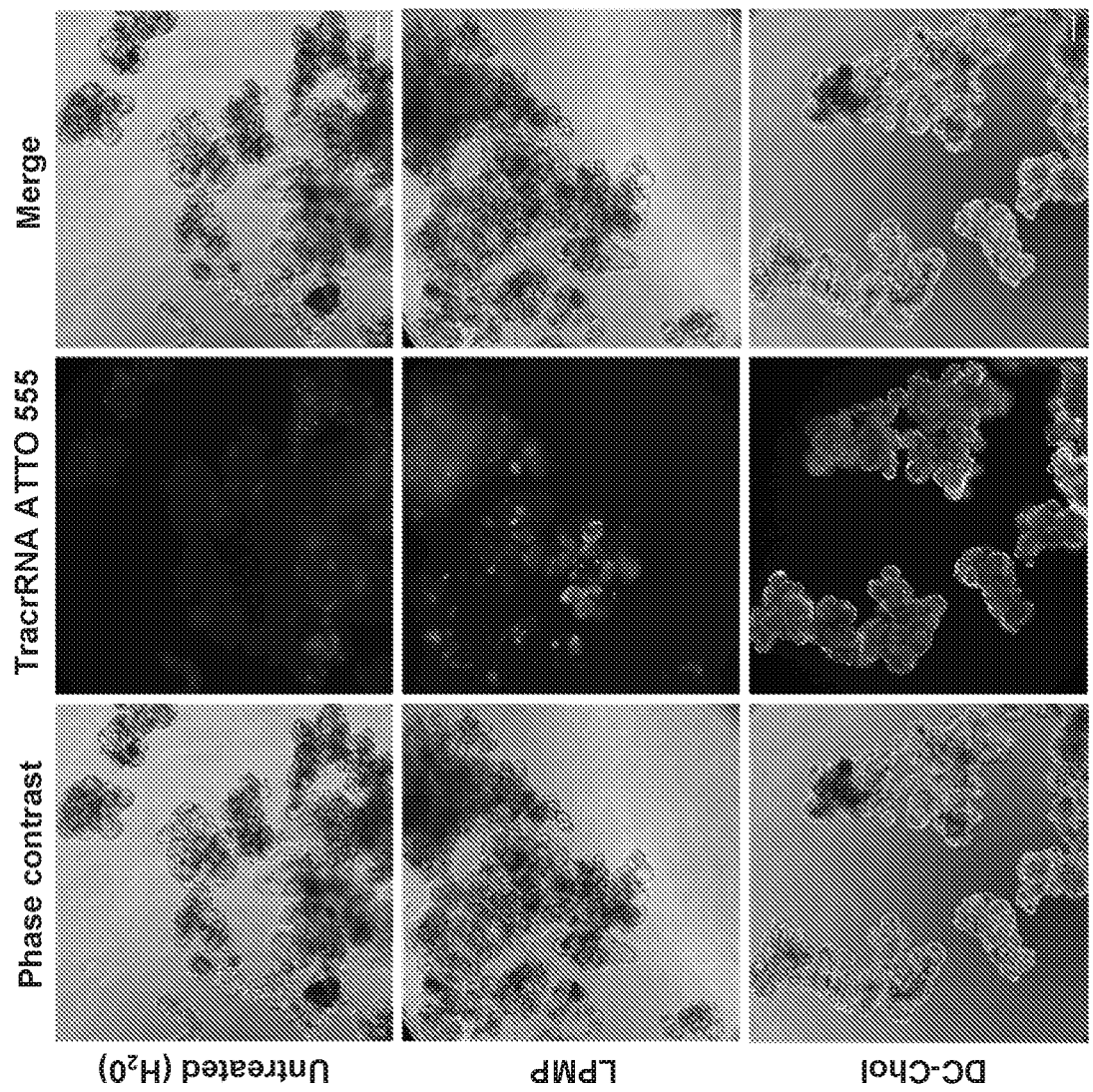
FIG. 16 is a set of photomicrographs showing phase contrast (left column), ATTO 550 fluorescence (center column), and merged views of maize Black Mexican Sweet (BMS) cells treated with LPMPs not comprising added lipids (center row) and LPMPs comprising 40% DC-cholesterol (DC-Chol). Cells that were treated with only H$_2$O are provided as a negative control (top panels). Uptake of LPMPs or LPMPs modified with DC-Cholesterol by a cell is indicated by the presence of the TracrRNA ATTO 550 signal in the cell. Scale bar: 100 µm.

For BMS cells treatments, 10 mL of the cell suspensions was taken to determine the percent Pack Cell Volume (PCV). The PCV is defined as the volume of cells divided by the total volume of the cell culture aliquot and is expressed as a percentage. Cells were centrifuged for 5 min at 3900 rpm, and the volume of the cell pellet was determined. The % PCV for BMS was 20%. For the uptake experiment, the % PCV of the cultures was adjusted to 4% by diluting cells in the medium as described above. LPMPs and LPMPs modified with DC-Cholesterol were loaded with TracrRNA labeled with ATTO 550 as described above, sterilized, and resuspended in sterile water. The mean size and concentration of the particles were analyzed by NanoFCM and were 104±25 nm and $2.54 \times 10^{11}$ LPMPs/mL for DC-Chol and 89±15 nm and $1.54 \times 10^{12}$ LPMPs/mL for unmodified LPMPs. The amount of TracrRNA ATTO 550 (IDT) in samples was quantified by Quant-iT™ RiboGreen®. 50 µL of both LPMPs and LPMP modified with DC-Cholesterol containing 433 ng of TracrRNA was added to an aliquot of 450 µL of plant cell suspension in a 24-well plate in duplicate. 50 µl of ultrapure sterile water was added to the cells and was used as a negative control. Cells were incubated for 3 hours at 24° C. in the dark and were washed three times with 1 mL ultrapure sterile water to remove particles that had not been taken up by cells. Cells were resuspended in 500 µL of ultrapure sterile water for imaging on an epifluorescence microscope (Olympus IX83). Compared to the negative control (ultrapure sterile water), which had no detectable fluorescence, a variable fluorescent signal could be detected in plant cells treated with LPMPs and LPMPs modified with DC-Cholesterol (FIG. 16). LPMPs modified with DC-Cholesterol displayed the strongest fluorescence signal, indicating this PMP modification had the highest delivery of TracrRNA to plant cells. Our data shows that modification of LPMPs with the cationic lipid DC-Cholesterol improved lemon LPMP uptake by plant cells in vitro.

Example 13: mRNA Loading and Delivery into Lipid-Reconstructed PMPs Using Cationic Lipids This example demonstrates the ability to load messenger RNA (mRNA) into lipid-reconstructed PMPs (LPMPs) modified with cationic lipids, and effectively deliver mRNA into human cells. In this example, DC-Cholesterol (3ß[N–(N',N'-dimethylaminoethane)-carbamoyl]cholesterol) was used as a model cationic lipid and lemon PMPs were used as a model PMP, mRNA encoding Firefly Luciferase (Fluc mRNA) was used as a model mRNA, and A549 (human lung epithelial carcinoma) cells as a model human cell line. LPMP particles containing mRNA were formulated using extrusion and microfluidics.

Experimental Protocol:

a) Modification of PMPs with Cationic Lipids

To prepare lipid-modified PMPs (LPMPs), lipids were extracted using the Bligh-Dyer method (Bligh and Dyer, *J Biolchem Physiol*, 37: 911-917, 1959) from a concentrated solution of lemon PMPs, isolated as described previously (Example 1 and Example 2), as described in Example 8. LPMPs were prepared by adding cationic lipids to PMP extracted lipid stock solution in chloroform:methanol (9:1) to 25% or 40% (w/w) of the total lipid and resuspended by vigorous mixing before drying.

b) Loading of Lipid-Modified PMPs with mRNA

For the preparation of LPMPs with DC-Cholesterol (40% w/w) via extrusion, mRNA dissolved in nuclease-free water was added to the dried lipid film at 35 µg of mRNA per 1 mg of PMP lipids and was left for 1 h at RT to hydrate. Resuspended lipid solution was subjected to 10 freeze-thaw cycles and extruded through 0.8 µm, 0.4 µm and 0.2 µm polycarbonate filters using a Mini Extruder (Avanti® Polar Lipids). LPMPs were dialyzed overnight against PBS in a dialysis device (Spectrum®) with a 100 kDa MWCO membrane. Free RNA was removed by ultracentrifugation. Modified PMPs were centrifuged for 30 min at 100,000 g at 4° C., supernatant was removed, and the pellet was washed with 1 mL PBS or water. Centrifugation was repeated as described above and the final PMP pellet was resuspended in a desired buffer (e.g. PBS). The size of the vesicles and final concentration was assessed by NanoFCM: DC-Cholesterol LPMPs (DC-Chol) were at a concentration of $2.4 \times 10^{10}$ PMPs/mL and had an average size of 107 nm+/−43 nm SD.

For the preparation of LPMPs via microfluidics, 1 mg of PMP lipids containing 40% (w/w) of DC-cholesterol was dissolved in 275 µL of DMF:MeOH (4:1) and sonicated for 10 min at 37° C. in a water bath sonicator. The PMP lipid solution (organic phase) was loaded into a 1 mL slip tip syringe (Becton Dickinson) and placed in a heating block set to 37° C. mounted to a microfluidics device. 35 µg of firefly luciferase (Fluc) mRNA was dissolved in 825 µL of Milli-Q® H$_2$O or PBS pH 7.4 to formulate the aqueous phase. The aqueous phase was loaded into 1 mL slip tip syringe (Becton Dickinson) and mounted to the microfluidics device (NanoAssemblr® IGNITE™, Precision Nanosystems). The aqueous and organic phases were mixed in the microfluidic device at a 3:1 volumetric ratio and at a 12 mL/min flowrate. The resulting LPMP particles were dialyzed against PBS in a Slide-A-Lyzer™ G2 Cassette (20 kDa MWCO) for 4-24 h at RT. As a positive control, mRNA lipid nanoparticles (LNP) were prepared by solubilizing with ethanol a mixture of C12-200, 2-distearoyl-sn-glycero-3phosphocholine (DSPC, Avanti® Polar Lipids, Alabaster, AL), 1,2-distearoyl-sn-glycero-3-phosphoethanolamine (DSPE, Avanti® Polar Lipids), 1,2-dioleoyl-sn-glycero-3-phosphocholine (DOPC, Avanti® Polar Lipids), 1,2-dioleoyl-sn-glycero-3-phosphoethanolamine (DOPE, Avanti® Polar Lipids), cholesterol (Sigma), and/or 1,2-dimyristoylsn-glycero-3-phosphoethanolamine-N-[methoxy(polyethylene glycol)-2000] (ammonium salt) (C14-PEG 2000, Avanti® Polar Lipids) at predetermined molar ratios, as described by Kauffman et al., *Nano Letters*, 15(11), 7300-7306, 2015. LNPs were formulated using microfluidics with the same settings and dialyzed in the same conditions as the LPMPs. Size of the vesicles and final concentration was assessed by NanoFCM. DC-Cholesterol LPMPs (DC-Chol) were at a concentration of $2.0 \times 10^{10}$ PMPs/mL and had an average size of 100 nm+/−34 nm SD. C12-200 LNP (C12 LNP) were at a concentration of $2.8 \times 10^{9}$ PMPs/mL and had an average size of 84.7 nm+/−30 nm SD.

RNA loading was determined by the Quant-iT™ RiboGreen® assay (Thermo Scientific). The RiboGreen® assay was performed according to the manufacturer's protocol in the presence of heparin (5 mg/mL) and 1% Triton™ X-100 to lyse LPMPs and release encapsulated cargo. DC-Cholesterol LPMPs prepared by the microfluidic method were able to efficiently load and encapsulate mRNA (FIGS. 17A and 17B).

c) Functional Delivery of Firefly Luciferase mRNA (Fluc) to Mammalian Cells (A549) by LPMP Modified with a Cationic Lipid (DC-Cholesterol)

Figure 17D:
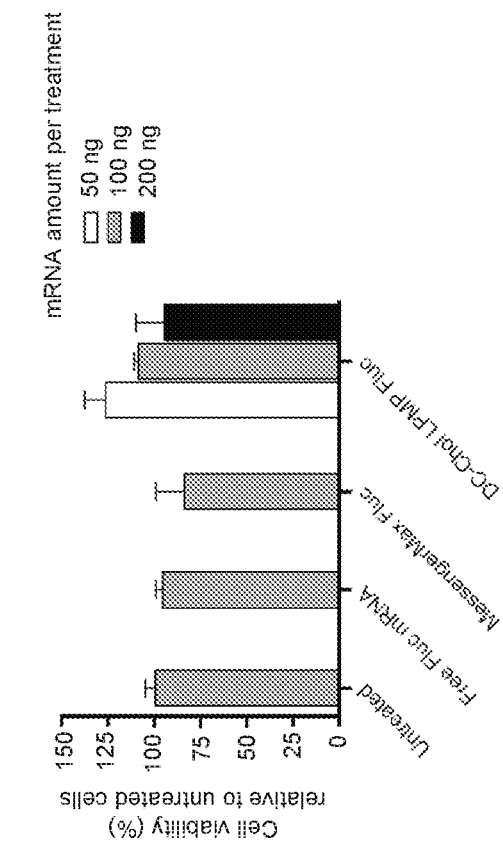
FIG. 17D is a bar graph showing cell viability (%) after transfection with DC-Cholesterol-modified LPMPs or a commercial transfection reagent (MessengerMax) containing Fluc mRNA.
Figure 17C:
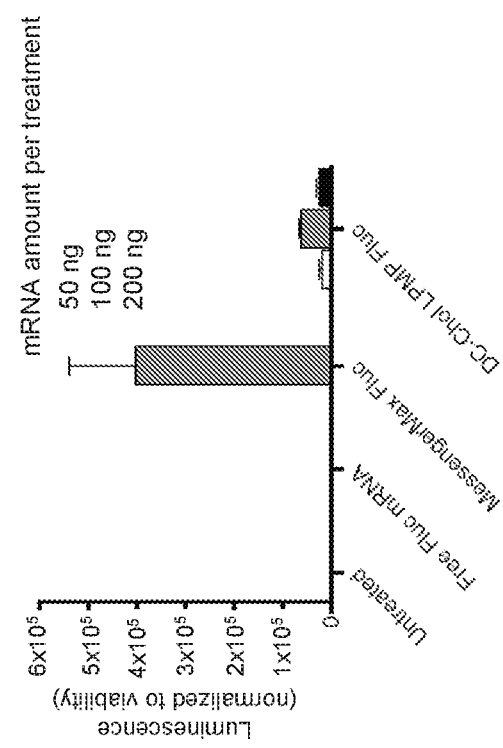
FIG. 17C is a bar graph showing the expression of firefly luciferase (Fluc) mRNA (mean luminescence normalized to viability ±SD; n=4) delivered to A549 cells by DC-Cholesterol-modified LPMPs or a commercial transfection reagent (MessengerMax). Cells were transfected for 24 h with 50 ng, 100 ng, or 200 ng of FLuc mRNA.

A549 cells (ATCC® CCL-184™) were cultured in Dulbecco's Modified Eagle's Medium (DMEM) (4500 mg/L glucose) supplemented with 10% heat-inactivated fetal bovine serum (hiFBS, Gibco) and penicillin/streptomycin at 37° C. and 5% $CO_2$. Cells were passaged every 3-4 days. For the experiments, 10,000 cells per well were seeded in a 96-well plate (Corning® Costar®) in 100 µL of medium one day before the experiment. DC-Cholesterol-modified LPMPs containing mRNA were formulated with microfluidics (NanoAssemblr® IGNITE™, Precision Nanosystems) and characterized as described above. DC-Cholesterol-modified LPMPs containing 50, 100 and 200 ng of FLuc mRNA were added to each well and incubated for 24 h. As a positive control, cells were transfected with 100 ng of Fluc mRNA using Lipofectamine MessengerMax (Thermo Scientific), according to the manufacturer's protocol. 100 ng of free Fluc mRNA was used as negative control. Cell Viability and FLuc expression were analyzed with a CellTiter-Fluor™ Cell Viability Assay (Promega) and a Bright-Glo™ Luciferase Assay System (Promega), according to the manufacturer's protocols. Fluorescence and luminescence were quantified using a SYNERGY™ H1 plate reader (BioTek Instruments). DC-Cholesterol-modified LPMPs showed functional delivery of mRNA to A549 cells, which resulted in the expression of Luciferase protein (FIG. 17C). No significant loss of cell viability upon transfection with mRNA LPMPs, as compared to untreated cells, was observed (FIG. 17D).

Example 14: Cellular Uptake of Natural and Reconstructed PMPs, with and without Cationic Lipid Modifications This example demonstrates the ability to incorporate lipids of different origins into PMPs, thereby altering their uptake by human cells. This example also demonstrates the difference in cellular uptake between natural and reconstructed PMPs. In this example, DOTAP (1,2-dioleoyl-3-trimethylammonium-propane) and DC-Cholesterol (3β[N—(N',N'-dimethylaminoethane)-carbamoyl]cholesterol) are used as model cationic lipids; lemon and grapefruit PMPs are used as model PMPs and lipids extracted from these PMPs are used for formation of reconstructed PMPs; and A549 cells are used as a model human cell line.

Experimental Protocol:

a) Reconstructed PMPs Demonstrate Higher Uptake than Natural PMPs

Lemon (LM) and grapefruit (GF) PMPs were produced and lipids were extracted as described in Example 8 and Example 9. Reconstructed lemon PMPs (recLM) and reconstructed grapefruit PMPs (recGF) were prepared using 2 mg of lemon lipids or 5.6 mg of grapefruit lipids at a final lipid concentration of 4 mg/mL and 9.3 mg/mL in UltaPure water, respectively. Dried lipid film was rehydrated in UltraPure™ DNase/RNase-Free Distilled Water (ThermoFisher, 10977023) for 2 h at RT in the dark. The resuspended lipid solution was subjected to sonication for 10 minutes at RT using a water bath sonicator, and extruded through 0.8 µm, 0.4 µm and 0.2 µm polycarbonate filters using a Mini Extruder (Avanti® Polar Lipids). All PMP formulations (i.e., reconstructed PMPs from extracted lipids and original PMPs from the same source) were labeled with green PKH67 lipophilic membrane dye (Sigma) according to the manufacturer's protocol, with some modifications. Briefly, PMPs ($5-7 \times 10^{13}$ particles/mL) resuspended in Dilute C (Dil.C) of the PKH26 labelling (1:1 ratio water:Dil.C) were mixed with PKH26 dye at a ratio of 1:500 (2 µl of 1 mM dye to 1 mL of solution) and incubated for 1.5 h at 37° C. in the dark. All unlabeled dye was washed away by ultracentrifugation (100,000 g, 1 h, UltraPure™ DNase/RNase-Free Distilled Water (ThermoFisher, 10977023), twice), and PKH67-labeled PMPs were sterilized using an 0.2 µm sterile filter. The final pellet was resuspended in sterile PBS and kept at 4° C. until further use. Fluorescent intensity and number of particles of PKH67-labeled PMPs were assessed by a SpectraMax® spectrophotometer (Ex/Em=485/510 nm) and by nano-flow cytometry (NanoFCM), respectively. Final PMP concentrations of PKH67-labeled PMPs (particles/mL) were determined by NanoFCM, using concentration standards provided by the manufacturer, and were as follows: $5.7 \times 10^{12}$ (recLM), $3.8 \times 10^{13}$ (LM), $1 \times 10^{13}$ (recGF), $1.8 \times 10^{13}$ (GF). The fluorescent intensity was 69183, 103529, 79465, 155459 fluorescent a.u./µL, respectively.

Figure 7:
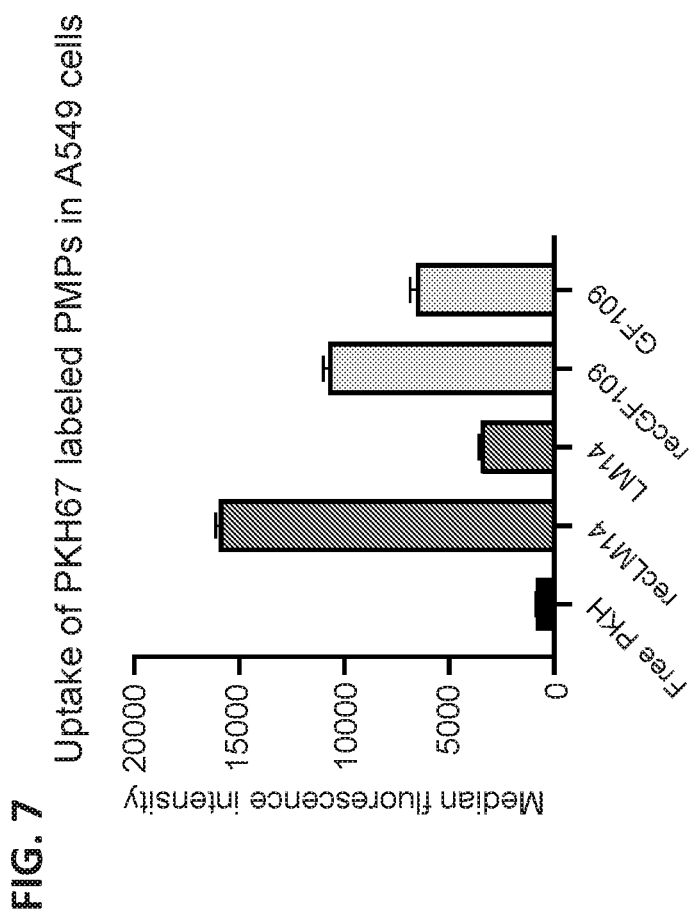
FIG. 7 is a bar graph showing uptake/association with human adenocarcinoma (A549) cells for lipid reconstructed PMPs and original PMPs from lemon (LM) and grapefruit (GF), as quantified by median fluorescence intensity of PKH67 dye using a flow cytometer (MACSQuant Analyzer 10). Free PKH67 dye was used as a control. Data are presented as mean relative fluorescence ±SD; n=3.

To determine the uptake efficiency of PKH26-labeled PMPs versus PKH26-labeled lipid-reconstructed PMPs, human A549 cells (ATCC® CCL-184™; adenocarcinomic human alveolar basal epithelial cells) were treated with the formulations for 2.5 h at 37° C. All formulations were normalized based on fluorescence intensity (180022 PKH67 fluorescent units/well). Free dye was used as a control. At the end of the incubation, cells were washed two times with ice cold PBS, detached by adding 50 µL Gibco TrypLE™ reagent per well (ThermoFisher), and incubated for 3 min. Then, 200 µL of ice cold FACS buffer (PBS containing 5% FBS) was added to neutralize the TrypLE™ reagent. Samples were collected and spun down at 1500 rpm (230 g) for 5 min at 4° C. To remove the supernatant, cells were washed with 1 mL of FACS buffer, and the centrifugation step was repeated one more time. Cells were resuspended in 150 µL of PBS supplemented with 0.5% of formaldehyde and incubated at least for 30 min at 4° C. prior to flow cytometry. The flow cytometry analysis was performed using a flow cytometer MACSQuant Analyzer 10 (Miltenyi Biotec). The analysis of PKH67-positive cells demonstrated increased association and uptake of lipid-reconstructed PMPs by cells compared to original PMPs for all sources (FIG. 7).

b) PMPs Modified with Cationic Lipids Demonstrate Higher Uptake

Lemon PMPs were produced and lipids were extracted as described in Example 8 and Example 9. Cationic lipids were added to 1 mg of PMP extracted lipid stock solution in chloroform:methanol (9:1) to amount to 40% (w/w) (DC-Chol, DOTAP) of the total lipid. The stock solution of DiI (a fluorescent lipophilic cationic indocarbocyanine dye from ThermoFisher) was prepared in anhydrous DMSO (10 mg/mL) and added to the lipid mixture at the final concentration of 1 mM (2.3 uL of DiI per 1 mg of lipids) upon vigorous mixing. Dried lipid film was prepared by evaporation of the solvent with a stream of inert gas (e.g., nitrogen) using a TurboVap® evaporator. Lipid-modified PMPs (LPMPs) without cargo were prepared by rehydration of the lipids in PBS followed by extrusion. Unincorporated dye was washed out twice with PBS using Nanosep® Centrifugal Devices (300 kDa MWCO, Pall Corporation), and DiI-labeled PMPs were concentrated by centrifugation at 15,000 g, 5 min, RT. Fluorescent intensity and number of particles of DiI-labeled lipid-modified LPMPs were assessed using a SpectraMax® spectrophotometer (Ex/Em=549/565 nm) and by nano-flow cytometry (NanoFCM), respectively. The final concentration and fluorescent intensity was $1.7 \times 10^{12}$ particles/mL with fluorescent intensity of 12902 fluorescent a.u./uL for DiI-labeled LPMPs; $3.08 \times 10^{11}$ particles/mL with 9450 a.u./µL for DC-Chol-LPMPs; and $6.54 \times 10^{10}$ particles/mL with 3169 a.u./µL for DOTAP-LPMPs.

Figure 18:
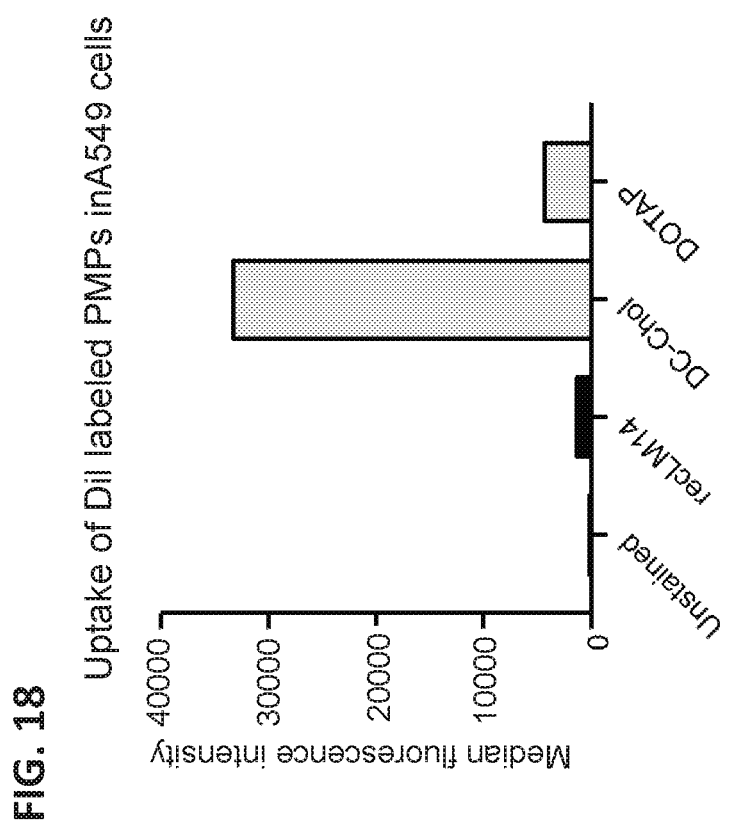
FIG. 18 is a bar graph showing uptake/association with human adenocarcinoma (A549) cells for reconstructed LM (recLM) PMPs containing 40% DOTAP or DC-Cholesterol as quantified by median fluorescence intensity of PKH67 dye using a flow cytometer (MACSQuant Analyzer 10). Free PKH67 dye was used as a control. Data are presented as mean relative fluorescence ±SD; n=3.
Figure 19B:
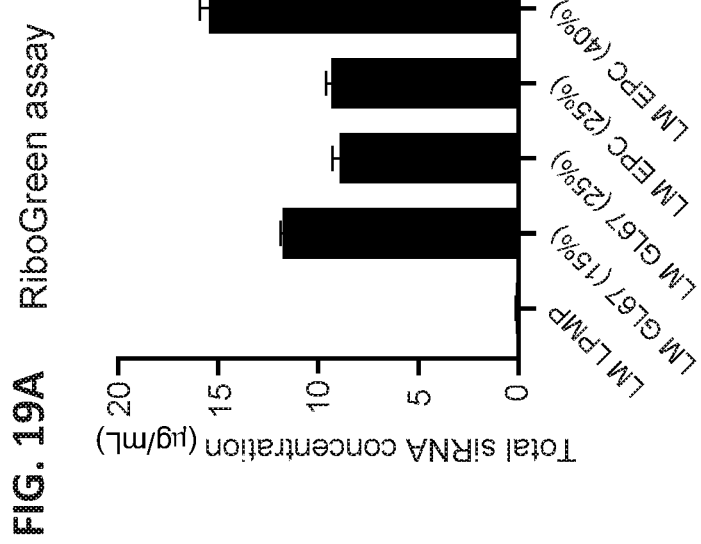
FIG. 19B is a bar graph showing the siRNA encapsulation efficacy (% difference in siRNA concentrations between intact and lysed (+Triton® X-100+Heparin) vesicles) for the LPMPs of FIG. 19A. Data are presented as Mean±SD.
Figure 19A:
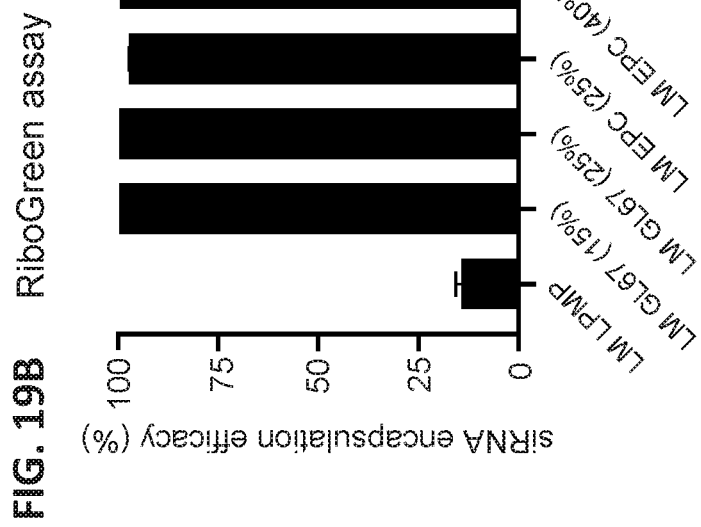
FIG. 19A is a bar graph showing total siRNA concentration (µg/mL) in lemon (LM) LPMPs modified with GL67 or ethyl PC (EPC) that have been formulated with 25 µg (about 1.5 nmol) of siRNA per 1 mg of PMP lipid using extrusion, as measured using a Quant-iT™ RiboGreen® analysis. Data are presented as Mean±SD.

To determine the PMP uptake efficiency of DiI-labeled lipid-modified PMPs versus lipid reconstructed PMPs, human A549 cells (adenocarcinomic human alveolar basal epithelial cells) were treated with the formulations as described in Example 14a. All formulations were normalized based on the fluorescence intensity (193306 DiI fluorescent units/well). Free dye was used as a control. The flow cytometry analysis was performed using a flow cytometer (MACSQuant® Analyzer 10 (Miltenyi Biotec)), as described above. Modification of LPMPs with DOTAP or DC-Chol increased uptake of the LPMPs by cells (FIG. 18).

Example 15: Improved Loading Using the Cationic Lipids GL67 and Ethyl PC

This example demonstrates the ability to increase the cargo loading capacity of PMPs by modification of the PMPs with cationic lipids. In this example, GL67 (N4-Cholesteryl-Spermine HCl Salt) and Ethyl PC (1-palmitoyl-2-oleoyl-sn-glycero-3-ethylphosphocholine) are used as model cationic lipids, lemon PMPs are used as model PMPs, and siRNA is used as a model negatively charged payload.

Experimental Protocol:

a) Modification of PMPs with Cationic Lipids

To prepare lipid-modified PMPs (LPMPs), lipids were extracted using the Bligh-Dyer method (Bligh and Dyer, *J Biolchem Physiol*, 37: 911-917, 1959) from a concentrated solution of lemon PMPs, isolated as described previously (Example 1 and Example 2). PMP extracted lipid stock solution in chloroform:methanol (9:1) was dried by evaporation of the solvent with a stream of inert gas (e.g. nitrogen) to prepare a lipid film. LPMPs were prepared by adding cationic lipids to PMP extracted lipid stock solution in chloroform:methanol (9:1) to amount to 15%, 25% or 40% (w/w) of total lipids and resuspended by vigorous mixing before drying.

b) Loading of Cationic Lipid-Modified PMPs with Negatively Charged Cargo siRNA dissolved in a nuclease-free water was added to the dried lipid film at 1.5 nmol per 1 mg of PMP lipids and was left for 1 h at RT to hydrate. The resuspended lipid solution was subjected to 10 freeze-thaw cycles and extruded through 0.8 µm, 0.4 µm and 0.2 µm polycarbonate filters using a Mini Extruder (Avanti® Polar Lipids). Modified PMPs were dialyzed over night against PBS in a dialysis device (Spectrum®) with a 100 kDa MWCO membrane. Free RNA was removed by ultracentrifugation. Modified PMPs were centrifuged for 30 min at 100,000 g at 4° C., the supernatant was removed, and the pellet was washed with 1 mL PBS or water. Centrifugation was repeated as described above, and the final PMP pellet was resuspended in a desired buffer (e.g. PBS). The concentration and size of the vesicles in the final solution was assessed by NanoFCM and was as follows: GL67 15%: $3.0 \times 10^{10}$ PMPs/mL, 130 nm+/−49 nm SD; GL67 25%, $2.3 \times 10^{10}$ PMPs/mL, 118 nm+/−25 nm SD; EPC 25%, $1.15 \times 10^{11}$ PMPs/mL, 105 nm+/−29 nm SD; EPC 40%, $6.0 \times 10^{10}$ PMPs/mL, 104 nm+/−33 nm SD. RNA loading was determined by a Quant-iT™ RiboGreen™ assay, performed according to manufacturer's protocol in the presence of heparin (5 mg/mL) and 1% Triton™ X-100 to lyse PMPs and release encapsulated cargo. Modification with GL67 and EPC enabled increased loading of negatively charged cargo (e.g. siRNA), as compared to LPMPs without cationic lipids (FIGS. 10A and 10B).

Example 16: Optimization of Lipid Ratios for mRNA Loading

This example demonstrates that PMP lipids can be formulated with ionizable lipids, sterols, and PEG lipids, and that such formulations can encapsulate mRNA. In this example, broccoli and grapefruit PMP lipids are used as model PMP lipids; C12-200 and MC3 are used as model ionizable lipids; sitosterol and cholesterol are used as model sterols, C14-PEG2k and C18-PEG2k are used as model PEGylated lipids, and CleanCap® firefly luciferase (FLuc) mRNA is used as a model mRNA. The example further demonstrates that these formulations can deliver an mRNA cargo to cells. Caco-2 (colorectal adenocarcinoma) cells are used as a model human cell line.

a) mRNA Loading of Ionizable Lipid-Modified Broccoli PMPs

Modified PMP compositions composed of an ionizable lipid, broccoli PMP lipids (extracted using the Bligh-Dyer method, as described in Example 7a), a sterol, and a PEGylated lipid at varying molar ratios were formulated as indicated in Tables 11-13 and loaded with mRNA. The molar ratio of broccoli PMPs was calculated by assuming a composition of 80% phospholipids (~800 g/mol) and 20% sterols (~400 g/mol). Lipids were solubilized in ethanol (organic phase) at the indicated molar ratios. Formulations containing DLin-MC3-DMA (MC3) were maintained at an N:P (amines of ionizable lipid:phosphates of mRNA) ratio of 6:1. Formulations containing C12-200 were maintained at ionizable lipid to mRNA N:P ratio of 15:1 or 30:1. An mRNA solution (aqueous phase, CleanCap® firefly luciferase (FLuc) mRNA: TriLink Biotechnologies) was prepared with RNAse-free water and 100 mM citrate buffer pH 3 (Teknova) for a final concentration of 50 mM citrate buffer.

The lipid mixture (organic phase) and mRNA solution (aqueous phase) were mixed at a 1:3 ratio by volume on the NanoAssemblr® IGNITE™ (Precision Nanosystems) at a total flow rate of 9 mL/minute. The resulting formulations were then loaded into Slide-A-Lyzer™ G2 dialysis cassettes (10k MWCO) and dialyzed in 200 times the sample volume of 1×PBS for 4 hours at room temperature with gentle stirring. The PBS was refreshed, and the formulations were further dialyzed for at least 14 hours at 4° C. with gentle stirring. The dialyzed formulations were then collected and concentrated by centrifugation at 3000×g for 30 minutes using Amicon® Ultra centrifugation filters (20k MWCO).

The concentrated formulations were sterilized using 0.2 µm pore size PES syringe filters (MilliporeSigma) and characterized for size, polydispersity index (PDI), and particle concentration using a Zetasizer Ultra (Malvern Panalytical) and for mRNA encapsulation efficiency using the Quant-iT™ RiboGreen® assay (Thermo Scientific) according to the manufacturer's protocol (Table 13).

Figure 8A:
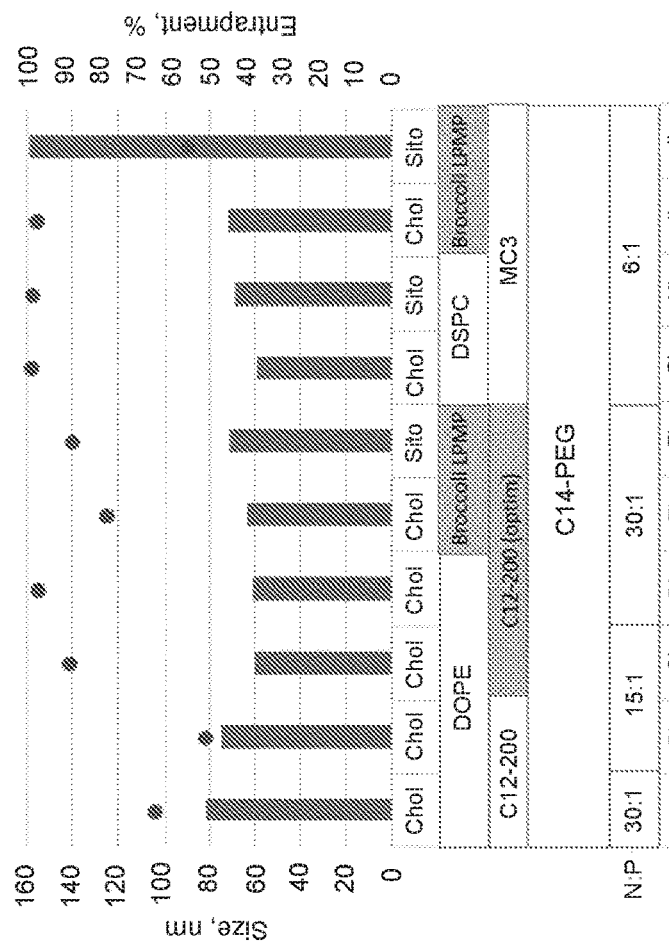
FIG. 8A is a bar graph showing the size (bars; left axis) of PMP compositions composed of C12-200, broccoli PMP lipids, cholesterol or sitosterol, and PEGylated lipids at a molar ratio of 50:10:38.5:1.5, respectively and the percent entrapment (dots; right axis) by the PMPs of CleanCap® firefly luciferase (FLuc) mRNA. Lipid nanoparticle (LNP) compositions comprising DOPE or DSPC in the place of PMP lipids are provided as positive controls. The lipid:mRNA ratio (w:w) was 20:1 for each composition. Formulations A-F are described in Table 11 herein.
Figure 8B:
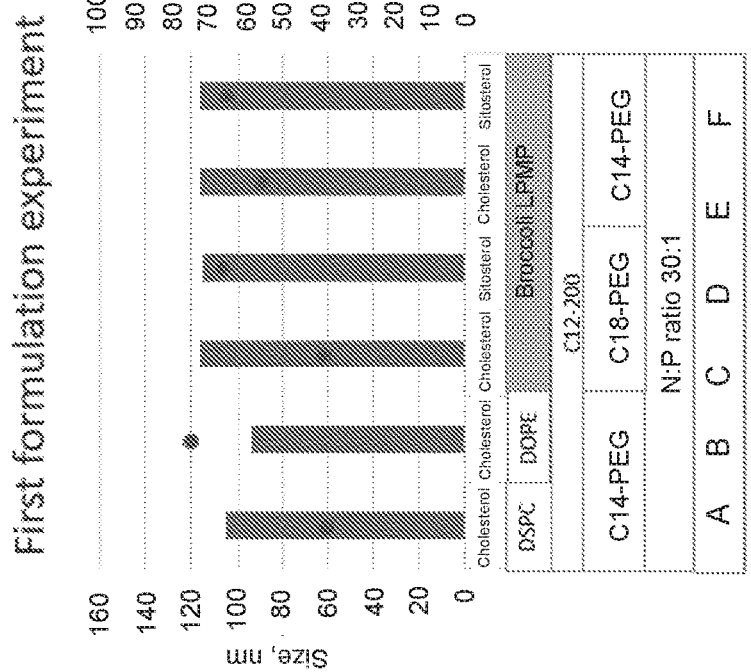
FIG. 8B is a bar graph showing the size (bars; left axis) of PMP compositions composed of C12-200 (optim: optimized ratio) or MC3, broccoli PMP lipids, cholesterol or sitosterol, and PEGylated lipids at a molar ratio of 50:10:38.5:1.5, respectively and the percent entrapment (dots; right axis) by the PMPs of CleanCap® FLuc mRNA. LNP compositions comprising DOPE or DSPC in the place of PMP lipids are provided as positive controls. The lipid:mRNA ratio (w:w) was 20:1 for each composition. Formulations A'-J' are described in Table 12 herein.

Optimizing the ratio of the ionizable lipids MC3 and C12-200 to PMP-derived lipids, as well as the use of a microfluidic system for PMP formulation, increased loading of negatively charged cargo (e.g., mRNA) and allowed the size of the nanoparticles to be controlled (Table 13, FIGS. 8A and 8B). Lipid nanoparticle (LNP) formulations comprising the structural lipids DOPE and DSPC in place of the PMP lipids were provided as positive controls. Particle formulation and nucleic acid encapsulation were not compromised in the formulations containing PMP lipids as compared to the DOPE and DSPC LNP controls (FIG. 8A and Table 11; FIG. 8B and Table 12).

TABLE 11

Lipid ratios in first formulation experiment

| Formulation | Cargo | N:P | Ionizable Lipid Name | mol % | Structural Lipid Name | mol % | Sterol Name |
|---|---|---|---|---|---|---|---|
| A | Fluc mRNA | 30:1 | C12-200 | 50 | DSPC | 10 | Cholesterol |
| B | Fluc mRNA | | C12-200 | 50 | DOPE | 10 | Cholesterol |
| C | Fluc mRNA | | C12-200 | 50 | Broccoli Lipids | 10 | Cholesterol |
| D | Fluc mRNA | | C12-200 | 50 | Broccoli Lipids | 10 | Sitosterol |
| E | Fluc mRNA | | C12-200 | 50 | Broccoli Lipids | 10 | Cholesterol |
| F | Fluc mRNA | | C12-200 | 50 | Broccoli Lipids | 10 | Sitosterol |

| Formulation | Sterol mol % | PEG Name | mol % | Size nm | PDI | Encapsulation % | Concentration Particles/ml |
|---|---|---|---|---|---|---|---|
| A | 38.5 | DMPE-PEG2k | 1.5 | 104.7 | 0.056 | 37.6 | 5.04E+12 |
| B | 38.5 | DMPE-PEG2k | 1.5 | 93.3 | 0.061 | 74.9 | 7.3E+12 |
| C | 38.5 | DSPE-PEG2k | 1.5 | 116.1 | 0.050 | 38.2 | 3E+12 |
| D | 38.5 | DSPE-PEG2k | 1.5 | 114.8 | 0.028 | 66.1 | 4.92E+12 |
| E | 38.5 | DMPE-PEG2k | 1.5 | 116.0 | 0.043 | 55.1 | 4.14E+12 |
| F | 38.5 | DMPE-PEG2k | 1.5 | 116.1 | 0.053 | 65.1 | 4.22E+12 |

TABLE 12

Lipid ratios in second formulation experiment

| Formulation | Content | N:P | Ionizable Lipid Name | mol % | Structural Lipid Name | mol % | Sterol Name |
|---|---|---|---|---|---|---|---|
| A' | Fluc mRNA | 30:1 | C12-200 | 50 | DOPE | 10 | Cholesterol |
| B' | Fluc mRNA | 15:1 | C12-200 | 50 | DOPE | 10 | Cholesterol |
| C' | Fluc mRNA | | C12-200 | 35 | DOPE | 16 | Cholesterol |
| D' | Fluc mRNA | 30:1 | C12-200 | 35 | DOPE | 16 | Cholesterol |
| E' | Fluc mRNA | | C12-200 | 35 | Broccoli Lipids | 16 | Cholesterol |
| F' | Fluc mRNA | | C12-200 | 35 | Broccoli Lipids | 16 | Sitosterol |
| G' | Fluc mRNA | 6:1 | MC3 | 50 | DSPC | 10 | Cholesterol |
| H' | Fluc mRNA | | MC3 | 50 | DSPC | 10 | Sitosterol |
| I' | Fluc mRNA | | MC3 | 50 | Broccoli Lipids | 10 | Cholesterol |
| J' | Fluc mRNA | | MC3 | 50 | Broccoli Lipids | 10 | Sitosterol |

| Formulation | Sterol mol % | PEG Name | mol % | Size nm | PDI | Encapsulation % | Concentration Particles/ml |
|---|---|---|---|---|---|---|---|
| A' | 38.5 | DMPE-PEG2k | 1.5 | 81.6 | 0.030 | 64.6 | 1.79e+13 |
| B' | 38.5 | DMPE-PEG2k | 1.5 | 74.8 | 0.108 | 50.6 | 9.90e+12 |
| C' | 46.5 | DMPE-PEG2k | 2.5 | 60.5 | 0.088 | 88.0 | 3.60e+13 |
| D' | 46.5 | DMPE-PEG2k | 2.5 | 60.9 | 0.063 | 96.4 | 5.70e+13 |
| E' | 46.5 | DMPE-PEG2k | 2.5 | 63.3 | 0.059 | 77.8 | 5.88e+13 |
| F' | 46.5 | DMPE-PEG2k | 2.5 | 71.2 | 0.067 | 87.2 | 4.45e+13 |
| G' | 38.5 | DMPE-PEG2k | 1.5 | 59.4 | 0.092 | 98.3 | 3.56e+13 |
| H' | 38.5 | DMPE-PEG2k | 1.5 | 68.5 | 0.103 | 97.9 | 3.70e+13 |
| I' | 38.5 | DMPE-PEG2k | 1.5 | 71.8 | 0.084 | 97.0 | 3.20e+13 |
| J' | 38.5 | DMPE-PEG2k | 1.5 | 158.9 | 0.311 | 55.7 | 1.09e+12 |

TABLE 13

Lipid ratios in PMP compositions loaded with mRNA and LNP controls

| Cargo | N:P | Ionizable Lipid Name | mol % | Structural Lipid Name | mol % | Cholesterol Name | mol % |
|---|---|---|---|---|---|---|---|
| Fluc mRNA | 30:1 | C12-200 | 50 | DSPC | 10 | Cholesterol | 38.5 |
| Fluc mRNA | | C12-200 | 50 | Broccoli lipids | 10 | Cholesterol | 38.5 |
| Fluc mRNA | | C12-200 | 50 | Broccoli lipids | 10 | Sitosterol | 38.5 |
| Fluc mRNA | | C12-200 | 50 | Broccoli lipids | 10 | Cholesterol | 38.5 |
| Fluc mRNA | | C12-200 | 50 | Broccoli lipids | 10 | Sitosterol | 38.5 |
| Fluc mRNA | | C12-200 | 50 | DOPE | 10 | Cholesterol | 38.5 |
| Fluc mRNA | 15:1 | C12-200 | 50 | DOPE | 10 | Cholesterol | 38.5 |
| Fluc mRNA | | C12-200 | 35 | DOPE | 16 | Cholesterol | 46.5 |
| Fluc mRNA | 30:1 | C12-200 | 35 | DOPE | 16 | Cholesterol | 46.5 |
| Fluc mRNA | | C12-200 | 35 | Broccoli lipids | 16 | Cholesterol | 46.5 |
| Fluc mRNA | | C12-200 | 35 | Broccoli lipids | 16 | Sitosterol | 46.5 |
| Fluc mRNA | 6:1 | MC3 | 50 | DSPC | 10 | Cholesterol | 38.5 |
| Fluc mRNA | | MC3 | 50 | DSPC | 10 | Sitosterol | 38.5 |
| Fluc mRNA | | MC3 | 50 | Broccoli lipids | 10 | Cholesterol | 38.5 |
| Fluc mRNA | | MC3 | 50 | Broccoli lipids | 10 | Sitosterol | 38.5 |
| Fluc mRNA | | MC3 | 50 | DSPC | 10 | Cholesterol | 38.5 |
| Fluc mRNA | | MC3 | 50 | DSPC | 10 | Cholesterol | 38.5 |

| Cargo | PEG Name | mol % | Size nm | PDI | Encapsulation % | Concentration Particles |
|---|---|---|---|---|---|---|
| Fluc mRNA | C14-PEG2k | 1.5 | 104.7 | 0.056 | 37.6 | 5.04E+12 |
| Fluc mRNA | C18-PEG2k | 1.5 | 116.1 | 0.05 | 38.2 | 3.00E+12 |
| Fluc mRNA | C18-PEG2k | 1.5 | 114.8 | 0.028 | 66.1 | 4.92E+12 |
| Fluc mRNA | C14-PEG2k | 1.5 | 116 | 0.043 | 55.1 | 4.14E+12 |
| Fluc mRNA | C14-PEG2k | 1.5 | 116.1 | 0.053 | 65.1 | 4.22E+12 |
| Fluc mRNA | C14-PEG2k | 1.5 | 81.6 | 0.03 | 64.6 | 1.79E+13 |
| Fluc mRNA | C14-PEG2k | 1.5 | 74.8 | 0.108 | 50.6 | 9.90E+12 |
| Fluc mRNA | C14-PEG2k | 2.5 | 60.5 | 0.088 | 88 | 3.60E+13 |
| Fluc mRNA | C14-PEG2k | 2.5 | 60.9 | 0.063 | 96.4 | 5.70E+13 |
| Fluc mRNA | C14-PEG2k | 2.5 | 63.3 | 0.059 | 77.8 | 5.88E+13 |
| Fluc mRNA | C14-PEG2k | 2.5 | 71.2 | 0.067 | 87.2 | 4.45E+13 |
| Fluc mRNA | C14-PEG2k | 1.5 | 59.4 | 0.092 | 98.3 | 3.56E+13 |
| Fluc mRNA | C14-PEG2k | 1.5 | 68.5 | 0.103 | 97.9 | 3.70E+13 |
| Fluc mRNA | C14-PEG2k | 1.5 | 71.8 | 0.084 | 97 | 3.20E+13 |
| Fluc mRNA | C14-PEG2k | 1.5 | 158.9 | 0.311 | 55.7 | 1.09E+12 |
| Fluc mRNA | C14-PEG2k | 1.5 | 69.3 | 0.241 | 93.8 | 3.59E+12 |
| Fluc mRNA | C14-PEG2k | 1.5 | 63.4 | 0.215 | 94.5 | 5.09E+12 | b) Delivery of pDNA-Loaded, Ionizable Lipid-Modified PMPs to Cells

Figure 9:
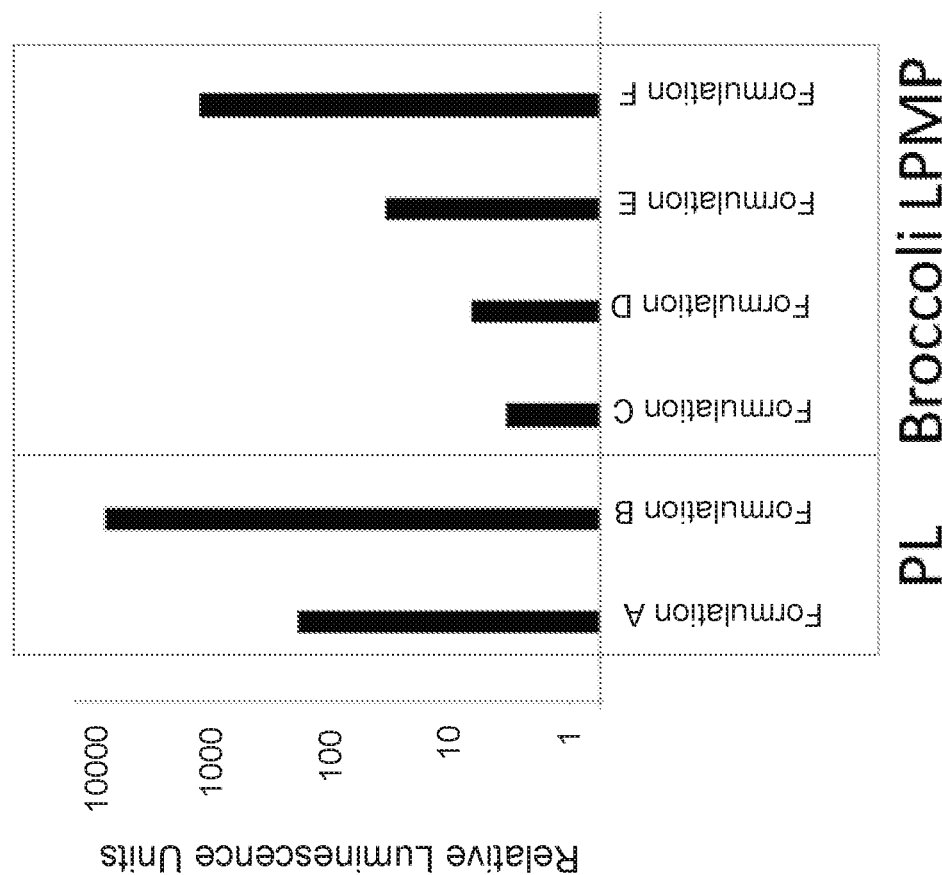
FIG. 9 is a bar graph showing the expression of luciferase (relative luminescence units (RLU)) in Caco-2 cells that were contacted with PMP compositions composed of broccoli PMP lipids, cholesterol, C12-200 or MC3, and DMPE-PEG2k and loaded with CleanCap® FLuc mRNA. LNP compositions comprising the synthetic phospholipids (PL) DOPE or DSPC in the place of PMP lipids are provided as positive controls. Formulations A-F are described in Table 11 herein.

The PMP formulations provided in Table 11 were delivered to a Caco-2 human cell line as described in Example 10a as a model for oral delivery. Uptake of the PMPs by the cells was measured as luciferase expression (relative luminescence units (RLU)) (FIG. 9). Cells treated with DOPE and DSPC LNPs were provided as positive controls.

Example 17: Optimization of Lipid Ratios for Plasmid Loading

This example demonstrates that PMP lipids can be formulated with ionizable lipids, sterols, and PEG lipids, and that such formulations can encapsulate plasmid DNA (pDNA). In this example, broccoli and grapefruit PMP lipids are used as model PMP lipids; C12-200 and MC3 are used as model ionizable lipids; sitosterol and cholesterol are used as model sterols, DMPE-PEG2k is used as a model PEGylated lipid, and gWiz™-Luc, a plasmid encoding luciferase, is used as a model pDNA. The example further demonstrates that these formulations can be delivered to cells. HeLa (cervical cancer) and MCF7 (breast cancer) cells are used as model human cell lines.

a) pDNA Loading of Ionizable Lipid-Modified PMPs

Modified PMP compositions composed of an ionizable lipid, broccoli or grapefruit PMP lipids, a sterol, and a PEGylated lipid at varying molar ratios were formulated as indicated in Table 14 and loaded with plasmid DNA (pDNA). Lipids were solubilized in ethanol (organic phase) at the indicated molar ratios. DLin-MC3-DMA (MC3) containing formulations were maintained at an N:P (amines of ionizable lipid:phosphates of pDNA) ratio of 6:1. Formulations containing C12-200 were maintained at ionizable lipid to pDNA N:P ratio of 15:1, 30:1, or 45:1. The plasmid DNA (pDNA) solution (aqueous phase, gWiz™-Luc (luciferase) pDNA: Aldevron®) was prepared with DNAse-free water and 100 mM citrate buffer pH 3 (Teknova) for a final concentration of 50 mM citrate buffer.

The lipid mix (organic phase) and pDNA solution (aqueous phase) were mixed at a 1:3 ratio by volume on the NanoAssemblr® IGNITE™ (Precision Nanosystems) at a total flow rate of 9 mL/minute. The resulting formulations were then loaded into Slide-A-Lyzer™ G2 dialysis cassettes (10k MWCO) and dialyzed in 200 times the sample volume of 1×PBS for 4 hours at room temperature with gentle stirring. The PBS was refreshed, and the formulations were further dialyzed for at least 14 hours at 4° C. with gentle stirring. The dialyzed formulations were then collected and concentrated by centrifugation at 3000×g for 30 minutes using Amicon® Ultra centrifugation filters (20k MWCO).

The concentrated formulations were sterilized using 0.2 µm pore size PES syringe filters (MilliporeSigma) and characterized for size, polydispersity index (PDI), and particle concentration using Zetasizer Ultra (Malvern Panalytical) and for pDNA encapsulation efficiency using the Quant-iT™ PicoGreen® dsDNA Assay Kit (ThermoFisher Scientific) according to the manufacturer's protocol (Table 14).

Optimizing the ratio of the ionizable lipids MC3 and C12-200 to PMP-derived lipids, as well as the use of a microfluidic system for PMP formulation, increased loading of negatively charged cargo (e.g., plasmid DNA) and allowed the size of the nanoparticles to be controlled (Table 14). LNP formulations comprising the structural lipids DOPE and DSPC in place of the PMP lipids were provided as positive controls.

TABLE 14

Lipid ratios in PMP compositions loaded with pDNA and LNP controls

| Cargo | N:P | Ionizable Lipid | | Structural Lipid | | Cholesterol | |
|---|---|---|---|---|---|---|---|
| | | Name | mol % | Name | mol % | Name | mol % |
| Fluc pDNA | 15:1 | C12-200 | 35 | DOPE | 16 | Cholesterol | 46.5 |
| Fluc pDNA | 30:1 | C12-200 | 35 | DOPE | 16 | Cholesterol | 46.5 |
| Fluc pDNA | | C12-200 | 35 | Broccoli lipids | 16 | Sitosterol | 46.5 |
| Fluc pDNA | | C12-200 | 35 | Broccoli lipids | 20 | Sitosterol | 42.5 |
| Fluc pDNA | | C12-200 | 50 | DOPE | 10 | Cholesterol | 38.5 |
| Fluc pDNA | | C12-200 | 50 | Broccoli lipids | 10 | Cholesterol | 38.5 |
| Fluc pDNA | 45:1 | C12-200 | 50 | Broccoli lipids | 10 | Cholesterol | 38.5 |
| Fluc pDNA | | C12-200 | 35 | Broccoli lipids | 16 | Cholesterol | 46.5 |
| Fluc pDNA | 30:1 | C12-200 | 50 | Grapefruit lipids | 10 | Cholesterol | 38.5 |
| Fluc pDNA | 6:1 | MC3 | 50 | DSPC | 12.5 | Cholesterol | 36 |
| Fluc pDNA | | MC3 | 50 | DSPC | 12.5 | Sitosterol | 36 |
| Fluc pDNA | | MC3 | 50 | Broccoli lipids | 10 | Cholesterol | 38.5 |
| Fluc pDNA | | MC3 | 50 | Broccoli lipids | 10 | Sitosterol | 38.5 |
| Fluc pDNA | | MC3 | 50 | Broccoli lipids | 12.5 | Cholesterol | 36 |
| Fluc pDNA | | MC3 | 50 | Grapefruit lipids | 12.5 | Cholesterol | 36 |

| Cargo | PEG | | Size | PDI | Encapsulation | Concentration |
|---|---|---|---|---|---|---|
| | Name | mol % | nm | — | % | Particles/ml |
| Fluc pDNA | DMPE-PEG2k | 2.5 | 80.2 | 0.19 | 51.1 | 7.40E+14 |
| Fluc pDNA | DMPE-PEG2k | 2.5 | 73.8 | 0.18 | 75 | 3.98E+14 |
| Fluc pDNA | DMPE-PEG2k | 2.5 | 73.1 | 0.11 | 5 | 1.80E+13 |
| Fluc pDNA | DMPE-PEG2k | 2.5 | 73.4 | 0.124 | 8.2 | 1.67E+13 |
| Fluc pDNA | DMPE-PEG2k | 1.5 | 125.8 | 0.099 | 53 | 1.84E+12 |
| Fluc pDNA | DMPE-PEG2k | 1.5 | 124.7 | 0.081 | 30.1 | 1.37E+12 |
| Fluc pDNA | DMPE-PEG2k | 1.5 | 134.3 | 0.076 | 39.4 | 1.28E+12 |
| Fluc pDNA | DMPE-PEG2k | 2.5 | 105.5 | 0.123 | 39.5 | 4.80E+12 |
| Fluc pDNA | DMPE-PEG2k | 1.5 | 130.5 | 0.185 | 43.6 | 8.16E+11 |
| Fluc pDNA | DMPE-PEG2k | 1.5 | 75.2 | 0.098 | 97.1 | 1.22E+13 |
| Fluc pDNA | DMPE-PEG2k | 1.5 | 83.2 | 0.11 | 96.5 | 7.50E+13 |
| Fluc pDNA | DMPE-PEG2k | 1.5 | 96.3 | 0.13 | 89.3 | 5.67E+12 |
| Fluc pDNA | DMPE-PEG2k | 1.5 | 100.3 | 0.2 | 82.3 | 5.12E+13 |
| Fluc pDNA | DMPE-PEG2k | 1.5 | 96 | 0.122 | 91.4 | 3.70E+13 |
| Fluc pDNA | DMPE-PEG2k | 1.5 | 87 | 0.104 | 96.8 | 6.67E+12 | b) Delivery of pDNA-Loaded, Ionizable Lipid-Modified PMPs to Cells

Figure 10:
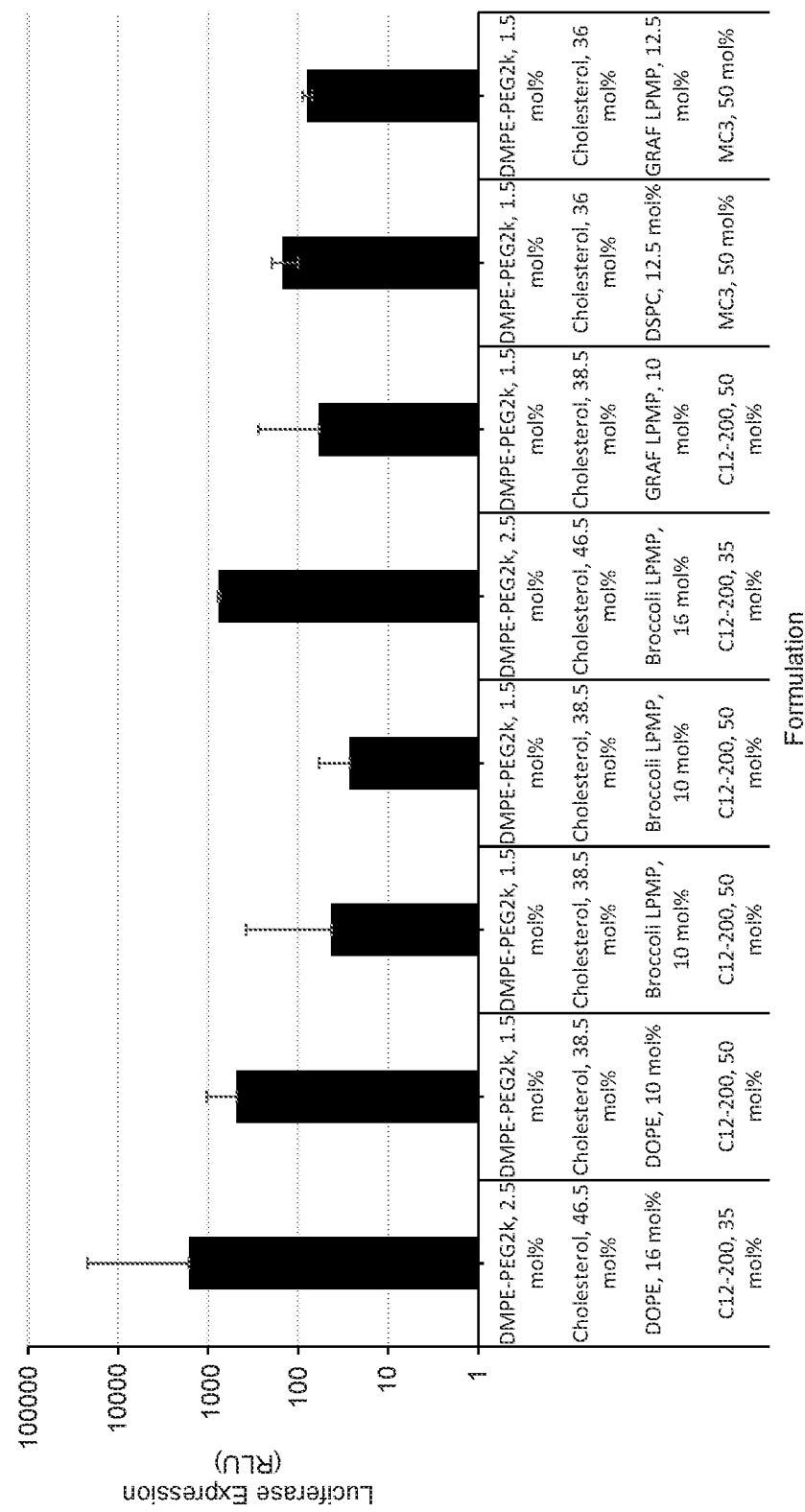
FIG. 10 is a bar graph showing the expression of luciferase (RLU) in HeLa cells that were contacted with PMP compositions composed of broccoli or grapefruit (GRAF) PMP lipids, cholesterol, C12-200 or MC3, and DMPE-PEG2k at the indicated molar ratios and loaded with gWiz™-Luc, a plasmid encoding luciferase. Compositions comprising DOPE or DSPC in the place of PMP lipids are provided as positive controls.
Figure 11:
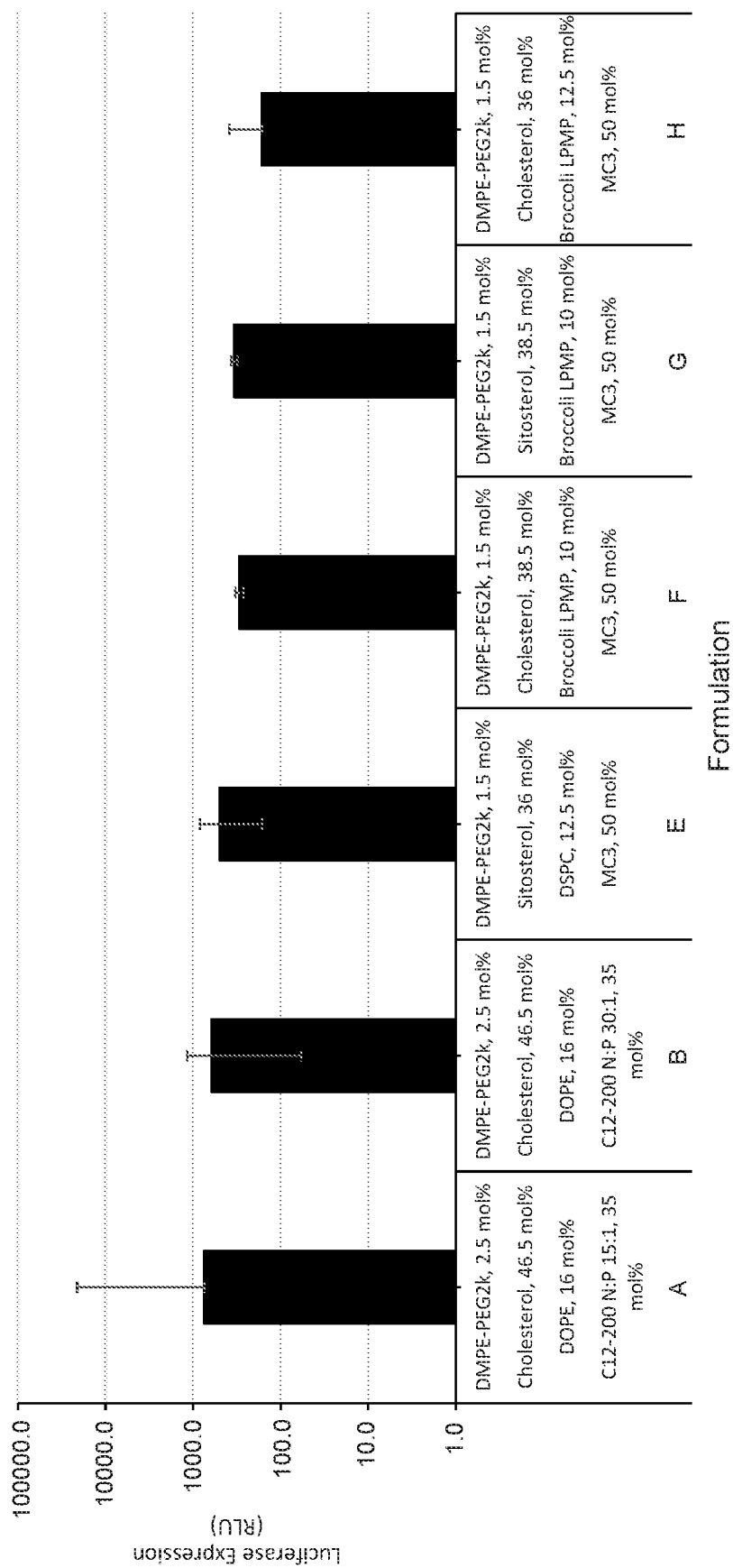
FIG. 11 is a bar graph showing the expression of luciferase (RLU) in MCF7 cells that were contacted with PMP compositions composed of broccoli PMP lipids, cholesterol or sitosterol, C12-200 or MC3, and DMPE-PEG2k at the indicated molar ratios and loaded with gWiz™-Luc. Compositions comprising DOPE or DSPC in the place of PMP lipids are provided as positive controls.

The PMP formulations provided in Table 14 were delivered to HeLa (cervical cancer) and MCF7 (breast cancer) human cell lines as described in Example 10a. Uptake of the PMPs by the cells was measured as luciferase expression (relative luminescence units (RLU)) (FIGS. 10 and 11). Cells treated with DOPE and DSPC LNPs were provided as positive controls.

Other Embodiments

Some embodiments of the invention are within the following numbered paragraphs.

1. A composition comprising a PMP modified to comprise a synthetic charged lipid, wherein the synthetic charged lipid is chosen from 1'-((2-(4-(2-((2-(bis(2-hydroxydodecyl)amino)ethyl) (2-hydroxydodecyl)amino)ethyl)piperazin-1-yl)ethyl)azanediyl)bis(dodecan-2-ol) (C12-200), DLin-MC3-DMA (MC3), dioleoyl-3-trimethylammonium propane (DODAP), DC-cholesterol, DOTAP, Ethyl PC, GL67, DLin-KC2-DMA (KC2), MD1 (cKK-E12), OF2, EPC, ZA3-Ep10, TT3, LP01, 5A2-SC8, Lipid 5 (Moderna), a cationic sulfonamide amino lipid, an amphiphilic zwitterionic amino lipid, DODAC, DOBAQ, YSK05, DOBAT, DOBAQ, DOPAT, DOMPAQ, DOAAQ, DMAP-BLP, DLinDMA, DODMA, DOTMA, DSDMA, DOSPA, DODAC, DOBAQ, DMRIE, DOTAP-cholesterol, GL67A, and 98N12-5, or combinations thereof.

2. A composition comprising a PMP modified to comprise a synthetic charged lipid, wherein the PMP is modified by reconstituting a lipid film comprising purified PMP lipids in the presence of a synthetic charged lipid, thereby producing a modified PMP that comprises the synthetic charged lipid, wherein the synthetic charged lipid is chosen from 1'-((2-(4-(2-((2-(bis(2-hydroxydodecyl)amino)ethyl) (2-hydroxydodecyl)amino)ethyl)piperazin-1-yl)ethyl)azanediyl)bis(dodecan-2-ol) (C12-200), DLin-MC3-DMA (MC3), dioleoyl-3-trimethylammonium propane (DODAP), DC-cholesterol, DOTAP, Ethyl PC, GL67, DLin-KC2-DMA (KC2), MD1 (cKK-E12), OF2, EPC, ZA3-Ep10, TT3, LP01, 5A2-SC8, Lipid 5 (Moderna), a cationic sulfonamide amino lipid, an amphiphilic zwitterionic amino lipid, DODAC, DOBAQ, YSK05, DOBAT, DOBAQ, DOPAT, DOMPAQ, DOAAQ, DMAP-BLP, DLinDMA, DODMA, DOTMA, DSDMA, DOSPA, DODAC, DOBAQ, DMRIE, DOTAP-cholesterol, GL67A, and 98N12-5, or combinations thereof.

3. The composition of paragraph 1 or 2, wherein the synthetic charged lipid is chosen from C12-200, MC3, DODAP, DC-cholesterol, DOTAP, Ethyl PC, GL67, KC2, MD1, OF2, EPC, ZA3-Ep10, TT3, LP01, 5A2-SC8, Lipid 5 (Moderna), a cationic sulfonamide amino lipid, and an amphiphilic zwitterionic amino lipid, or combinations thereof.

4. The composition of paragraph 3, wherein the synthetic charged lipid is chosen from C12-200, MC3, DODAP, and DC-cholesterol, or combinations thereof.

5. The composition of any one of paragraphs 1-4, wherein the modified PMP further comprises a sterol.

6. The composition of any one of paragraphs 1-5, wherein the modified PMP further comprises a PEGylated lipid.

7. The composition of any one of paragraphs 1-6, wherein the modified PMP further comprises a sterol and a PEGylated lipid.

8. The composition of paragraph 5 or 7, wherein the sterol is cholesterol or sitosterol.

9. The composition of any one of paragraphs 6-8, wherein the PEGylated lipid is C14-PEG2k, C18-PEG2k, or DMPE-PEG2k.

10. The composition of paragraph 9, wherein the synthetic charged lipid, purified PMP lipids, sterol, and PEGylated lipid comprise about 30%-75%, about 10%-20%, about 35%-50%, and about 1%-3%, respectively, of the lipids in the modified PMP.

11. The composition of paragraph 10, wherein the synthetic charged lipid, purified PMP lipids, sterol, and PEGylated lipid are formulated at a molar ratio of 50:10:38.5:1.5.

12. The composition of any one of paragraphs 1-11, wherein the synthetic charged lipid is C12-200.

13. The composition of paragraph 12, wherein a lipid membrane of the modified PMPs comprises 25% C12-200.

14. The composition of any one of paragraphs 1-11, wherein the synthetic charged lipid is MC3.

15. The composition of paragraph 14, wherein a lipid membrane of the modified PMPs comprises 40% MC3.

16. The composition of any one of paragraphs 1-11, wherein the synthetic charged lipid is DC-cholesterol.

17. The composition of paragraph 16, wherein a lipid membrane of the modified PMPs comprises 20% DC-cholesterol.

18. The composition of paragraph 16, wherein a lipid membrane of the modified PMPs comprises 40% DC-cholesterol.

19. The composition of any one of paragraphs 1-11, wherein the synthetic charged lipid is DOTAP.

20. The composition of paragraph 19, wherein a lipid membrane of the modified PMPs comprises 25% DOTAP.

21. The composition of any one of paragraphs 1-15, wherein the synthetic charged lipid is an ionizable lipid and the composition has a zeta potential of greater than −40 mV at pH 4 when in the absence of cargo.

22. The composition of paragraph 21, wherein the composition has a zeta potential of greater than 0 mV at pH 4 when in the absence of cargo.

23. The composition of paragraph 22, wherein the composition has a zeta potential of greater than 20 mV at pH 4 when in the absence of cargo.

24. The composition of paragraph 23, wherein the composition has a zeta potential of greater than 30 mV at pH 4 when in the absence of cargo.

25. The composition of paragraph 24, wherein the composition has a zeta potential of about 40 mV at pH 4 when in the absence of cargo.

26. The composition of any one of paragraphs 1-20, wherein the composition has a zeta potential of greater than −30 mV when in the absence of cargo.

27. The composition of paragraph 26, wherein the composition has a zeta potential of greater than −20 mV when in the absence of cargo.

28. The composition of paragraph 27, wherein the composition has a zeta potential of greater than −5 mV when in the absence of cargo.

29. The composition of paragraph 28, wherein the composition has a zeta potential of greater than 0 mV when in the absence of cargo.

30. The composition of paragraph 29, wherein the composition has a zeta potential of about 30 mV when in the absence of cargo.

31. The composition of any one of paragraphs 1-30, wherein the modified PMPs comprise a heterologous functional agent.

32. The composition of paragraph 31, wherein the heterologous functional agent is encapsulated by the modified PMPs.

33. The composition of paragraph 31, wherein the heterologous functional agent is embedded on the surface of the modified PMPs.

34. The composition of paragraph 31, wherein the heterologous functional agent is conjugated to the surface of the modified PMPs.

35. The composition of any one of paragraphs 31-34, wherein the heterologous functional agent is a polynucleotide.

36. The composition of paragraph 35, wherein the polynucleotide is chosen from an mRNA, an siRNA or siRNA precursor, a microRNA (miRNA) or miRNA precursor, a plasmid, a Dicer substrate small interfering RNA (dsiRNA), a short hairpin RNA (shRNA), an asymmetric interfering RNA (aiRNA), a peptide nucleic acid (PNA), a morpholino, a locked nucleic acid (LNA), a piwi-interacting RNA (piRNA), a ribozyme, a deoxyribozyme (DNAzyme), an aptamer, a circular RNA (circRNA), a guide RNA (gRNA), or a DNA molecule encoding any of these RNAs.

37. The composition of paragraph 36, wherein the polynucleotide is an mRNA.

38. The composition of paragraph 36, wherein the polynucleotide is an siRNA or a precursor thereof.

39. The composition of paragraph 36, wherein the polynucleotide is a plasmid.

40. The composition of any one of paragraphs 1-39, wherein the encapsulation efficiency of the polynucleotide by the modified PMP is at least 5%, 10%, 15%, 20%, 30%, 40%, 50%, 60%, 70%, 80%, 90%, 95%, 98%, 99%, or more than 99%.

41. The composition of any one of paragraphs 1-40, wherein the modified PMPs are lipid reconstructed PMPs (LPMPs).

42. The composition of paragraph 41, wherein the LPMP is produced by a method comprising lipid extrusion.

43. The composition of paragraph 42, wherein the LPMP is produced by a method comprising processing a solution comprising a lipid extract of the PMPs in a microfluidics device comprising an aqueous phase, thereby producing the LPMPs.

44. The composition of paragraph 43, wherein the aqueous phase comprises a heterologous functional agent.

45. The composition of any one of paragraphs 1-44, wherein the modified PMPs have increased cell uptake.

46. The composition of paragraph 45, wherein the increased cell uptake is an increased cell uptake of at least 1%, 2%, 5%, 10%, 15%, 20%, 30%, 40%, 50%, 60%, 70%, 80%, 90%, or 100% relative to the cell uptake of the unmodified PMP.

47. The composition of paragraph 45 or 46, wherein the cell is a mammalian cell.

48. The composition of paragraph 47, wherein the mammalian cell is a human cell.

49. The composition of paragraph 45 or 46, wherein the cell is a plant cell.

50. The composition of paragraph 45 or 46, wherein the cell is a bacterial cell.

51. The composition of paragraph 45 or 46, wherein the cell is a fungal cell.

52. A method for delivering a PMP to a target cell, the method comprising introducing a composition that comprises a PMP comprising a synthetic charged lipid to the target cell, wherein the synthetic charged lipid is chosen from 1'-((2-(4-(2-((2-(bis(2-hydroxydodecyl)amino)ethyl) (2-hydroxydodecyl)amino)ethyl)piperazin-1-yl)ethyl) azanediyl)bis(dodecan-2-ol) (C12-200), DLin-MC3-DMA (MC3), dioleoyl-3-trimethylammonium propane (DODAP), DC-cholesterol, DOTAP, Ethyl PC, GL67, DLin-KC2-DMA (KC2), MD1 (cKK-E12), OF2, EPC, ZA3-Ep10, TT3, LP01, 5A2-SC8, Lipid 5 (Moderna), a cationic sulfonamide amino lipid, an amphiphilic zwitterionic amino lipid, DODAC, DOBAQ, YSK05, DOBAT, DOBAQ, DOPAT, DOMPAQ, DOAAQ, DMAP-BLP, DLinDMA, DODMA, DOTMA, DSDMA, DOSPA, DODAC, DOBAQ, DMRIE, DOTAP-cholesterol, GL67A, and 98N12-5, or combinations thereof.

53. The method of paragraph 52, wherein the synthetic charged lipid is chosen from C12-200, MC3, DODAP, DC-cholesterol, DOTAP, Ethyl PC, GL67, KC2, MD1, OF2, EPC, ZA3-Ep10, TT3, LP01, 5A2-SC8, Lipid 5 (Moderna), a cationic sulfonamide amino lipid, and an amphiphilic zwitterionic amino lipid, or combinations thereof.

54. The method of paragraph 53, wherein the synthetic charged lipid is chosen from C12-200, MC3, DODAP, and DC-cholesterol, or combinations thereof.

55. The method of any one of paragraphs 52-54, wherein the PMP further comprises a sterol.

56. The method of any one of paragraphs 52-55, wherein the PMP further comprises a PEGylated lipid.

57. The method of any one of paragraphs 52-56, wherein the PMP further comprises a sterol and a PEGylated lipid.

58. The method of paragraph 55 or 57, wherein the sterol is cholesterol or sitosterol.

59. The method of any one of paragraphs 56-58, wherein the PEGylated lipid is C14-PEG2k, C18-PEG2k, or DMPE-PEG2k.

60. The method of paragraph 57, wherein the synthetic charged lipid, purified PMP lipids, sterol, and PEGylated lipid comprise about 30%-75%, about 10%-20%, about 35%-50%, and about 1%-3%, respectively, of the lipids in the PMP.

61. The method of paragraph 60, wherein the synthetic charged lipid, purified PMP lipids, sterol, and PEGylated lipid are formulated at a molar ratio of 50:10:38.5:1.5.

62. The method of any one of paragraphs 52-61, wherein the synthetic charged lipid is C12-200.

63. The method of paragraph 62, wherein a lipid membrane of the PMP comprises 25% C12-200.

64. The method of any one of paragraphs 52-61, wherein the synthetic charged lipid is MC3.

65. The method of paragraph 64, wherein a lipid membrane of the PMP comprises 40% MC3.

66. The method of any one of paragraphs 52-61, wherein the synthetic charged lipid is DC-cholesterol.

67. The method of paragraph 66, wherein a lipid membrane of the PMP comprises 20% DC-cholesterol.

68. The method of any one of paragraphs 52-61, wherein a lipid membrane of the PMP comprises 40% DC-cholesterol.

69. The method of any one of paragraphs 52-61, wherein the synthetic charged lipid is DOTAP.

70. The method of paragraph 69, wherein a lipid membrane of the PMP comprises 25% DOTAP.

71. The method of any one of paragraphs 52-70, wherein the synthetic charged lipid is an ionizable lipid and the composition comprising the PMP has a zeta potential of greater than −40 mV at pH 4 when in the absence of cargo.

72. The method of paragraph 71, wherein the composition comprising the PMP has a zeta potential of greater than 0 mV at pH 4 when in the absence of cargo.

73. The method of paragraph 72, wherein the composition comprising the PMP has a zeta potential of greater than 20 mV at pH 4 when in the absence of cargo.

74. The method of paragraph 73, wherein the composition comprising the PMP has a zeta potential of greater than 30 mV at pH 4 when in the absence of cargo.

75. The method of paragraph 74, wherein the composition comprising the PMP has a zeta potential of about 40 mV at pH 4 when in the absence of cargo.

76. The method of any one of paragraphs 52-70, wherein the composition comprising the PMP has a zeta potential of greater than −30 mV when in the absence of cargo.

77. The method of paragraph 76, wherein the composition comprising the PMP has a zeta potential of greater than −20 mV when in the absence of cargo.

78. The method of paragraph 77, wherein the composition comprising the PMP has a zeta potential of greater than −5 mV when in the absence of cargo.

79. The method of paragraph 78, wherein the composition comprising the PMP has a zeta potential of greater than 0 mV when in the absence of cargo.

80. The method of paragraph 79, wherein the composition comprising the PMP has a zeta potential of about 30 mV when in the absence of cargo.

81. The method of any one of paragraphs 52-80, wherein the PMP comprises a heterologous functional agent.

82. The method of paragraph 81, wherein the heterologous functional agent is encapsulated by the PMP.

83. The method of paragraph 81, wherein the heterologous functional agent is embedded on the surface of the PMP.

84. The method of paragraph 81, wherein the heterologous functional agent is conjugated to the surface of the PMP.

85. The method of any one of paragraphs 81-84, wherein the heterologous functional agent is a polynucleotide.

86. The method of paragraph 85, wherein the polynucleotide is chosen from an mRNA, an siRNA or siRNA precursor, a miRNA or miRNA precursor, a plasmid, a dsiRNA, a shRNA, an aiRNA, a PNA, a morpholino, a LNA, a piRNA, a ribozyme, a DNAzyme, an aptamer, a circRNA, a gRNA, or a DNA molecule encoding any of these RNAs.

87. The method of paragraph 86, wherein the polynucleotide is an mRNA.

88. The method of paragraph 86, wherein the polynucleotide is an siRNA or a precursor thereof. 89. The method of paragraph 86, wherein the polynucleotide is a plasmid.

90. The method of any one of paragraphs 81-89, wherein the encapsulation efficiency of the polynucleotide by the PMP is at least 5%, 10%, 15%, 20%, 30%, 40%, 50%, 60%, 70%, 80%, 90%, 95%, 98%, 99%, or more than 99%.

91. The method of any one of paragraphs 52-90, wherein the PMP is a lipid reconstructed PMP (LPMP).

92. The method of any one of paragraphs 52-91, wherein the PMP has increased cell uptake.

93. The method of paragraph 92, wherein the increased cell uptake is an increased cell uptake of at least 1%, 2%, 5%, 10%, 15%, 20%, 30%, 40%, 50%, 60%, 70%, 80%, 90%, or 100% relative to the cell uptake of the unmodified PMP.

94. The method of paragraph 92 or 93, wherein the cell is a mammalian cell.

95. The method of paragraph 94, wherein the mammalian cell is a human cell.

96. The method of paragraph 92 or 93, wherein the cell is a plant cell.

97. The method of paragraph 92 or 93, wherein the cell is a bacterial cell.

98. The method of paragraph 92 or 93, wherein the cell is a fungal cell.

99. A method of increasing the fitness of a plant, the method comprising delivering to the plant an effective amount of the composition of any one of paragraphs 1-51, wherein the method increases the fitness of the plant relative to an untreated plant.

100. The method of paragraph 99, wherein the modified PMP comprises an agricultural agent.

101. The method of paragraph 99 or 100, wherein the plant is a plant of agricultural or horticultural importance.

102. The method of paragraph 101, wherein the plant is a soybean plant, a wheat plant, or a corn plant.

103. A method of decreasing the fitness of a plant, the method comprising delivering to the plant an effective amount of the composition of any one of paragraphs 1-51, wherein the method decreases the fitness of the plant relative to an untreated plant.

104. The method of paragraph 103, wherein the modified PMP comprises an agricultural agent.

105. The method of paragraph 104, wherein the plant is a weed.

106. The method of any one of paragraphs 99-105, wherein the composition is delivered to a leaf, seed, embryo, ovule, meristem, microspore, root, fruit, shoot, pollen, or flower of the plant.

107. A method of increasing the fitness of a mammal, the method comprising delivering to the mammal an effective amount of the composition of any one of paragraphs 1-51, wherein the method increases the fitness of the mammal relative to an untreated mammal.

108. The method of paragraph 107, wherein the modified PMP comprises a heterologous therapeutic agent.

109. The method of paragraph 107 or 108, wherein the mammal is a human.

110. A composition comprising a plurality of modified PMPs having a zeta potential of greater than or equal to −30 mV when in the absence of cargo.

111. A composition comprising a plurality of modified PMPs having a zeta potential of greater than −40 mV at pH 4 when in the absence of cargo.

112. The composition of paragraph 110 or 111, wherein the composition has a net positive zeta potential when in the absence of cargo.

113. The composition of any one of paragraphs 110-112, wherein the composition comprises an exogenous lipid.

114. The composition of paragraph 113, wherein the exogenous lipid is an ionizable lipid.

115. The composition of paragraph 114, wherein the ionizable lipid is C12-200.

116. The composition of paragraph 114, wherein the ionizable lipid is MC3.

117. The composition of paragraph 113, wherein the exogenous lipid is a cationic lipid.

118. The composition of paragraph 117, wherein the cationic lipid is DOTAP.

119. The composition of paragraph 117, wherein the cationic lipid is DC-cholesterol.

120. The composition of any one of paragraphs 111-119, wherein the composition has a zeta potential of greater than 0 mV at pH 4 when in the absence of cargo.

121. The composition of paragraph 120, wherein the composition has a zeta potential of greater than 20 mV at pH 4 when in the absence of cargo.

122. The composition of paragraph 121, wherein the composition has a zeta potential of about 40 mV at pH 4 when in the absence of cargo.

123. The composition of any one of paragraphs 110-122, wherein the modified PMPs further comprise a cargo.

124. The composition of paragraph 123, wherein the cargo is a heterologous functional agent.

125. The composition of paragraph 124, wherein the heterologous functional agent is a polynucleotide.

126. The composition of paragraph 125, wherein the polynucleotide is chosen from an mRNA, an siRNA or siRNA precursor, a miRNA or miRNA precursor, a plasmid, a dsiRNA, a shRNA, an aiRNA, a PNA, a morpholino, a LNA, a piRNA, a ribozyme, a DNAzyme, an aptamer, a circRNA, a gRNA, or a DNA molecule encoding any of these RNAs.

127. The composition of any one of paragraphs 1-51 or 110-126, wherein zeta potential is measured by electrophoretic light scattering.

128. A method for delivering a cargo to a cell, the method comprising contacting a cell with the composition of any one of paragraphs 1-51 or 110-127.

129. A method for increasing uptake of a cargo by a cell, the method comprising contacting a cell with the composition of any one of paragraphs 1-51 or 110-127.

130. A method for fusing a composition to a cell, the method comprising contacting a cell with the composition of any one of paragraphs 1-51 or 110-127.

131. A method for delivering a composition to a cell wall, the method comprising contacting a cell with the composition of any one of paragraphs 1-51 or 110-127.

132. A method for modulating gene expression in a cell, the method comprising contacting a cell with the composition of any one of paragraphs 1-51 or 110-127.

133. A composition comprising a plurality of lipid reconstructed PMPs (LPMPs), wherein the LPMPs are produced by a process comprising the steps of:
 (a) providing a plurality of purified PMPs;
 (b) processing the plurality of PMPs to produce a lipid film;
 (c) reconstituting the lipid film in an organic solvent, wherein the organic solvent is dimethylformamide: methanol (DMF:MeOH), thereby producing a lipid solution; and (d) processing the lipid solution of step (c) in a microfluidics device comprising an aqueous phase, thereby producing the LPMPs.

134. The composition of paragraph 133, wherein the LPMPs further comprise an exogenous lipid.

135. The composition of paragraph 134, wherein the exogenous lipid is added to the preparation prior to step (b).

136. The composition of paragraph 134 or 135, wherein the exogenous lipid is a synthetic charged lipid.

137. The composition of paragraph 136, wherein the synthetic charged lipid is chosen from 1'-((2-(4-(2-((2-(bis(2-hydroxydodecyl)amino)ethyl) (2-hydroxydodecyl)amino)ethyl)piperazin-1-yl)ethyl)azanediyl)bis(dodecan-2-ol) (C12-200), DLin-MC3-DMA (MC3), dioleoyl-3-trimethylammonium propane (DODAP), DC-cholesterol, DOTAP, Ethyl PC, GL67, DLin-KC2-DMA (KC2), MD1 (cKK-E12), OF2, EPC, ZA3-Ep10, TT3, LP01, 5A2-SC8, Lipid 5 (Moderna), a cationic sulfonamide amino lipid, an amphiphilic zwitterionic amino lipid, DODAC, DOBAQ, YSK05, DOBAT, DOBAQ, DOPAT, DOMPAQ, DOAAQ, DMAP-BLP, DLinDMA, DODMA, DOTMA, DSDMA, DOSPA, DODAC, DOBAQ, DMRIE, DOTAP-cholesterol, GL67A, and 98N12-5, or combinations thereof.

138. The composition of paragraph 137, wherein the synthetic charged lipid is chosen from C12-200, MC3, DODAP, DC-cholesterol, DOTAP, Ethyl PC, GL67, KC2, MD1, OF2, EPC, ZA3-Ep10, TT3, LP01, 5A2-SC8, Lipid 5 (Moderna), a cationic sulfonamide amino lipid, and an amphiphilic zwitterionic amino lipid, or combinations thereof.

139. The composition of paragraph 138, wherein the synthetic charged lipid is chosen from C12-200, MC3, DODAP, and DC-cholesterol, or combinations thereof.

140. The composition of any one of paragraphs 133-139, wherein the aqueous phase comprises a citrate buffer having a pH of about 3.2.

141. The composition of any one of paragraphs 133-140, wherein aqueous phase and the lipid solution are mixed at a 3:1 volumetric ratio.

142. The composition of any one of paragraphs 133-141, wherein the LPMPs comprise a heterologous functional agent.

143. The composition of paragraph 142, wherein the heterologous functional agent is a polynucleotide.

144. The composition of paragraph 143, wherein the polynucleotide is chosen from an mRNA, an siRNA or siRNA precursor, a miRNA or miRNA precursor, a plasmid, a dsiRNA, a shRNA, an aiRNA, a PNA, a morpholino, a LNA, a piRNA, a ribozyme, a DNAzyme, an aptamer, a circRNA, a gRNA, or a DNA molecule encoding any of these RNAs.

145. The composition of any one of paragraphs 142-144, wherein the heterologous functional agent is comprised by the aqueous phase.

146. The composition of any one of paragraphs 133-145, wherein the LPMPs further comprise a sterol.

147. The composition of any one of paragraphs 133-146, wherein the LPMPs further comprise a
PEGylated lipid.

148. The composition of any one of paragraphs 133-147, wherein the LPMPs further comprise a sterol and a PEGylated lipid.

149. The composition of paragraph 146 or 148, wherein the sterol is cholesterol or sitosterol.

150. The composition of any one of paragraphs 147-149, wherein the PEGylated lipid is C14-PEG2k, C18-PEG2k, or DMPE-PEG2k.

151. A method for making LPMPs, the method comprising:
(a) providing a plurality of purified PMPs;
(b) processing the plurality of PMPs to produce a lipid film;
(c) reconstituting the lipid film in an organic solvent, wherein the organic solvent is dimethylformamide:methanol (DMF:MeOH), thereby producing a lipid solution; and
(d) processing the lipid solution of step (c) in a microfluidics device comprising an aqueous phase, thereby producing the LPMPs.

152. The method of paragraph 151, wherein the LPMPs further comprise an exogenous lipid.

153. The method of paragraph 151 or 152, wherein the exogenous lipid is added to the preparation prior to step (b).

154. The method of paragraph 152 or 153, wherein the exogenous lipid is a synthetic charged lipid.

155. The method of paragraph 154, wherein the synthetic charged lipid is chosen from 1'-((2-(4-(2-((2-(bis(2-hydroxydodecyl)amino)ethyl) (2-hydroxydodecyl)amino)ethyl)piperazin-1-yl)ethyl)azanediyl)bis(dodecan-2-ol) (C12-200), DLin-MC3-DMA (MC3), dioleoyl-3-trimethylammonium propane (DODAP), DC-cholesterol, DOTAP, Ethyl PC, GL67, DLin-KC2-DMA (KC2), MD1 (cKK-E12), OF2, EPC, ZA3-Ep10, TT3, LP01, 5A2-SC8, Lipid 5 (Moderna), a cationic sulfonamide amino lipid, an amphiphilic zwitterionic amino lipid, DODAC, DOBAQ, YSK05, DOBAT, DOBAQ, DOPAT, DOMPAQ, DOAAQ, DMAP-BLP, DLinDMA, DODMA, DOTMA, DSDMA, DOSPA, DODAC, DOBAQ, DMRIE, DOTAP-cholesterol, GL67A, and 98N12-5, or combinations thereof.

156. The method of paragraph 155, wherein the synthetic charged lipid is chosen from C12-200, MC3, DODAP, DC-cholesterol, DOTAP, Ethyl PC, GL67, KC2, MD1, OF2, EPC, ZA3-Ep10, TT3, LP01, 5A2-SC8, Lipid 5 (Moderna), a cationic sulfonamide amino lipid, and an amphiphilic zwitterionic amino lipid, or combinations thereof.

157. The method of paragraph 156, wherein the synthetic charged lipid is chosen from C12-200, MC3, DODAP, and DC-cholesterol, or combinations thereof.

158. The method of any one of paragraphs 151-157, wherein the aqueous phase comprises water, PBS, or a citrate buffer.

159. The method of any one of paragraphs 151-158, wherein the aqueous phase and the lipid solution are mixed at a 3:1 volumetric ratio.

160. The method of any one of paragraphs 151-159, wherein the LPMPs comprise a heterologous functional agent.

161. The method of paragraph 160, wherein the heterologous functional agent is a polynucleotide.

162. The method of paragraph 161, wherein the polynucleotide is chosen from an mRNA, an siRNA or siRNA precursor, a miRNA or miRNA precursor, a plasmid, a dsiRNA, a shRNA, an aiRNA, a PNA, a morpholino, a LNA, a piRNA, a ribozyme, a DNAzyme, an aptamer, a circRNA, a gRNA, or a DNA molecule encoding any of these RNAs.

163. The method of any one of paragraphs 160-162, wherein the heterologous functional agent is comprised by the aqueous phase.

164. The method of any one of paragraphs 151-163, wherein the LPMPs further comprise a sterol.

165. The method of any one of paragraphs 151-164, wherein the LPMPs further comprise a PEGylated lipid.

166. The method of any one of paragraphs 151-165, wherein the LPMPs further comprise a sterol and a PEGylated lipid.

167. The composition of paragraph 164 or 166, wherein the sterol is cholesterol or sitosterol.

168. The composition of any one of paragraphs 165-167, wherein the PEGylated lipid is C14-PEG2k, C18-PEG2k, or DMPE-PEG2k.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Other embodiments are within the claims.

APPENDIX

Table 13: Plant EV-Markers

| Example Species | Accession No. | Protein Name |
| --- | --- | --- |
| *Arabidopsis thaliana* | C0LGG8 | Probable LRR receptor-like serine/threonine-protein kinase At1g53430 (EC 2.7.11.1) |
| *Arabidopsis thaliana* | F4HQT8 | Uncharacterized protein |
| *Arabidopsis thaliana* | F4HWU0 | Protein kinase superfamily protein |
| *Arabidopsis thaliana* | F4IO82 | Bifunctional inhibitor/lipid-transfer protein/seed storage 2S albumin superfamily protein |
| *Arabidopsis thaliana* | F4I3M3 | Kinase with tetratricopeptide repeat domain-containing protein |
| *Arabidopsis thaliana* | F4IB62 | Leucine-rich repeat protein kinase family protein |
| *Arabidopsis thaliana* | O03042 | Ribulose bisphosphate carboxylase large chain (RuBisCO large subunit) (EC 4.1.1.39) |
| *Arabidopsis thaliana* | O03986 | Heat shock protein 90-4 (AtHSP90.4) (AtHsp90-4) (Heat shock protein 81-4) (Hsp81-4) |
| *Arabidopsis thaliana* | O04023 | Protein SRC2 homolog (AtSRC2) |
| *Arabidopsis thaliana* | O04309 | Jacalin-related lectin 35 (JA-responsive protein 1) (Myrosinase-binding protein-like At3g16470) |
| *Arabidopsis thaliana* | O04314 | PYK10-binding protein 1 (Jacalin-related lectin 30) (Jasmonic acid-induced protein) |
| *Arabidopsis thaliana* | O04922 | Probable glutathione peroxidase 2 (EC 1.11.1.9) |
| *Arabidopsis thaliana* | O22126 | Fasciclin-like arabinogalactan protein 8 (AtAGP8) |
| *Arabidopsis thaliana* | O23179 | Patatin-like protein 1 (AtPLP1 (EC 3.1.1.—) (Patatin-related phospholipase A IIgamma) (pPLAIIg) (Phospholipase A IVA) (AtPLAIVA) |
| *Arabidopsis thaliana* | O23207 | Probable NAD(P)H dehydrogenase (quinone) FQR1-like 2 (EC 1.6.5.2) |
| *Arabidopsis thaliana* | O23255 | Adenosylhomocysteinase 1 (AdoHcyase 1) (EC 3.3.1.1) (Protein EMBRYO DEFECTIVE 1395) (Protein HOMOLOGY-DEPENDENT GENE SILENCING 1) (S-adenosyl-L-homocysteine hydrolase 1) (SAH hydrolase 1) |
| *Arabidopsis thaliana* | O23482 | Oligopeptide transporter 3 (AtOPT3) |
| *Arabidopsis thaliana* | O23654 | V-type proton ATPase catalytic subunit A (V-ATPase subunit A) (EC 3.6.3.14) (V-ATPase 69 kDa subunit) (Vacuolar H(+)-ATPase subunit A) (Vacuolar proton pump subunit alpha) |
| *Arabidopsis thaliana* | O48788 | Probable inactive receptor kinase At2g26730 |
| *Arabidopsis thaliana* | O48963 | Phototropin-1 (EC 2.7.11.1) (Non-phototropic hypocotyl protein 1) (Root phototropism protein 1) |
| *Arabidopsis thaliana* | O49195 | Vegetative storage protein 1 |
| *Arabidopsis thaliana* | O50008 | 5-methyltetrahydropteroyltriglutamate--homocysteine methyltransferase 1 (EC 2.1.1.14) (Cobalamin-independent methionine synthase 1) (AtMS1) (Vitamin-B12-independent methionine synthase 1) |
| *Arabidopsis thaliana* | O64696 | Putative uncharacterized protein At2g34510 |
| *Arabidopsis thaliana* | O65572 | Carotenoid 9,10(9',10')-cleavage dioxygenase 1 (EC 1.14.99.n4) (AtCCD1) (Neoxanthin cleavage enzyme NC1) (AtNCED1) |
| *Arabidopsis thaliana* | O65660 | PLAT domain-containing protein 1 (AtPLAT1) (PLAT domain protein 1) |
| *Arabidopsis thaliana* | O65719 | Heat shock 70 kDa protein 3 (Heat shock cognate 70 kDa protein 3) (Heat shock cognate protein 70-3) (AtHsc70-3) (Heat shock protein 70-3) (AtHsp70-3) |
| *Arabidopsis thaliana* | O80517 | Uclacyanin-2 (Blue copper-binding protein II) (BCB II) (Phytocyanin 2) (Uclacyanin-II) |
| *Arabidopsis thaliana* | O80576 | At2g44060 (Late embryogenesis abundant protein, group 2) (Similar to late embryogenesis abundant proteins) |
| *Arabidopsis thaliana* | O80725 | ABC transporter B family member 4 (ABC transporter ABCB.4) (AtABCB4) (Multidrug resistance protein 4) (P-glycoprotein 4) |
| *Arabidopsis thaliana* | O80837 | Remorin (DNA-binding protein) |
| *Arabidopsis thaliana* | O80852 | Glutathione S-transferase F9 (AtGSTF9) (EC 2.5.1.18) (AtGSTF7) (GST class-phi member 9) |
| *Arabidopsis thaliana* | O80858 | Expressed protein (Putative uncharacterized protein At2g30930) (Putative uncharacterized protein At2g30930; F7F1.14) |

APPENDIX-continued

Table 13: Plant EV-Markers

| | | |
|---|---|---|
| *Arabidopsis thaliana* | O80939 | L-type lectin-domain containing receptor kinase IV.1 (*Arabidopsis thaliana* lectin-receptor kinase e) (AthlecRK-e) (LecRK-IV.1) (EC 2.7.11.1) (Lectin Receptor Kinase 1) |
| *Arabidopsis thaliana* | O80948 | Jacalin-related lectin 23 (Myrosinase-binding protein-like At2g39330) |
| *Arabidopsis thaliana* | O82628 | V-type proton ATPase subunit G1 (V-ATPase subunit G1) (Vacuolar H(+)-ATPase subunit G isoform 1) (Vacuolar proton pump subunit G1) |
| *Arabidopsis thaliana* | P10795 | Ribulose bisphosphate carboxylase small chain 1A, chloroplastic (RuBisCO small subunit 1A) (EC 4.1.1.39) |
| *Arabidopsis thaliana* | P10896 | Ribulose bisphosphate carboxylase/oxygenase activase, chloroplastic (RA) (RuBisCO activase) |
| *Arabidopsis thaliana* | P17094 | 60S ribosomal protein L3-1 (Protein EMBRYO DEFECTIVE 2207) |
| *Arabidopsis thaliana* | P19456 | ATPase 2, plasma membrane-type (EC 3.6.3.6) (Proton pump 2) |
| *Arabidopsis thaliana* | P20649 | ATPase 1, plasma membrane-type (EC 3.6.3.6) (Proton pump 1) |
| *Arabidopsis thaliana* | P22953 | Probable mediator of RNA polymerase II transcription subunit 37e (Heat shock 70 kDa protein 1) (Heat shock cognate 70 kDa protein 1) (Heat shock cognate protein 70-1) (AtHsc70-1) (Heat shock protein 70-1) (AtHsp70-1) (Protein EARLY-RESPONSIVE TO DEHYDRATION 2) |
| *Arabidopsis thaliana* | P23586 | Sugar transport protein 1 (Glucose transporter) (Hexose transporter 1) |
| *Arabidopsis thaliana* | P24636 | Tubulin beta-4 chain (Beta-4-tubulin) |
| *Arabidopsis thaliana* | P25696 | Bifunctional enolase 2/transcriptional activator (EC 4.2.1.11) (2-phospho-D-glycerate hydro-lyase 2) (2-phosphoglycerate dehydratase 2) (LOW EXPRESSION OF OSMOTICALLY RESPONSIVE GENES 1) |
| *Arabidopsis thaliana* | P25856 | Glyceraldehyde-3-phosphate dehydrogenase GAPA1, chloroplastic (EC 1.2.1.13) (NADP-dependent glyceraldehydephosphate dehydrogenase A subunit 1) |
| *Arabidopsis thaliana* | P28186 | Ras-related protein RABE1c (AtRABE1c) (Ras-related protein Ara-3) (Ras-related protein Rab8A) (AtRab8A) |
| *Arabidopsis thaliana* | P30302 | Aquaporin PIP2-3 (Plasma membrane intrinsic protein 2-3) (AtPIP2; 3) (Plasma membrane intrinsic protein 2c) (PIP2c) (RD28-PIP) (TMP2C) (Water stress-induced tonoplast intrinsic protein) (WSI-TIP) [Cleaved into: Aquaporin PIP2-3, N-terminally processed] |
| *Arabidopsis thaliana* | P31414 | Pyrophosphate-energized vacuolar membrane proton pump 1 (EC 3.6.1.1) (Pyrophosphate-energized inorganic pyrophosphatase 1) (H(+)-PPase 1) (Vacuolar proton pyrophosphatase 1) (Vacuolar proton pyrophosphatase 3) |
| *Arabidopsis thaliana* | P32961 | Nitrilase 1 (EC 3.5.5.1) |
| *Arabidopsis thaliana* | P38666 | 60S ribosomal protein L24-2 (Protein SHORT VALVE 1) |
| *Arabidopsis thaliana* | P39207 | Nucleoside diphosphate kinase 1 (EC 2.7.4.6) (Nucleoside diphosphate kinase I) (NDK I) (NDP kinase I) (NDPK I) |
| *Arabidopsis thaliana* | P42643 | 14-3-3-like protein GF14 chi (General regulatory factor 1) |
| *Arabidopsis thaliana* | P42737 | Beta carbonic anhydrase 2, chloroplastic (AtbCA2) (AtbetaCA2) (EC 4.2.1.1) (Beta carbonate dehydratase 2) |
| *Arabidopsis thaliana* | P42759 | Dehydrin ERD10 (Low-temperature-induced protein LTI45) |
| *Arabidopsis thaliana* | P42761 | Glutathione S-transferase F10 (AtGSTF10) (EC 2.5.1.18) (AtGSTF4) (GST class-phi member 10) (Protein EARLY RESPONSE TO DEHYDRATION 13) |
| *Arabidopsis thaliana* | P42763 | Dehydrin ERD14 |
| *Arabidopsis thaliana* | P42791 | 60S ribosomal protein L18-2 |
| *Arabidopsis thaliana* | P43286 | Aquaporin PIP2-1 (Plasma membrane intrinsic protein 2-1) (AtPIP2; 1) (Plasma membrane intrinsic protein 2a) (PIP2a) [Cleaved into: Aquaporin PIP2-1, N-terminally processed] |
| *Arabidopsis thaliana* | P46286 | 60S ribosomal protein L8-1 (60S ribosomal protein L2) (Protein EMBRYO DEFECTIVE 2296) |
| *Arabidopsis thaliana* | P46422 | Glutathione S-transferase F2 (AtGSTF2) (EC 2.5.1.18) (24 kDa auxin-binding protein) (AtPM24) (GST class-phi member 2) |
| *Arabidopsis thaliana* | P47998 | Cysteine synthase 1 (EC 2.5.1.47) (At.OAS.5-8) (Beta-substituted Ala synthase 1; 1) (ARAth-Bsas1; 1) (CSase A) (AtCS-A) (Cys-3A) (O-acetylserine (thiol)-lyase 1) (OAS-TL A) (O-acetylserine sulfhydrylase) (Protein ONSET OF LEAF DEATH 3) |
| *Arabidopsis thaliana* | P48347 | 14-3-3-like protein GF14 epsilon (General regulatory factor 10) |
| *Arabidopsis thaliana* | P48491 | Triosephosphate isomerase, cytosolic (TIM) (Triose-phosphate isomerase) (EC 5.3.1.1) |
| *Arabidopsis thaliana* | P50318 | Phosphoglycerate kinase 2, chloroplastic (EC 2.7.2.3) |
| *Arabidopsis thaliana* | P53492 | Actin-7 (Actin-2) |
| *Arabidopsis thaliana* | P54144 | Ammonium transporter 1 member 1 (AtAMT1; 1) |
| *Arabidopsis thaliana* | P92963 | Ras-related protein RABB1c (AtRABB1c) (Ras-related protein Rab2A) (AtRab2A) |
| *Arabidopsis thaliana* | P93004 | Aquaporin PIP2-7 (Plasma membrane intrinsic protein 2-7) (AtPIP2; 7) (Plasma membrane intrinsic protein 3) (Salt stress-induced major intrinsic protein) [Cleaved into: Aquaporin PIP2-7, N-terminally processed] |

APPENDIX-continued

Table 13: Plant EV-Markers

| | | |
|---|---|---|
| *Arabidopsis thaliana* | P93025 | Phototropin-2 (EC 2.7.11.1) (Defective in chloroplast avoidance protein 1) (Non-phototropic hypocotyl 1-like protein 1) (AtKin7) (NPH1-like protein 1) |
| *Arabidopsis thaliana* | P93819 | Malate dehydrogenase 1, cytoplasmic (EC 1.1.1.37) (Cytosolic NAD-dependent malate dehydrogenase 1) (cNAD-MDH1) (Cytosolic malate dehydrogenase 1) (Cytosolic MDH1) |
| *Arabidopsis thaliana* | Q03250 | Glycine-rich RNA-binding protein 7 (AtGR-RBP7) (AtRBG7) (Glycine-rich protein 7) (AtGRP7) (Protein COLD, CIRCADIAN RHYTHM, AND RNA BINDING 2) (Protein CCR2) |
| *Arabidopsis thaliana* | Q05431 | L-ascorbate peroxidase 1, cytosolic (AP) (AtAPx01) (EC 1.11.1.11) |
| *Arabidopsis thaliana* | Q06611 | Aquaporin PIP1-2 (AtPIP1; 2) (Plasma membrane intrinsic protein 1b) (PIP1b) (Transmembrane protein A) (AthH2) (TMP-A) |
| *Arabidopsis thaliana* | Q07488 | Blue copper protein (Blue copper-binding protein) (AtBCB) (Phytocyanin 1) (Stellacyanin) |
| *Arabidopsis thaliana* | Q0WLB5 | Clathrin heavy chain 2 |
| *Arabidopsis thaliana* | Q0WNJ6 | Clathrin heavy chain 1 |
| *Arabidopsis thaliana* | Q1ECE0 | Vesicle-associated protein 4-1 (Plant VAP homolog 4-1) (AtPVA41) (Protein MEMBRANE-ASSOCIATED MANNITOL-INDUCED) (AtMAMI) (VAMP-associated protein 4-1) |
| *Arabidopsis thaliana* | Q38882 | Phospholipase D alpha 1 (AtPLDalpha1) (PLD alpha 1) (EC 3.1.4.4) (Choline phosphatase 1) (PLDalpha) (Phosphatidylcholine-hydrolyzing phospholipase D 1) |
| *Arabidopsis thaliana* | Q38900 | Peptidyl-prolyl cis-trans isomerase CYP19-1 (PPIase CYP19-1) (EC 5.2.1.8) (Cyclophilin of 19 kDa 1) (Rotamase cyclophilin-3) |
| *Arabidopsis thaliana* | Q39033 | Phosphoinositide phospholipase C 2 (EC 3.1.4.11) (Phosphoinositide phospholipase PLC2) (AtPLC2) (PI-PLC2) |
| *Arabidopsis thaliana* | Q39085 | Delta(24)-sterol reductase (EC 1.3.1.72) (Cell elongation protein DIMINUTO) (Cell elongation protein Dwarf1) (Protein CABBAGE1) (Protein ENHANCED VERY-LOW-FLUENCE RESPONSE 1) |
| *Arabidopsis thaliana* | Q39228 | Sugar transport protein 4 (Hexose transporter 4) |
| *Arabidopsis thaliana* | Q39241 | Thioredoxin H5 (AtTrxh5) (Protein LOCUS OF INSENSITIVITY TO VICTORIN 1) (Thioredoxin 5) (AtTRX5) |
| *Arabidopsis thaliana* | Q39258 | V-type proton ATPase subunit E1 (V-ATPase subunit E1) (Protein EMBRYO DEFECTIVE 2448) (Vacuolar H(+)-ATPase subunit E isoform 1) (Vacuolar proton pump subunit E1) |
| *Arabidopsis thaliana* | Q42112 | 60S acidic ribosomal protein P0-2 |
| *Arabidopsis thaliana* | Q42403 | Thioredoxin H3 (AtTrxh3) (Thioredoxin 3) (AtTRX3) |
| *Arabidopsis thaliana* | Q42479 | Calcium-dependent protein kinase 3 (EC 2.7.11.1) (Calcium-dependent protein kinase isoform CDPK6) (AtCDPK6) |
| *Arabidopsis thaliana* | Q42547 | Catalase-3 (EC 1.11.1.6) |
| *Arabidopsis thaliana* | Q56WH1 | Tubulin alpha-3 chain |
| *Arabidopsis thaliana* | Q56WK6 | Patellin-1 |
| *Arabidopsis thaliana* | Q56X75 | CASP-like protein 4D2 (AtCASPL4D2) |
| *Arabidopsis thaliana* | Q56ZI2 | Patellin-2 |
| *Arabidopsis thaliana* | Q7Y208 | Glycerophosphodiester phosphodiesterase GDPDL1 (EC 3.1.4.46) (Glycerophosphodiester phosphodiesterase-like 1) (ATGDPDL1) (Glycerophosphodiesterase-like 3) (Protein SHV3-LIKE 2) |
| *Arabidopsis thaliana* | Q84VZ5 | Uncharacterized GPI-anchored protein At5g19240 |
| *Arabidopsis thaliana* | Q84WU7 | Eukaryotic aspartyl protease family protein (Putative uncharacterized protein At3g51330) |
| *Arabidopsis thaliana* | Q8GUL8 | Uncharacterized GPI-anchored protein At5g19230 |
| *Arabidopsis thaliana* | Q8GYA4 | Cysteine-rich receptor-like protein kinase 10 (Cysteine-rich RLK10) (EC 2.7.11.—) (Receptor-like protein kinase 4) |
| *Arabidopsis thaliana* | Q8GYN5 | RPM1-interacting protein 4 |
| *Arabidopsis thaliana* | Q8GZ99 | At5g49760 (Leucine-rich repeat protein kinase family protein) (Leucine-rich repeat receptor-like protein kinase) (Putative receptor protein kinase) |
| *Arabidopsis thaliana* | Q8L636 | Sodium/calcium exchanger NCL (Na(+)/Ca(2+)-exchange protein NCL) (Protein NCX-like) (AtNCL) |
| *Arabidopsis thaliana* | Q8L7S1 | At1g45200 (At1g45200/At1g45200) (Triacylglycerol lipase-like 1) |
| *Arabidopsis thaliana* | Q8LAA6 | Probable aquaporin PIP1-5 (AtPIP1; 5) (Plasma membrane intrinsic protein 1d) (PIP1d) |
| *Arabidopsis thaliana* | Q8LCP6 | Endoglucanase 10 (EC 3.2.1.4) (Endo-1,4-beta glucanase 10) |
| *Arabidopsis thaliana* | Q8RWV0 | Transketolase-1, chloroplastic (TK) (EC 2.2.1.1) |
| *Arabidopsis thaliana* | Q8S8Q6 | Tetraspanin-8 |
| *Arabidopsis thaliana* | Q8VZG8 | MDIS1-interacting receptor like kinase 2 (AtMIK2) (Probable LRR receptor-like serine/threonine-protein kinase At4g08850) (EC 2.7.11.1) |

APPENDIX-continued

Table 13: Plant EV-Markers

| | | |
|---|---|---|
| Arabidopsis thaliana | Q8VZU2 | Syntaxin-132 (AtSYP132) |
| Arabidopsis thaliana | Q8W4E2 | V-type proton ATPase subunit B3 (V-ATPase subunit B3) (Vacuolar H(+)-ATPase subunit B isoform 3) (Vacuolar proton pump subunit B3) |
| Arabidopsis thaliana | Q8W4S4 | V-type proton ATPase subunit a3 (V-ATPase subunit a3) (V-type proton ATPase 95 kDa subunit a isoform 3) (V-ATPase 95 kDa isoform a3) (Vacuolar H(+)-ATPase subunit a isoform 3) (Vacuolar proton pump subunit a3) (Vacuolar proton translocating ATPase 95 kDa subunit a isoform 3) |
| Arabidopsis thaliana | Q93VG5 | 40S ribosomal protein S8-1 |
| Arabidopsis thaliana | Q93XY5 | Tetraspanin-18 (TOM2A homologous protein 2) |
| Arabidopsis thaliana | Q93YS4 | ABC transporter G family member 22 (ABC transporter ABCG.22) (AtABCG22) (White-brown complex homolog protein 23) (AtWBC23) |
| Arabidopsis thaliana | Q93Z08 | Glucan endo-1,3-beta-glucosidase 6 (EC 3.2.1.39) ((1->3)-beta-glucan endohydrolase 6) ((1->3)-beta-glucanase 6) (Beta-1,3-endoglucanase 6) (Beta-1,3-glucanase 6) |
| Arabidopsis thaliana | Q940M8 | 3-oxo-5-alpha-steroid 4-dehydrogenase (DUF1295) (At1g73650/F25P22_7) |
| Arabidopsis thaliana | Q944A7 | Probable serine/threonine-protein kinase At4g35230 (EC 2.7.11.1) |
| Arabidopsis thaliana | Q944G5 | Protein NRT1/PTR FAMILY 2.10 (AtNPF2.10) (Protein GLUCOSINOLATE TRANSPORTER-1) |
| Arabidopsis thaliana | Q94AZ2 | Sugar transport protein 13 (Hexose transporter 13) (Multicopy suppressor of snf4 deficiency protein 1) |
| Arabidopsis thaliana | Q94BT2 | Auxin-induced in root cultures protein 12 |
| Arabidopsis thaliana | Q94CE4 | Beta carbonic anhydrase 4 (AtbCA4) (AtbetaCA4) (EC 4.2.1.1) (Beta carbonate dehydratase 4) |
| Arabidopsis thaliana | Q94KI8 | Two pore calcium channel protein 1 (Calcium channel protein 1) (AtCCH1) (Fatty acid oxygenation up-regulated protein 2) (Voltage-dependent calcium channel protein TPC1) (AtTPC1) |
| Arabidopsis thaliana | Q96262 | Plasma membrane-associated cation-binding protein 1 (AtPCAP1) (Microtubule-destabilizing protein 25) |
| Arabidopsis thaliana | Q9C5Y0 | Phospholipase D delta (AtPLDdelta) (PLD delta) (EC 3.1.4.4) |
| Arabidopsis thaliana | Q9C7F7 | Non-specific lipid transfer protein GPI-anchored 1 (AtLTPG-1) (Protein LTP-GPI-ANCHORED 1) |
| Arabidopsis thaliana | Q9C821 | Proline-rich receptor-like protein kinase PERK15 (EC 2.7.11.1) (Proline-rich extensin-like receptor kinase 15) (AtPERK15) |
| Arabidopsis thaliana | Q9C8G5 | CSC1-like protein ERD4 (Protein EARLY-RESPONSIVE TO DEHYDRATION STRESS 4) |
| Arabidopsis thaliana | Q9C9C5 | 60S ribosomal protein L6-3 |
| Arabidopsis thaliana | Q9CAR7 | Hypersensitive-induced response protein 2 (AtHIR2) |
| Arabidopsis thaliana | Q9FFH6 | Fasciclin-like arabinogalactan protein 13 |
| Arabidopsis thaliana | Q9FGT8 | Temperature-induced lipocalin-1 (AtTIL1) |
| Arabidopsis thaliana | Q9FJ62 | Glycerophosphodiester phosphodiesterase GDPDL4 (EC 3.1.4.46) (Glycerophosphodiester phosphodiesterase-like 4) (ATGDPDL4) (Glycerophosphodiesterase-like 1) (Protein SHV3-LIKE 1) |
| Arabidopsis thaliana | Q9FK68 | Ras-related protein RABA1c (AtRABA1c) |
| Arabidopsis thaliana | Q9FKS8 | Lysine histidine transporter 1 |
| Arabidopsis thaliana | Q9FM65 | Fasciclin-like arabinogalactan protein 1 |
| Arabidopsis thaliana | Q9FNH6 | NDR1/HIN1-like protein 3 |
| Arabidopsis thaliana | Q9FRL3 | Sugar transporter ERD6-like 6 |
| Arabidopsis thaliana | Q9FWR4 | Glutathione S-transferase DHAR1, mitochondrial (EC 2.5.1.18) (Chloride intracellular channel homolog 1) (CLIC homolog 1) (Glutathione-dependent dehydroascorbate reductase 1) (AtDHAR1) (GSH-dependent dehydroascorbate reductase 1) (mtDHAR) |
| Arabidopsis thaliana | Q9FX54 | Glyceraldehyde-3-phosphate dehydrogenase GAPC2, cytosolic (EC 1.2.1.12) (NAD-dependent glyceraldehydephosphate dehydrogenase C subunit 2) |
| Arabidopsis thaliana | Q9LE22 | Probable calcium-binding protein CML27 (Calmodulin-like protein 27) |
| Arabidopsis thaliana | Q9LEX1 | At3g61050 (CaLB protein) (Calcium-dependent lipid-binding (CaLB domain) family protein) |
| Arabidopsis thaliana | Q9LF79 | Calcium-transporting ATPase 8, plasma membrane-type (EC 3.6.3.8) (Ca(2+)-ATPase isoform 8) |
| Arabidopsis thaliana | Q9LJG3 | GDSL esterase/lipase ESM1 (EC 3.1.1.—) (Extracellular lipase ESM1) (Protein EPITHIOSPECIFIER MODIFIER 1) (AtESM1) |
| Arabidopsis thaliana | Q9LJI5 | V-type proton ATPase subunit d1 (V-ATPase subunit d1) (Vacuolar H(+)-ATPase subunit d isoform 1) (Vacuolar proton pump subunit d1) |
| Arabidopsis thaliana | Q9LME4 | Probable protein phosphatase 2C 9 (AtPP2C09) (EC 3.1.3.16) (Phytochrome-associated protein phosphatase 2C) (PAPP2C) |

APPENDIX-continued

Table 13: Plant EV-Markers

| | | |
|---|---|---|
| *Arabidopsis thaliana* | Q9LNP3 | At1g17620/F11A6_23 (F1L3.32) (Late embryogenesis abundant (LEA) hydroxyproline-rich glycoprotein family) (Putative uncharacterized protein At1g17620) |
| *Arabidopsis thaliana* | Q9LNW1 | Ras-related protein RABA2b (AtRABA2b) |
| *Arabidopsis thaliana* | Q9LQU2 | Protein PLANT CADMIUM RESISTANCE 1 (AtPCR1) |
| *Arabidopsis thaliana* | Q9LQU4 | Protein PLANT CADMIUM RESISTANCE 2 (AtPCR2) |
| *Arabidopsis thaliana* | Q9LR30 | Glutamate--glyoxylate aminotransferase 1 (AtGGT2) (EC 2.6.1.4) (Alanine aminotransferase GGT1) (EC 2.6.1.2) (Alanine--glyoxylate aminotransferase GGT1) (EC 2.6.1.44) (Alanine-2-oxoglutarate aminotransferase 1) (EC 2.6.1.—) |
| *Arabidopsis thaliana* | Q9LSI9 | Inactive LRR receptor-like serine/threonine-protein kinase BIR2 (Protein BAK1-INTERACTING RECEPTOR-LIKE KINASE 2) |
| *Arabidopsis thaliana* | Q9LSQ5 | NAD(P)H dehydrogenase (quinone) FQR1 (EC 1.6.5.2) (Flavodoxin-like quinone reductase 1) |
| *Arabidopsis thaliana* | Q9LUT0 | Protein kinase superfamily protein (Putative uncharacterized protein At3g17410) (Serine/threonine protein kinase-like protein) |
| *Arabidopsis thaliana* | Q9LV48 | Proline-rich receptor-like protein kinase PERK1 (EC 2.7.11.1) (Proline-rich extensin-like receptor kinase 1) (AtPERK1) |
| *Arabidopsis thaliana* | Q9LX65 | V-type proton ATPase subunit H (V-ATPase subunit H) (Vacuolar H(+)-ATPase subunit H) (Vacuolar proton pump subunit H) |
| *Arabidopsis thaliana* | Q9LYG3 | NADP-dependent malic enzyme 2 (AtNADP-ME2) (NADP-malic enzyme 2) (EC 1.1.1.40) |
| *Arabidopsis thaliana* | Q9M088 | Glucan endo-1,3-beta-glucosidase 5 (EC 3.2.1.39) ((1->3)-beta-glucan endohydrolase 5) ((1->3)-beta-glucanase 5) (Beta-1,3-endoglucanase 5) (Beta-1,3-glucanase 5) |
| *Arabidopsis thaliana* | Q9M2D8 | Uncharacterized protein At3g61260 |
| *Arabidopsis thaliana* | Q9M386 | Late embryogenesis abundant (LEA) hydroxyproline-rich glycoprotein family (Putative uncharacterized protein At3g54200) (Putative uncharacterized protein F24B22.160) |
| *Arabidopsis thaliana* | Q9M390 | Protein NRT1/PTR FAMILY 8.1 (AtNPF8.1) (Peptide transporter PTR1) |
| *Arabidopsis thaliana* | Q9M5P2 | Secretory carrier-associated membrane protein 3 (AtSC3) (Secretory carrier membrane protein 3) |
| *Arabidopsis thaliana* | Q9M8T0 | Probable inactive receptor kinase At3g02880 |
| *Arabidopsis thaliana* | Q9SDS7 | V-type proton ATPase subunit C (V-ATPase subunit C) (Vacuolar H(+)-ATPase subunit C) (Vacuolar proton pump subunit C) |
| *Arabidopsis thaliana* | Q9SEL6 | Vesicle transport v-SNARE 11 (AtVTI11) (Protein SHOOT GRAVITROPISM 4) (Vesicle soluble NSF attachment protein receptor VTI1a) (AtVTI1a) (Vesicle transport v-SNARE protein VTI1a) |
| *Arabidopsis thaliana* | Q9SF29 | Syntaxin-71 (AtSYP71) |
| *Arabidopsis thaliana* | Q9SF85 | Adenosine kinase 1 (AK 1) (EC 2.7.1.20) (Adenosine 5'-phosphotransferase 1) |
| *Arabidopsis thaliana* | Q9SIE7 | PLAT domain-containing protein 2 (AtPLAT2) (PLAT domain protein 2) |
| *Arabidopsis thaliana* | Q9SIM4 | 60S ribosomal protein L14-1 |
| *Arabidopsis thaliana* | Q9SIU8 | Probable protein phosphatase 2C 20 (AtPP2C20) (EC 3.1.3.16) (AtPPC3; 1.2) |
| *Arabidopsis thaliana* | Q9SJ81 | Fasciclin-like arabinogalactan protein 7 |
| *Arabidopsis thaliana* | Q9SKB2 | Leucine-rich repeat receptor-like serine/threonine/tyrosine-protein kinase SOBIR1 (EC 2.7.10.1) (EC 2.7.11.1) (Protein EVERSHED) (Protein SUPPRESSOR OF BIR1-1) |
| *Arabidopsis thaliana* | Q9SKR2 | Synaptotagmin-1 (NTMC2T1.1) (Synaptotagmin A) |
| *Arabidopsis thaliana* | Q9SLF7 | 60S acidic ribosomal protein P2-2 |
| *Arabidopsis thaliana* | Q9SPE6 | Alpha-soluble NSF attachment protein 2 (Alpha-SNAP2) (N-ethylmaleimide-sensitive factor attachment protein alpha 2) |
| *Arabidopsis thaliana* | Q9SRH6 | Hypersensitive-induced response protein 3 (AtHIR3) |
| *Arabidopsis thaliana* | Q9SRY5 | Glutathione S-transferase F7 (EC 2.5.1.18) (AtGSTF8) (GST class-phi member 7) (Glutathione S-transferase 11) |
| *Arabidopsis thaliana* | Q9SRZ6 | Cytosolic isocitrate dehydrogenase [NADP] (EC 1.1.1.42) |
| *Arabidopsis thaliana* | Q9SSK5 | MLP-like protein 43 |
| *Arabidopsis thaliana* | Q9SU13 | Fasciclin-like arabinogalactan protein 2 |
| *Arabidopsis thaliana* | Q9SU40 | Monocopper oxidase-like protein SKU5 (Skewed roots) |
| *Arabidopsis thaliana* | Q9SUR6 | Cystine lyase CORI3 (EC 4.4.1.35) (Protein CORONATINE INDUCED 3) (Protein JASMONIC ACID RESPONSIVE 2) (Tyrosine aminotransferase CORI3) |
| *Arabidopsis thaliana* | Q9SVC2 | Syntaxin-122 (AtSYP122) (Synt4) |
| *Arabidopsis thaliana* | Q9SVF0 | Putative uncharacterized protein AT4g38350 (Putative uncharacterized protein F22I13.120) |
| *Arabidopsis thaliana* | Q9SW40 | Major facilitator superfamily protein (Putative uncharacterized protein AT4g34950) (Putative uncharacterized protein T11I11.190) |

APPENDIX-continued

Table 13: Plant EV-Markers

| | | |
|---|---|---|
| *Arabidopsis thaliana* | Q9SYT0 | Annexin D1 (AnnAt1) (Annexin A1) |
| *Arabidopsis thaliana* | Q9SZ11 | Glycerophosphodiester phosphodiesterase GDPDL3 (EC 3.1.4.46) (Glycerophosphodiester phosphodiesterase-like 3) (ATGDPDL3) (Glycerophosphodiesterase-like 2) (Protein MUTANT ROOT HAIR 5) (Protein SHAVEN 3) |
| *Arabidopsis thaliana* | Q9SZN1 | V-type proton ATPase subunit B2 (V-ATPase subunit B2) (Vacuolar H(+)-ATPase subunit B isoform 2) (Vacuolar proton pump subunit B2) |
| *Arabidopsis thaliana* | Q9SZP6 | AT4g38690/F20M13_250 (PLC-like phosphodiesterases superfamily protein) (Putative uncharacterized protein AT4g38690) (Putative uncharacterized protein F20M13.250) |
| *Arabidopsis thaliana* | Q9SZR1 | Calcium-transporting ATPase 10, plasma membrane-type (EC 3.6.3.8) (Ca(2+)-ATPase isoform 10) |
| *Arabidopsis thaliana* | Q9T053 | Phospholipase D gamma 1 (AtPLDgamma1) (PLD gamma 1) (EC 3.1.4.4) (Choline phosphatase) (Lecithinase D) (Lipophosphodiesterase II) |
| *Arabidopsis thaliana* | Q9T076 | Early nodulin-like protein 2 (Phytocyanin-like protein) |
| *Arabidopsis thaliana* | Q9T0A0 | Long chain acyl-CoA synthetase 4 (EC 6.2.1.3) |
| *Arabidopsis thaliana* | Q9T0G4 | Putative uncharacterized protein AT4g10060 (Putative uncharacterized protein T5L19.190) |
| *Arabidopsis thaliana* | Q9XEE2 | Annexin D2 (AnnAt2) |
| *Arabidopsis thaliana* | Q9XGM1 | V-type proton ATPase subunit D (V-ATPase subunit D) (Vacuolar H(+)-ATPase subunit D) (Vacuolar proton pump subunit D) |
| *Arabidopsis thaliana* | Q9XI93 | At1g13930/F16A14.27 (F16A14.14) (F7A19.2 protein) (Oleosin-B3-like protein) |
| *Arabidopsis thaliana* | Q9XIE2 | ABC transporter G family member 36 (ABC transporter ABCG.36) (AtABCG36) (Pleiotropic drug resistance protein 8) (Protein PENETRATION 3) |
| *Arabidopsis thaliana* | Q9ZPZ4 | Putative uncharacterized protein (Putative uncharacterized protein At1g09310) (T31J12.3 protein) |
| *Arabidopsis thaliana* | Q9ZQX4 | V-type proton ATPase subunit F (V-ATPase subunit F) (V-ATPase 14 kDa subunit) (Vacuolar H(+)-ATPase subunit F) (Vacuolar proton pump subunit F) |
| *Arabidopsis thaliana* | Q9ZSA2 | Calcium-dependent protein kinase 21 (EC 2.7.11.1) |
| *Arabidopsis thaliana* | Q9ZSD4 | Syntaxin-121 (AtSYP121) (Syntaxin-related protein At-Syr1) |
| *Arabidopsis thaliana* | Q9ZV07 | Probable aquaporin PIP2-6 (Plasma membrane intrinsic protein 2-6) (AtPIP2; 6) (Plasma membrane intrinsic protein 2e) (PIP2e) [Cleaved into: Probable aquaporin PIP2-6, N-terminally processed] |
| *Arabidopsis thaliana* | Q9ZVF3 | MLP-like protein 328 |
| *Arabidopsis thaliana* | Q9ZWA8 | Fasciclin-like arabinogalactan protein 9 |
| *Arabidopsis thaliana* | Q9ZSD4 | SYR1, Syntaxin Related Protein 1, also known as SYP121, PENETRATION1/PEN1 (Protein PENETRATION 1) |
| *Citrus lemon* | A1ECK0 | Putative glutaredoxin |
| *Citrus lemon* | A9YVC9 | Pyrophosphate--fructose 6-phosphate 1-phosphotransferase subunit beta (PFP) (EC 2.7.1.90) (6-phosphofructokinase, pyrophosphate dependent) (PPi-PFK) (Pyrophosphate-dependent 6-phosphofructose-1-kinase) |
| *Citrus lemon* | B2YGY1 | Glycosyltransferase (EC 2.4.1.—) |
| *Citrus lemon* | B6DZD3 | Glutathione S-transferase Tau2 (Glutathione transferase Tau2) |
| *Citrus lemon* | C3VIC2 | Translation elongation factor |
| *Citrus lemon* | C8CPS0 | Importin subunit alpha |
| *Citrus lemon* | D3JWB5 | Flavanone 3-hydroxylase |
| *Citrus lemon* | E0ADY2 | Putative caffeic acid O-methyltransferase |
| *Citrus lemon* | E5DK62 | ATP synthase subunit alpha (Fragment) |
| *Citrus lemon* | E9M5S3 | Putative L-galactose-1-phosphate phosphatase |
| *Citrus lemon* | F1CGQ9 | Heat shock protein 90 |
| *Citrus lemon* | F8WL79 | Aminopeptidase (EC 3.4.11.—) |
| *Citrus lemon* | F8WL86 | Heat shock protein |
| *Citrus lemon* | K9JG59 | Abscisic acid stress ripening-related protein |
| *Citrus lemon* | Q000W4 | Fe(III)-chelate reductase |
| *Citrus lemon* | Q39538 | Heat shock protein (Fragment) |
| *Citrus lemon* | Q5UEN6 | Putative signal recognition particle protein |
| *Citrus lemon* | Q8GV08 | Dehydrin |
| *Citrus lemon* | Q8L893 | Cytosolic phosphoglucomutase (Fragment) |
| *Citrus lemon* | Q8S990 | Polygalacturonase-inhibiting protein |
| *Citrus lemon* | Q8W3U6 | Polygalacturonase-inhibitor protein |
| *Citrus lemon* | Q93XL8 | Dehydrin COR15 |
| *Citrus lemon* | Q941Q1 | Non-symbiotic hemoglobin class 1 |
| *Citrus lemon* | Q9MBF3 | Glycine-rich RNA-binding protein |
| *Citrus lemon* | Q9SP55 | V-type proton ATPase subunit G (V-ATPase subunit G) (Vacuolar proton pump subunit G) |
| *Citrus lemon* | Q9THJ8 | Ribulose bisphosphate carboxylase large chain (EC 4.1.1.39) (Fragment) |

APPENDIX-continued

Table 13: Plant EV-Markers

| | | |
|---|---|---|
| Citrus lemon | Q9ZST2 | Pyrophosphate--fructose 6-phosphate 1-phosphotransferase subunit alpha (PFP) (6-phosphofructokinase, pyrophosphate dependent) (PPi-PFK) (Pyrophosphate-dependent 6-phosphofructose-1-kinase) |
| Citrus lemon | Q9ZWH6 | Polygalacturonase inhibitor |
| Citrus lemon | S5DXI9 | Nucleocapsid protein |
| Citrus lemon | S5NFC6 | GTP cyclohydrolase |
| Citrus lemon | V4RG42 | Uncharacterized protein |
| Citrus lemon | V4RGP4 | Uncharacterized protein |
| Citrus lemon | V4RHN8 | Uncharacterized protein |
| Citrus lemon | V4RJ07 | Uncharacterized protein |
| Citrus lemon | V4RJK9 | Adenosylhomocysteinase (EC 3.3.1.1) |
| Citrus lemon | V4RJM1 | Uncharacterized protein |
| Citrus lemon | V4RJX1 | 40S ribosomal protein S6 |
| Citrus lemon | V4RLB2 | Uncharacterized protein |
| Citrus lemon | V4RMX8 | Uncharacterized protein |
| Citrus lemon | V4RNA5 | Uncharacterized protein |
| Citrus lemon | V4RP81 | Glycosyltransferase (EC 2.4.1.—) |
| Citrus lemon | V4RPZ5 | Adenylyl cyclase-associated protein |
| Citrus lemon | V4RTN9 | Histone H4 |
| Citrus lemon | V4RUZ4 | Phosphoserine aminotransferase (EC 2.6.1.52) |
| Citrus lemon | V4RVF6 | Uncharacterized protein |
| Citrus lemon | V4RXD4 | Uncharacterized protein |
| Citrus lemon | V4RXG2 | Uncharacterized protein |
| Citrus lemon | V4RYA0 | Uncharacterized protein |
| Citrus lemon | V4RYE3 | Uncharacterized protein |
| Citrus lemon | V4RYH3 | Uncharacterized protein |
| Citrus lemon | V4RYX8 | Uncharacterized protein |
| Citrus lemon | V4RZ12 | Coatomer subunit beta' |
| Citrus lemon | V4RZ89 | Uncharacterized protein |
| Citrus lemon | V4RZE3 | Uncharacterized protein |
| Citrus lemon | V4RZF3 | 1,2-dihydroxy-3-keto-5-methylthiopentene dioxygenase (EC 1.13.11.54) (Acireductone dioxygenase (Fe(2+)-requiring)) (ARD) (Fe-ARD) |
| Citrus lemon | V4RZM7 | Uncharacterized protein |
| Citrus lemon | V4RZX6 | Uncharacterized protein |
| Citrus lemon | V4S1V0 | Uncharacterized protein |
| Citrus lemon | V4S2B6 | Uncharacterized protein |
| Citrus lemon | V4S2N1 | Uncharacterized protein |
| Citrus lemon | V4S2S5 | Uncharacterized protein (Fragment) |
| Citrus lemon | V4S346 | Uncharacterized protein |
| Citrus lemon | V4S3T8 | Uncharacterized protein |
| Citrus lemon | V4S409 | Cyanate hydratase (Cyanase) (EC 4.2.1.104) (Cyanate hydrolase) (Cyanate lyase) |
| Citrus lemon | V4S4E4 | Histone H2B |
| Citrus lemon | V4S4F6 | Flavin-containing monooxygenase (EC 1.—.—.—) |
| Citrus lemon | V4S4J1 | Uncharacterized protein |
| Citrus lemon | V4S4K9 | Uncharacterized protein |
| Citrus lemon | V4S535 | Proteasome subunit alpha type (EC 3.4.25.1) |
| Citrus lemon | V4S5A8 | Isocitrate dehydrogenase [NADP] (EC 1.1.1.42) |
| Citrus lemon | V4S5G8 | Uncharacterized protein |
| Citrus lemon | V4S5I6 | Uncharacterized protein |
| Citrus lemon | V4S5N4 | Uncharacterized protein (Fragment) |
| Citrus lemon | V4S5Q3 | Uncharacterized protein |
| Citrus lemon | V4S5X8 | Uncharacterized protein |
| Citrus lemon | V4S5Y1 | Uncharacterized protein |
| Citrus lemon | V4S6P4 | Calcium-transporting ATPase (EC 3.6.3.8) |
| Citrus lemon | V4S6W0 | Uncharacterized protein |
| Citrus lemon | V4S6W7 | Uncharacterized protein (Fragment) |
| Citrus lemon | V4S6Y4 | Uncharacterized protein |
| Citrus lemon | V4S773 | Ribosomal protein L19 |
| Citrus lemon | V4S7U0 | Uncharacterized protein |
| Citrus lemon | V4S7U5 | Uncharacterized protein |
| Citrus lemon | V4S7W4 | Pyruvate kinase (EC 2.7.1.40) |
| Citrus lemon | V4S885 | Uncharacterized protein |
| Citrus lemon | V4S8T3 | Peptidyl-prolyl cis-trans isomerase (PPIase) (EC 5.2.1.8) |
| Citrus lemon | V4S920 | Uncharacterized protein |
| Citrus lemon | V4S999 | Uncharacterized protein |
| Citrus lemon | V4S9G5 | Phosphoglycerate kinase (EC 2.7.2.3) |
| Citrus lemon | V4S9Q6 | Beta-amylase (EC 3.2.1.2) |
| Citrus lemon | V4SA44 | Serine/threonine-protein phosphatase (EC 3.1.3.16) |
| Citrus lemon | V4SAE0 | Alpha-1,4 glucan phosphorylase (EC 2.4.1.1) |
| Citrus lemon | V4SAF6 | Uncharacterized protein |
| Citrus lemon | V4SAI9 | Eukaryotic translation initiation factor 3 subunit M (eIF3m) |
| Citrus lemon | V4SAJ5 | Ribosomal protein |
| Citrus lemon | V4SAR3 | Uncharacterized protein |
| Citrus lemon | V4SB37 | Uncharacterized protein |
| Citrus lemon | V4SBI0 | Elongation factor 1-alpha |

APPENDIX-continued

Table 13: Plant EV-Markers

| | | |
|---|---|---|
| *Citrus lemon* | V4SBI8 | D-3-phosphoglycerate dehydrogenase (EC 1.1.1.95) |
| *Citrus lemon* | V4SBL9 | Polyadenylate-binding protein (PABP) |
| *Citrus lemon* | V4SBR1 | S-formylglutathione hydrolase (EC 3.1.2.12) |
| *Citrus lemon* | V4SBR6 | Uncharacterized protein |
| *Citrus lemon* | V4SCG7 | Uncharacterized protein |
| *Citrus lemon* | V4SCJ2 | Uncharacterized protein |
| *Citrus lemon* | V4SCQ6 | Peptidyl-prolyl cis-trans isomerase (PPIase) (EC 5.2.1.8) |
| *Citrus lemon* | V4SDJ8 | Uncharacterized protein |
| *Citrus lemon* | V4SE41 | Protein DETOXIFICATION (Multidrug and toxic compound extrusion protein) |
| *Citrus lemon* | V4SE90 | Uncharacterized protein |
| *Citrus lemon* | V4SED1 | Succinate dehydrogenase [ubiquinone] flavoprotein subunit, mitochondrial (EC 1.3.5.1) |
| *Citrus lemon* | V4SEI1 | Uncharacterized protein |
| *Citrus lemon* | V4SEN9 | Uncharacterized protein |
| *Citrus lemon* | V4SEX8 | Uncharacterized protein |
| *Citrus lemon* | V4SF31 | Uncharacterized protein |
| *Citrus lemon* | V4SF69 | 40S ribosomal protein S24 |
| *Citrus lemon* | V4SF76 | Cysteine synthase (EC 2.5.1.47) |
| *Citrus lemon* | V4SFK3 | Uncharacterized protein |
| *Citrus lemon* | V4SFL4 | Uncharacterized protein |
| *Citrus lemon* | V4SFW2 | Uncharacterized protein |
| *Citrus lemon* | V4SGC9 | Uncharacterized protein |
| *Citrus lemon* | V4SGJ4 | Uncharacterized protein |
| *Citrus lemon* | V4SGN4 | Uncharacterized protein |
| *Citrus lemon* | V4SGV6 | Uncharacterized protein |
| *Citrus lemon* | V4SGV7 | Uncharacterized protein |
| *Citrus lemon* | V4SHH1 | Plasma membrane ATPase (EC 3.6.3.6) (Fragment) |
| *Citrus lemon* | V4SHI2 | Uncharacterized protein |
| *Citrus lemon* | V4SHJ3 | Uncharacterized protein |
| *Citrus lemon* | V4SI86 | Uncharacterized protein |
| *Citrus lemon* | V4SI88 | Uncharacterized protein |
| *Citrus lemon* | V4SIA2 | Uncharacterized protein |
| *Citrus lemon* | V4SIC1 | Phospholipase D (EC 3.1.4.4) |
| *Citrus lemon* | V4SJ14 | Uncharacterized protein |
| *Citrus lemon* | V4SJ48 | Uncharacterized protein |
| *Citrus lemon* | V4SJ69 | Uncharacterized protein |
| *Citrus lemon* | V4SJD9 | Uncharacterized protein |
| *Citrus lemon* | V4SJS7 | Uncharacterized protein |
| *Citrus lemon* | V4SJT5 | Uncharacterized protein |
| *Citrus lemon* | V4SKA2 | Uncharacterized protein |
| *Citrus lemon* | V4SKG4 | Glucose-6-phosphate isomerase (EC 5.3.1.9) |
| *Citrus lemon* | V4SKJ1 | Uncharacterized protein |
| *Citrus lemon* | V4SL90 | Uncharacterized protein |
| *Citrus lemon* | V4SLC6 | Proteasome subunit beta type (EC 3.4.25.1) |
| *Citrus lemon* | V4SLI7 | Uncharacterized protein |
| *Citrus lemon* | V4SLQ6 | Uncharacterized protein |
| *Citrus lemon* | V4SMD8 | Uncharacterized protein |
| *Citrus lemon* | V4SMN7 | Uncharacterized protein |
| *Citrus lemon* | V4SMV5 | Uncharacterized protein |
| *Citrus lemon* | V4SN00 | Uncharacterized protein |
| *Citrus lemon* | V4SNA9 | Uncharacterized protein |
| *Citrus lemon* | V4SNC1 | Uncharacterized protein |
| *Citrus lemon* | V4SNC4 | Aconitate hydratase (Aconitase) (EC 4.2.1.3) |
| *Citrus lemon* | V4SNZ3 | Uncharacterized protein |
| *Citrus lemon* | V4SP86 | Uncharacterized protein |
| *Citrus lemon* | V4SPM1 | 40S ribosomal protein S12 |
| *Citrus lemon* | V4SPW4 | 40S ribosomal protein S4 |
| *Citrus lemon* | V4SQ71 | Uncharacterized protein |
| *Citrus lemon* | V4SQ89 | Uncharacterized protein |
| *Citrus lemon* | V4SQ92 | Uncharacterized protein |
| *Citrus lemon* | V4SQC7 | Peroxidase (EC 1.11.1.7) |
| *Citrus lemon* | V4SQG3 | Uncharacterized protein |
| *Citrus lemon* | V4SR15 | Uncharacterized protein |
| *Citrus lemon* | V4SRN3 | Transmembrane 9 superfamily member |
| *Citrus lemon* | V4SS09 | Uncharacterized protein |
| *Citrus lemon* | V4SS11 | Uncharacterized protein |
| *Citrus lemon* | V4SS50 | Uncharacterized protein |
| *Citrus lemon* | V4SSB6 | Uncharacterized protein |
| *Citrus lemon* | V4SSB8 | Proteasome subunit alpha type (EC 3.4.25.1) |
| *Citrus lemon* | V4SSL7 | Uncharacterized protein |
| *Citrus lemon* | V4SSQ1 | Uncharacterized protein |
| *Citrus lemon* | V4SST6 | Uncharacterized protein |
| *Citrus lemon* | V4SSW9 | Uncharacterized protein |
| *Citrus lemon* | V4SSX5 | Uncharacterized protein |
| *Citrus lemon* | V4SU82 | Uncharacterized protein |
| *Citrus lemon* | V4SUD3 | Uncharacterized protein |
| *Citrus lemon* | V4SUL7 | Uncharacterized protein |

APPENDIX-continued

Table 13: Plant EV-Markers

| | | |
|---|---|---|
| *Citrus lemon* | V4SUP3 | Uncharacterized protein |
| *Citrus lemon* | V4SUT4 | UDP-glucose 6-dehydrogenase (EC 1.1.1.22) |
| *Citrus lemon* | V4SUY5 | Uncharacterized protein |
| *Citrus lemon* | V4SV60 | Serine/threonine-protein phosphatase (EC 3.1.3.16) |
| *Citrus lemon* | V4SV61 | Uncharacterized protein |
| *Citrus lemon* | V4SVI5 | Proteasome subunit alpha type (EC 3.4.25.1) |
| *Citrus lemon* | V4SVI6 | Uncharacterized protein |
| *Citrus lemon* | V4SW04 | Uncharacterized protein (Fragment) |
| *Citrus lemon* | V4SWD9 | Uncharacterized protein |
| *Citrus lemon* | V4SWJ0 | 40S ribosomal protein S3a |
| *Citrus lemon* | V4SWQ9 | Uncharacterized protein |
| *Citrus lemon* | V4SWR9 | Uncharacterized protein |
| *Citrus lemon* | V4SWU9 | Fructose-bisphosphate aldolase (EC 4.1.2.13) |
| *Citrus lemon* | V4SX11 | Uncharacterized protein |
| *Citrus lemon* | V4SX99 | Uncharacterized protein |
| *Citrus lemon* | V4SXC7 | Proteasome subunit alpha type (EC 3.4.25.1) |
| *Citrus lemon* | V4SXQ5 | Uncharacterized protein |
| *Citrus lemon* | V4SXW1 | Beta-adaptin-like protein |
| *Citrus lemon* | V4SXY9 | Uncharacterized protein |
| *Citrus lemon* | V4SY74 | Uncharacterized protein |
| *Citrus lemon* | V4SY90 | Uncharacterized protein |
| *Citrus lemon* | V4SY93 | Uncharacterized protein |
| *Citrus lemon* | V4SYH9 | Uncharacterized protein |
| *Citrus lemon* | V4SYK6 | Uncharacterized protein |
| *Citrus lemon* | V4SZ03 | Uncharacterized protein |
| *Citrus lemon* | V4SZ73 | Uncharacterized protein |
| *Citrus lemon* | V4SZI9 | Uncharacterized protein |
| *Citrus lemon* | V4SZX7 | Uncharacterized protein |
| *Citrus lemon* | V4T057 | Ribosomal protein L15 |
| *Citrus lemon* | V4T0V5 | Eukaryotic translation initiation factor 3 subunit A (eIF3a) (Eukaryotic translation initiation factor 3 subunit 10) |
| *Citrus lemon* | V4T0Y1 | Uncharacterized protein |
| *Citrus lemon* | V4T1Q6 | Uncharacterized protein |
| *Citrus lemon* | V4T1U7 | Uncharacterized protein |
| *Citrus lemon* | V4T2D9 | Uncharacterized protein |
| *Citrus lemon* | V4T2M6 | Tubulin beta chain |
| *Citrus lemon* | V4T3G2 | Uncharacterized protein |
| *Citrus lemon* | V4T3P3 | 6-phosphogluconate dehydrogenase, decarboxylating (EC 1.1.1.44) |
| *Citrus lemon* | V4T3V9 | Uncharacterized protein |
| *Citrus lemon* | V4T3Y6 | Uncharacterized protein |
| *Citrus lemon* | V4T4H3 | Uncharacterized protein |
| *Citrus lemon* | V4T4I7 | Uncharacterized protein |
| *Citrus lemon* | V4T4M7 | Superoxide dismutase [Cu—Zn] (EC 1.15.1.1) |
| *Citrus lemon* | V4T539 | Uncharacterized protein |
| *Citrus lemon* | V4T541 | Uncharacterized protein |
| *Citrus lemon* | V4T576 | Uncharacterized protein |
| *Citrus lemon* | V4T5E1 | Uncharacterized protein |
| *Citrus lemon* | V4T5I3 | Uncharacterized protein |
| *Citrus lemon* | V4T5W7 | Uncharacterized protein |
| *Citrus lemon* | V4T6T5 | 60S acidic ribosomal protein P0 |
| *Citrus lemon* | V4T722 | Uncharacterized protein |
| *Citrus lemon* | V4T785 | Uncharacterized protein |
| *Citrus lemon* | V4T7E2 | Uncharacterized protein |
| *Citrus lemon* | V4T7I7 | Uncharacterized protein |
| *Citrus lemon* | V4T7N0 | Proteasome subunit beta type (EC 3.4.25.1) |
| *Citrus lemon* | V4T7N4 | Uncharacterized protein |
| *Citrus lemon* | V4T7T2 | Uncharacterized protein |
| *Citrus lemon* | V4T7W5 | Uncharacterized protein |
| *Citrus lemon* | V4T825 | Uncharacterized protein |
| *Citrus lemon* | V4T846 | Uncharacterized protein |
| *Citrus lemon* | V4T8E9 | S-acyltransferase (EC 2.3.1.225) (Palmitoyltransferase) |
| *Citrus lemon* | V4T8G2 | Uncharacterized protein |
| *Citrus lemon* | V4T8G9 | Chorismate synthase (EC 4.2.3.5) |
| *Citrus lemon* | V4T8Y6 | Uncharacterized protein |
| *Citrus lemon* | V4T8Y8 | Uncharacterized protein |
| *Citrus lemon* | V4T939 | Carboxypeptidase (EC 3.4.16.—) |
| *Citrus lemon* | V4T957 | Uncharacterized protein |
| *Citrus lemon* | V4T998 | Uncharacterized protein |
| *Citrus lemon* | V4T9B9 | Uncharacterized protein |
| *Citrus lemon* | V4T9Y7 | Uncharacterized protein |
| *Citrus lemon* | V4TA70 | Uncharacterized protein |
| *Citrus lemon* | V4TAF6 | Uncharacterized protein |
| *Citrus lemon* | V4TB09 | Uncharacterized protein |
| *Citrus lemon* | V4TB32 | Uncharacterized protein |
| *Citrus lemon* | V4TB89 | Uncharacterized protein |
| *Citrus lemon* | V4TBN7 | Phosphoinositide phospholipase C (EC 3.1.4.11) |
| *Citrus lemon* | V4TBQ3 | Uncharacterized protein |

APPENDIX-continued

Table 13: Plant EV-Markers

| | | |
|---|---|---|
| *Citrus lemon* | V4TBS4 | Uncharacterized protein |
| *Citrus lemon* | V4TBU3 | Uncharacterized protein |
| *Citrus lemon* | V4TCA6 | Uncharacterized protein |
| *Citrus lemon* | V4TCL3 | Uncharacterized protein |
| *Citrus lemon* | V4TCS5 | Pectate lyase (EC 4.2.2.2) |
| *Citrus lemon* | V4TD99 | Uncharacterized protein |
| *Citrus lemon* | V4TDB5 | Uncharacterized protein |
| *Citrus lemon* | V4TDI2 | Uncharacterized protein |
| *Citrus lemon* | V4TDY3 | Serine/threonine-protein kinase (EC 2.7.11.1) |
| *Citrus lemon* | V4TE72 | Uncharacterized protein |
| *Citrus lemon* | V4TE95 | Uncharacterized protein |
| *Citrus lemon* | V4TEC0 | Uncharacterized protein |
| *Citrus lemon* | V4TED8 | Uncharacterized protein |
| *Citrus lemon* | V4TES4 | Uncharacterized protein |
| *Citrus lemon* | V4TEY9 | Uncharacterized protein |
| *Citrus lemon* | V4TF24 | Proteasome subunit alpha type (EC 3.4.25.1) |
| *Citrus lemon* | V4TF52 | Uricase (EC 1.7.3.3) (Urate oxidase) |
| *Citrus lemon* | V4TFV8 | Catalase (EC 1.11.1.6) |
| *Citrus lemon* | V4TGU1 | Uncharacterized protein |
| *Citrus lemon* | V4TH28 | Uncharacterized protein |
| *Citrus lemon* | V4TH78 | Reticulon-like protein |
| *Citrus lemon* | V4THM9 | Uncharacterized protein |
| *Citrus lemon* | V4TIU2 | Ribulose-phosphate 3-epimerase (EC 5.1.3.1) |
| *Citrus lemon* | V4TIW6 | Uncharacterized protein |
| *Citrus lemon* | V4TIY6 | Uncharacterized protein |
| *Citrus lemon* | V4TIZ5 | Uncharacterized protein |
| *Citrus lemon* | V4TJ75 | Uncharacterized protein |
| *Citrus lemon* | V4TJC3 | Uncharacterized protein |
| *Citrus lemon* | V4TJQ9 | Uncharacterized protein |
| *Citrus lemon* | V4TK29 | NEDD8-activating enzyme E1 regulatory subunit |
| *Citrus lemon* | V4TL04 | Uncharacterized protein |
| *Citrus lemon* | V4TLL5 | Uncharacterized protein |
| *Citrus lemon* | V4TLP6 | Uncharacterized protein |
| *Citrus lemon* | V4TM00 | Uncharacterized protein |
| *Citrus lemon* | V4TM19 | Uncharacterized protein |
| *Citrus lemon* | V4TMB7 | Uncharacterized protein (Fragment) |
| *Citrus lemon* | V4TMD1 | Uncharacterized protein |
| *Citrus lemon* | V4TMD6 | Uncharacterized protein |
| *Citrus lemon* | V4TMV4 | Uncharacterized protein |
| *Citrus lemon* | V4TN30 | Uncharacterized protein |
| *Citrus lemon* | V4TN38 | Uncharacterized protein |
| *Citrus lemon* | V4TNY8 | Uncharacterized protein |
| *Citrus lemon* | V4TP87 | Carbonic anhydrase (EC 4.2.1.1) (Carbonate dehydratase) |
| *Citrus lemon* | V4TPM1 | Homoserine dehydrogenase (HDH) (EC 1.1.1.3) |
| *Citrus lemon* | V4TQB6 | Uncharacterized protein |
| *Citrus lemon* | V4TQM7 | Uncharacterized protein |
| *Citrus lemon* | V4TQR2 | Uncharacterized protein |
| *Citrus lemon* | V4TQV9 | Uncharacterized protein |
| *Citrus lemon* | V4TS21 | Proteasome subunit beta type (EC 3.4.25.1) |
| *Citrus lemon* | V4TS28 | Annexin |
| *Citrus lemon* | V4TSD8 | Uncharacterized protein (Fragment) |
| *Citrus lemon* | V4TSF8 | Uncharacterized protein |
| *Citrus lemon* | V4TSI9 | Uncharacterized protein |
| *Citrus lemon* | V4TT89 | Uncharacterized protein |
| *Citrus lemon* | V4TTA0 | Uncharacterized protein |
| *Citrus lemon* | V4TTR8 | Uncharacterized protein |
| *Citrus lemon* | V4TTV4 | Uncharacterized protein |
| *Citrus lemon* | V4TTZ7 | Uncharacterized protein |
| *Citrus lemon* | V4TU54 | Uncharacterized protein |
| *Citrus lemon* | V4TVB6 | Uncharacterized protein |
| *Citrus lemon* | V4TVG1 | Eukaryotic translation initiation factor 5A (eIF-5A) |
| *Citrus lemon* | V4TVJ4 | Profilin |
| *Citrus lemon* | V4TVM6 | Uncharacterized protein |
| *Citrus lemon* | V4TVM9 | Uncharacterized protein |
| *Citrus lemon* | V4TVP7 | Uncharacterized protein |
| *Citrus lemon* | V4TVT8 | Uncharacterized protein |
| *Citrus lemon* | V4TW14 | Uncharacterized protein |
| *Citrus lemon* | V4TWG9 | T-complex protein 1 subunit delta |
| *Citrus lemon* | V4TWU1 | Probable bifunctional methylthioribulose-1-phosphate dehydratase/enolase-phosphatase E1 [Includes: Enolase-phosphatase E1 (EC 3.1.3.77) (2,3-diketo-5-methylthio-1-phosphopentane phosphatase); Methylthioribulose-1-phosphate dehydratase (MTRu-1-P dehydratase) (EC 4.2.1.109)] |
| *Citrus lemon* | V4TWX8 | Uncharacterized protein |
| *Citrus lemon* | V4TXH0 | Glutamate decarboxylase (EC 4.1.1.15) |
| *Citrus lemon* | V4TXK9 | Uncharacterized protein |
| *Citrus lemon* | V4TXU9 | Thiamine thiazole synthase, chloroplastic (Thiazole biosynthetic enzyme) |

APPENDIX-continued

Table 13: Plant EV-Markers

| | | |
|---|---|---|
| *Citrus lemon* | V4TY40 | Uncharacterized protein |
| *Citrus lemon* | V4TYJ6 | Uncharacterized protein |
| *Citrus lemon* | V4TYP5 | 60S ribosomal protein L13 |
| *Citrus lemon* | V4TYP6 | Uncharacterized protein |
| *Citrus lemon* | V4TYR6 | Uncharacterized protein |
| *Citrus lemon* | V4TYZ8 | Tubulin alpha chain |
| *Citrus lemon* | V4TZ91 | Guanosine nucleotide diphosphate dissociation inhibitor |
| *Citrus lemon* | V4TZA8 | Uncharacterized protein |
| *Citrus lemon* | V4TZJ1 | Uncharacterized protein |
| *Citrus lemon* | V4TZK5 | Uncharacterized protein |
| *Citrus lemon* | V4TZP2 | Uncharacterized protein |
| *Citrus lemon* | V4TZT8 | Uncharacterized protein |
| *Citrus lemon* | V4TZU3 | Mitogen-activated protein kinase (EC 2.7.11.24) |
| *Citrus lemon* | V4TZU5 | Dihydrolipoyl dehydrogenase (EC 1.8.1.4) |
| *Citrus lemon* | V4TZZ0 | Uncharacterized protein |
| *Citrus lemon* | V4U003 | Eukaryotic translation initiation factor 3 subunit K (eIF3k) (eIF-3 p25) |
| *Citrus lemon* | V4U068 | Uncharacterized protein |
| *Citrus lemon* | V4U088 | Uncharacterized protein |
| *Citrus lemon* | V4U0J7 | Uncharacterized protein |
| *Citrus lemon* | V4U133 | Uncharacterized protein |
| *Citrus lemon* | V4U1A8 | Uncharacterized protein |
| *Citrus lemon* | V4U1K1 | Xylose isomerase (EC 5.3.1.5) |
| *Citrus lemon* | V4U1M1 | Uncharacterized protein |
| *Citrus lemon* | V4U1V0 | Uncharacterized protein |
| *Citrus lemon* | V4U1X7 | Uncharacterized protein |
| *Citrus lemon* | V4U1X9 | Proteasome subunit beta type (EC 3.4.25.1) |
| *Citrus lemon* | V4U251 | Uncharacterized protein |
| *Citrus lemon* | V4U283 | Uncharacterized protein |
| *Citrus lemon* | V4U2E4 | Uncharacterized protein |
| *Citrus lemon* | V4U2F7 | Uncharacterized protein |
| *Citrus lemon* | V4U2H8 | Uncharacterized protein |
| *Citrus lemon* | V4U2L0 | Malate dehydrogenase (EC 1.1.1.37) |
| *Citrus lemon* | V4U2L2 | Uncharacterized protein |
| *Citrus lemon* | V4U2W4 | V-type proton ATPase subunit C |
| *Citrus lemon* | V4U3L2 | Uncharacterized protein |
| *Citrus lemon* | V4U3W8 | Uncharacterized protein |
| *Citrus lemon* | V4U412 | Uncharacterized protein |
| *Citrus lemon* | V4U4K2 | Uncharacterized protein |
| *Citrus lemon* | V4U4M4 | Uncharacterized protein |
| *Citrus lemon* | V4U4N5 | Eukaryotic translation initiation factor 6 (eIF-6) |
| *Citrus lemon* | V4U4S9 | Uncharacterized protein |
| *Citrus lemon* | V4U4X3 | Serine hydroxymethyltransferase (EC 2.1.2.1) |
| *Citrus lemon* | V4U4Z9 | Uncharacterized protein |
| *Citrus lemon* | V4U500 | Uncharacterized protein |
| *Citrus lemon* | V4U5B0 | Eukaryotic translation initiation factor 3 subunit E (eIF3e) (Eukaryotic translation initiation factor 3 subunit 6) |
| *Citrus lemon* | V4U5B8 | Glutathione peroxidase |
| *Citrus lemon* | V4U5R5 | Citrate synthase |
| *Citrus lemon* | V4U5Y8 | Uncharacterized protein |
| *Citrus lemon* | V4U6I5 | ATP synthase subunit beta (EC 3.6.3.14) |
| *Citrus lemon* | V4U6Q8 | Uncharacterized protein |
| *Citrus lemon* | V4U706 | Uncharacterized protein |
| *Citrus lemon* | V4U717 | Uncharacterized protein |
| *Citrus lemon* | V4U726 | Uncharacterized protein |
| *Citrus lemon* | V4U729 | Uncharacterized protein |
| *Citrus lemon* | V4U734 | Serine/threonine-protein phosphatase (EC 3.1.3.16) |
| *Citrus lemon* | V4U7G7 | Uncharacterized protein |
| *Citrus lemon* | V4U7H5 | Uncharacterized protein |
| *Citrus lemon* | V4U7R1 | Potassium transporter |
| *Citrus lemon* | V4U7R7 | Mitogen-activated protein kinase (EC 2.7.11.24) |
| *Citrus lemon* | V4U833 | Malic enzyme |
| *Citrus lemon* | V4U840 | Uncharacterized protein |
| *Citrus lemon* | V4U8C3 | Uncharacterized protein |
| *Citrus lemon* | V4U8J1 | 3-phosphoshikimate 1-carboxyvinyltransferase (EC 2.5.1.19) |
| *Citrus lemon* | V4U8J8 | T-complex protein 1 subunit gamma |
| *Citrus lemon* | V4U995 | Uncharacterized protein |
| *Citrus lemon* | V4U999 | Uncharacterized protein |
| *Citrus lemon* | V4U9C7 | Eukaryotic translation initiation factor 3 subunit D (eIF3d) (Eukaryotic translation initiation factor 3 subunit 7) (eIF-3-zeta) |
| *Citrus lemon* | V4U9G8 | Proline iminopeptidase (EC 3.4.11.5) |
| *Citrus lemon* | V4U9L1 | Uncharacterized protein |
| *Citrus lemon* | V4UA63 | Phytochrome |
| *Citrus lemon* | V4UAC8 | Uncharacterized protein |
| *Citrus lemon* | V4UAR4 | Uncharacterized protein |
| *Citrus lemon* | V4UB30 | Uncharacterized protein |
| *Citrus lemon* | V4UBK8 | V-type proton ATPase subunit a |
| *Citrus lemon* | V4UBL3 | Coatomer subunit alpha |

APPENDIX-continued

Table 13: Plant EV-Markers

| | | |
|---|---|---|
| *Citrus lemon* | V4UBL5 | Uncharacterized protein (Fragment) |
| *Citrus lemon* | V4UBM0 | Uncharacterized protein |
| *Citrus lemon* | V4UBZ8 | Aspartate aminotransferase (EC 2.6.1.1) |
| *Citrus lemon* | V4UC72 | Uncharacterized protein |
| *Citrus lemon* | V4UC97 | Beta-glucosidase (EC 3.2.1.21) |
| *Citrus lemon* | V4UCE2 | Uncharacterized protein |
| *Citrus lemon* | V4UCT9 | Acetyl-coenzyme A synthetase (EC 6.2.1.1) |
| *Citrus lemon* | V4UCZ1 | Uncharacterized protein |
| *Citrus lemon* | V4UE34 | Uncharacterized protein |
| *Citrus lemon* | V4UE78 | Uncharacterized protein |
| *Citrus lemon* | V4UER3 | Uncharacterized protein |
| *Citrus lemon* | V4UET6 | Uncharacterized protein |
| *Citrus lemon* | V4UEZ6 | Uncharacterized protein |
| *Citrus lemon* | V4UFD0 | Uncharacterized protein |
| *Citrus lemon* | V4UFG8 | Uncharacterized protein |
| *Citrus lemon* | V4UFK1 | Uncharacterized protein |
| *Citrus lemon* | V4UG68 | Eukaryotic translation initiation factor 3 subunit I (eIF3i) |
| *Citrus lemon* | V4UGB0 | Uncharacterized protein |
| *Citrus lemon* | V4UGH4 | Uncharacterized protein |
| *Citrus lemon* | V4UGL9 | Uncharacterized protein |
| *Citrus lemon* | V4UGQ0 | Ubiquitinyl hydrolase 1 (EC 3.4.19.12) |
| *Citrus lemon* | V4UH00 | Uncharacterized protein |
| *Citrus lemon* | V4UH48 | Uncharacterized protein |
| *Citrus lemon* | V4UH77 | Proteasome subunit alpha type (EC 3.4.25.1) |
| *Citrus lemon* | V4UHD8 | Uncharacterized protein |
| *Citrus lemon* | V4UHD9 | Uncharacterized protein |
| *Citrus lemon* | V4UHF1 | Uncharacterized protein |
| *Citrus lemon* | V4UHZ5 | Uncharacterized protein |
| *Citrus lemon* | V4UI07 | 40S ribosomal protein S8 |
| *Citrus lemon* | V4UI34 | Eukaryotic translation initiation factor 3 subunit L (eIF3l) |
| *Citrus lemon* | V4UIF1 | Uncharacterized protein |
| *Citrus lemon* | V4UIN5 | Uncharacterized protein |
| *Citrus lemon* | V4UIX8 | Uncharacterized protein |
| *Citrus lemon* | V4UJ12 | Uncharacterized protein |
| *Citrus lemon* | V4UJ42 | Uncharacterized protein |
| *Citrus lemon* | V4UJ63 | Uncharacterized protein |
| *Citrus lemon* | V4UJB7 | Uncharacterized protein (Fragment) |
| *Citrus lemon* | V4UJC4 | Uncharacterized protein |
| *Citrus lemon* | V4UJX0 | Phosphotransferase (EC 2.7.1.—) |
| *Citrus lemon* | V4UJY5 | Uncharacterized protein |
| *Citrus lemon* | V4UK18 | Uncharacterized protein |
| *Citrus lemon* | V4UK52 | Uncharacterized protein |
| *Citrus lemon* | V4UKM9 | Uncharacterized protein |
| *Citrus lemon* | V4UKS4 | Uncharacterized protein |
| *Citrus lemon* | V4UKV6 | 40S ribosomal protein SA |
| *Citrus lemon* | V4UL30 | Pyrophosphate-fructose 6-phosphate 1-phosphotransferase subunit beta (PFP) (EC 2.7.1.90) (6-phosphofructokinase, pyrophosphate dependent) (PPi-PFK) (Pyrophosphate-dependent 6-phosphofructose-1-kinase) |
| *Citrus lemon* | V4UL39 | Uncharacterized protein |
| *Citrus lemon* | V4ULH9 | Uncharacterized protein |
| *Citrus lemon* | V4ULL2 | Uncharacterized protein |
| *Citrus lemon* | V4ULS0 | Uncharacterized protein |
| *Citrus lemon* | V4UMU7 | Uncharacterized protein |
| *Citrus lemon* | V4UN36 | Uncharacterized protein |
| *Citrus lemon* | V4UNT5 | Uncharacterized protein |
| *Citrus lemon* | V4UNW1 | Uncharacterized protein |
| *Citrus lemon* | V4UP89 | Uncharacterized protein |
| *Citrus lemon* | V4UPE4 | Uncharacterized protein |
| *Citrus lemon* | V4UPF7 | Uncharacterized protein |
| *Citrus lemon* | V4UPK0 | Uncharacterized protein |
| *Citrus lemon* | V4UPX5 | Uncharacterized protein |
| *Citrus lemon* | V4UQ58 | Uncharacterized protein |
| *Citrus lemon* | V4UQF6 | Uncharacterized protein |
| *Citrus lemon* | V4UR21 | Uncharacterized protein |
| *Citrus lemon* | V4UR80 | Uncharacterized protein |
| *Citrus lemon* | V4URK3 | Uncharacterized protein |
| *Citrus lemon* | V4URT3 | Uncharacterized protein |
| *Citrus lemon* | V4US96 | Uncharacterized protein |
| *Citrus lemon* | V4USQ8 | Uncharacterized protein |
| *Citrus lemon* | V4UT16 | Uncharacterized protein |
| *Citrus lemon* | V4UTC6 | Uncharacterized protein |
| *Citrus lemon* | V4UTC8 | Uncharacterized protein |
| *Citrus lemon* | V4UTP6 | Uncharacterized protein |
| *Citrus lemon* | V4UTY0 | Proteasome subunit alpha type (EC 3.4.25.1) |
| *Citrus lemon* | V4UU96 | Uncharacterized protein |
| *Citrus lemon* | V4UUB6 | Uncharacterized protein |
| *Citrus lemon* | V4UUJ9 | Aminopeptidase (EC 3.4.11.—) |

APPENDIX-continued

Table 13: Plant EV-Markers

| | | |
|---|---|---|
| *Citrus lemon* | V4UUK6 | Uncharacterized protein |
| *Citrus lemon* | V4UV09 | Uncharacterized protein |
| *Citrus lemon* | V4UV83 | Lysine--tRNA ligase (EC 6.1.1.6) (Lysyl-tRNA synthetase) |
| *Citrus lemon* | V4UVJ5 | Diacylglycerol kinase (DAG kinase) (EC 2.7.1.107) |
| *Citrus lemon* | V4UW03 | Uncharacterized protein |
| *Citrus lemon* | V4UW04 | Uncharacterized protein |
| *Citrus lemon* | V4UWR1 | Uncharacterized protein |
| *Citrus lemon* | V4UWV8 | Uncharacterized protein |
| *Citrus lemon* | V4UX36 | Uncharacterized protein |
| *Citrus lemon* | V4V003 | Uncharacterized protein |
| *Citrus lemon* | V4V0J0 | 40S ribosomal protein S26 |
| *Citrus lemon* | V4V1P8 | Uncharacterized protein |
| *Citrus lemon* | V4V4V0 | Uncharacterized protein |
| *Citrus lemon* | V4V5T8 | Ubiquitin-fold modifier 1 |
| *Citrus lemon* | V4V600 | Uncharacterized protein |
| *Citrus lemon* | V4V622 | Aldehyde dehydrogenase |
| *Citrus lemon* | V4V6W1 | Uncharacterized protein |
| *Citrus lemon* | V4V6Z2 | Uncharacterized protein |
| *Citrus lemon* | V4V738 | Uncharacterized protein |
| *Citrus lemon* | V4V8H5 | Vacuolar protein sorting-associated protein 35 |
| *Citrus lemon* | V4V9P6 | Eukaryotic translation initiation factor 3 subunit F (eIF3f) (eIF-3-epsilon) |
| *Citrus lemon* | V4V9V7 | Clathrin heavy chain |
| *Citrus lemon* | V4V9X3 | Uncharacterized protein |
| *Citrus lemon* | V4VAA3 | Superoxide dismutase (EC 1.15.1.1) |
| *Citrus lemon* | V4VAF3 | Uncharacterized protein |
| *Citrus lemon* | V4VBQ0 | Uncharacterized protein (Fragment) |
| *Citrus lemon* | V4VCL1 | Proteasome subunit beta type (EC 3.4.25.1) |
| *Citrus lemon* | V4VCZ9 | Uncharacterized protein |
| *Citrus lemon* | V4VDK1 | Peptidylprolyl isomerase (EC 5.2.1.8) |
| *Citrus lemon* | V4VEA1 | Uncharacterized protein |
| *Citrus lemon* | V4VEB3 | Alanine--tRNA ligase (EC 6.1.1.7) (Alanyl-tRNA synthetase) (AlaRS) |
| *Citrus lemon* | V4VEE3 | Glutamine synthetase (EC 6.3.1.2) |
| *Citrus lemon* | V4VFM3 | Uncharacterized protein |
| *Citrus lemon* | V4VFN5 | Proteasome subunit beta type (EC 3.4.25.1) |
| *Citrus lemon* | V4VGD6 | Uncharacterized protein |
| *Citrus lemon* | V4VGL9 | Uncharacterized protein |
| *Citrus lemon* | V4VHI6 | Uncharacterized protein |
| *Citrus lemon* | V4VIP4 | Uncharacterized protein |
| *Citrus lemon* | V4VJT4 | Uncharacterized protein |
| *Citrus lemon* | V4VK14 | Uncharacterized protein |
| *Citrus lemon* | V4VKI5 | Protein-L-isoaspartate O-methyltransferase (EC 2.1.1.77) |
| *Citrus lemon* | V4VKP2 | Glyceraldehyde-3-phosphate dehydrogenase (EC 1.2.1.—) |
| *Citrus lemon* | V4VL73 | Acyl-coenzyme A oxidase |
| *Citrus lemon* | V4VLL7 | Uncharacterized protein |
| *Citrus lemon* | V4VN43 | Uncharacterized protein (Fragment) |
| *Citrus lemon* | V4VQH3 | Methylenetetrahydrofolate reductase (EC 1.5.1.20) |
| *Citrus lemon* | V4VTC9 | Uncharacterized protein (Fragment) |
| *Citrus lemon* | V4VTT4 | Uncharacterized protein |
| *Citrus lemon* | V4VTY7 | Uncharacterized protein |
| *Citrus lemon* | V4VU14 | Uncharacterized protein |
| *Citrus lemon* | V4VU32 | Uncharacterized protein |
| *Citrus lemon* | V4VUK6 | S-(hydroxymethyl)glutathione dehydrogenase (EC 1.1.1.284) |
| *Citrus lemon* | V4VVR8 | Uncharacterized protein |
| *Citrus lemon* | V4VXE2 | Uncharacterized protein |
| *Citrus lemon* | V4VY37 | Phosphomannomutase (EC 5.4.2.8) |
| *Citrus lemon* | V4VYC0 | Uncharacterized protein |
| *Citrus lemon* | V4VYV1 | Uncharacterized protein |
| *Citrus lemon* | V4VZ80 | Uncharacterized protein |
| *Citrus lemon* | V4VZJ7 | Uncharacterized protein |
| *Citrus lemon* | V4W2P2 | Alpha-mannosidase (EC 3.2.1.—) |
| *Citrus lemon* | V4W2Z9 | Chloride channel protein |
| *Citrus lemon* | V4W378 | Uncharacterized protein |
| *Citrus lemon* | V4W4G3 | Uncharacterized protein |
| *Citrus lemon* | V4W5F1 | Uncharacterized protein |
| *Citrus lemon* | V4W5N8 | Uncharacterized protein |
| *Citrus lemon* | V4W5U2 | Uncharacterized protein |
| *Citrus lemon* | V4W6G1 | Uncharacterized protein |
| *Citrus lemon* | V4W730 | Uncharacterized protein |
| *Citrus lemon* | V4W7J4 | Obg-like ATPase 1 |
| *Citrus lemon* | V4W7L5 | Uncharacterized protein |
| *Citrus lemon* | V4W8C5 | Uncharacterized protein |
| *Citrus lemon* | V4W8C9 | Uncharacterized protein |
| *Citrus lemon* | V4W8D3 | Uncharacterized protein |
| *Citrus lemon* | V4W951 | Uncharacterized protein |
| *Citrus lemon* | V4W9F6 | 60S ribosomal protein L18a |
| *Citrus lemon* | V4W9G2 | Uncharacterized protein (Fragment) |

APPENDIX-continued

Table 13: Plant EV-Markers

| | | |
|---|---|---|
| Citrus lemon | V4W9L3 | Uncharacterized protein |
| Citrus lemon | V4W9Y8 | Uncharacterized protein |
| Citrus lemon | V4WAP9 | Coatomer subunit beta (Beta-coat protein) |
| Citrus lemon | V4WBK6 | Cytochrome b-c1 complex subunit 7 |
| Citrus lemon | V4WC15 | Malic enzyme |
| Citrus lemon | V4WC19 | Uncharacterized protein |
| Citrus lemon | V4WC74 | Uncharacterized protein |
| Citrus lemon | V4WC86 | Serine/threonine-protein phosphatase 2A 55 kDa regulatory subunit B |
| Citrus lemon | V4WCS4 | GTP-binding nuclear protein |
| Citrus lemon | V4WD80 | Aspartate aminotransferase (EC 2.6.1.1) |
| Citrus lemon | V4WDK0 | Uncharacterized protein |
| Citrus lemon | V4WDK3 | ATP-dependent 6-phosphofructokinase (ATP-PFK) (Phosphofructokinase) (EC 2.7.1.11) (Phosphohexokinase) |
| Citrus lemon | V4WE00 | Uncharacterized protein |
| Citrus lemon | V4WEE3 | Uncharacterized protein |
| Citrus lemon | V4WEN2 | Uncharacterized protein |
| Citrus lemon | V4WG97 | Autophagy-related protein |
| Citrus lemon | V4WGV2 | Uncharacterized protein |
| Citrus lemon | V4WGW5 | Uridine kinase (EC 2.7.1.48) |
| Citrus lemon | V4WHD4 | Uncharacterized protein |
| Citrus lemon | V4WHF8 | Sucrose synthase (EC 2.4.1.13) |
| Citrus lemon | V4WHK2 | Pectinesterase (EC 3.1.1.11) |
| Citrus lemon | V4WHQ4 | Uncharacterized protein |
| Citrus lemon | V4WHT6 | Uncharacterized protein |
| Citrus lemon | V4WJ93 | Uncharacterized protein |
| Citrus lemon | V4WJA9 | Uncharacterized protein |
| Citrus lemon | V4WJB1 | Uncharacterized protein |
| Citrus lemon | V9HXG3 | Protein disulfide-isomerase (EC 5.3.4.1) |
| Citrus lemon | W8Q8K1 | Putative inorganic pyrophosphatase |
| Citrus lemon | W8QJL0 | Putative isopentenyl pyrophosphate isomerase |

| Grape | Accession Number | Identified Proteins |
|---|---|---|
| Grape | A5C5K3 (+2) | Adenosylhomocysteinase |
| Grape | Q9M6B5 | Alcohol dehydrogenase 6 |
| Grape | A3FA65 (+1) | Aquaporin PIP1; 3 |
| Grape | Q0MX13 (+2) | Aquaporin PIP2; 2 |
| Grape | A3FA69 (+4) | Aquaporin PIP2; 4 |
| Grape | A5AFS1 (+2) | Elongation factor 1-alpha |
| Grape | UPI0001985702 | elongation factor 2 |
| Grape | D7T227 | Enolase |
| Grape | D7TJ12 | Enolase |
| Grape | A5B118 (+1) | Fructose-bisphosphate aldolase |
| Grape | E0CQ39 | Glucose-6-phosphate isomerase |
| Grape | D7TW04 | Glutathione peroxidase |
| Grape | A1YW90 (+3) | Glutathione S-transferase |
| Grape | A5BEW0 | Histone H4 |
| Grape | UPI00015C9A6A | HSC70-1 (heat shock cognate 70 kDa protein 1); ATP binding isoform 1 |
| Grape | D7FBC0 (+1) | Malate dehydrogenase |
| Grape | D7TBH4 | Malic enzyme |
| Grape | A5ATB7 (+1) | Methylenetetrahydrofolate reductase |
| Grape | A5JPK7 (+1) | Monodehydroascorbate reductase |
| Grape | A5AKD8 | Peptidyl-prolyl cis-trans isomerase |
| Grape | A5BQN6 | Peptidyl-prolyl cis-trans isomerase |
| Grape | A5CAF6 | Phosphoglycerate kinase |
| Grape | Q09VU3 (+1) | Phospholipase D |
| Grape | D7SK33 | Phosphorylase |
| Grape | A5AQ89 | Profilin |
| Grape | C5DB50 (+2) | Putative 2,3-bisphosphoglycerate-independent phosphoglycerate mutase |
| Grape | D7TIZ5 | Pyruvate kinase |
| Grape | A5BV65 | Triosephosphate isomerase |
| Grapefruit | G8Z362 (+1) | (E)-beta-farnesene synthase |
| Grapefruit | Q5CD81 | (E)-beta-ocimene synthase |
| Grapefruit | D0UZK1 (+2) | 1,2 rhamnosyltransferase |
| Grapefruit | A7ISD3 | 1,6-rhamnosyltransferase |
| Grapefruit | Q80H98 | 280 kDa protein |
| Grapefruit | Q15GA4 (+2) | 286 kDa polyprotein |
| Grapefruit | D7NHW9 | 2-phospho-D-glycerate hydrolase |
| Grapefruit | D0EAL9 | 349 kDa polyprotein |
| Grapefruit | Q9DTG5 | 349-kDa polyprotein |
| Grapefruit | O22297 | Acidic cellulase |
| Grapefruit | Q8H986 | Acidic class I chitinase |
| Grapefruit | D3GQL0 | Aconitate hydratase 1 |
| Grapefruit | K7N8A0 | Actin |
| Grapefruit | A8W8Y0 | Alcohol acyl transferase |

APPENDIX-continued

Table 13: Plant EV-Markers

| | | |
|---|---|---|
| Grapefruit | Q84V85 | Allene oxide synthase |
| Grapefruit | F8WL79 | Aminopeptidase |
| Grapefruit | Q09MG5 | Apocytochrome f |
| Grapefruit | J7EIR8 | Ascorbate peroxidase |
| Grapefruit | B9VRH6 | Ascorbate peroxidase |
| Grapefruit | G9I820 | Auxin-response factor |
| Grapefruit | J7ICW8 | Beta-amylase |
| Grapefruit | Q8L5Q9 | Beta-galactosidase |
| Grapefruit | A7BG60 | Beta-pinene synthase |
| Grapefruit | C0KLD1 | Beta-tubulin |
| Grapefruit | Q9IQZ1 | Capsid protein |
| Grapefruit | Q3SAK9 | Capsid protein |
| Grapefruit | D2U833 | Cation chloride cotransporter |
| Grapefruit | C3VPJ0 (+3) | Chalcone synthase |
| Grapefruit | D5LM39 | Chloride channel protein |
| Grapefruit | Q9M4U0 | Cinnamate 4-hydroxylase CYP73 |
| Grapefruit | Q39627 | Citrin |
| Grapefruit | G2XKD3 | Coat protein |
| Grapefruit | Q3L2I6 | Coat protein |
| Grapefruit | D5FV16 | CRT/DRE binding factor |
| Grapefruit | Q8H6S5 | CTV.2 |
| Grapefruit | Q8H6Q8 | CTV.20 |
| Grapefruit | Q8H6Q7 | CTV.22 |
| Grapefruit | Q1I1D7 | Cytochrome P450 |
| Grapefruit | Q7Y045 | Dehydrin |
| Grapefruit | F8WLD2 | DNA excision repair protein |
| Grapefruit | Q09MI8 | DNA-directed RNA polymerase subunit beta" |
| Grapefruit | D2WKC9 | Ethylene response 1 |
| Grapefruit | D2WKD2 | Ethylene response sensor 1 |
| Grapefruit | D7PVG7 | Ethylene-insensitive 3-like 1 protein |
| Grapefruit | G3CHK8 | Eukaryotic translation initiation factor 3 subunit E |
| Grapefruit | A9NJG4 (+3) | Fatty acid hydroperoxide lyase |
| Grapefruit | B8Y9B5 | F-box family protein |
| Grapefruit | Q000W4 | Fe(III)-chelate reductase |
| Grapefruit | Q6Q3H4 | Fructokinase |
| Grapefruit | F8WL95 | Gag-pol polyprotein |
| Grapefruit | Q8L5K4 | Gamma-terpinene synthase, chloroplastic |
| Grapefruit | Q9SP43 | Glucose-1-phosphate adenylyltransferase |
| Grapefruit | Q3HM93 | Glutathione S-transferase |
| Grapefruit | D0VEW6 | GRAS family transcription factor |
| Grapefruit | F8WL87 | Heat shock protein |
| Grapefruit | H9NHK0 | Hsp90 |
| Grapefruit | Q8H6R4 | Jp18 |
| Grapefruit | G3CHK6 | Leucine-rich repeat family protein |
| Grapefruit | B2YGX9 (+1) | Limonoid UDP-glucosyltransferase |
| Grapefruit | Q05KK0 | MADS-box protein |
| Grapefruit | F8WLB4 | Mechanosensitive ion channel domain-containing protein |
| Grapefruit | Q5CD82 | Monoterpene synthase |
| Grapefruit | F8WLC4 | MYB transcription factor |
| Grapefruit | A5YWA9 | NAC domain protein |
| Grapefruit | Q09MC9 | NAD(P)H-quinone oxidoreductase subunit 5, chloroplastic |
| Grapefruit | Q8H6R9 | NBS-LRR type disease resistance protein |
| Grapefruit | Q8H6S0 | NBS-LRR type disease resistance protein |
| Grapefruit | Q8H6R6 | NBS-LRR type disease resistance protein |
| Grapefruit | J9WR93 | p1a |
| Grapefruit | Q1X8V8 | P23 |
| Grapefruit | E7DSS0 (+4) | P23 |
| Grapefruit | G0Z9I6 | p27 |
| Grapefruit | I3XHN0 | p33 |
| Grapefruit | B8YDL3 | p33 protein |
| Grapefruit | B9VB22 | p33 protein |
| Grapefruit | P87587 | P346 |
| Grapefruit | B9VB56 | p349 protein |
| Grapefruit | I3RWW7 | p349 protein |
| Grapefruit | B9VB20 | p349 protein |
| Grapefruit | Q9WID7 | p349 protein |
| Grapefruit | Q2XP16 | P353 |
| Grapefruit | O04886 (+1) | Pectinesterase 1 |
| Grapefruit | F8WL74 | Peptidyl-prolyl cis-trans isomerase |
| Grapefruit | Q0ZA67 | Peroxidase |
| Grapefruit | F1CT41 | Phosphoenolpyruvate carboxylase |
| Grapefruit | B1PBV7 (+2) | Phytoene synthase |
| Grapefruit | Q9ZWQ8 | Plastid-lipid-associated protein, chloroplastic |
| Grapefruit | Q94FM1 | Pol polyprotein |
| Grapefruit | Q94FM0 | Pol polyprotein |
| Grapefruit | G9I825 | Poly C-binding protein |
| Grapefruit | O64460 (+7) | Polygalacturonase inhibitor |
| Grapefruit | I3XHM8 | Polyprotein |

APPENDIX-continued

Table 13: Plant EV-Markers

| | | |
|---|---|---|
| Grapefruit | C0STR9 | Polyprotein |
| Grapefruit | H6U1F0 | Polyprotein |
| Grapefruit | B8QHP8 | Polyprotein |
| Grapefruit | I3V6C0 | Polyprotein |
| Grapefruit | C0STS0 | Polyprotein |
| Grapefruit | K0FGH5 | Polyprotein |
| Grapefruit | Q3HWZ1 | Polyprotein |
| Grapefruit | F8WLA5 | PPR containing protein |
| Grapefruit | Q06652 (+1) | Probable phospholipid hydroperoxide glutathione peroxidase |
| Grapefruit | P84177 | Profilin |
| Grapefruit | Q09MB4 | Protein ycf2 |
| Grapefruit | A8C183 | PSI reaction center subunit II |
| Grapefruit | A5JVP6 | Putative 2b protein |
| Grapefruit | D0EFM2 | Putative eukaryotic translation initiation factor 1 |
| Grapefruit | Q18L98 | Putative gag-pol polyprotein |
| Grapefruit | B5AMI9 | Putative movement protein |
| Grapefruit | A1ECK5 | Putative multiple stress-responsive zinc-finger protein |
| Grapefruit | B5AMJ0 | Putative replicase polyprotein |
| Grapefruit | I7CYN5 | Putative RNA-dependent RNA polymerase |
| Grapefruit | Q8RVR2 | Putative terpene synthase |
| Grapefruit | B5TE89 | Putative uncharacterized protein |
| Grapefruit | Q8JVF3 | Putative uncharacterized protein |
| Grapefruit | F8WLB0 | Putative uncharacterized protein ORF43 |
| Grapefruit | A5JVP4 | Putative viral replicase |
| Grapefruit | M1JAW3 | Replicase |
| Grapefruit | H6VXK8 | Replicase polyprotein |
| Grapefruit | J9UF50 (+1) | Replicase protein 1a |
| Grapefruit | J9RV45 | Replicase protein 2a |
| Grapefruit | Q5EGG5 | Replicase-associated polyprotein |
| Grapefruit | G9I823 | RNA recognition motif protein 1 |
| Grapefruit | J7EPC0 | RNA-dependent RNA polymerase |
| Grapefruit | Q6DN67 | RNA-directed RNA polymerase L |
| Grapefruit | A9CQM4 | SEPALLATA1 homolog |
| Grapefruit | Q9SLS2 | Sucrose synthase |
| Grapefruit | Q9SLV8 (+1) | Sucrose synthase |
| Grapefruit | Q38JC1 | Temperature-induced lipocalin |
| Grapefruit | D0ELH6 | Tetratricopeptide domain-containing thioredoxin |
| Grapefruit | D2KU75 | Thaumatin-like protein |
| Grapefruit | C3VIC2 | Translation elongation factor |
| Grapefruit | D5LY07 | Ubiquitin/ribosomal fusion protein |
| Grapefruit | C6KI43 | UDP-glucosyltransferase family 1 protein |
| Grapefruit | A0FKR1 | Vacuolar citrate/H+ symporter |
| Grapefruit | Q944C8 | Vacuolar invertase |
| Grapefruit | Q9MB46 | V-type proton ATPase subunit E |
| Grapefruit | F8WL82 | WD-40 repeat family protein |
| *Helianthuus annuus* | HanXRQChr03g0080391 | Hsp90 |
| *Helianthuus annuus* | HanXRQChr13g0408351 | Hsp90 |
| *Helianthuus annuus* | HanXRQChr13g0408441 | Hsp90 |
| *Helianthuus annuus* | HanXRQChr14g0462551 | Hsp90 |
| *Helianthuus annuus* | HanXRQChr02g0044471 | Hsp70 |
| *Helianthuus annuus* | HanXRQChr02g0044481 | Hsp70 |
| *Helianthuus annuus* | HanXRQChr05g0132631 | Hsp70 |
| *Helianthuus annuus* | HanXRQChr05g0134631 | Hsp70 |
| *Helianthuus annuus* | HanXRQChr05g0134801 | Hsp70 |
| *Helianthuus annuus* | HanXRQChr10g0299441 | glutathione S-transferase |
| *Helianthuus annuus* | HanXRQChr16g0516291 | glutathione S-transferase |
| *Helianthuus annuus* | HanXRQChr03g0091431 | lactate/malate dehydrogenase |
| *Helianthuus annuus* | HanXRQChr13g0421951 | lactate/malate dehydrogenase |
| *Helianthuus annuus* | HanXRQChr10g0304821 | lactate/malate dehydrogenase |
| *Helianthuus annuus* | HanXRQChr12g0373491 | lactate/malate dehydrogenase |
| *Helianthuus annuus* | HanXRQChr01g0031071 | small GTPase superfamily, Rab type |
| *Helianthuus annuus* | HanXRQChr01g0031091 | small GTPase superfamily, Rab type |
| *Helianthuus annuus* | HanXRQChr02g0050791 | small GTPase superfamily, Rab type |
| *Helianthuus annuus* | HanXRQChr11g0353711 | small GTPase superfamily, Rab type |
| *Helianthuus annuus* | HanXRQChr13g0402771 | small GTPase superfamily, Rab type |
| *Helianthuus annuus* | HanXRQChr07g0190171 | isocitrate/isopropylmalate dehydrogenase |
| *Helianthuus annuus* | HanXRQChr16g0532251 | isocitrate/isopropylmalate dehydrogenase |
| *Helianthuus annuus* | HanXRQChr03g0079131 | phosphoenolpyruvate carboxylase |
| *Helianthuus annuus* | HanXRQChr15g0495261 | phosphoenolpyruvate carboxylase |
| *Helianthuus annuus* | HanXRQChr13g0388931 | phosphoenolpyruvate carboxylase |
| *Helianthuus annuus* | HanXRQChr14g0442731 | phosphoenolpyruvate carboxylase |
| *Helianthuus annuus* | HanXRQChr15g0482381 | UTP--glucose-1-phosphate uridylyltransferase |
| *Helianthuus annuus* | HanXRQChr16g0532261 | UTP--glucose-1-phosphate uridylyltransferase |
| *Helianthuus annuus* | HanXRQChr05g0135591 | tubulin |
| *Helianthuus annuus* | HanXRQChr06g0178921 | tubulin |
| *Helianthuus annuus* | HanXRQChr08g0237071 | tubulin |
| *Helianthuus annuus* | HanXRQChr11g0337991 | tubulin |

APPENDIX-continued

Table 13: Plant EV-Markers

| | | |
|---|---|---|
| *Helianthuus annuus* | HanXRQChr13g0407921 | tubulin |
| *Helianthuus annuus* | HanXRQChr05g0145191 | tubulin |
| *Helianthuus annuus* | HanXRQChr07g0187021 | tubulin |
| *Helianthuus annuus* | HanXRQChr07g0189811 | tubulin |
| *Helianthuus annuus* | HanXRQChr09g0253681 | tubulin |
| *Helianthuus annuus* | HanXRQChr10g0288911 | tubulin |
| *Helianthuus annuus* | HanXRQChr11g0322631 | tubulin |
| *Helianthuus annuus* | HanXRQChr12g0367231 | tubulin |
| *Helianthuus annuus* | HanXRQChr13g0386681 | tubulin |
| *Helianthuus annuus* | HanXRQChr13g0393261 | tubulin |
| *Helianthuus annuus* | HanXRQChr12g0371591 | ubiquitin |
| *Helianthuus annuus* | HanXRQChr12g0383641 | ubiquitin |
| *Helianthuus annuus* | HanXRQChr17g0569881 | ubiquitin |
| *Helianthuus annuus* | HanXRQChr06g0171511 | photosystem II HCF136, stability/assembly factor |
| *Helianthuus annuus* | HanXRQChr17g0544921 | photosystem II HCF136, stability/assembly factor |
| *Helianthuus annuus* | HanXRQChr16g0526461 | proteasome B-type subunit |
| *Helianthuus annuus* | HanXRQChr17g0565551 | proteasome B-type subunit |
| *Helianthuus annuus* | HanXRQChr05g0149801 | proteasome B-type subunit |
| *Helianthuus annuus* | HanXRQChr09g0241421 | proteasome B-type subunit |
| *Helianthuus annuus* | HanXRQChr11g0353161 | proteasome B-type subunit |
| *Helianthuus annuus* | HanXRQChr16g0506311 | proteinase inhibitor family I3 (Kunitz) |
| *Helianthuus annuus* | HanXRQChr16g0506331 | proteinase inhibitor family I3 (Kunitz) |
| *Helianthuus annuus* | HanXRQChr09g0265401 | metallopeptidase (M10 family) |
| *Helianthuus annuus* | HanXRQChr09g0265411 | metallopeptidase (M10 family) |
| *Helianthuus annuus* | HanXRQChr05g0154561 | ATPase, AAA-type |
| *Helianthuus annuus* | HanXRQChr08g0235061 | ATPase, AAA-type |
| *Helianthuus annuus* | HanXRQChr09g0273921 | ATPase, AAA-type |
| *Helianthuus annuus* | HanXRQChr16g0498881 | ATPase, AAA-type |
| *Helianthuus annuus* | HanXRQChr02g0058711 | oxoacid dehydrogenase acyltransferase |
| *Helianthuus annuus* | HanXRQChr08g0214191 | oxoacid dehydrogenase acyltransferase |
| *Helianthuus annuus* | HanXRQChr08g0208631 | small GTPase superfamily, SAR1-type |
| *Helianthuus annuus* | HanXRQChr11g0331441 | small GTPase superfamily, SAR1-type |
| *Helianthuus annuus* | HanXRQChr12g0371571 | small GTPase superfamily, SAR1-type |
| *Helianthuus annuus* | HanXRQChr12g0383571 | small GTPase superfamily, SAR1-type |
| *Helianthuus annuus* | HanXRQChr14g0446771 | small GTPase superfamily, SAR1-type |
| *Helianthuus annuus* | HanXRQChr17g0539461 | small GTPase superfamily, SAR1-type |
| *Helianthuus annuus* | HanXRQChr17g0548271 | small GTPase superfamily, SAR1-type |
| *Helianthuus annuus* | HanXRQChr17g0569871 | small GTPase superfamily, SAR1-type |
| *Helianthuus annuus* | HanXRQChr10g0311201 | ATPase, V1 complex, subunit A |
| *Helianthuus annuus* | HanXRQChr12g0359711 | ATPase, V1 complex, subunit A |
| *Helianthuus annuus* | HanXRQChr04g0124671 | fructose-1,6-bisphosphatase |
| *Helianthuus annuus* | HanXRQChr06g0176631 | fructose-1,6-bisphosphatase |
| *Helianthuus annuus* | HanXRQCPg0579861 | photosystem II PsbD/D2, reaction centre |
| *Helianthuus annuus* | HanXRQChr00c0439g0574731 | photosystem II PsbD/D2, reaction centre |
| *Helianthuus annuus* | HanXRQChr04g0099321 | photosystem II PsbD/D2, reaction centre |
| *Helianthuus annuus* | HanXRQChr08g0210231 | photosystem II PsbD/D2, reaction centre |
| *Helianthuus annuus* | HanXRQChr11g0326671 | photosystem II PsbD/D2, reaction centre |
| *Helianthuus annuus* | HanXRQChr17g0549121 | photosystem II PsbD/D2, reaction centre |
| *Helianthuus annuus* | HanXRQCPg0579731 | photosystem II protein D1 |
| *Helianthuus annuus* | HanXRQChr00c0126g0571821 | photosystem II protein D1 |
| *Helianthuus annuus* | HanXRQChr00c0165g0572191 | photosystem II protein D1 |
| *Helianthuus annuus* | HanXRQChr00c0368g0574171 | photosystem II protein D1 |
| *Helianthuus annuus* | HanXRQChr00c0454g0574931 | photosystem II protein D1 |
| *Helianthuus annuus* | HanXRQChr00c0524g0575441 | photosystem II protein D1 |
| *Helianthuus annuus* | HanXRQChr00c0572g0575941 | photosystem II protein D1 |
| *Helianthuus annuus* | HanXRQChr09g0257281 | photosystem II protein D1 |
| *Helianthuus annuus* | HanXRQChr11g0326571 | photosystem II protein D1 |
| *Helianthuus annuus* | HanXRQChr11g0327051 | photosystem II protein D1 |
| *Helianthuus annuus* | HanXRQChr16g0503941 | photosystem II protein D1 |
| *Helianthuus annuus* | HanXRQCPg0580061 | photosystem II cytochrome b559 |
| *Helianthuus annuus* | HanXRQChr01g0020331 | photosystem II cytochrome b559 |
| *Helianthuus annuus* | HanXRQChr10g0283581 | photosystem II cytochrome b559 |
| *Helianthuus annuus* | HanXRQChr10g0284271 | photosystem II cytochrome b559 |
| *Helianthuus annuus* | HanXRQChr10g0289291 | photosystem II cytochrome b559 |
| *Helianthuus annuus* | HanXRQChr10g0318171 | photosystem II cytochrome b559 |
| *Helianthuus annuus* | HanXRQChr11g0326851 | photosystem II cytochrome b559 |
| *Helianthuus annuus* | HanXRQChr16g0529011 | photosystem II cytochrome b559 |
| *Helianthuus annuus* | HanXRQChr08g0219051 | chlorophyll A-B binding protein |
| *Helianthuus annuus* | HanXRQChr12g0370841 | chlorophyll A-B binding protein |
| *Helianthuus annuus* | HanXRQChr02g0053151 | chlorophyll A-B binding protein |
| *Helianthuus annuus* | HanXRQChr02g0053161 | chlorophyll A-B binding protein |
| *Helianthuus annuus* | HanXRQCPg0580051 | cytochrome f |
| *Helianthuus annuus* | HanXRQChr01g0020341 | cytochrome f |
| *Helianthuus annuus* | HanXRQChr10g0283571 | cytochrome f |
| *Helianthuus annuus* | HanXRQChr10g0284261 | cytochrome f |
| *Helianthuus annuus* | HanXRQChr10g0289281 | cytochrome f |
| *Helianthuus annuus* | HanXRQChr10g0318181 | cytochrome f |
| *Helianthuus annuus* | HanXRQChr11g0326841 | cytochrome f |

APPENDIX-continued

Table 13: Plant EV-Markers

| | | |
|---|---|---|
| *Helianthuus annuus* | HanXRQChr15g0497521 | cytochrome f |
| *Helianthuus annuus* | HanXRQChr06g0163851 | ribosomal protein |
| *Helianthuus annuus* | HanXRQChr09g0252071 | ribosomal protein |
| *Helianthuus annuus* | HanXRQChr12g0374041 | ribosomal protein |
| *Helianthuus annuus* | HanXRQChr04g0128141 | ribosomal protein |
| *Helianthuus annuus* | HanXRQChr05g0163131 | ribosomal protein |
| *Helianthuus annuus* | HanXRQChr03g0076971 | ribosomal protein |
| *Helianthuus annuus* | HanXRQChr05g0159851 | ribosomal protein |
| *Helianthuus annuus* | HanXRQChr05g0159971 | ribosomal protein |
| *Helianthuus annuus* | HanXRQChr11g0324631 | ribosomal protein |
| *Helianthuus annuus* | HanXRQChr13g0408051 | ribosomal protein |
| *Helianthuus annuus* | HanXRQChr03g0089331 | ribosomal protein |
| *Helianthuus annuus* | HanXRQChr13g0419951 | ribosomal protein |
| *Helianthuus annuus* | HanXRQChr15g0497041 | ribosomal protein |
| *Helianthuus annuus* | HanXRQChr16g0499761 | ribosomal protein |
| *Helianthuus annuus* | HanXRQChr04g0106961 | ribosomal protein |
| *Helianthuus annuus* | HanXRQChr06g0175811 | ribosomal protein |
| *Helianthuus annuus* | HanXRQChr04g0122771 | ribosomal protein |
| *Helianthuus annuus* | HanXRQChr09g0245691 | ribosomal protein |
| *Helianthuus annuus* | HanXRQChr16g0520021 | ribosomal protein |
| *Helianthuus annuus* | HanXRQChr03g0060471 | ribosomal protein |
| *Helianthuus annuus* | HanXRQChr14g0429531 | ribosomal protein |
| *Helianthuus annuus* | HanXRQChr06g0171911 | ribosomal protein |
| *Helianthuus annuus* | HanXRQChr15g0479091 | ribosomal protein |
| *Helianthuus annuus* | HanXRQChr15g0479101 | ribosomal protein |
| *Helianthuus annuus* | HanXRQChr17g0543641 | ribosomal protein |
| *Helianthuus annuus* | HanXRQChr17g0543661 | ribosomal protein |
| *Helianthuus annuus* | HanXRQChr04g0105831 | ribosomal protein |
| *Helianthuus annuus* | HanXRQChr09g0258341 | ribosomal protein |
| *Helianthuus annuus* | HanXRQChr10g0287141 | ribosomal protein |
| *Helianthuus annuus* | HanXRQChr15g0463911 | ribosomal protein |
| *Helianthuus annuus* | HanXRQChr03g0076171 | ribosomal protein |
| *Helianthuus annuus* | HanXRQChr05g0159291 | ribosomal protein |
| *Helianthuus annuus* | HanXRQChr13g0407551 | ribosomal protein |
| *Helianthuus annuus* | HanXRQChr12g0380701 | ribosomal protein |
| *Helianthuus annuus* | HanXRQChr15g0477271 | ribosomal protein |
| *Helianthuus annuus* | HanXRQChr17g0545211 | ribosomal protein |
| *Helianthuus annuus* | HanXRQChr17g0570741 | ribosomal protein |
| *Helianthuus annuus* | HanXRQChr17g0570761 | ribosomal protein |
| *Helianthuus annuus* | HanXRQChr02g0044021 | ribosomal protein |
| *Helianthuus annuus* | HanXRQChr05g0152871 | ribosomal protein |
| *Helianthuus annuus* | HanXRQChr01g0012781 | ribosomal protein |
| *Helianthuus annuus* | HanXRQChr08g0230861 | ribosomal protein |
| *Helianthuus annuus* | HanXRQChr13g0391831 | ribosomal protein |
| *Helianthuus annuus* | HanXRQChr11g0337791 | bifunctional trypsin/alpha-amylase inhibitor |
| *Helianthuus annuus* | HanXRQChr10g0312371 | 2-oxoacid dehydrogenase acyltransferase |
| *Helianthuus annuus* | HanXRQChr09g0276191 | acid phosphatase (class B) |
| *Helianthuus annuus* | HanXRQChr05g0142271 | aldose-1-epimerase |
| *Helianthuus annuus* | HanXRQChr14g0439791 | alpha-D-phosphohexomutase |
| *Helianthuus annuus* | HanXRQChr09g0251071 | alpha-L-fucosidase |
| *Helianthuus annuus* | HanXRQChr05g0147371 | annexin |
| *Helianthuus annuus* | HanXRQChr09g0247561 | Asp protease (Peptidase family A1) |
| *Helianthuus annuus* | HanXRQChr13g0409681 | berberine-bridge enzyme (S)-reticulin: oxygen oxido-reductase |
| *Helianthuus annuus* | HanXRQChr10g0295971 | beta-hydroxyacyl-(acyl-carrier-protein) dehydratase |
| *Helianthuus annuus* | HanXRQChr13g0412571 | carbohydrate esterase family 13 - CE13 (pectin acylesterase - PAE) |
| *Helianthuus annuus* | HanXRQChr12g0360101 | carbohydrate esterase family 8 - CE8 (pectin methylesterase - PME) |
| *Helianthuus annuus* | HanXRQChr01g0019231 | carbonic anhydrase |
| *Helianthuus annuus* | HanXRQChr02g0036611 | cellular retinaldehyde binding/alpha-tocopherol transport |
| *Helianthuus annuus* | HanXRQChr10g0313581 | chaperonin Cpn60 |
| *Helianthuus annuus* | HanXRQChr09g0251791 | chlathrin |
| *Helianthuus annuus* | HanXRQChr11g0329811 | chlorophyll A-B binding protein |
| *Helianthuus annuus* | HanXRQChr13g0398861 | cobalamin (vitamin B12)-independent methionine synthase |
| *Helianthuus annuus* | HanXRQChr10g0298981 | cyclophilin |
| *Helianthuus annuus* | HanXRQChr04g0103281 | Cys protease (papain family) |
| *Helianthuus annuus* | HanXRQChr09g0268361 | cytochrome P450 |
| *Helianthuus annuus* | HanXRQChr17g0535591 | dirigent protein |
| *Helianthuus annuus* | HanXRQChr03g0065901 | expansin |
| *Helianthuus annuus* | HanXRQChr11g0336761 | expressed protein (cupin domain, seed storage protein domain) |
| *Helianthuus annuus* | HanXRQChr10g0280931 | expressed protein (cupin domain, seed storage protein domain) |
| *Helianthuus annuus* | HanXRQChr10g0288971 | expressed protein (cupin domain, seed storage protein domain) |
| *Helianthuus annuus* | HanXRQChr12g0380361 | expressed protein (cupin domain, seed storage protein domain) |
| *Helianthuus annuus* | HanXRQChr09g0254381 | expressed protein (cupin domain, seed storage protein domain) |

APPENDIX-continued

Table 13: Plant EV-Markers

| | | |
|---|---|---|
| *Helianthuus annuus* | HanXRQChr04g0112711 | expressed protein (cupin domain, seed storage protein domain) |
| *Helianthuus annuus* | HanXRQChr07g0196131 | expressed protein (cupin domain, seed storage protein domain) |
| *Helianthuus annuus* | HanXRQChr10g0301281 | expressed protein (cupin domain, seed storage protein domain) |
| *Helianthuus annuus* | HanXRQChr10g0301931 | expressed protein (cupin domain, seed storage protein domain) |
| *Helianthuus annuus* | HanXRQChr13g0404461 | expressed protein (cupin domain) |
| *Helianthuus annuus* | HanXRQChr01g0015821 | expressed protein (DUF642) |
| *Helianthuus annuus* | HanXRQChr03g0065301 | expressed protein (Gnk2-homologous domain, antifungal protein of Ginkgo seeds) |
| *Helianthuus annuus* | HanXRQChr03g0068311 | expressed protein (LRR domains) |
| *Helianthuus annuus* | HanXRQChr10g0291371 | expressed protein (LRR domains) |
| *Helianthuus annuus* | HanXRQChr03g0075061 | fasciclin-like arabinogalactan protein (FLA) |
| *Helianthuus annuus* | HanXRQChr08g0221961 | ferritin |
| *Helianthuus annuus* | HanXRQChr09g0257521 | FMN-dependent dehydrogenase |
| *Helianthuus annuus* | HanXRQChr14g0441641 | fructose-bisphosphate aldolase |
| *Helianthuus annuus* | HanXRQChr10g0312621 | germin |
| *Helianthuus annuus* | HanXRQChr09g0244271 | glucose-methanol-choline oxidoreductase |
| *Helianthuus annuus* | HanXRQChr03g0061571 | glutamate synthase |
| *Helianthuus annuus* | HanXRQChr05g0144801 | glyceraldehyde 3-phosphate dehydrogenase |
| *Helianthuus annuus* | HanXRQChr17g0550211 | glycerophosphoryl diester phosphodiesterase |
| *Helianthuus annuus* | HanXRQChr06g0175391 | glycoside hydrolase family 16 - GH16 (endoxyloglucan transferase) |
| *Helianthuus annuus* | HanXRQChr11g0351571 | glycoside hydrolase family 17 - GH17 (beta-1,3-glucosidase) |
| *Helianthuus annuus* | HanXRQChr05g0141461 | glycoside hydrolase family 18 - GH18 |
| *Helianthuus annuus* | HanXRQChr09g0276721 | glycoside hydrolase family 19 - GH19 |
| *Helianthuus annuus* | HanXRQChr02g0046191 | glycoside hydrolase family 2 - GH2 |
| *Helianthuus annuus* | HanXRQChr16g0524981 | glycoside hydrolase family 20 - GH20 (N-acetyl-beta-glucosaminidase) |
| *Helianthuus annuus* | HanXRQChr11g0322851 | glycoside hydrolase family 27 - GH27 (alpha-galactosidase/melibiase) |
| *Helianthuus annuus* | HanXRQChr10g0293191 | glycoside hydrolase family 3 - GH3 |
| *Helianthuus annuus* | HanXRQChr16g0511881 | glycoside hydrolase family 31 - GH31 (alpha-xylosidase) |
| *Helianthuus annuus* | HanXRQChr14g0461441 | glycoside hydrolase family 32 - GH32 (vacuolar invertase) |
| *Helianthuus annuus* | HanXRQChr13g0423671 | glycoside hydrolase family 35 - GH35 (beta-galactosidase) |
| *Helianthuus annuus* | HanXRQChr10g0319301 | glycoside hydrolase family 35 - GH35 (beta-galactosidase) |
| *Helianthuus annuus* | HanXRQChr09g0256531 | glycoside hydrolase family 38 - GH38 (alpha-mannosidase) |
| *Helianthuus annuus* | HanXRQChr11g0320901 | glycoside hydrolase family 5 - GH5 (glucan-1,3-beta glucosidase) |
| *Helianthuus annuus* | HanXRQChr05g0130491 | glycoside hydrolase family 51 - GH51 (alpha-arabinofuranosidase) |
| *Helianthuus annuus* | HanXRQChr10g0314191 | glycoside hydrolase family 79 - GH79 (endo-beta-glucuronidase/heparanase |
| *Helianthuus annuus* | HanXRQChr13g0397411 | homologous to *A. thaliana* PMR5 (Powdery Mildew Resistant) (carbohydrate acylation) |
| *Helianthuus annuus* | HanXRQChr14g0444681 | inhibitor family I3 (Kunitz-P family) |
| *Helianthuus annuus* | HanXRQChr14g0445181 | lactate/malate dehydrogenase |
| *Helianthuus annuus* | HanXRQChr17g0564111 | lectin (D-mannose) |
| *Helianthuus annuus* | HanXRQChr17g0558861 | lectin (PAN-2 domain) |
| *Helianthuus annuus* | HanXRQChr02g0039251 | lipase acylhydrolase (GDSL family) |
| *Helianthuus annuus* | HanXRQChr01g0000161 | lipid transfer protein/trypsin-alpha amylase inhibitor |
| *Helianthuus annuus* | HanXRQChr02g0047121 | mannose-binding lectin |
| *Helianthuus annuus* | HanXRQChr10g0303361 | mitochondrial carrier protein |
| *Helianthuus annuus* | HanXRQChr15g0489551 | multicopper oxidase |
| *Helianthuus annuus* | HanXRQChr05g0135581 | neutral/alkaline nonlysosomal ceramidase |
| *Helianthuus annuus* | HanXRQChr01g0017621 | nucleoside diphosphate kinase |
| *Helianthuus annuus* | HanXRQChr10g0295991 | peroxidase |
| *Helianthuus annuus* | HanXRQChr13g0398251 | peroxiredoxin |
| *Helianthuus annuus* | HanXRQChr11g0333171 | phosphate-induced (phi) protein 1 |
| *Helianthuus annuus* | HanXRQChr03g0060421 | phosphodiesterase/nucleotide pyrophosphatase/phosphate transferase |
| *Helianthuus annuus* | HanXRQChr03g0078011 | phosphofructokinase |
| *Helianthuus annuus* | HanXRQChr13g0408831 | phosphoglycerate kinase |
| *Helianthuus annuus* | HanXRQChr10g0286701 | phosphoglycerate mutase |
| *Helianthuus annuus* | HanXRQChr06g0171591 | photosystem II PsbP, oxygen evolving complex |
| *Helianthuus annuus* | HanXRQChr14g0434951 | plastid lipid-associated protein/fibrillin conserved domain |
| *Helianthuus annuus* | HanXRQChr05g0146621 | plastocyanin (blue copper binding protein) |
| *Helianthuus annuus* | HanXRQChr11g0330251 | polyphenol oxidase |
| *Helianthuus annuus* | HanXRQChr04g0094541 | proteasome A-type subunit |
| *Helianthuus annuus* | HanXRQChr03g0081271 | proteasome B-type subunit |
| *Helianthuus annuus* | HanXRQChr12g0356851 | purple acid phosphatase |
| *Helianthuus annuus* | HanXRQChr15g0485781 | pyridoxal phosphate-dependent transferase |
| *Helianthuus annuus* | HanXRQChr11g0336791 | ribosomal protein |
| *Helianthuus annuus* | HanXRQChr11g0330521 | ribosomal protein |
| *Helianthuus annuus* | HanXRQChr11g0326801 | ribulose bisphosphate carboxylase, large subunit |
| *Helianthuus annuus* | HanXRQChr16g0523951 | ribulose-1,5-bisphosphate carboxylase small subunit |

APPENDIX-continued

Table 13: Plant EV-Markers

| | | |
|---|---|---|
| *Helianthuus annuus* | HanXRQChr01g0022151 | S-adenosyl-L-homocysteine hydrolase |
| *Helianthuus annuus* | HanXRQChr14g0454811 | S-adenosylmethionine synthetase |
| *Helianthuus annuus* | HanXRQChr04g0109991 | SCP-like extracellular protein (PR-1) |
| *Helianthuus annuus* | HanXRQChr03g0072241 | Ser carboxypeptidase (Peptidase family S10) |
| *Helianthuus annuus* | HanXRQChr12g0377221 | Ser protease (subtilisin) (Peptidase family S8) |
| *Helianthuus annuus* | HanXRQChr02g0055581 | superoxide dismutase |
| *Helianthuus annuus* | HanXRQChr15g0493261 | thaumatin (PR5) |
| *Helianthuus annuus* | HanXRQChr16g0532531 | transketolase |
| *Helianthuus annuus* | HanXRQChr07g0197421 | translation elongation factor EFTu/EF1A |
| *Helianthuus annuus* | HanXRQChr06g0173951 | translationally controlled tumour protein |

What is claimed is:

1. A method for making lipid reconstructed plant messenger packs (LPMPs), the method comprising reconstituting a film comprising purified lipids derived from a plant source in the presence of a synthetic charged lipid, thereby producing a LPMP that comprises the synthetic charged lipid, wherein the synthetic charged lipid is chosen from 1'-((2-(4-(2-((2-(bis(2-hydroxydodecyl)amino)ethyl) (2-hydroxydodecyl)amino)ethyl)piperazin-1-yl)ethyl)azanediyl) bis(dodecan-2-ol) (C12-200), DLin-MC3-DMA (MC3), dioleoyl-3-trimethylammonium propane (DODAP), DC-cholesterol, DOTAP, Ethyl PC, GL67, DLin-KC2-DMA (KC2), MD1 cKK-E12 (MD1), OF2, EPC, ZA3-Ep10, TT3, LP01, 5A2-SC8, heptadecan-9-yl 8-((2-hydroxyethyl)(8-(nonyloxy)-8-oxooctyl)amino)octanoate, a cationic sulfonamide amino lipid, an amphiphilic zwitterionic amino lipid, DODAC, DOBAQ, YSK05, DOBAT, DOBAQ, DOPAT, DOMPAQ, DOAAQ, DMAP-BLP, DLinDMA, DODMA, DOTMA, DSDMA, DOSPA, DODAC, DOBAQ, DMRIE, DOTAP-cholesterol, GL67A, and 98N12-5, or combinations thereof.

2. The method of claim 1, wherein the synthetic charged lipid is chosen from C12-200, MC3, DODAP, DC-cholesterol, DOTAP, Ethyl PC, GL67, KC2, MD1, OF2, EPC, ZA3-Ep10, TT3, LP01, 5A2-SC8, heptadecan-9-yl 8-((2-hydroxyethyl)(8-(nonyloxy)-8-oxooctyl)amino)octanoate, a cationic sulfonamide amino lipid, and an amphiphilic zwitterionic amino lipid, or combinations thereof.

3. The method of claim 2, wherein the synthetic charged lipid is chosen from C12-200, MC3, DODAP, and DC-cholesterol, or combinations thereof.

4. The method of claim 1, wherein the reconstitution is performed in the presence of a sterol, thereby producing a LPMP that comprises a synthetic charged lipid and a sterol.

5. The method of claim 4, wherein the sterol is cholesterol or sitosterol.

6. The method of claim 1, wherein the reconstitution is performed in the presence of a PEGylated lipid, thereby producing a LPMP that comprises a synthetic charged lipid and a PEGylated lipid.

7. The method of claim 6, wherein the PEGylated lipid is C14-PEG2k, C18-PEG2k, or DMPE-PEG2k.

8. The method of claim 1, wherein the reconstitution is performed in the presence of a sterol and a PEGylated lipid, thereby producing a LPMP that comprises a synthetic charged lipid, a sterol, and a PEGylated lipid.

9. The method of claim 8, wherein the synthetic charged lipid, lipids derived from a plant source, sterol, and PEGylated lipid comprise a molar ratio of about 30%-75%, about 10%-20%, about 35%-50%, and about 1%-3%, respectively, of the lipids in the LPMP.

10. The method of claim 9, wherein the synthetic charged lipid, lipids derived from a plant source, sterol, and PEGylated lipid are formulated at a molar ratio of 50:10:38.5:1.5.

11. The method of claim 1, wherein the LPMPs comprise a heterologous polynucleotide.

12. The method of claim 11, wherein the heterologous polynucleotide is an mRNA, a siRNA or a precursor thereof, a microRNA (miRNA) or a precursor thereof, a viral RNA, or a plasmid.

13. The method of claim 11, wherein the encapsulation efficiency of the heterologous polynucleotide by the LPMP is at least 5%, 10%, 15%, 20%, 30%, 40%, 50%, 60%, 70%, 80%, 90%, 95%, 98%, 99%, or more than 99%.

14. The method of claim 1, wherein the LPMP is formulated for delivery to an animal.

15. The method of claim 1, wherein the LPMP is formulated for delivery to a plant.

* * * * *

```
                            SEQUENCE LISTING

<160> NUMBER OF SEQ ID NOS: 12

<210> SEQ ID NO 1
<211> LENGTH: 3
<212> TYPE: DNA
<213> ORGANISM: Streptococcus pyogenes
<220> FEATURE:
<221> NAME/KEY: misc_feature
<222> LOCATION: (1)..(1)
<223> OTHER INFORMATION: n is a, c, g, or t

<400> SEQUENCE: 1 ngg                                                                        3

<210> SEQ ID NO 2
<211> LENGTH: 6
<212> TYPE: DNA
<213> ORGANISM: Streptococcus thermophilus
<220> FEATURE:
<221> NAME/KEY: misc_feature
<222> LOCATION: (1)..(2)
<223> OTHER INFORMATION: n is a, c, g, or t

<400> SEQUENCE: 2 nnagaa                                                                     6

<210> SEQ ID NO 3
<211> LENGTH: 5
<212> TYPE: DNA
<213> ORGANISM: Streptococcus thermophilus
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 3 nggng                                                                      5

<210> SEQ ID NO 4
<211> LENGTH: 7
<212> TYPE: DNA
<213> ORGANISM: Neisseria meningitidis
<220> FEATURE:
<221> NAME/KEY: misc_feature
<222> LOCATION: (1)..(3)
<223> OTHER INFORMATION: n is a, c, g, or t

<400> SEQUENCE: 4 nnngatt                                                                    7
```

```
<210> SEQ ID NO 5
<211> LENGTH: 3
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: n is a, c, g, or t

<400> SEQUENCE: 5 ttn                                                                         3

<210> SEQ ID NO 6
<211> LENGTH: 3
<212> TYPE: DNA
<213> ORGANISM: Artificial Sequence
<220> FEATURE:
<223> OTHER INFORMATION: Synthetic Construct

<400> SEQUENCE: 6 cta                                                                         3

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
ccaggtgggg cttatgcatc                                                      20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
ccacaccaag gcttgaaccc                                                      20

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
ggccggattc acgaaacggt                                                      20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
cgtcgagatt ggcagttggc                                                      20

<210> SEQ ID NO 11
```

```
<211> LENGTH: 25
<212> TYPE: DNA
<213> ORGANISM: Artificial Sequence
<220> FEATURE:
<223> OTHER INFORMATION: Synthetic Construct

<400> SEQUENCE: 11
tctgccctat caactttcga tggta                                              25

<210> SEQ ID NO 12
<211> LENGTH: 25
<212> TYPE: DNA
<213> ORGANISM: Artificial Sequence
<220> FEATURE:
<223> OTHER INFORMATION: Synthetic Construct

<400> SEQUENCE: 12
aatttgcgcg cctgctgcct tcctt                                              25
```